US011680263B2

(12) United States Patent
Chen et al.

(10) Patent No.: US 11,680,263 B2
(45) Date of Patent: *Jun. 20, 2023

(54) MICRO-RNAS AND COMPOSITIONS COMPRISING SAME FOR THE TREATMENT AND DIAGNOSIS OF SEROTONIN-, ADRENALIN-, NORADRENALIN-, GLUTAMATE-, AND CORTICOTROPIN-RELEASING HORMONE-ASSOCIATED MEDICAL CONDITIONS

(71) Applicant: Yeda Research and Development Co. Ltd., Rehovot (IL)

(72) Inventors: Alon Chen, Rehovot (IL); Orna Issler, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 121 days.

This patent is subject to a terminal disclaimer.

(21) Appl. No.: 17/227,483

(22) Filed: Apr. 12, 2021

(65) Prior Publication Data

US 2021/0230597 A1    Jul. 29, 2021

Related U.S. Application Data

(62) Division of application No. 16/180,083, filed on Nov. 5, 2018, now Pat. No. 10,975,373, which is a division of application No. 15/111,539, filed as application No. PCT/IL2015/050132 on Feb. 5, 2015, now Pat. No. 10,125,365.

(60) Provisional application No. 61/935,912, filed on Feb. 5, 2014.

(51) Int. Cl.
| C12N 15/113 | (2010.01) |
| C12Q 1/6883 | (2018.01) |
| C12N 15/11  | (2006.01) |
| C07H 21/02  | (2006.01) |

(52) U.S. Cl.
CPC .......... *C12N 15/113* (2013.01); *C12N 15/111* (2013.01); *C12Q 1/6883* (2013.01); *C12N 2310/141* (2013.01); *C12N 2320/30* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 8,951,983 B2 | 2/2015 | Hornstein et al. |
| 9,150,858 B2 | 10/2015 | Chen et al. |
| 9,301,981 B2 | 4/2016 | Hornstein et al. |
| 10,125,365 B2 | 11/2018 | Chen et al. |
| 2009/0075258 A1 | 3/2009 | Latham et al. |
| 2009/0092980 A1 | 4/2009 | Arenz et al. |
| 2009/0131356 A1 | 5/2009 | Bader et al. |
| 2009/0208564 A1 | 8/2009 | Li et al. |
| 2010/0222413 A1 | 9/2010 | Stoffel et al. |
| 2010/0227908 A1 | 9/2010 | Cairns |
| 2010/0240665 A1 | 9/2010 | Eckhardt et al. |
| 2012/0093936 A1 | 4/2012 | Lindenberg et al. |
| 2012/0100569 A1 | 4/2012 | Liu et al. |
| 2014/0163089 A1 | 6/2014 | Chen et al. |
| 2016/0000821 A1 | 1/2016 | Chen et al. |
| 2016/0348101 A1 | 12/2016 | Chen et al. |
| 2017/0037404 A1 | 2/2017 | Brown et al. |
| 2018/0147233 A1 | 5/2018 | Chen et al. |
| 2019/0055561 A1 | 2/2019 | Chen et al. |
| 2019/0167712 A1 | 6/2019 | Chen et al. |
| 2022/0265696 A1 | 8/2022 | Chen et al. |

FOREIGN PATENT DOCUMENTS

| CN | 101448958 | 6/2009 |
| CN | 101590243 | 12/2009 |
| EP | 2298359 | 3/2011 |
| JP | 2010-537639 | 12/2010 |
| JP | 2012-525146 | 10/2012 |
| JP | 2017-506228 | 3/2017 |
| WO | WO 2007/033023 | 3/2007 |
| WO | WO 2007/109236 | 9/2007 |
| WO | WO 2007/147409 | 12/2007 |
| WO | WO 2009/079790 | 7/2009 |
| WO | WO 2009/148137 | 12/2009 |
| WO | WO 2011/131693 | 10/2011 |
| WO | WO 2013/018060 | 2/2013 |
| WO | WO 2013/116589 | 8/2013 |
| WO | WO 2014/064257 | 5/2014 |
| WO | WO 2014/064258 | 5/2014 |

(Continued)

OTHER PUBLICATIONS

Examination Report dated Jan. 28, 2022 From the Serviço Publico Federal, Ministerio da Economia, Institute Nacional da Propriedade Industrial do Brasil Re. Application No. BR1120140027374. (5 Pages).
International Search Report and the Written Opinion dated Mar. 6, 2022 From the International Searching Authority Re. Application No. PCT/IL2022/050075. (15 Pages).
Taipaleenmaki et al. "Targeting of Runx2 by miRNA-135 and miRNA-203 Impairs Progression of Breast Cancer and Metastatic Bone Disease", Cancer Research, 75(7):1433-1444, Apr. 1, 2015.
Applicant-Initiated Interview Summary dated Feb. 20, 2015 From the U.S. Patent and Trademark Office Re. U.S. Appl. No. 14/236,928.
Communication Pursuant to Article 94(3) EPC dated Sep. 8, 2017 From the European Patent Office Re. Application No. 15710264.1. (7 Pages).

(Continued)

*Primary Examiner* — Sean McGarry

(57) ABSTRACT

A method of treating a bipolar disorder in a subject in need thereof is disclosed. The method comprising administering to the subject sa therapeutically effective amount of a miR-135, a precursor thereof or a nucleic acid molecule encoding said miR-135 or said precursor thereof, thereby treating the bipolar disorder. Methods of diagnosing a mood disorder in a human subject and of monitoring treatment of an anti-depressant drug or a medicament for the treatment of a mood disorder are also disclosed.

9 Claims, 66 Drawing Sheets

Specification includes a Sequence Listing.

(56) References Cited

FOREIGN PATENT DOCUMENTS

| WO | WO 2015/118537 | 8/2015 |
|----|----------------|--------|
| WO | WO 2022/153322 | 7/2022 |

OTHER PUBLICATIONS

Communication Pursuant to Article 94(3) EPC dated Feb. 16, 2018 From the European Patent Office Re. Application No. 15710264.1. (6 Pages).
Communication Pursuant to Article 94(3) EPC dated Mar. 18, 2019 Fromthe European Patent Office Re. Application No. 15710264.1. (9 Pages).
Communication Pursuant to Article 94(3) EPC dated May 19, 2016 From the European Patent Office Re. Application No. 12759827.4.
Communication Pursuant to Article 94(3) EPC dated Apr. 23, 2020 From the European Patent Office Re. Application No. 15710264.1. (7 Pages).
Communication Pursuant to Article 94(3) EPC dated May 27, 2020 From the European Patent Office Re. Application No. 19164042.4. (3 Pages).
Communication Pursuant to Article 94(3) EPC dated Jul. 29, 2015 From the European Patent Office Re. Application No. 12759827.4.
Communication Relating to the Results of the Partial International Search dated Dec. 5, 2012 From the International Searching Authority Re. Application No. PCT/IB2012/053971.
Communication Relating to the Results of the Partial International Search dated May 20, 2015 Fromthe International Searching Authority Re. Application No. PCT/IL2015/050132.
European Search Report and the European Search Opinion dated Jul. 12, 2019 Fromthe European Patent Office Re. Application No. 19164042.4. (6 Pages).
European Search Report and the European Search Opinion dated Jul. 26, 2017 Fromthe European Patent Office Re. Application No. 17163200.3. (9 Pages).
Examination Report dated Jan. 13, 2021 From the Servico Publico Federal, Ministerio da Economia, hrstituto Nacional da Propriedade Industrial do Brasil RE Application No. BR1120140027374. ( 4 Pages).
Final Official Action dated Jun. 17, 2020 from the U.S. Patent and Trademark Office Re. U.S. Appl. No. 16/273,215. (11 pages).
International Preliminary Report on Patentability dated Feb. 13, 2014 From the International Bureau of WIPO Re. Application No. PCT/IB2012/053971.
International Preliminary Report on Patentability dated Aug. 18, 2016 From the International Bureau of WIPO Re. Application No. PCT/IL2015/050132.
International Search Report and the Written Opinion dated Aug. 3, 2015 From the International Searching Authority Re. Application No. PCT/IL2015/050132.
International Search Report and the Written Opinion dated Feb. 7, 2013 From the International Searching Authority Re. Application No. PCT/IB2012/053971.
Notice of Reason for Rejection dated Mar. 25, 2016 From the Japanese Patent Office Re. Application No. 2014-523434 and Its Translation Into English.
Notice of Reasons for Refusal dated Nov. 14, 2018 From the Japan Patent Office Re. Application No. 2016-549799 and Its Translation Into English. (12 Pages).
Notice of Reasons for Refusal dated Jul. 21, 2020 From the Japan Patent Office Re. Application No. 2016-549799 and Its Translation Into English. (18 Pages).
Notice of Reasons for Refusal dated Apr. 28, 2020 From the Japan Patent Office Re. Application No. 2019-114138 and Its Translation Into English. (9 Pages).
Notice of Reasons for Refusal dated Dec. 28, 2020 From the Japan Patent Office Re. Application No. 2016-549799 and Its Machine Translation Into English. (3 Pages).
Notification of Office Action and Search Report dated Aug. 5, 2019 Fromthe National Intellectual Property Administration of the People's Republic of China Re. Application No. 201710223993.2 and Its Translation Into English. (19 Pages).
Notification of Office Action and Search Report dated Dec. 12, 2018 From the National Intellectual Property Administration of the People's Republic of China Re. Application No. 201580018229.0 and Its Translation Into English. (20 Pages).
Office Action and Search Report dated Feb. 25, 2015 From The State Intellectual Property Office of the People's Republic of China Re. Application No. 201280048952.X and Its Translation Into English.
Office Action dated Jun. 2, 2019 From the Israel Patent Office Re. Application No. 246942 and Its Translation Into English. (7 Pages).
Office Action dated May 3, 2017 Fromthe Israel Patent Office Re. Application No. 230814. (2 Pages).
Office Action dated Dec. 5, 2016 From the Israel Patent Office Re. Application No. 230814 and Its Translation Into English. (9 Pages).
Office Action dated Nov. 17, 2015 From The State Intellectual Property Office of the People's Republic of China Re. Application No. 201280048952.X and Its Translation Into English.
Office Action dated Feb. 24, 2020 From the Israel Patent Office Re. Application No. 246942 and Its Translation Into English. (5 Pages).
Official Action dated Apr. 2, 2021 Fromthe U.S. Patent and Trademark Office Re. U.S. Appl. No. 16/273,215. (21 Pages).
Official Action dated Feb. 8, 2017 Fromthe U.S. Patent and Trademark Office Re. U.S. Appl. No. 14/856,697. (19 pages).
Official Action dated Jul. 9, 2018 From the U.S. Patent and Trademark Office Re. U.S. Appl. No. 15/873,998. (19 pages).
Official Action dated Jun. 12, 2020 from the U.S. Patent and Trademark Office Re. U.S. Appl. No. 16/180,083. (35 pages).
Official Action dated Dec. 14, 2014 From the U.S. Patent and Trademark Office Re. U.S. Appl. No. 14/236,928.
Official Action dated Jun. 16, 2017 From the U.S. Patent and Trademark Office Re. U.S. Appl. No. 14/856,697. (8 pages).
Official Action dated Nov. 22, 2019 From the U.S. Patent and Trademark Office Re. U.S. Appl. No. 16/273,215. (24 pages).
Official Action dated Sep. 28, 2017 From tire U.S. Patent and Trademark Office Re. U.S. Appl. No. 15/111,539. (22 pages).
Official Action dated Jan. 30, 2018 From the U.S. Patent and Trademark Office Re. U.S. Appl. No. 15/111,539. (9 pages).
Decision of Rejection dated Aug. 30, 2016 From the Japan Patent Office Re. Application No. 2014-523434 and Its Translation Into English.
Requisition by the Examiner dated Jan. 18, 2021 From the Innovation, Science and Economic Development Canada, Canadian Intellectual Property Office Re. Application No. 2,936,158, (11 Pages).
Requisition by the Examiner dated Jun. 18, 2019 Fromthe Innovation, Science and Economic Development Canada, Canadian Intellectual Property Office Re. Application No. 2844012. (5 Pages).
Requisition by the Examiner dated Jun. 19, 2018 Fromthe Innovation, Science and Economic Development Canada, Canadian Intellectual Property Office Re. Application No. 2,844,012. (4 Pages).
Restriction Official Action dated Sep. 24, 2014 From the U.S. Patent and Trademark Office Re. U.S. Appl. No. 14/236,928.
Search Report and Opinion dated Aug. 14, 2020 Fromthe Servico Publico Federal, Ministerio da Economia, Instituto Nacional da Propriedade Industrial do Brasil Re. Application No. BR112016018145-0 and Its Translation of Opinion Into English. (6 Pages).
Translation dated Jan. 28, 2021 of Examination Report dated Jan. 13, 2021 From the Servico Publico Federal, Ministerio da Economia, Instituto Nacional da Propriedade Industrial do Brasil Re. Application No. BR1120140027374. (2 Pages).
Aluru et al. "Developmental Exposure to Valproic Acid Alters the Expression of MicroRNAs Involved in Neurodevelopment in Zebrafish", Neurotoxicology and Teratology, XP002739185, 40: 46-58, Nov. 2013. p. 51, Fig.3.
American Psychiatric Association "Bipolar and Related Disorders", Diagnostic and Statistical Manual of Mental Disorders, DSM-5™, 5th Ed., p. 123-154, 2013.
American Psychiatric Association "Depressive Disorders", Diagnostic and Statistical Manual of Mental Disorders, DSM-5™, 5th Ed., p. 155-188, 2013.

(56) References Cited

OTHER PUBLICATIONS

American Psychiatric Association "DSM-5™: Contents", Diagnostic and Statistical Manual of Mental Disorders, 5th Ed., 3 P., 2013.
Barkus et al. "Hippocampal NMDA Receptors and a Anxiety: At the Interface Between Cognition and Emotion", European Journal of Pharmacology, 626(1):49-56, Jan. 10, 2010.
Baudry et al. "MiR-16 Targets the Serotonin Transporter: A New Facet for Adaptive Responses to Antidepressants", Science, XP055045625, 329(5998): 1537-1541, Sep. 17, 2010.
Curtis et al. "Genome Scan of Pedigrees Multiply Affected With Bipolar Disorder Provides Further Support for the Presence of a Susceptibility Locus on Chromosome 12q23-q24, and Suggests the Presence of Additional Loci on 1p and 1q", Psychiatry Genetics, 13(2): 77-84, Jun. 2003.
Detera-Wadleigh et al. "A High-Density Genome Scan Detects Evidence for a Bipolar-Disorder Susceptibility Locus on 13q32 and Other Potential Loci on 1q32 and 18p11.2", Proc. Natl. Acad. Sci. USA, 96(10): 5604-5609, May 11, 1999.
Dwivedi "Evidence Demonstrating Role of MicroRNAs in the Etiopathology of Major Depression", Journal of Chemical Neuroanatomy, XP028277207, 42(2): 142-156, Apr. 6, 2011. Abstract.
Ekholm et al. "Evidence of Susceptibility Loci on 4q32 and 15p12 for Bipolar Disorder", Human Molecular Genetics, 12(15): 1907-1915, Aug. 1, 2003.
Finnerty et al. "The MiR-15/107 Group of MicroRNA Genes: Evolutionary Biology, Cellular Functions, and Roles in Human Diseases", Journal of Molecular Biology, XP027306154, 402(3): 491-509, Available Online Aug. 1, 2010. Fig.7.
Fluegge et al. "5HT1A-Receptors and Behaviour Under Chronic Stress: Selective Counteraction by Testosterone", European Journal of Neuroscience, 10(8): 2685-2693, Aug. 31, 1998.
Franberg et al. "Involvement of 5-HT2A Receptor and Alpha2-Adrenoceptor Blockade in the Asenapine-Induced Elevation of Prefrontal Cortical Monoamine Outflow", Synapse, PX055403380. 66(7): 650-660, Published Online Feb. 23, 2012.
Gillespie et al. "Risk and Resilience: Genetic and Environmental Influences on Development of the Stress Response", Depression and Anxiety, XP055391931, 26(11): 984-992, Published Online Sep. 11, 2009. Fig.6.
Gould et al. "Animal Models of Bipolar Disorder and Mood Stabilizer Efficacy", Neuroscience and Biobehavioral Reviews, 31(6): 825-831, Jan. 2007.
Green et al. "Mutational Analysis of Two Positional Candidate Susceptibility Genes for Bipolar Disorder on Chromosome 12q23-q24: Phenylalanine Hvdroxylase and HumanLIM-Homcobox LHXS", Psychiatry Genetics, 13(2): 97-101, Jun. 2003.
Holleman et al. "MiR-135a Contributes to Paclitaxel Resistance in Tumor Cells Both In Vitro and In Vivo", Oncogene, XP055046005, 30(43): 4386-4398, Published Online May 9, 2011.
Issler et al. "Determiningthe Role ofMicroRNAs in Psychiatric Disorders", Nature Reviews Neuroscience, 16(4): 201-212, Apr. 2015.
Issler et al. "MicroRNA 135 Is Essential for Chronic Stress Resiliency, Antidepressant Efficacy, and Intact Serotonenenergic Activity", Neuron, 83(2): 344-360, Jul. 16, 2014.
Japanese Society of Mood Disorders "Bipolar Disorders", Guideline for Treatment. Japanese Society for Mood Disorders, I(Chap.1): 1-25, Mar. 31, 2012.
Kanba et al. "Guideline for Treatment of Bipolar Disorder by the Japanese Society of Mood Disorders, 2012", Psychiatry and Clinical Neurosciences 67: 285-300, 2013.
Kloosterman et al. "Cloning and Expression of New MicroRNAs from Zebrafish", Nucleic Acids Research, 34(9): 2558-2569, May 12, 2006.
Kosik "The Neuronal MicroRNA System", Nature Reviews Neuroscience, 7(12): 911-920, Dec. 2006.
Krishnan et al. "The Molecular Neurobiology ofDepression", Nature, 455(7215): 894-902, Oct. 16, 2008.

Lee et al. "MiR-19, MiR-101 and MiR-130 Co-Regulate ATXN1 Levels to Potentially Modulate SCA1 Pathogenesis", Nature Neuroscience, XP055051782, 11(10): 1137-1139, Oct. 1, 2008.
Li et al. "A MicroRNA Signature For a BMP2-Induced Osteoblast Lineage Commitment Program", Proceedings of National Academy of Sciences (PNAS), 105(37): 13906-13911, Sep. 16, 2008.
Mahmood et al. "Serotonin and Bipolar Disorder", Journal of Affective Disorders, 66: 1-11, 2001.
McMahon et al. "Meta-Analysis of Genome-Wide Association Data Detects a Risk Locus for Major Mood Disorders on Chromosome 3p21.1", Nature Genetics. 42(2): 128-131, Published Online Jan. 17, 2020.
Meerson et al. "Changes in Brain MicroRNAs Contributes to Cholinergic Stress Reactions", Journal of Molecular Neuroscience, XP055051770, 40(1-2): 47-55, Published Online Aug. 27, 2009. Fig.2, Table 1.
Meza-Sosa et al. "Role of MicroRNAs in Central Nervous System Development and Pathology", Journal of Neuroscience Research, XP55113622, 90: 1-12, Jan. 15, 2012. p. 8-9.
Michelsen et al. "The Dorsal Raphe Nucleus—From Silver Stainings to a Role in Depression", Brain Research Reviews, 55(2): 329-342, Oct. 31, 2007.
Millan "MicroRNA in the Regulation and Expression of Serotonergic Transmission in the Brain and Other Tissues", Current Opinion in Pharmacology, 11(1): 11 -22, Published Online Feb. 21, 2011.
Miller et al. "MicroRNA Dysregulation in Psychiatric Disease". Brain Research, XP055045628, 1338: 89-99, Published Online Mar. 18, 2010.
Moskvina et al. "Gene-Wide Analyses of Genome-Wide Association Datasets: Evidence for Multiple Common Risk Alleles for Schizophrenia and Bipolar Disorder and for Overlap in Genetic Risk", Molecular Psychiatry, 14(3): 252-260, Published Online Dec. 9, 2008.
Muinos-Gimeno et al. "Human MicroRNAs MiR-22, MiR-138-2, MiR-148a, and MiR-488 Arc Associated With Panic Disorder and Regulate Several Anxiety Candidate Genes and Related Pathways", Biological Psychiatry, XP028154304, 69(6): 526-533, Published Online Dec. 17, 2010. Tables 1, 2.
O'Connor et al. "Little Things on Which Happiness Depends: MicroRNAs as Novel Therapeutic Targets for the Treatment of Anxiety and Depression", Molecular Psychiatry, 17(4): 359-376, Publisehd Online Dec. 20, 2011.
Olive et al. "MiR-19 Is a Key Oncogenic Component of Mir-17-92". Genes & Development, XP055038529, 23(24): 2839-2849, Dec. 15, 2009.
Petracco et al. "MicroRNA 135 Regulates HOXA10 Expression in Endometriosis", Journal of Clinical Endocrinology & Metabolism, XP055187310, 96(12): 1925-1933, Dec. 1, 2011.
Presutti et al. "Non Coding RNA and Brain", BMC Neuroscience, 7(Suppl.1): S5-1-S5-12, Oct. 30, 2006.
Rasmussen et al. "Functional Studies of MicroRNA Based on Knockdown Using Locked Nucleic Acid Probes", Nature Methods 4,: 2 P., Apr. 2007.
Reich et al. "Differential Effects of Chronic Unpredictable Stress on Hippocampal CB1 Receptors in Male and Female Rats", Behavioural Brain Research. 203: 264-269, 2009.
Riester et al. "ACTH-Dependent Regulation of MicroRNA as Endogenous Modulators of Glucocorticoid Receptor Expression in the Adrenal Gland", Endocrinology, XP055051630, 153(1): 212-222, Nov. 29, 2011.
Saba et al. Dopamine-Regulated Micro RNA MiR-181 a Controls GluA2 Surface Expression in Hippocampal Neurons, Molecular and Cellular Biology,32(3): 619-632, Dec. 5, 2011.
Scott et al. "Genome-Wide Association and Meta-Analysis of Bipolar Disorder in Individuals of European Ancestry", Proc. Natl. Acad. Sci. USA, PNAS, 106(18): 7501-7506, May 5, 2009.
Toyoda "Social Defeat Models in Animal Science: What We Have Learned From Rodent Models". Animal Science Journal—Nihon Chikusan Gakkaiho, XP055687242, 88(7): 944-952, Apr. 24, 2017.
Volk et al. "MicroRNA-19b Assocaites With Ago2 in the Amygdala Following Chronic Stress and Regulates the Adrenergic Receptor Beta 1", The Journal of Neuroscience, XP055469360, 34(45): 15070-15082, Published Online Nov. 5, 2014.

(56) References Cited

OTHER PUBLICATIONS

Vreugdenhil et al. "MicroRNA 18 and 124a Down-Regulate the Glucocorticoid Receptor: Implications for Glucocorticoid Responsiveness in the Brain", Endocrinology, XP055051775, 150(5): 2220-2228, May 1, 2009.
Xun et al. "A Controlled Study on Venlafaxine and Lithium Augmentation in Major Depressive Disorder With Non-Responder to Selective Serotonin Reuptake Inhibitors", Journal of Clinical Psychiatry, 23(1): 42-44, Jul. 29, 2013. English Abstract.
Zhang et al. "miR-181a Involves in the Hippocampus-Dependent Memory Formation via PRKAA1" Scientific Reports 7 (8480): 1-11, Aug. 16, 2017.
Notification of Office Action and Search Report date Dec. 13, 2022 From the State Intellectual Property Office of the People's Republic of China Re. Application No. 202010626254.X and Claims. (8 Pages).
Xu et al. "Upregulation of miR-135b Is Involved in the Impaired Osteogenic Differentiation of Mesenchymal Stem Cells Derived from Multiple Myeloma Patients", Plose One. 8(11): e79752 1-11, Nov. 6, 2013.
Translation dated Jan. 5, 2023 of Notification of Office Action and Search Report dated Dec. 13, 2022 From the National Intellectual Property Administration of the People's Republic of China Re. Application No. 202010626254.X. (10 Pages).
Technical Examination Report dated Aug. 4, 2022 from the National Institute of Industrial Property of Brazil Re. Application No. BR 11 2016 018145 0 with an English Summary. (10 pages).
Examination Report dated Dec. 12, 2022 From the Servico Publico Federal, Ministerio da Economia, Instituto Nacional da Propriedade Industrial do Brasil RE Application No. BR12 2022 008902 0 and Its Summary In English. (9 Pages).

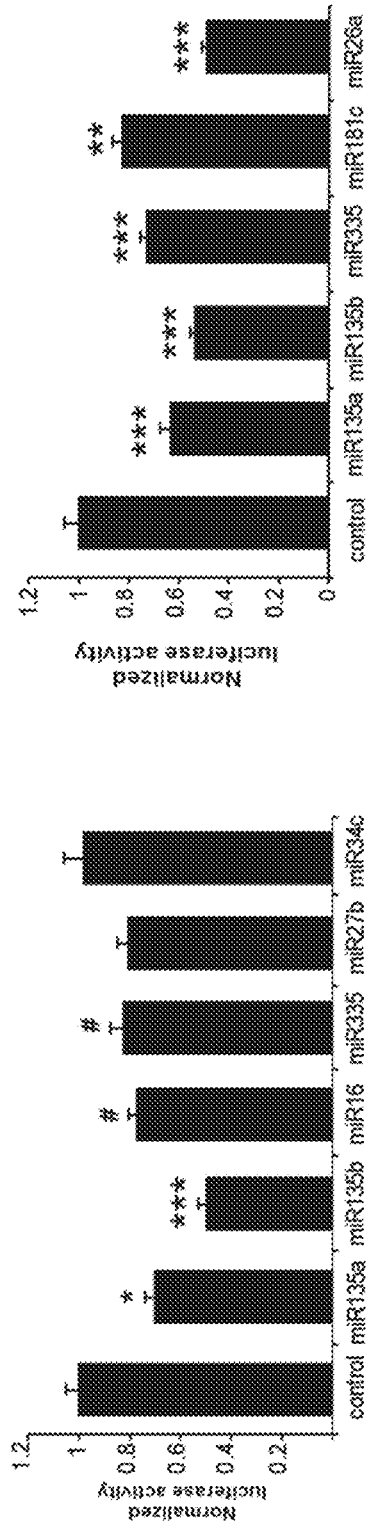

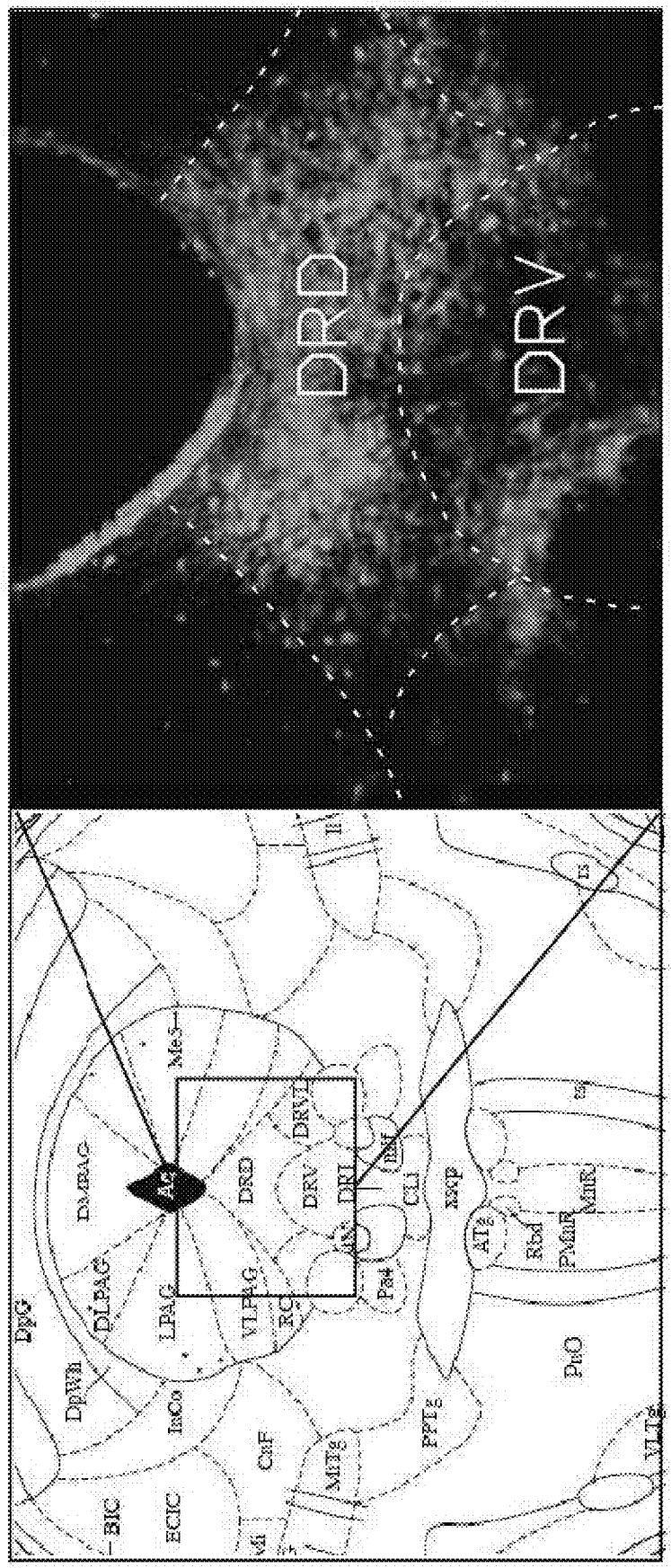

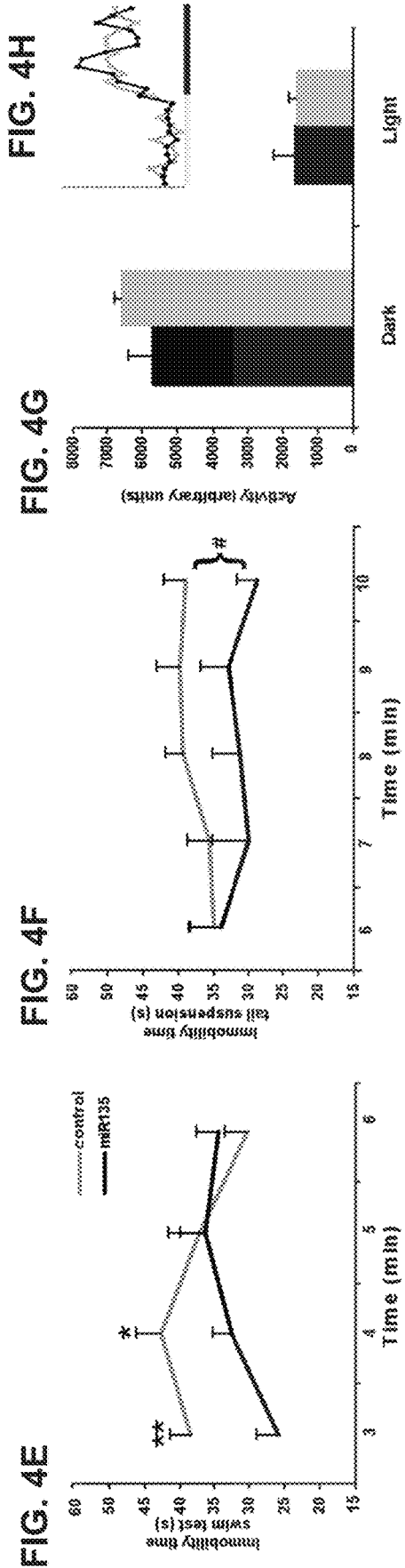

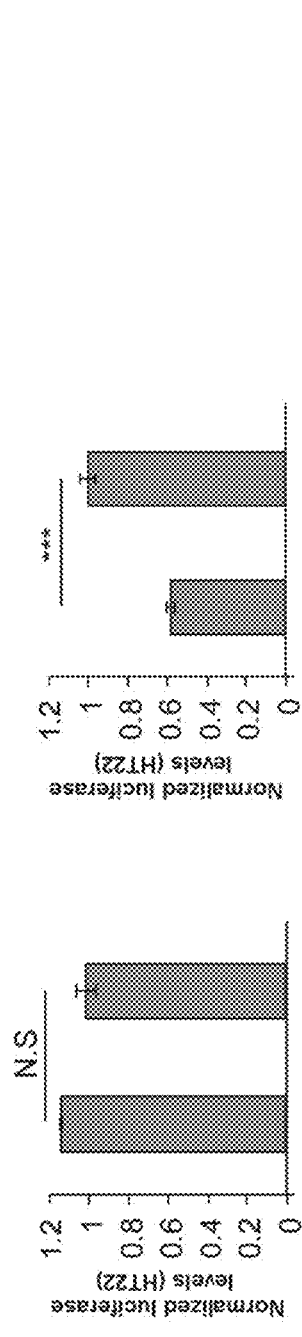
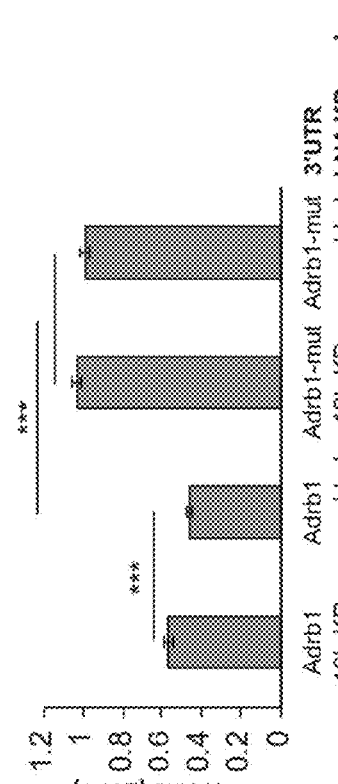
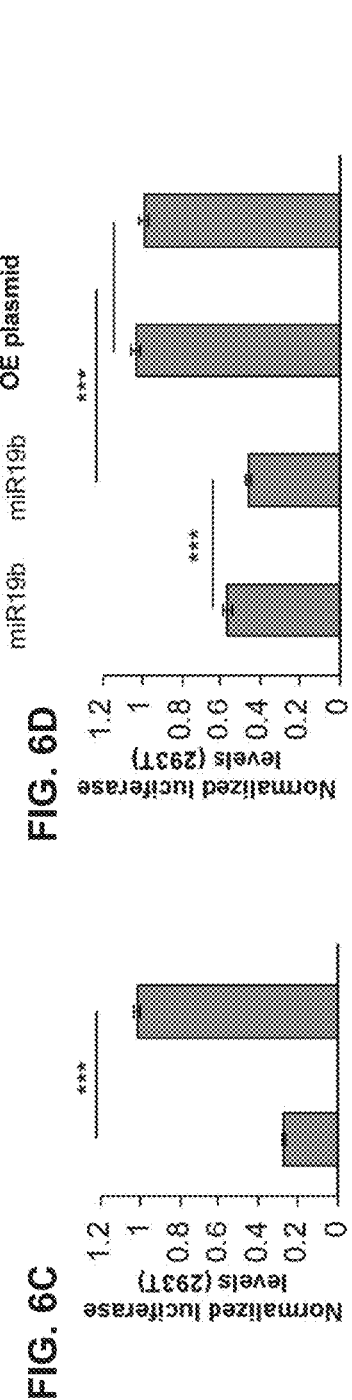
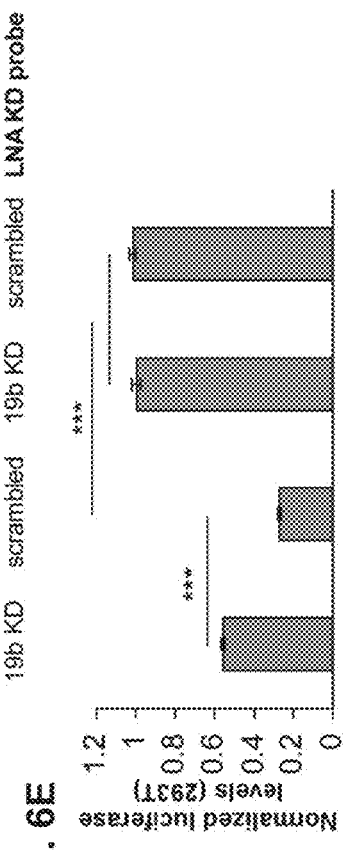
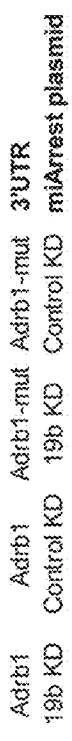

FIG. 10

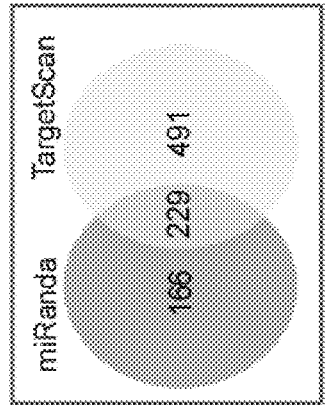

| | |
|---|---|
| SLC33A1 | solute carrier family 33 (acetyl-CoA transporter), member 1 |
| FOXP2 | forkhead box P2 |
| ADCY2 | adenylate cyclase 2 (brain) |
| ADCY6 | adrenergic, alpha-2C-, receptor |
| BDNF | brain-derived neurotrophic factor |
| GRIA1 | glutamate receptor, ionotropic, AMPA 1 |
| GRIA3 | glutamate receptor, ionotropic, AMPA 3 |
| GRIK3 | glutamate receptor, ionotropic, kainate 3 |
| GRM5 | glutamate receptor, metabotropic 5 |
| NUFIP2 | nuclear fragile X mental retardation protein interacting protein 2 |
| CACNB4 | calcium channel, voltage-dependent, beta 4 subunit |
| SLC1A1 | solute carrier family 1 (neuronal/epithelial high affinity glutamate transporter, system Xag), member 1 |
| GDNF | glial cell line derived neurotrophic factor |
| KCNH5 | potassium voltage-gated channel, subfamily H (eag-related), member 5 |
| CREB1 | cAMP responsive element binding protein 1 |
| FXR1H | fragile X mental retardation gene 1, autosomal homolog |
| GAD2 | glutamic acid decarboxylase 2 |
| FMR1 | fragile X mental retardation syndrome 1 homolog |
| HTR2C | 5-hydroxytryptamine (serotonin) receptor 2C |
| HDAC9 | histone deacetylase 9 |

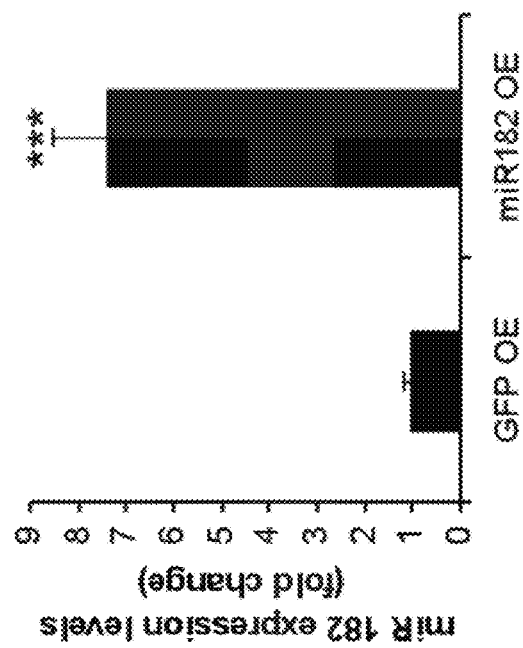
FIG. 11B
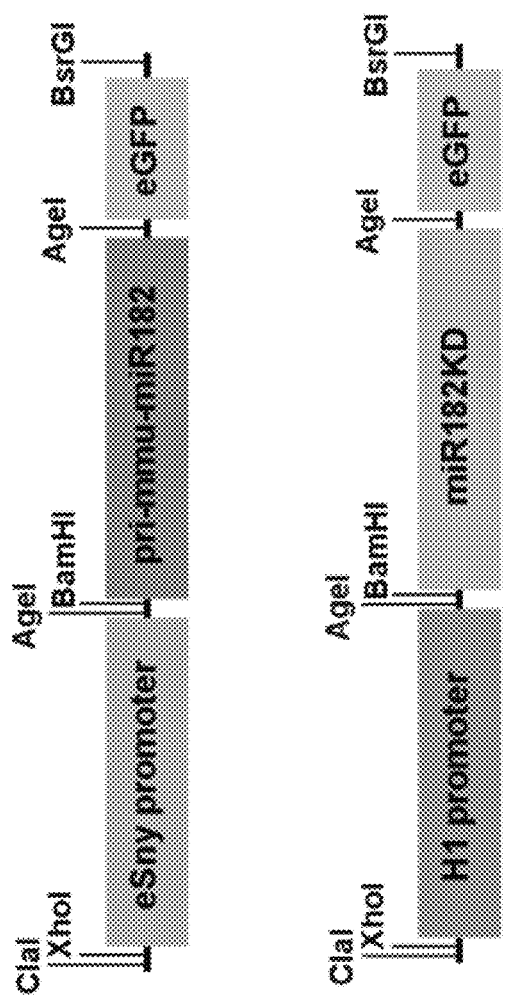
FIG. 11A
FIG. 11C

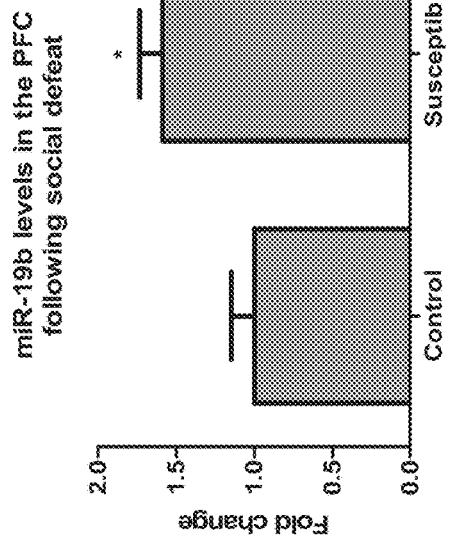
FIG. 13A
FIG. 13B
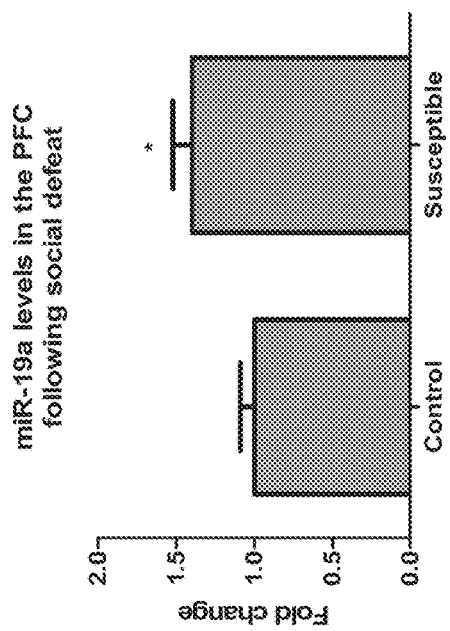
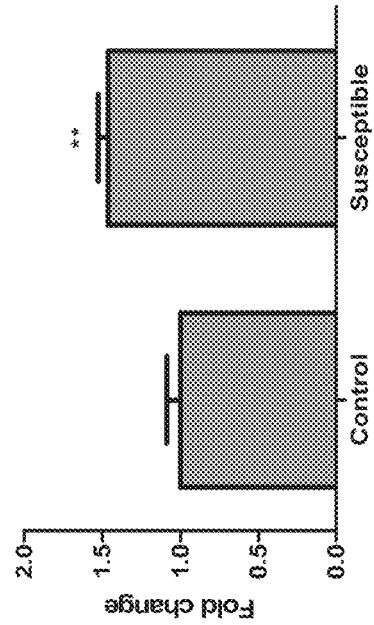
FIG. 13C
FIG. 13D
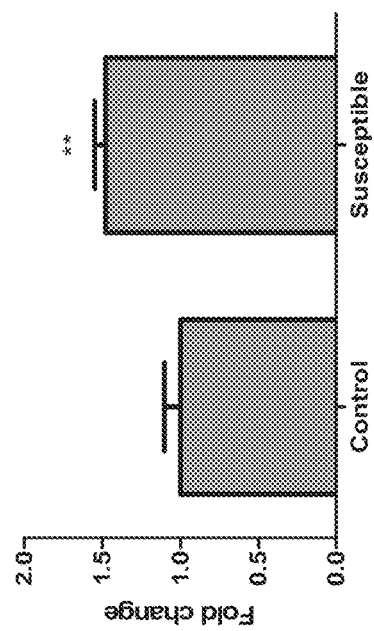

Incorporated from Hill M.N. and McEwen B.S. Proc of the Nat Acad of Sci of the USA (2009) 106:4579-4580

Incorporated from Meister G. et al., Molecular cell (2004) 15:185-197

Susceptible

Resilient

Habituation

Unfamiliar mouse

FIG. 20C

Conserved miR-15 binding site

Mouse FKBP5 3' UTR 1952 bases

| Species | Sequence | SEQ ID NO |
|---|---|---|
| Mouse | --UGACCACCUGCUGCUGGGGGGGGU | SEQ ID NO: 95 |
| Rabbit | -CAGCCACCCUGCUGCUGCUGCCAGUGGG | SEQ ID NO: 96 |
| Human | CAGCCCCCCUGCUGCUGCCCGGAGGG | SEQ ID NO: 97 |
| Chimpanzee | CAGCC-CCCUGCUGCUGCCGGAGGG | SEQ ID NO: 98 |
| Rhesus | CAGCC-CCCUGCUGCUGCCCAGAGGG | SEQ ID NO: 99 |
| Bushbaby | CAGCC-ACCUGCUGCUGCCCAGUGAG | SEQ ID NO: 100 |
| Hedgehog | CCACC-ACCUGCUGCUGCCCAGAGCU | SEQ ID NO: 101 |
| Dog | CAGCC-ACCUGCUGCUGCCCAGCGUG | SEQ ID NO: 102 |
| Horse | CAGCC-ACCUGCUGCUGCCCAGUGCU | SEQ ID NO: 103 |
| Cow | CACCC-ACCUGCUGCUGCCCAGUGCG | SEQ ID NO: 104 |
| Armadillo | AAGCA-ACCUGCUGCUGCCCAGGU | SEQ ID NO: 105 |
| Elephant | CAACC-ACCUGCUGCUGCCCAGUGCA | SEQ ID NO: 106 |
| Tenrec | CAUCC-CCCUGCUGCUGCCCAGCACA | SEQ ID NO: 107 |
| Opossum | UAGCC-CCCUGCUGCUACCCAUUGCC | SEQ ID NO: 108 |
| Chicken | CCAGC-CCAGUGCUGCCGGCUGCG | SEQ ID NO: 109 |

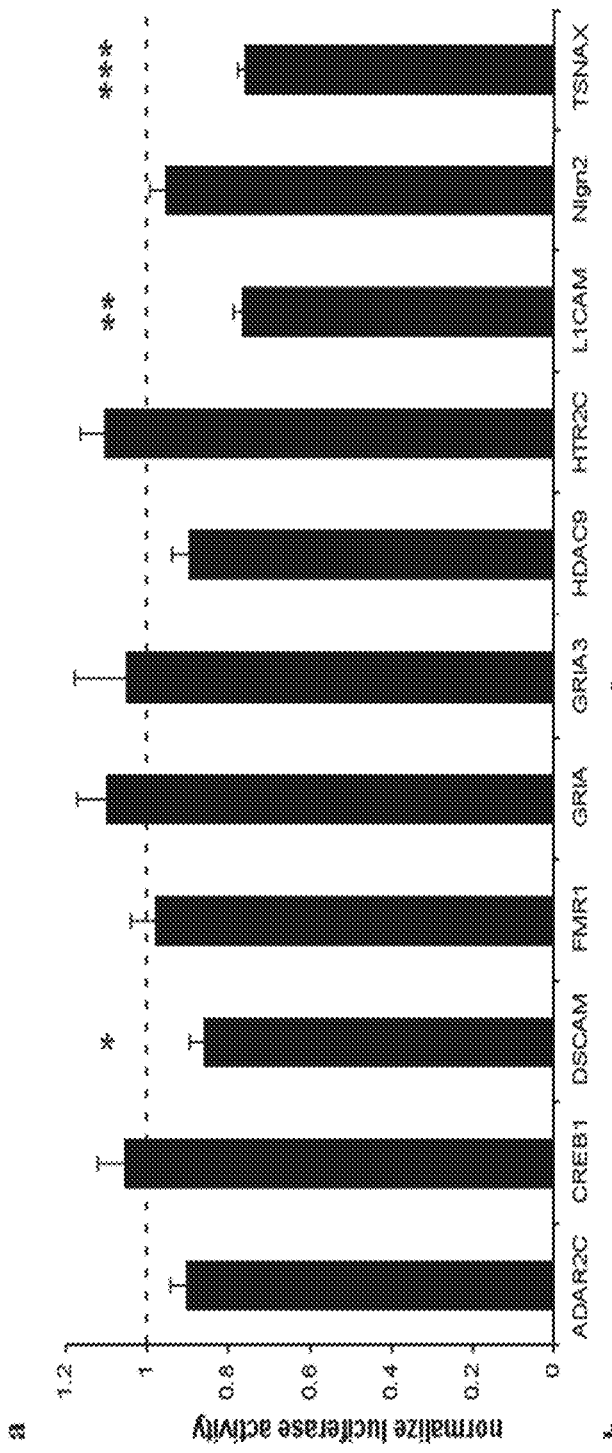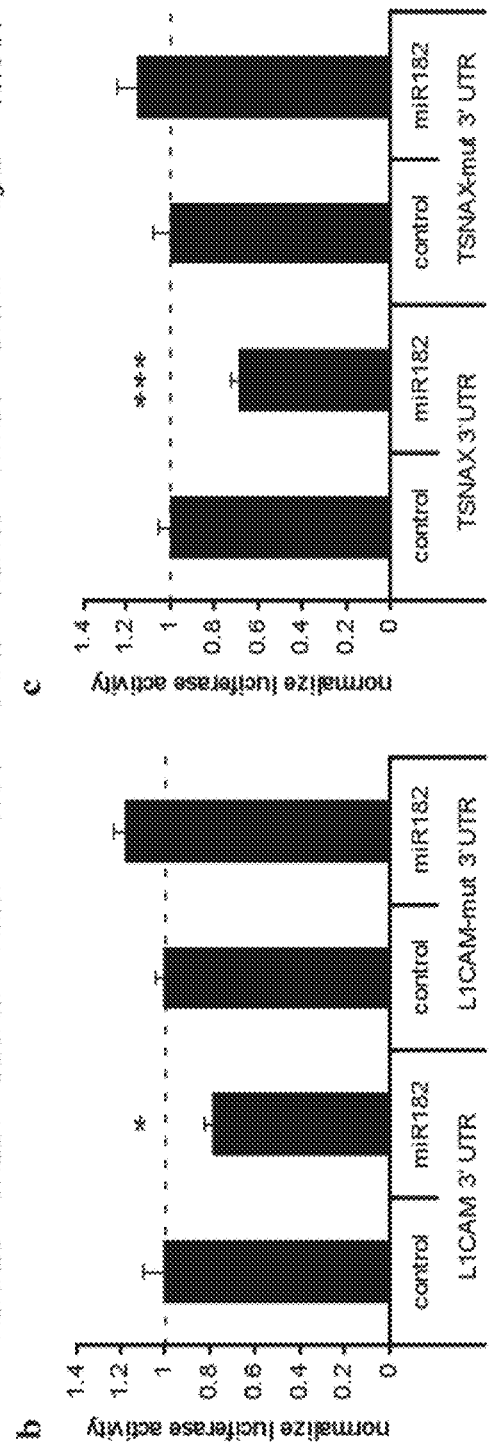
FIG. 27
FIG. 28
FIG. 29

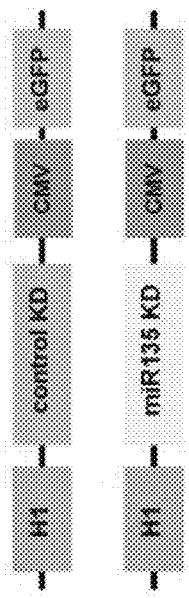
FIG. 30C
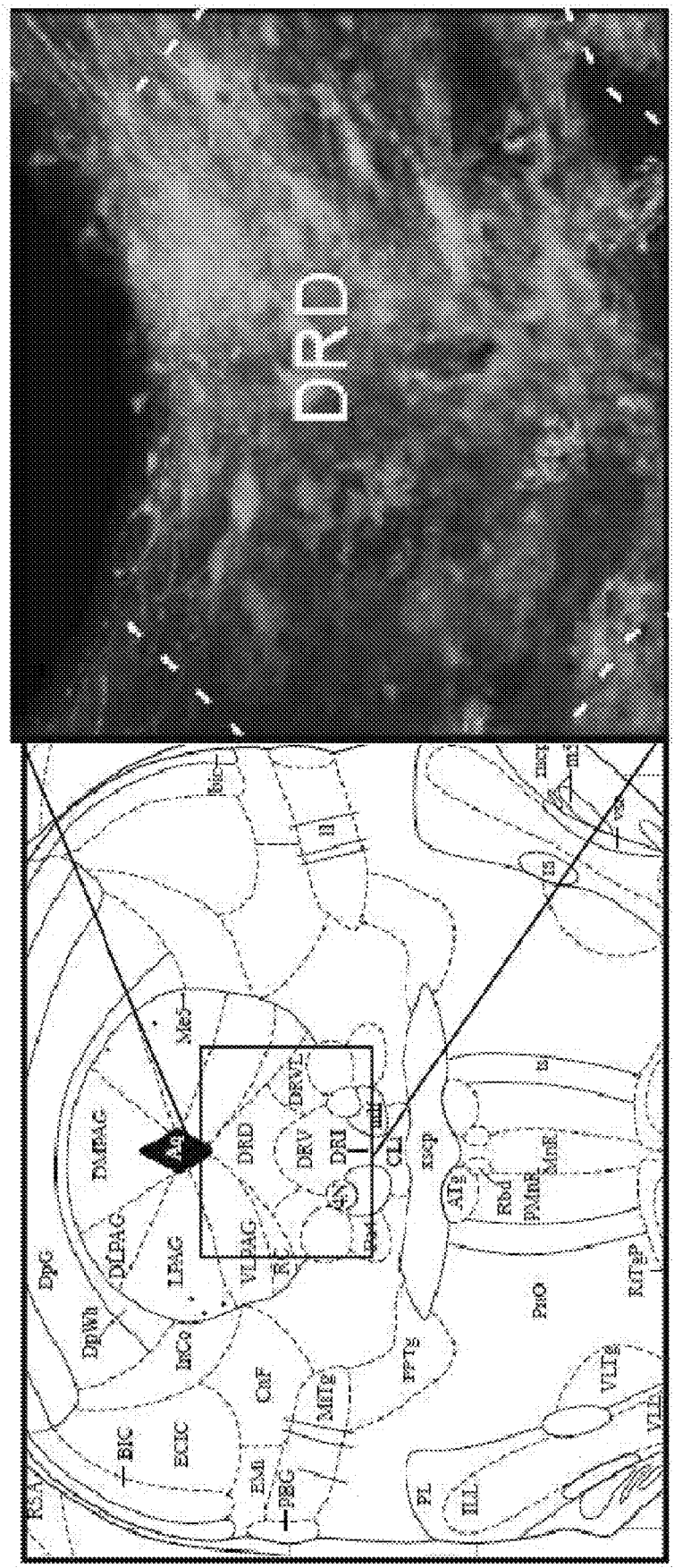
FIG. 30D
FIG. 30E

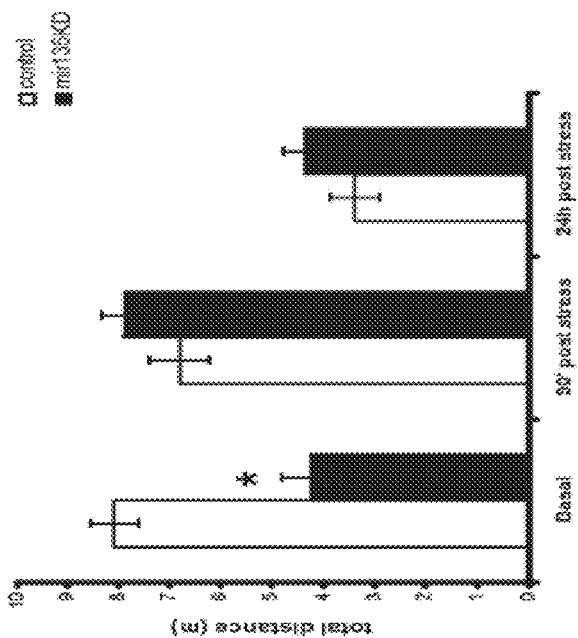
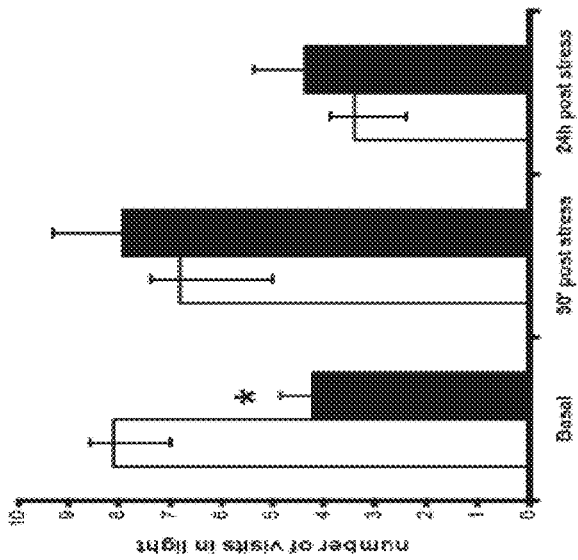
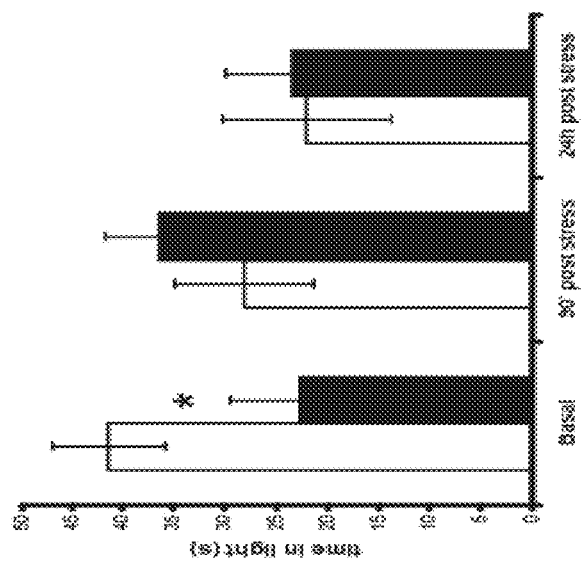

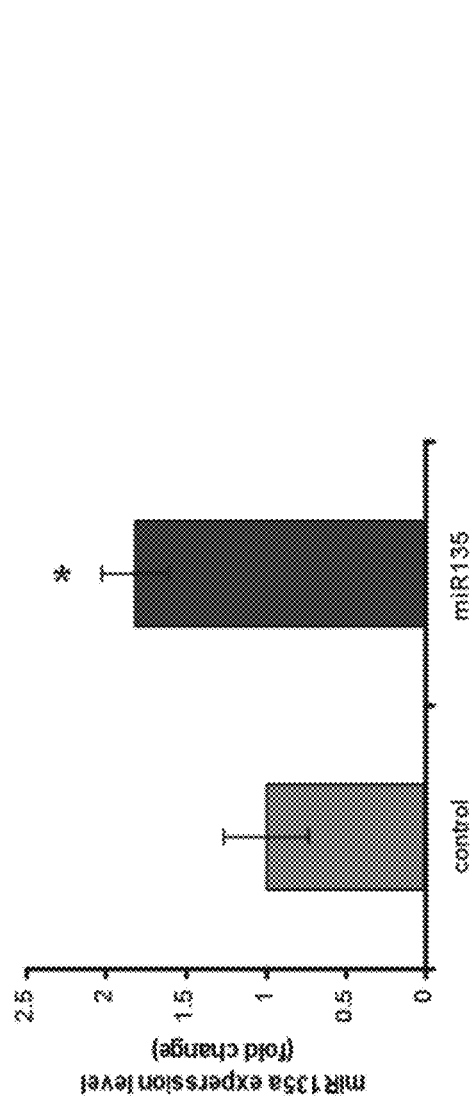
FIG. 33A
FIG. 33B
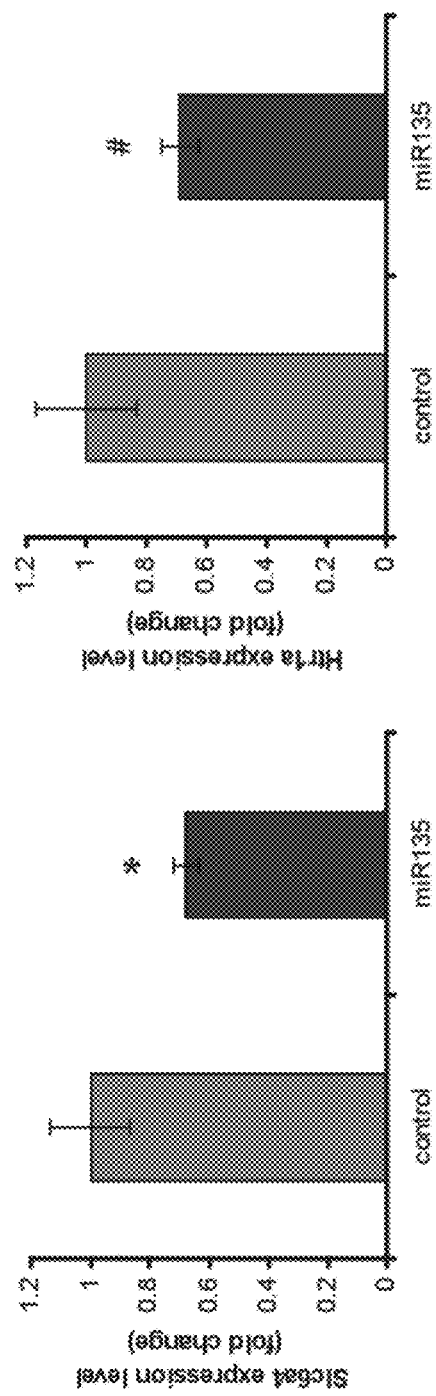
FIG. 33C

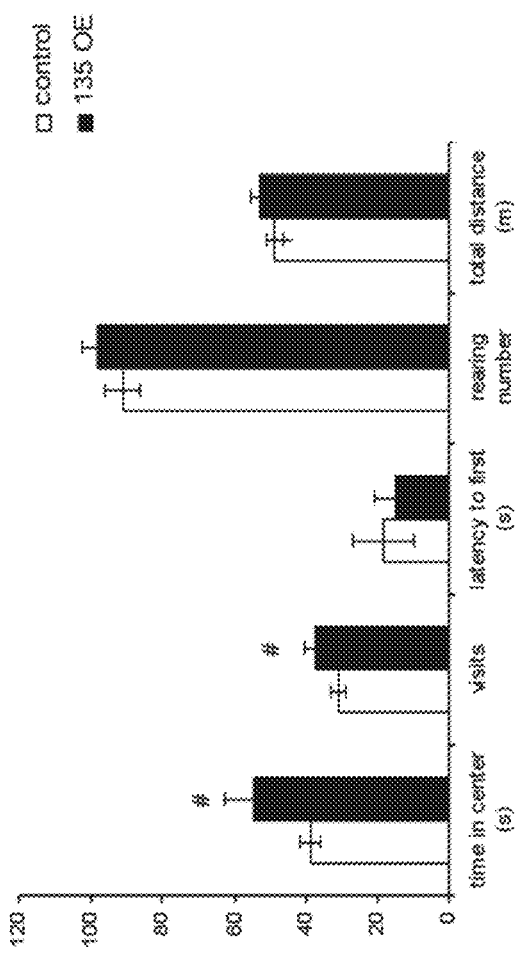
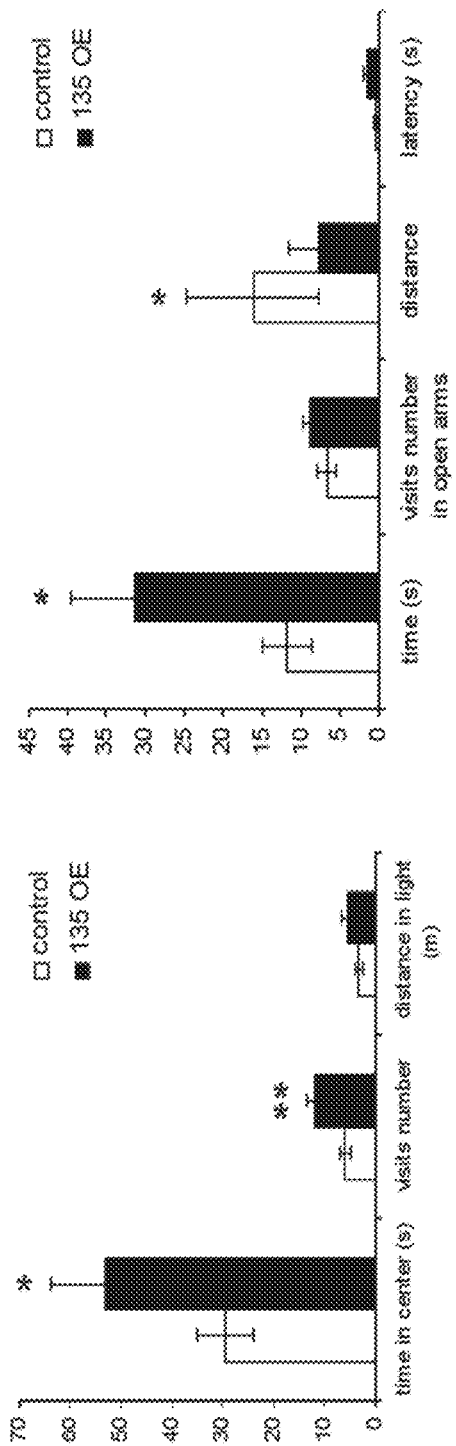
FIG. 34A
FIG. 34B
FIG. 34C

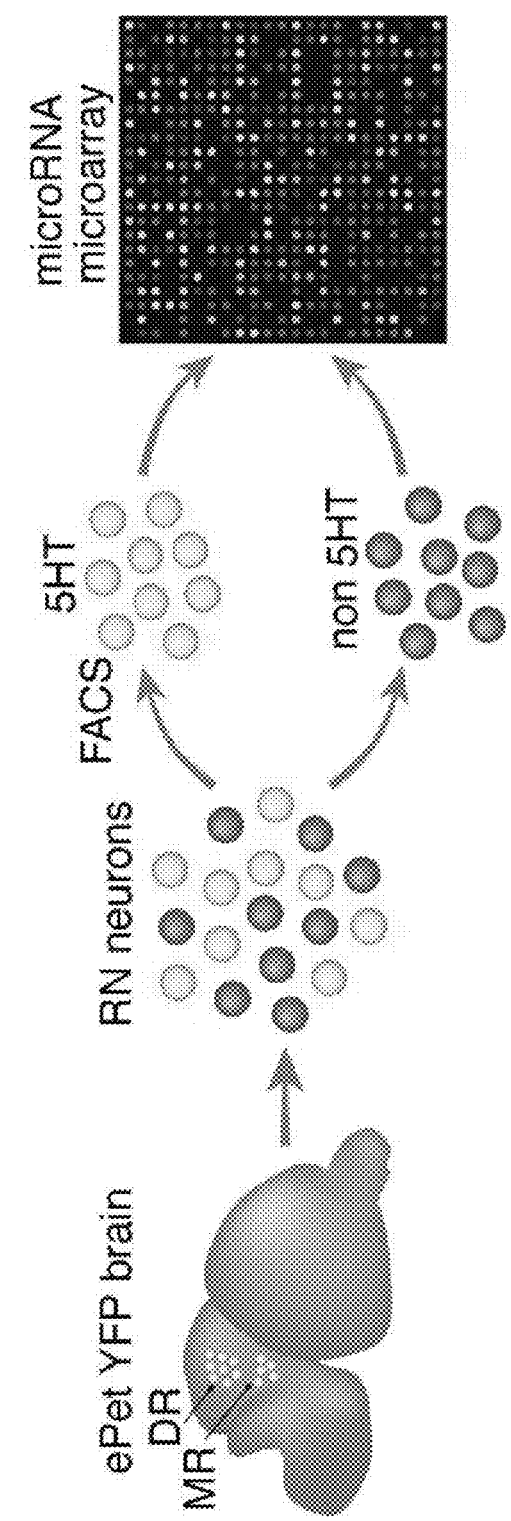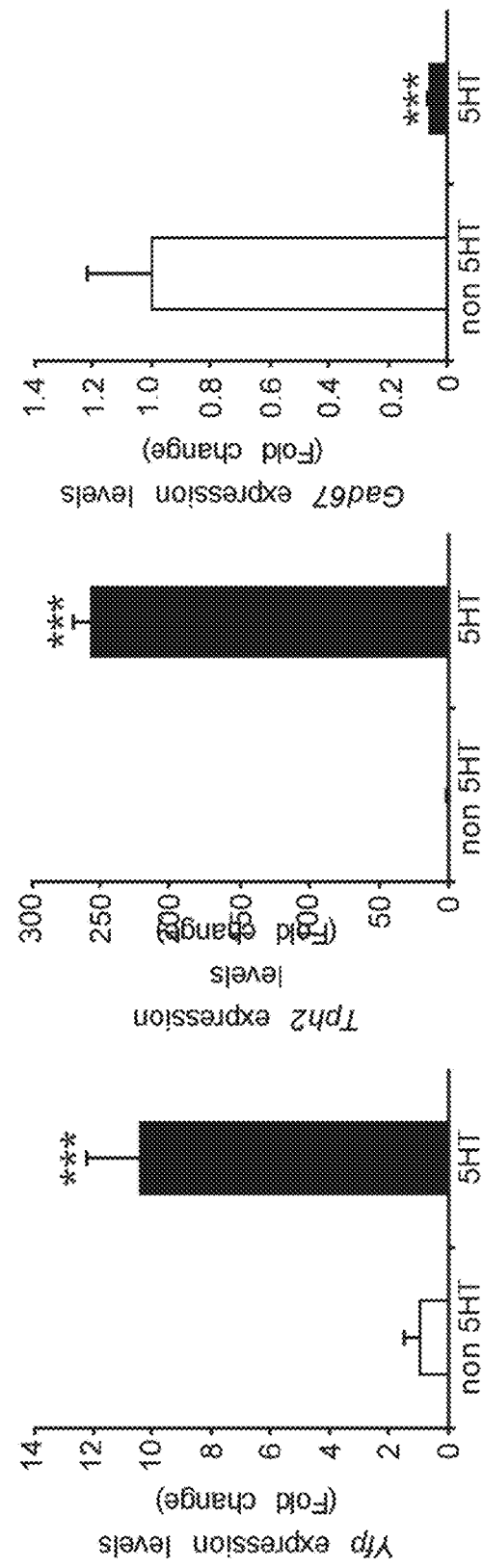
FIG. 35A
FIG. 35B
FIG. 35C
FIG. 35D

FIG. 36A pre-miR135a-1, mice chromosome 9:106,056,455-106,056,544

```
Mouse     a- g- - - - - - - gcct cact gt tct cat gct tt t cat gat t ct - at t gct cgc- t cat at a- gggat t ggag- ccgt g  gcgt ac- ggt gaggat a
Human     a- g- - - - - - - gcct cgct gt tct ct cta gct tt t cat gat t ct - act gct cac- t cat at a- gggat t ggag- ccgt g  gcgcac- ggcggggaca
Orangutan a- g- - - - - - - gcct cgct gt tct ct cta gct tt t cat gat t ct - act gct cac- t cat at a- gggat t ggag- ccgt g  gcgcac- ggcggggaca
Dog       a- g- - - - - - - gcct cgct gt tct ct cat gct tt t cat gat t ct - act gct cac- t cat at a- gggat t ggag- ccgt g  gcgt ac- ggcggggacg
Horse     a- g- - - - - - - gcct cgct gt tct ct at gct tt t cat gat t ct - act gct cac- t cat at a- gggat t ggag- ccgt g  gcgcac- ggcggggggg
Opossum   - - - - - - - - - - ct ggact at at ggc g gt at cca t g t gat ccc- gct gct cat - t cacat g- gggat t ggat - gt ac- - - - cac- aacaggaca
Chicken   - - - - g- gccgagcat ggagcgcct cat at ggct t t at t cca t g t gat at - acat cccgct t cat at - gggat t gaag- ccgt g  caagc- gct gggt cc
```

SEQ ID NO: 169— mouse
SEQ ID NO: 170— human
SEQ ID NO: 171— orangutan
SEQ ID NO: 172— dog
SEQ ID NO: 173— horse
SEQ ID NO: 174— opossum
SEQ ID NO: 175— chicken

FIG. 36B pre-miR135a-2, mice chromosome 10:91,543,831-91,534,930

```
Mouse     t gaat t t t cacaat gt at t t cat ggct t ccat ccct acat gagac- t t t at t acgat acat agagct aaagcact agagt gaat t t at ct
Rat       t gaat t t t cacaat gt at t t cat ggct t ccat ccct acat gagac- t t t at t acgat acat agagcat aaagcact agagt gaat t t at ct
Human     t gat t t t t cacaat gt at t t cat ggct t ccat ccct acat gagac- t t t at t act at acat agagcat aaagcact agagt gaat t t at ct
Orangutan t gat t t t t cacaat gt at t t cat ggct t ccat ccct acat gagac- t t t at t act at acat agagcat aaagcact agagt gaat t t at ct
Dog       t gat t t t t cacaat gt at t t cat ggct t ccat ccct acat gagac- t t t at t act at acat agagcat aaagcact agagt gaat t t at ct
Horse     t gat t t t t cacaat gt at t t cat ggct t ccat ccct acat gagac- t t t at t act at acat agagcat aaagcact agagt gaat t t at ct
```

SEQ ID NO: 176— mouse
SEQ ID NO: 177— rat
SEQ ID NO: 178— human
SEQ ID NO: 179— orangutan SEQ ID NO: 180— dog
SEQ ID NO: 181— horse
SEQ ID NO: 182— opossum (not shown)
SEQ ID NO: 183— chicken (not shown)

FIG. 36C pre-miR135b, mice chromosome 1:134,094,665-134,094,761

```
Mouse      cg-----ctctgctggccatggctgctgctccgaactcatgtgctgctgttgctccgaactcatgtagggctaaaagccatgtagggctacagtgagggcaag-----ctcc
Rat        cg-----ctctgctggccatggctgctgctccgaactcatgtgctgctgttgctccgaactcatgtagggctaaaagccatgtagggctacagtgagggcaag-----ctcc
Human      ca-----ctctgctggccatggctgctgctccaaactcatgtgctgctgttgctccaaactcatgtagggctaaaagccatgtagggctacagtgagggcgagc-----tctcc
Orangutan  ca-----ctctgctggccatggctgctgctccaaactcatgtgctgctgttgctccaaactcatgtagggctaaaagccatgtagggctacagtgagggcaagc----ctctcc
Dog        ag-----ctctgctggccatggctgctgctctaatcatgtgctgctgttgctctaatcatgtagggctaaaagccatgtagggctacagtgagggcgtgc----ctcttctcc
Horse      ag-----ctctgctggccatggctgctgctctaatcatgtgctgctgttgctctaaacatgtagggctaaaagccatgtagggctacagtgagggcgctgc-tccttctcc
Opossum    ag--ctctctgctggccatggctgctgctcccaactcatgtgctgctgttgctcccaactcatgtagggctaaaagccatgtagggctacagggagggag----agcctc..
Chicken    taagccctctgctggtcggtctgctcatggctcattcatccataatgtgctttcctaactcatgtagggcgaaaagccatgtagggctactcaggggaggg-------ac..
```

SEQ ID NO: 184— mouse      SEQ ID NO: 188— dog
SEQ ID NO: 185— rat      SEQ ID NO: 189— horse
SEQ ID NO: 186— human      SEQ ID NO: 190— opossum
SEQ ID NO: 187— orangutan      SEQ ID NO: 191— chicken miR135a 5' UAUGGCUUUUUAUUCCUAUGUGA 3'  SEQ ID NO: 212
miR135b 5' UAUGGCUUUUCAUUCCUAUGUGA 3'  SEQ ID NO: 213

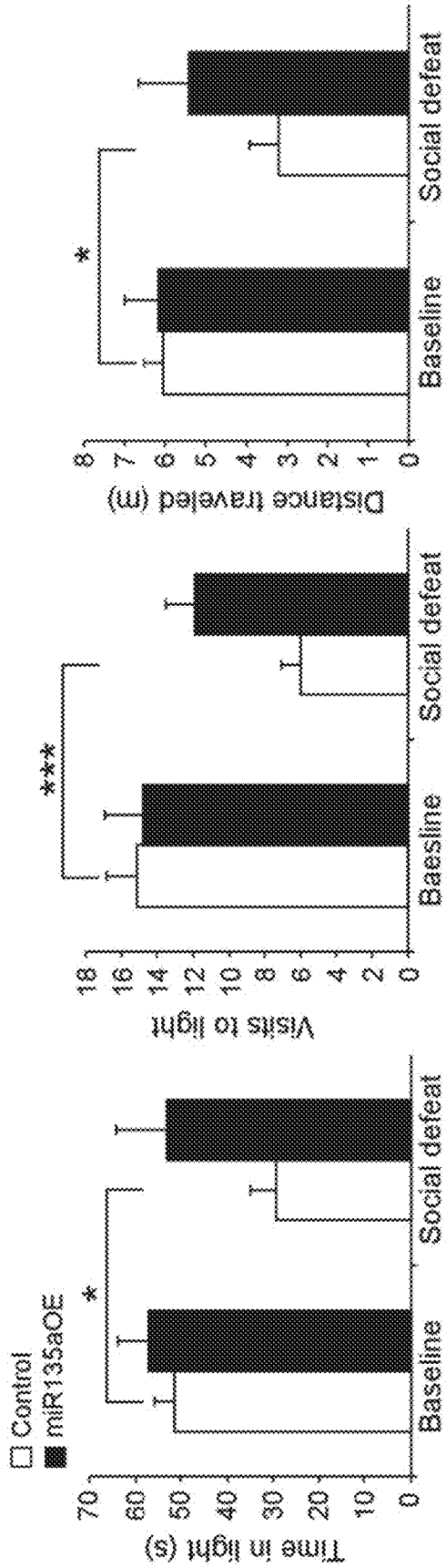
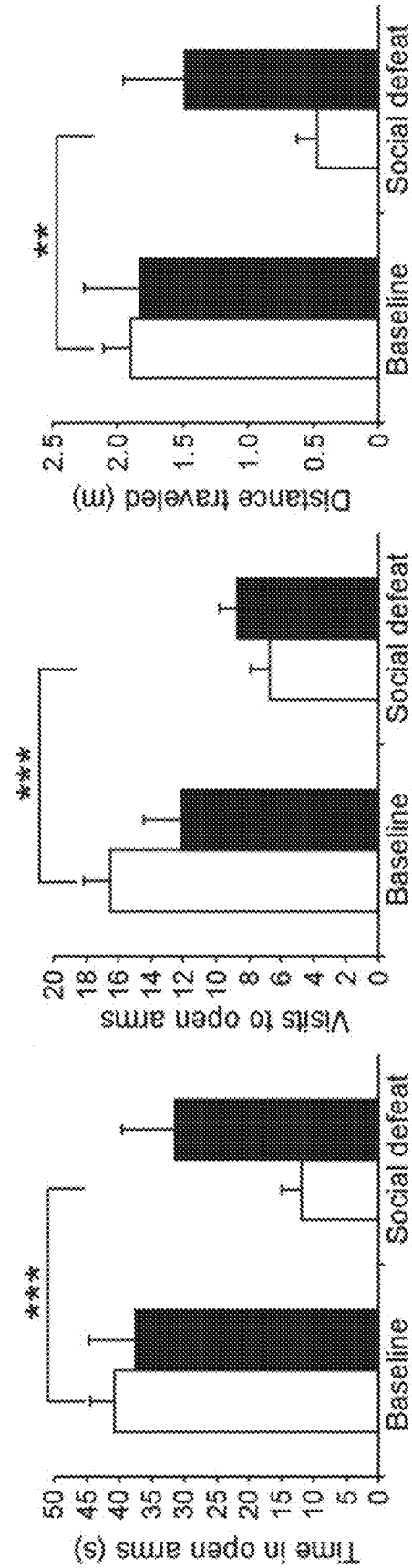
FIG. 38E  FIG. 38F  FIG. 38G
FIG. 38H  FIG. 38I  FIG. 38J

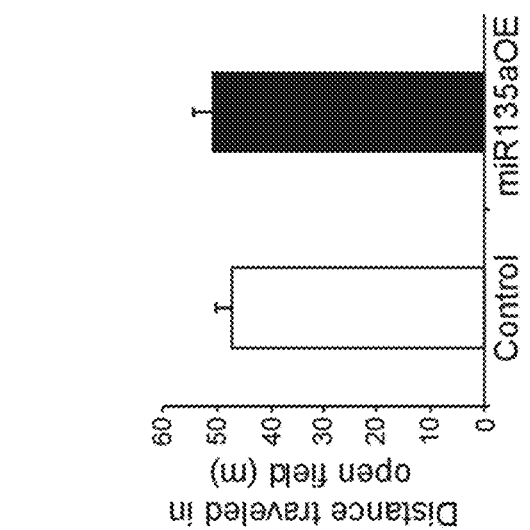
FIG. 38M
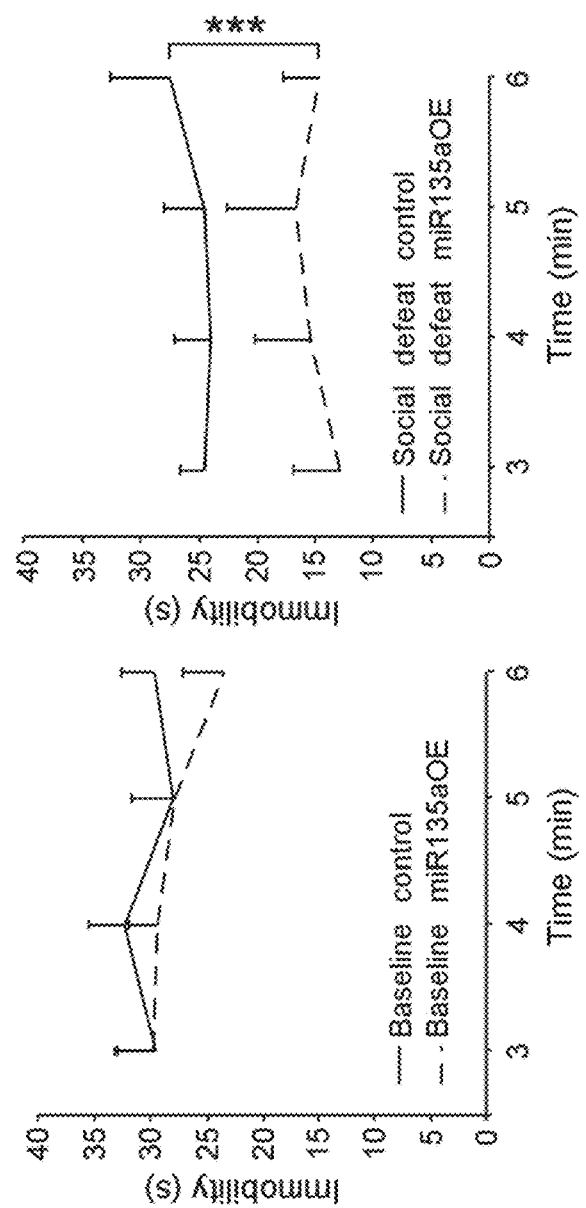
FIG. 38L
FIG. 38K

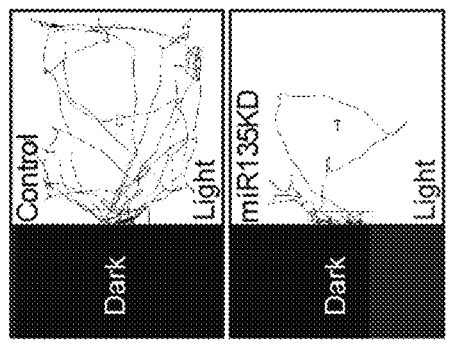
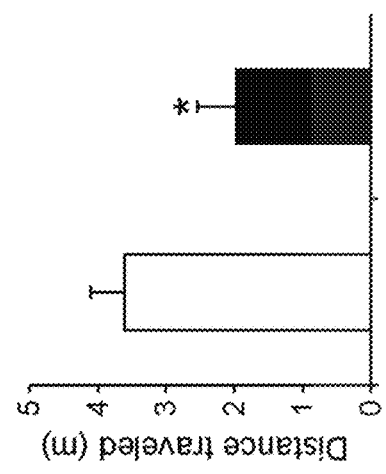
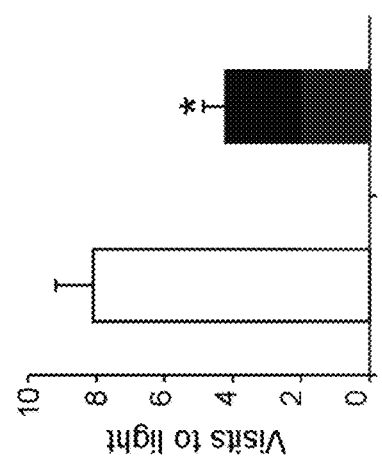
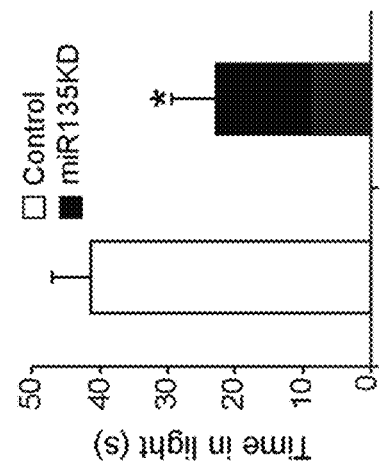

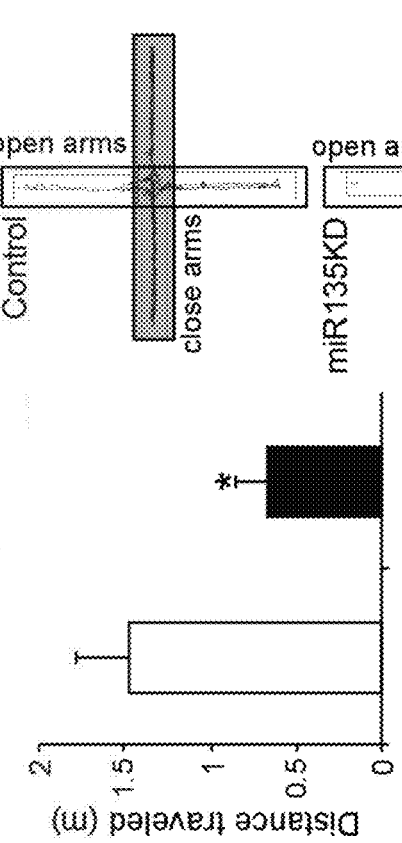
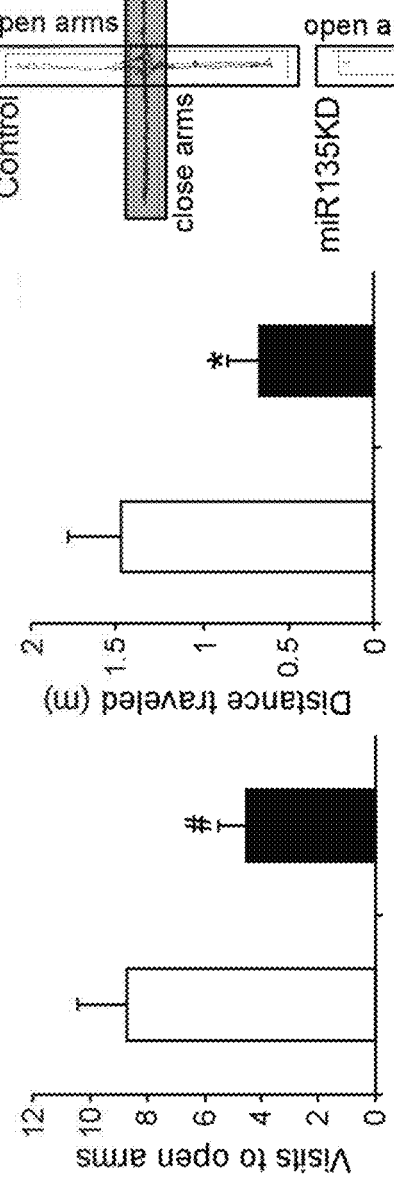
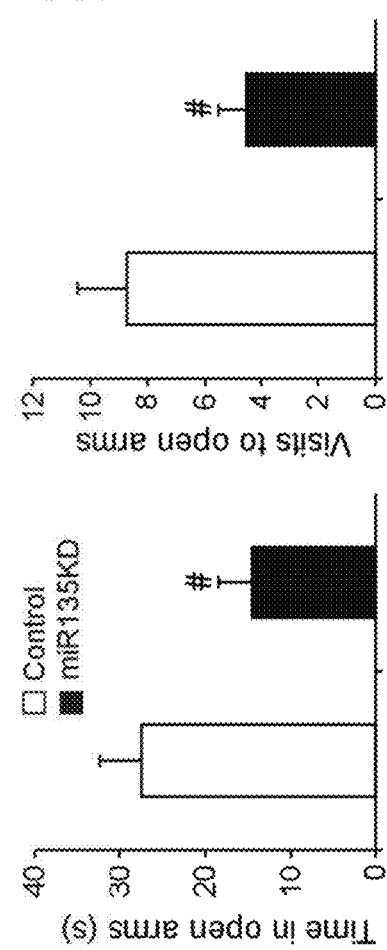
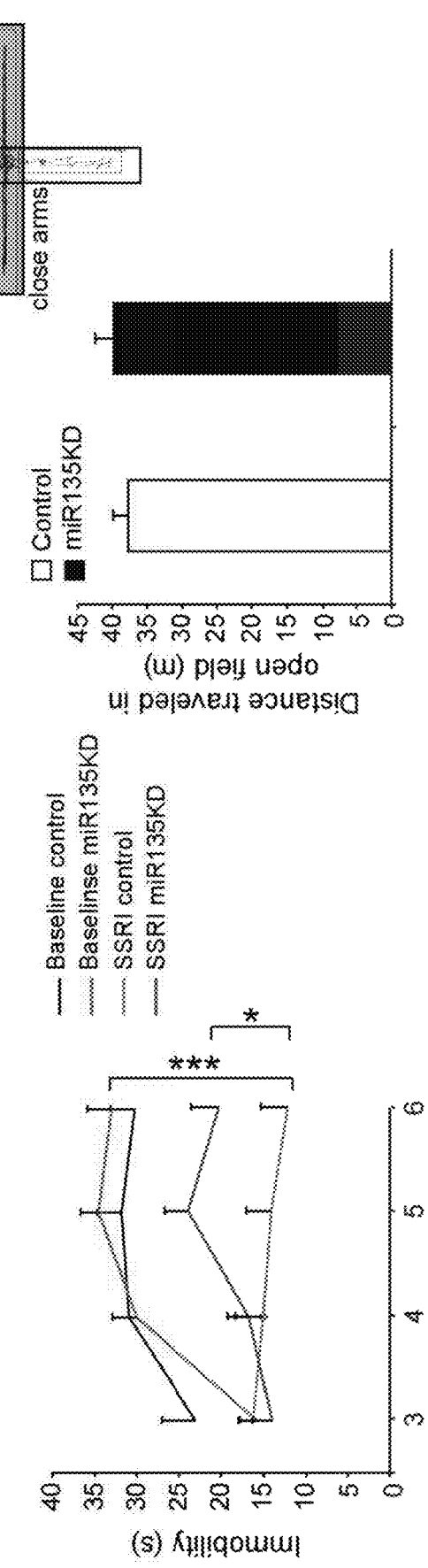

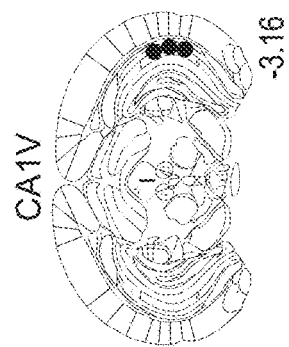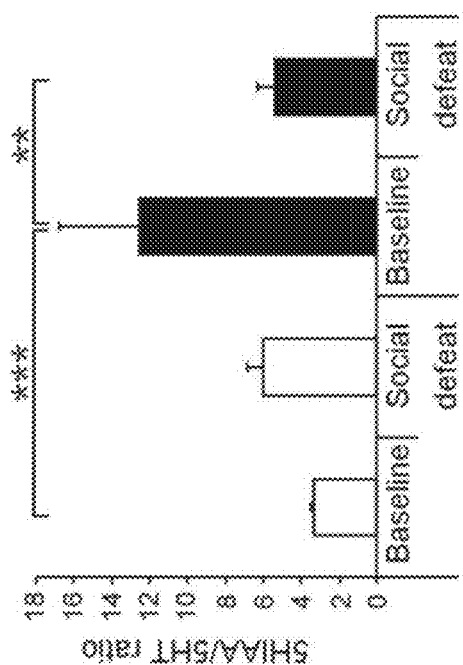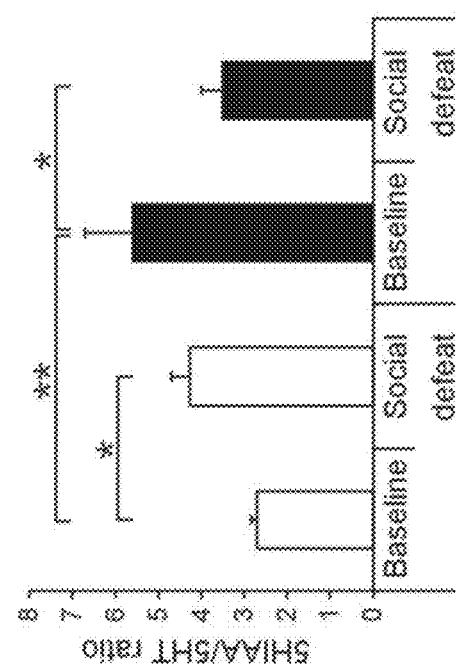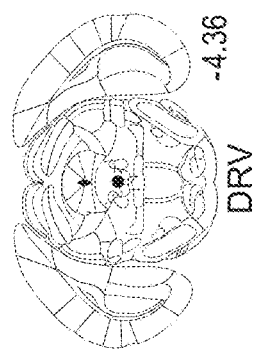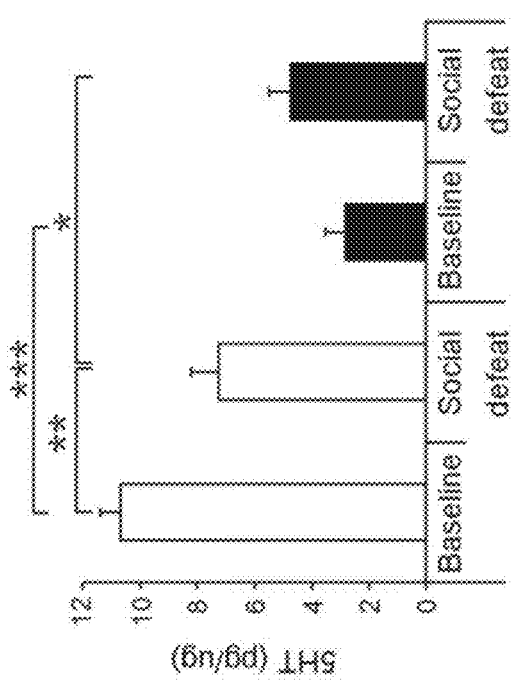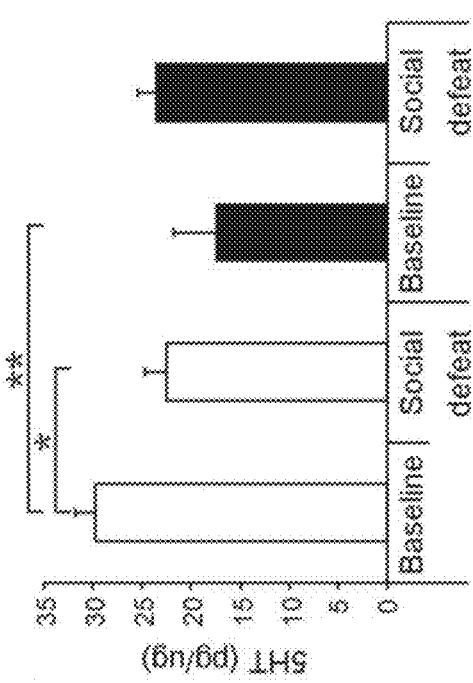

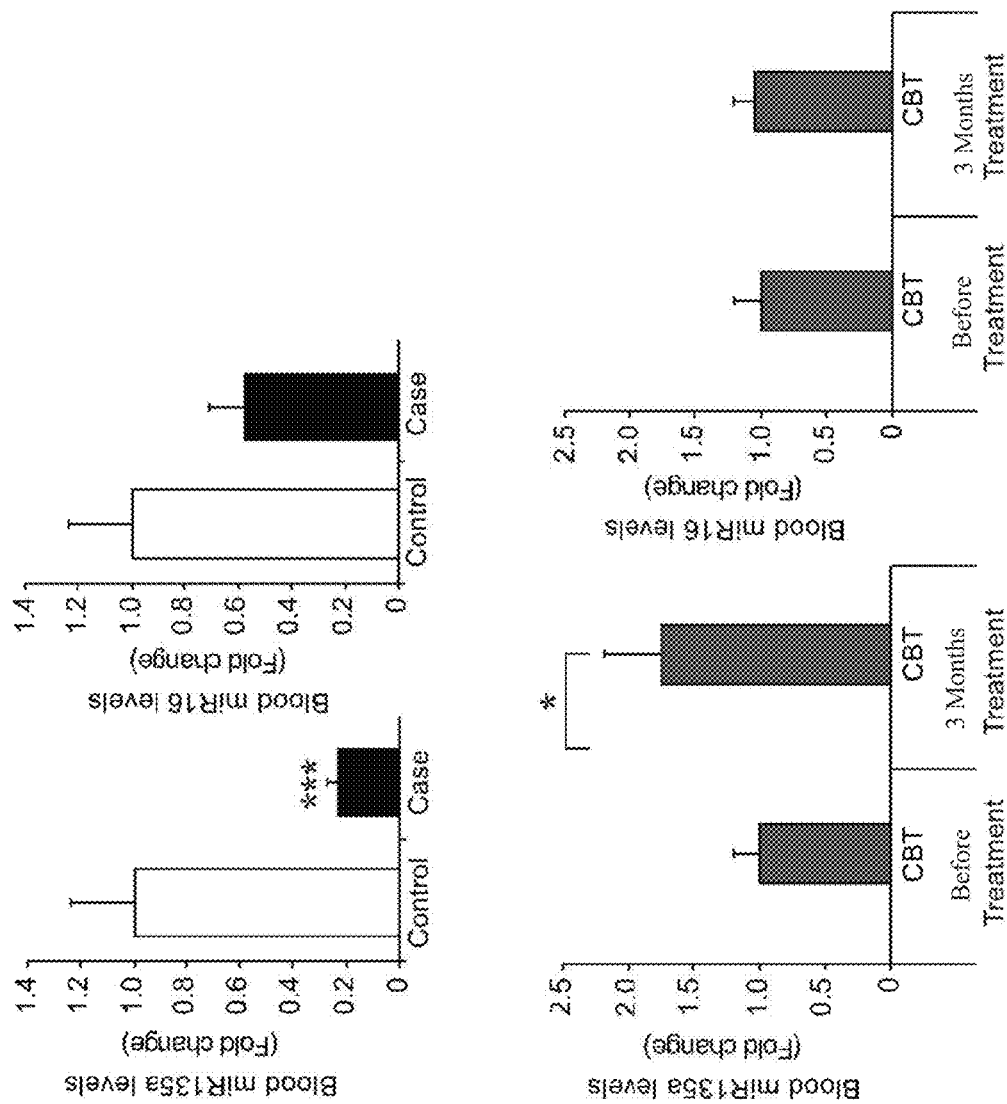

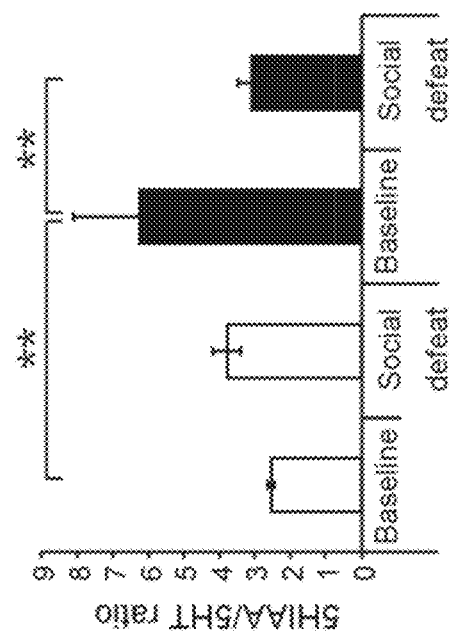
FIG. 42A
FIG. 42B
FIG. 42C
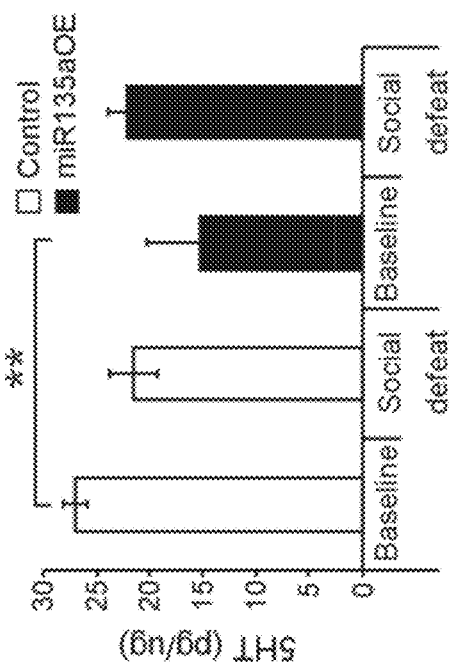
FIG. 42D
FIG. 42E
FIG. 42F
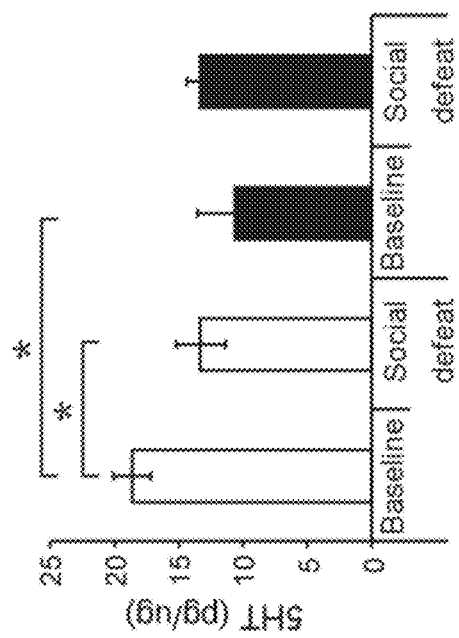

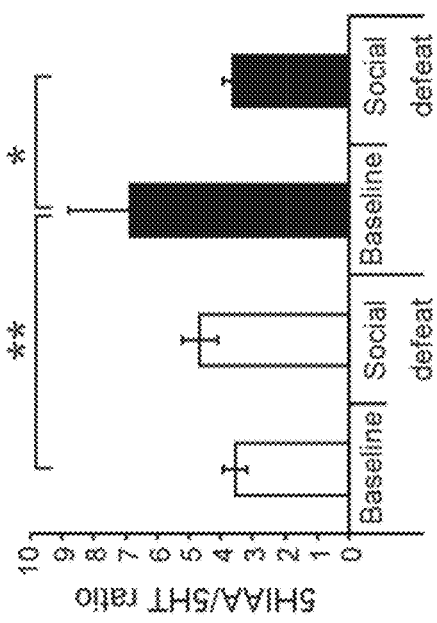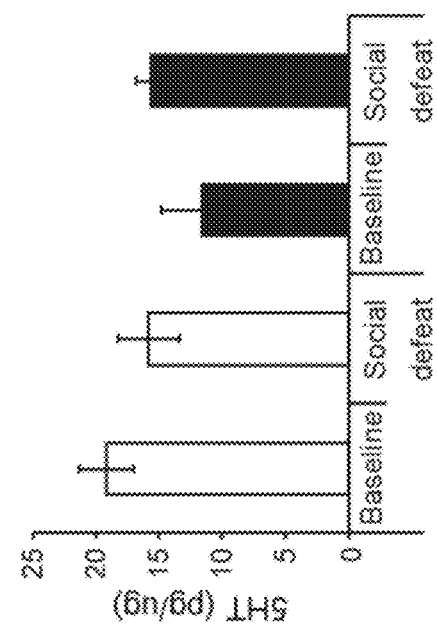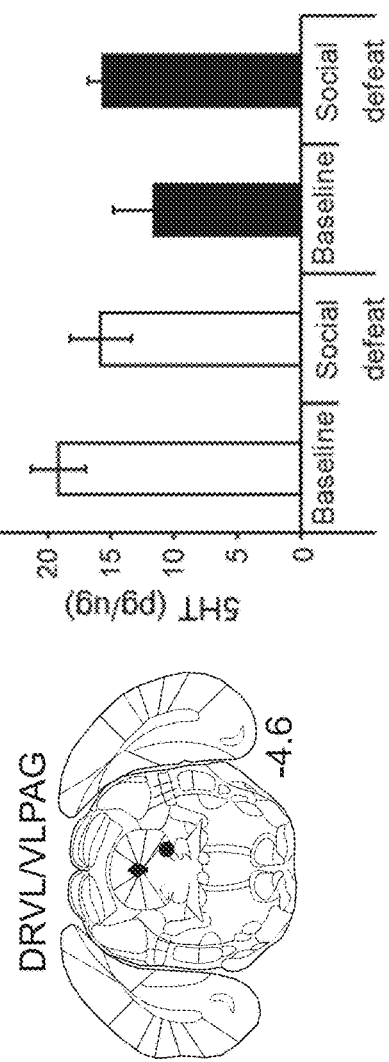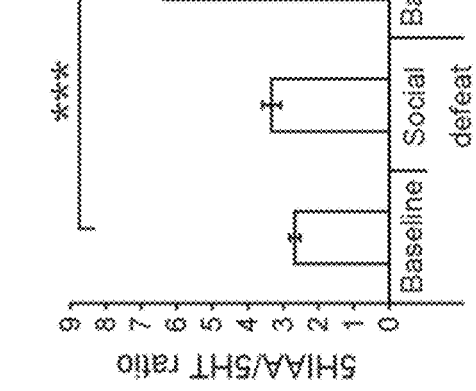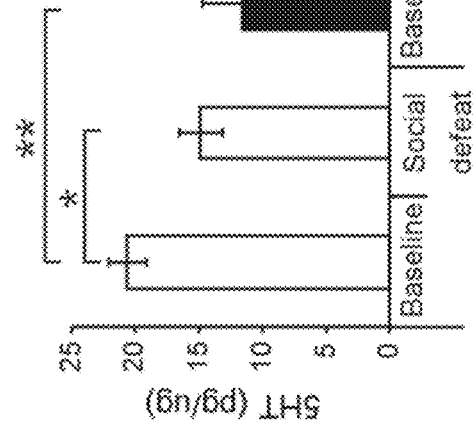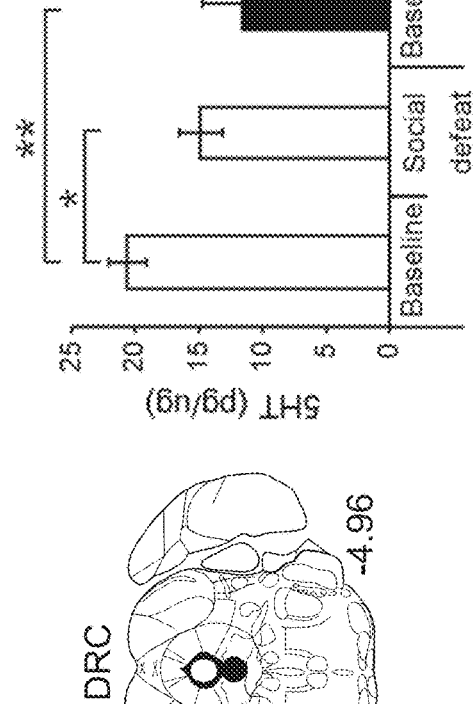

FIG. 44

| oligo no | Sequence | SEQ ID NO |
|---|---|---|
| OLG-135-001 | 5'Ph/UAUGGCUUUUAUUCCUAUGUGA | 194 |
| OLG-135-002 | UAUAGGGAUUGGAGCCGUGGCG | 195 |
| OLG-135-003 | UCAUAUAGGGAUUGGAGCCGUG | 196 |
| OLG-135-004 | UCACAUAGGAAUAAAAGCCAUA | 197 |
| OLG-135-005 | 5'Ph/UAUGGCUUUUUAUUCCUAUGUGA | 198 |
| OLG-135-006 | UAUAGGGAUUGGAGCCGUGGCG | 199 |
| OLG-135-007 | 5'Ph/UAUGGCUUUUAUUCCUAUGUGA | 200 |
| OLG-135-008 | 5'Ph/UAAUUUAAGCUUCUUUGUUCUGG | 201 |
| OLG-135-009 | CCAGAACAAAGAAGCUUAAAUUA | 202 |
| OLG-135-010 | 5'Ph/UAUGGCUUUUCAUUCCUAUGUGA | 203 |
| OLG-135-011 | AUGUAGGGCUAAAGCCAUGGG | 204 |
| OLG-135-012 | UCAUGUAGGGCUAAAAGCCAUG | 205 |
| OLG-135-013 | UCACAUAGGAAUGAAAAGCCAUA | 206 |
| OLG-135-014 | 5'Ph/UAUGGCUUUUCAUUCCUAUGUGA | 207 |
| OLG-135-015 | AUGUAGGGCUAAAAGCCAUGG | 208 |
| OLG-135-016 | 5'Ph/UAUGGCUUUUCAUUCCUAUGUGA | 209 |

5'Ph  5' phosphorylation
  2' O-Methyl
bold underline

MICRO-RNAS AND COMPOSITIONS COMPRISING SAME FOR THE TREATMENT AND DIAGNOSIS OF SEROTONIN-, ADRENALIN-, NORADRENALIN-, GLUTAMATE-, AND CORTICOTROPIN-RELEASING HORMONE-ASSOCIATED MEDICAL CONDITIONS

RELATED APPLICATIONS

This application is a division of U.S. patent application Ser. No. 16/180,083 filed on Nov. 5, 2018, which is a division of U.S. patent application Ser. No. 15/111,539 filed on Jul. 14, 2016, now U.S. Pat. No. 10,125,365, which is a National Phase of PCT Patent Application No. PCT/IL2015/050132 having International Filing Date of Feb. 5, 2015, which claims the benefit of priority under 35 USC § 119(e) of U.S. Provisional Patent Application No. 61/935,912 filed on Feb. 5, 2014.

The contents of the above applications are all incorporated by reference as if fully set forth herein in their entirety.

SEQUENCE LISTING STATEMENT

The ASCII file, entitled 87414SequenceListing.txt, created on Apr. 12, 2021, comprising 48,606 bytes, submitted concurrently with the filing of this application is incorporated herein by reference.

FIELD AND BACKGROUND OF THE INVENTION

The present invention, in some embodiments thereof, relates to microRNAs and, more particularly, but not exclusively, to the use of same for disease diagnosis, treatment and monitoring treatment.

Mood disorders, such as major depression, and anxiety disorders represent some of the most common and proliferating health problems worldwide effecting about 10% of the population. Despite many decades of research, the mechanisms behind depression onset, susceptibility and available therapies are only partially understood. Currently only about a third of patients respond to available treatments, therefore, there is a great need for better understanding of the pathology.

The current dogma regarding the etiology of depression is of a complex interaction between environmental factors and genetic predisposition, suggesting a mechanistic role for epigenetic processes.

Serotonin (5HT) is a monoamine neurotransmitter produced in the brain by the raphe nucleus (RN), which project extensively throughout the brain to modulate variety of cognitive, emotional and physiological functions. The link between dysregulated serotonergic activity and depression is well established [Michelsen K A. et al., Brain Res Rev (2007) 55(2):329-42]. The levels of 5HT, as well as the genetic circuitry in charge of it production, secretion, reuptake and deactivating, are dysregulated in depression. Furthermore, most currently available antidepressant drugs target the function of 5HT system related proteins, resulting in increased 5HT levels in the synapse [Krishnan V and Nestler E J, Nature (2008) 455: 894-902]. Available therapeutics require a long period of administration before relief of symptoms is observed.

MicroRNAs (miRs) are a subset of endogenous small (approximately 22 nucleotide) noncoding RNA molecules that repress gene expression post-transcriptionally. MiRs are transcribed as primary-miR molecules that are processed in the cell nucleus into precursor miRs with stem loop structures, which are exported to the cytoplasm where they are further processed into the active mature miRs. The mature miR is subsequently incorporated into the RNA-induced silencing complex and function primarily by binding to the 3'untranslated regions (3'UTRs) of specific mRNA molecules. Binding occurs via the seed sequence, a 6-8 nucleotides sequence at the 5' end of the miR, that base pairs to a complementary seed match sequence on the target mRNA 3' UTR. Binding of a miR leads to direct mRNA destabilization or translational repression, ultimately resulting in reduced protein levels of target gene.

MiRs are abundant in the nervous system, and initial research has mainly focused on neurons in the context of development, cancer and neurodegenerative disorders and normal process such as plasticity [Kosik K S. Nat Rev Neurosci (2006) 7:911-20]. Several miR-screening studies have reported that miR levels in various adult rodents or human brain structures are affected by a range of behavioral and pharmacological manipulations [O'Connor R. M. et al., Mol Psychiatry (2012) 17: 359-376]. Additionally, it has been suggested that miRs play a role in psychiatric disorders such as schizophrenia, autism and also depression and anxiety, both in humans and in mouse models [Miller B H and Wahlestedt C, Brain Res (2010) 1338: 89-99]. Several studies have recently demonstrated the involvement of miRs in regulating 5HT related genes [Millan M J. Curr Opin Pharmacol (2011) 11(1):11-22] revealing the emerging role of miRs in the regulation of 5HT system and their potential association with depression related disorders.

U.S. Patent Application No. 20100222413 (to Stoffel M. et al.) discloses chemically modified oligonucleotides for modulating expression of microRNAs. U.S. 20100222413 further discloses methods for silencing microRNAs (e.g. miR-122, miR-16, miR-192 and miR-194) for the treatment of diseases of the central nervous system.

SUMMARY OF THE INVENTION

According to an aspect of some embodiments of the present invention there is provided a method of treating a bipolar disorder in a subject in need thereof, the method comprising administering to the subject therapeutically effective amount of a miR-135, a precursor thereof or a nucleic acid molecule encoding the miR-135 or the precursor thereof, thereby treating the bipolar disorder.

According to an aspect of some embodiments of the present invention there is provided a use of a therapeutically effective amount of a miR-135, a precursor thereof or a nucleic acid molecule encoding the miR-135 or the precursor thereof for the manufacture of a medicament identified for treating a bipolar disease in a subject in need thereof.

According to an aspect of some embodiments of the present invention there is provided an article of manufacture comprising a packaging material packaging an agent selected from the group consisting of a miR-135, a precursor thereof and a nucleic acid molecule encoding the miR-135 or the precursor thereof and a medicament for the treatment of a bipolar disorder.

According to an aspect of some embodiments of the present invention there is provided a method of monitoring treatment of an anti-depressant drug or a medicament for the treatment of a mood disorder, the method comprising: (a) treating a human subject in need thereof with an anti-depressant drug or a medicament for the treatment of a mood disorder; and (b) measuring an expression level of a miR- 135 in biological sample of the human subject prior to and following the treatment, wherein a higher expression level of the miR-135 following the treatment by the anti-depressant drug or the medicament for the treatment of the mood disorder as compared to the expression level of the miR-135 prior to the treatment by the anti-depressant drug or the medicament for the treatment of the mood disorder is indicative of the efficient treatment.

According to an aspect of some embodiments of the present invention there is provided a method of diagnosing a mood disorder in a human subject in need thereof, the method comprising measuring an expression level of a miR-135 in a biological sample of the human subject, wherein a lower expression level of the miR-135 as compared to that in a biological sample of a healthy human subject is indicative of the mood disorder.

According to an aspect of some embodiments of the present invention there is provided an isolated polynucleotide comprising a miR-135 wherein the miR-135 comprises a modification selected from the group consisting of a locked nucleic acid (LNA) and a 2'-Fluoroarabinooligonucleotides (FANA).

According to an aspect of some embodiments of the present invention there is provided an isolated polynucleotide comprising a modified miR135 selected from the group consisting of SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208 and SEQ ID NO: 209.

According to an aspect of some embodiments of the present invention there is provided an isolated polynucleotide comprising a microRNA selected from the group consisting of miR-335, miR-181, miR-182, miR-26, miR-27, miR-15 and miR-19 wherein the microRNA comprises a modification selected from the group consisting of a locked nucleic acid (LNA) and a 2'-Fluoroarabinooligonucleotides (FANA).

According to an aspect of some embodiments of the present invention there is provided a pharmaceutical composition comprising the isolated polynucleotide of some embodiments of the invention, and a pharmaceutically acceptable carrier.

According to an aspect of some embodiments of the present invention there is provided a method of upregulating an expression of a gene selected from the group consisting of adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (Drosophila) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt1l); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3); and zinc finger, BED domain containing 4 (Zbed4) in a neuroglia cell, the method comprising: (a) downregulating an activity or expression of a miR-135 or a precursor thereof in the neuroglia cell; and (b) measuring an expression of the gene in the neuroglia cell, thereby upregulating the expression of the gene.

According to an aspect of some embodiments of the present invention there is provided a method of downregulating an expression of a gene selected from the group consisting of adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (Drosophila) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt1l); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3); and zinc finger, BED domain containing 4 (Zbed4) in a neuroglia cell, the method comprising: (a) upregulating an activity or expression of a miR-135 or a precursor thereof in the neuroglia cell; and (b) measuring an expression of the gene in the neuroglia cell, thereby downregulating the expression of the gene.

According to an aspect of some embodiments of the present invention there is provided a method of treating a medical condition in which an elevation of serotonin level is therapeutically beneficial in a subject in need thereof, the method comprising administering to the subject an agent capable of downregulating an activity or expression of a miR-135 target selected from the group consisting of adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (*Drosophila*) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt1l); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3); and zinc finger, BED domain containing 4 (Zbed4), wherein said agent is not miR-135, thereby treating the medical condition.

According to some embodiments of the invention, the medical condition is selected from the group consisting of a bipolar disorder, a depression, a major depression, an anxiety, a stress, a fatigue, an impaired cognitive function, a panic attack, a compulsive behavior, an addiction, a social phobia, a schizophrenia, a sleep disorder, an eating disorder, a growth disorder and a reproduction disorder.

According to some embodiments of the invention, the miR-135 is selected from the group consisting of miR-135a and miR-135b.

According to some embodiments of the invention, the miR-135 is as set forth in SEQ ID NO: 58-62.

According to some embodiments of the invention, the miR-135 comprises miR-135* as set forth in SEQ ID NO: 192-193.

According to some embodiments of the invention, the miR-135 comprises a modification selected from the group consisting of a modified sugar-phosphate backbone and a modified base.

According to some embodiments of the invention, the miR-135 comprises a modification in both a sugar and an internucleoside linkage.

According to some embodiments of the invention, the modification is selected from the group consisting of a phosphorothioate, a chiral phosphorothioate, a phosphorodithioate, a phosphotriester, an aminoalkyl phosphotriester, a methyl phosphonate, an alkyl phosphonate, a chiral phosphonate, a phosphinate, a phosphoramidate, an aminoalkylphosphoramidate, a thionophosphoramidate, a thionoalkylphosphonate, a thionoalkylphosphotriester, a boranophosphate, a phosphodiester, a 2'-O-methoxyethyl, a 2'-O-methyl, a 2'-fluoro, a locked nucleic acid (LNA), a peptide nucleic acid (PNA) and a 2'-Fluoroarabinooligonucleotides (FANA).

According to some embodiments of the invention, the miR-135 is as set forth in SEQ ID NO: 194-209.

According to some embodiments of the invention, the bipolar disorder is selected from the group consisting of Bipolar I, Bipolar II, Rapid-cycling bipolar disorder, Cyclothymia and Bipolar Disorder Not Otherwise Specified (BD-NOS).

According to some embodiments of the invention, the miR-135 is selected from the group consisting of SEQ ID NO: 58, SEQ ID NO: 59, SEQ ID NO: 60, SEQ ID NO: 61 and SEQ ID NO: 62.

According to some embodiments of the invention, the miR-135 comprises miR-135* selected from the group consisting of SEQ ID NO: 192 and SEQ ID NO: 193.

According to some embodiments of the invention, the miR-135 is selected from the group consisting of SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208 and SEQ ID NO: 209.

According to some embodiments of the invention, the medicament for the treatment of a bipolar disorder is selected from the group consisting of a lithium, an antipsychotic medicament and a mood stabilizer medicament.

According to some embodiments of the invention, the method further comprises (c) treating the human subject when a higher expression level of the miR-135 is observed in step (b).

According to some embodiments of the invention, the method further comprises obtaining a biological sample from the human subject prior to the treating.

According to some embodiments of the invention, the mood disorder comprises a bipolar disorder.

According to some embodiments of the invention, the anti-depressant drug is selected from the group consisting of selective serotonin reuptake inhibitors (SSRI), tricyclic anti-depressants and noradrenaline reuptake inhibitors (NRI).

According to some embodiments of the invention, the medicament for the treatment of the mood disorder is selected from the group consisting of a lithium, an antipsychotic medicament and a mood stabilizer medicament.

According to some embodiments of the invention, the biological sample is selected from the group consisting of a whole blood, a serum, a plasma and white blood cells.

According to some embodiments of the invention, the mood disorder is selected from the group consisting of a bipolar disorder, a depression, a major depression, an anxiety, a stress, a fatigue, an impaired cognitive function, a panic attack, a compulsive behavior, an addiction, a social phobia, a schizophrenia, a sleep disorder and an eating disorder.

According to some embodiments of the invention, the miR-135 is selected from the group consisting of miR-135a or miR-135b.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1I depict microRNA expression in serotonin (5HT) neurons. FIG. 1A is a graphic illustration of differentially expressed miRNAs in 5HT neurons. Lowess normalized values are depicted as ln2 fold change of spot intensity plotted against average log intensities (MA plot); FIG. 1B is a validation of array results in miRs real time PCR indicating increased levels of miR-375 in the 5HT neurons compared to control. n=5 5HT cells, n=4 non 5HT. Bars represent mean±s.e.m. P=0.0071; FIG. 1C is a validation of array results in miRs real time PCR indicating decreased levels of miR-135a in the 5HT neurons compared to control. N=5 5HT cells, n=4 non 5HT. P=0.0075; FIG. 1D is a van diagram representing crossing bioinformatics predictions for Slc6a4 with 5HT microarray results and listing miRs chosen for in vitro testing; FIG. 1E is a van diagram representing crossing bioinformatics predictions for Htr1a with 5HT microarray results and listing miRs chosen for in vitro testing; FIG. 1F is a van diagram representing crossing bioinformatics predictions for Tph2 with 5HT microarray results and listing miRs chosen for in vitro testing; FIG. 1G is a van diagram representing crossing bioinformatics predictions for MaoA with 5HT microarray results and listing miRs chosen for in vitro testing; FIG. 1H is a graph illustrating luciferase reporter assay results indicating that miR-181c and miR-27b may target Tph2 3'UTR; and FIG. 1I is a graph illustrating luciferase reporter assay results indicating that miR-27b may target Htr1a MaoA.

FIGS. 2A-2H depict microRNA targeting of Slc6a4 3'UTR (SEQ ID NO: 25) and Htr1a 3'UTR (SEQ ID NO: 27). FIG. 2A is an illustration of miR-135a and miR-135b (SEQ ID NOs: 24 and 26, respectively) targeting of Slc6a4 3'UTR; FIG. 2B is an illustration of miR-135a and miR-135b (SEQ ID NOs: 24 and 26, respectively) targeting of Htr1a 3'UTR; FIG. 2C is a graph illustrating luciferase reporter assay results indicating that miR-135a and miR-135b may target Slc6a4 3'UTR. Luciferase assay data depicts *renilla* luciferase activity normalized to the activity of a co-transfected firefly luciferase reporter in HEK293 cells transfected with 3'UTR of the gene described and an empty vector, or a vector over-expressing a specific miR. Bars represent mean±s.e.m. *P=0.014, *P=0.0002, for miR-16 #p<0.0535, for miR-27 #P=0.0967; FIG. 2D is a graph illustrating luciferase reporter assay results indicating that miR-135a, miR-135b, miR-335, miR-181C and miR-26a may target Htr1a 3'UTR. *P<0.0001, P=0.0029; FIG. 2E is an illustration of slc6a4 3'UTR conservation of the seed matches for miR-135 (SEQ ID NOs: 27-41); FIG. 2F is an illustration of Htr1a 3'UTR seed matches for miR-135 (SEQ ID NOs: 42-54), indicating seed 1 appearing only in mouse 3' UTR, and seed 2 is highly conserved; FIG. 2G is a graph illustrating that mutation in miR-135 seed match in slc6a4 3'UTR blocked the repressor effect of miR-135a and miR-135b. *P<0.0001, P=0.0032; and FIG. 2H is a graph illustrating mutation in miR-135 seed matches in Htr1a 3' UTR individually and both together, indicating miR-135b targets Htr1a via both the seed matches and miR-135a only by seed 2. *P<0.0001.

FIGS. 3A-3F depict miR-135a and miR-135b levels under different conditions. FIG. 3A is a graph illustrating down-regulation of miR-135a levels in the RN following acute stress. Bars represent mean±s.e.m. (n=8 in the 0 group, n=10 in the 90 group and n=9 in the 24 group) ***P<0.0001, *P=0.0357; FIG. 3B is a graph illustrating down-regulation of miR-135b levels in the RN following acute stress. *P<0.0001, P=0.0055; FIG. 3C is a graph illustrating up-regulation of miR-135a levels in the RN following acute and chronic imipramine administration independently from whether the mice were exposed to social defeat. (n=8 in control chronic saline and control chronic imipramine, n=7 acute imipramine, n=11 social defeat chronic saline, n=9 in the social defeat chronic imipramine) P=0.003; FIG. 3D is a graph illustrating up-regulation of miR-135b levels in the RN following acute and chronic imipramine administration independently from whether the mice were exposed to social defeat. P=0.0093; FIG. 3E is a graph illustrating increase in miR-135a levels in the RN following acute or chronically administered SSRI, and not NRI or saline. (n=8 in each group apart from acute saline n=7) ***P<0.0001; FIG. 3F is a graph illustrating an unaltered miR-135b levels in the RN following acute or chronically administered SSRI or NRI.

FIGS. 4A-4H depict in vivo over-expression of miR-135b. FIG. 4A is a schematic illustration of lentiviruses for over-expression of miR-135b; FIG. 4B is a graph illustrating real time PCR results indicating over-expression of miR-135b in vivo in the dorsal raphae nucleus (DRN) of adult mice. Bars represent mean±s.e.m. (n=5 GFP injected and n=3 miR-135 OE) P=0.0032; FIGS. 4C-4D are illustrations of a DRN injection site by demonstration of GFP staining at injections site. (Section map adopted from Paxinos); FIG. 4E is a graph illustrating decreased immobility time in the forest swim test in mice over-expressing miR-135b in the RN compared to control mice. (n=9 control n=9 miR-135) P=0.0088 in minute 3 and P=0.00330 for minute 4; FIG. 4F is a graph illustrating decreased immobility time in the tail suspension test in mice over-expressing miR-135b in the RN compared to control mice. P=0.07351; FIGS. 4G-4H are graphs illustrating no difference in home cage locomotion in of mice over-expressing miR-135b in the RN compared to controls.

FIG. 5 depicts ADRb1 3'UTR cloned following the luciferase gene. Illustration of intact (top) ADRb1 3'UTR, harboring four miR-19 binding sites, and mutant (bottom) form of ADRb1 3'UTR, lacking all four miR-19 binding sites, cloned downstream to the luciferase gene in Psicheck2 plasmid.

FIGS. 6A-6E depict that miR-19b targets ADRb1 3'UTR via seed matches on its 3' UTR; FIGS. 6A-6B are graphs illustrating normalized luciferase levels measured in HT22 cells that express low endogenous miR-19 levels following transfection with (FIG. 6A) GFP plasmid or (FIG. 6B) pre-miR-19b overexpression (OE) plasmid; FIGS. 6C-6E are graphs illustrating normalized luciferase levels measured in HEK293T cells that express high endogenous miR-19 levels. Transfection with (FIG. 6C) control plasmid, (FIG. 6D) miR-19b knockdown (KD) probe or scrambled probe as control, and (FIG. 6E) transfection with miR-19b miArrest plasmid or control miArrest plasmid. ***P<0.005. Renilla luciferase activity was normalized by firefly luciferase expression levels and presented as ratio of activity achieved by the mutant form of Adrb1-3'UTR (Adrb1-mut) at the presence of control treatment.

FIGS. 7A-7D depict differential expression of miRNA in the amygdale. FIGS. 7A-7B are graphs illustrating differential expression of miRNA in the amygdala 90 minutes following acute stress. FIG. 7A illustrates agilent array results. FIG. 7B illustrates affymetrix array results. Normalized values are depicted as log 2 ratio (stress vs. control) of spot intensity plotted against average intensities across conditions (N=2, 2). The intensity of each miRNA was calculated as the average normalized intensity across biological repeats. miR-15a and miR-15b are indicated in red. miR-124, a well-established neuronal marker not affected by the stress protocol is indicated in white; FIG. 7C illustrates that miR-15a and miR-15b have a semi-conserved seed match on corticotropin releasing hormone type 1 receptor 3'UTR [CRHR1, adapted from targetscan(dot)org]; and FIG. 7D is a graph illustrating luciferase activity measured in HEK293T cells co-transfected with miR-15b-EGFP overexpressing or GFP expressing plasmid and a luciferase reporter plasmid controlled by CRFR1-3'UTR. Renilla luciferase activity was normalized by firefly luciferase expression levels.

FIG. 10 is a van diagram representing in silico bioinformatics predictions for miR-182 targets in two algorithms, and list of potential target genes highly relevant for normal and pathological neuronal function appearing in this prediction.

FIGS. 11A-11C depict over-expression or knockdown of miR-182. FIG. 11A is a schematic illustration of lentiviruses for over-expression of miR-182; FIG. 11B is a graph illustrating real time PCR results indicating over-expression of miR-182 in vitro in N2A cell line; and FIG. 11C is a schematic illustration of lentiviruses for knockdown of miR-182.

Figure 12A:
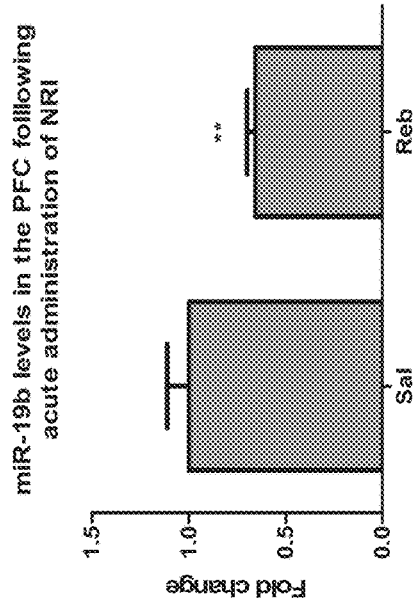
Figure 12C:
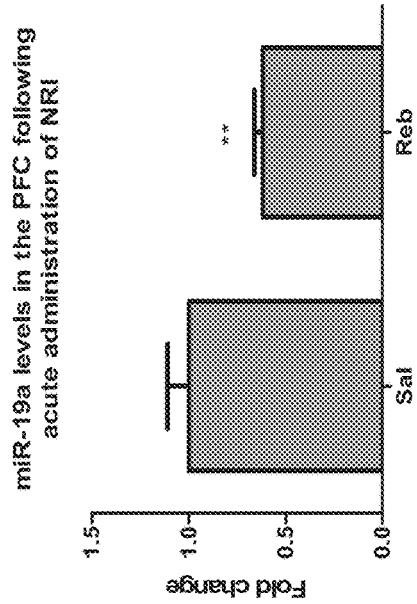
Figure 12B:
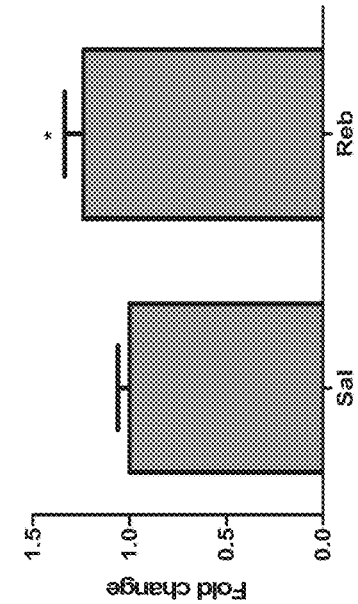
Figure 12D:
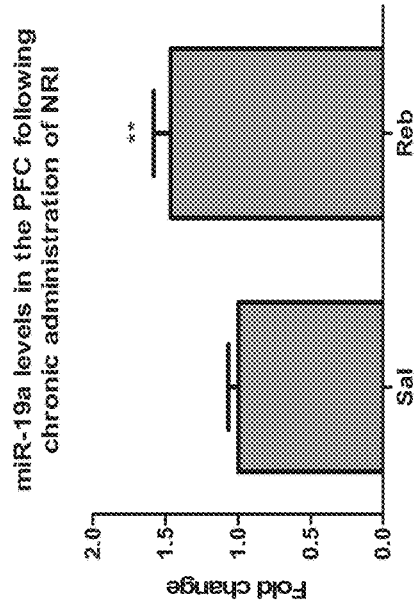

FIGS. 12A-12D depict miR-19 levels in the PFC following NRI administration. The NRI reboxetine was administrated either acutely (once) or chronically (for 18 days). Of note, miR-19a and miR-19b levels decreased in the PFC following acute administration of NRI (FIG. 12A and FIG. 12B, respectively) but increased following chronic administration of NRI (FIG. 12C and FIG. 12D, respectively).

FIGS. 13A-13D depict miR-19 levels in the PFC and amygdala of mice subjected to social defeat. miR-19a and miR-19b levels were measured in samples from amygdala taken from mice that were subjected to social defeat paradigm. Of note, miR-19a and miR-19b levels in the PFC were elevated in mice categorized as being "Susceptible" to social defeat relative to control mice (FIG. 13A and FIG. 13B, respectively). miR-19 levels were also elevated in the amygdala of mice categorized as being "Susceptible" to social defeat relative to control mice (FIG. 13C and FIG. 13D, respectively).

Figure 14:
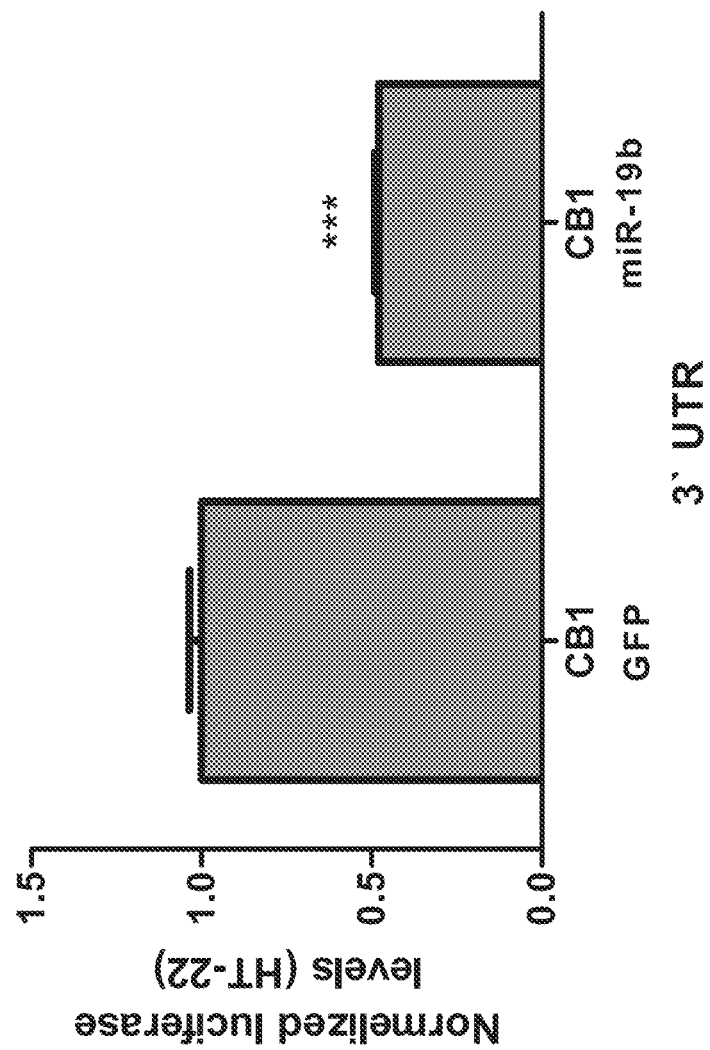

FIG. 14 depicts miRNA-19b targeting CB1 3'UTR. Transfection of HT-22 cells with CB1 3' UTR and plasmids overexpressing either miR-19b or GFP control lead to a 50% decrease in normalized luciferase levels.

Figure 15A:
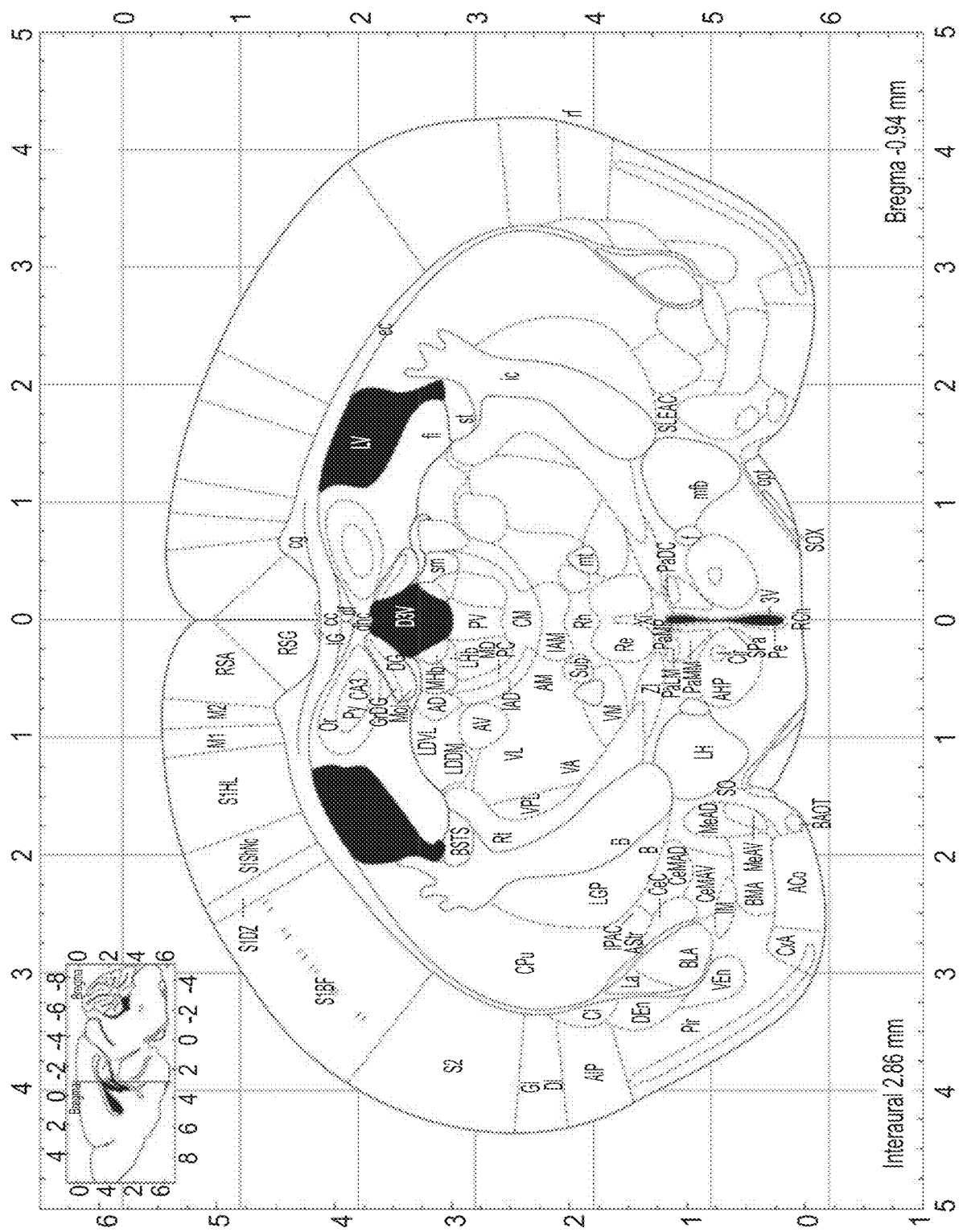
Figure 15B:
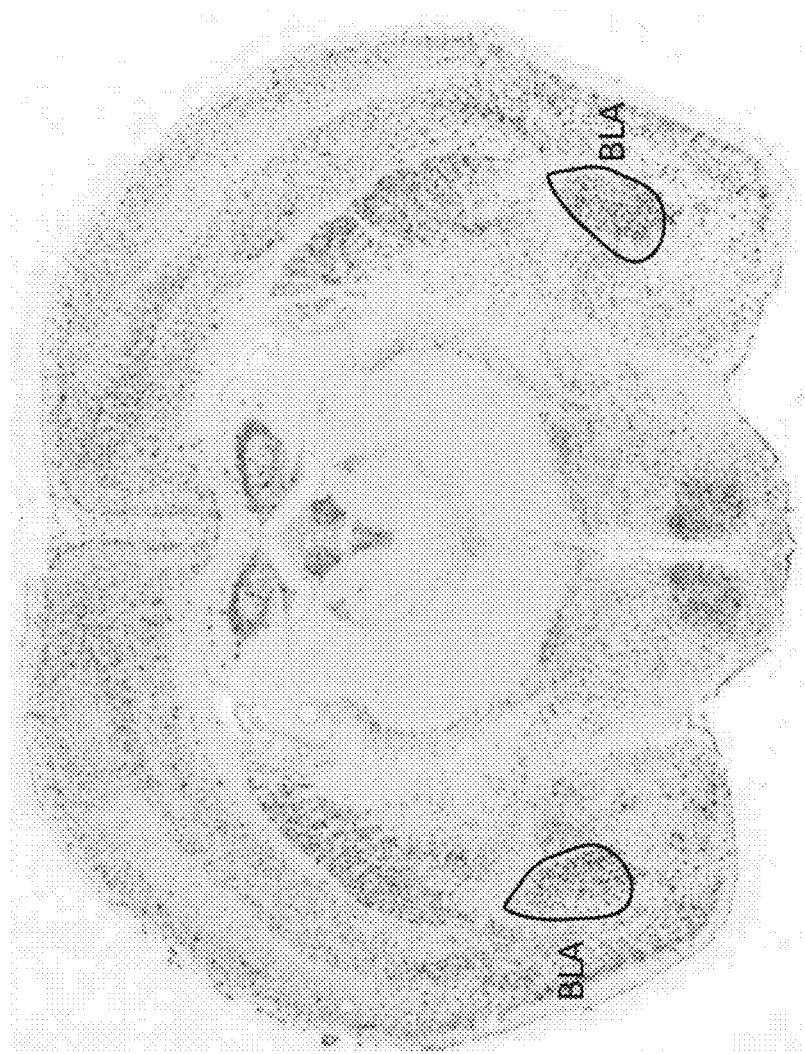

FIGS. 15A-15B are schematic illustrations of a coronal section of the mouse brain. FIG. 15A shows several nuclei in the brain including the BLA (adapted from the mouse brain by Paxinos and Franklin); FIG. 15B shows a CB1 distribution in the brain (adapted from Allen Brain Atlas www(dot)mouse(dot)brain-map(dot)org/). Of note, it is evident by this distribution that CB1 is abundant in the BLA.

Figure 16:
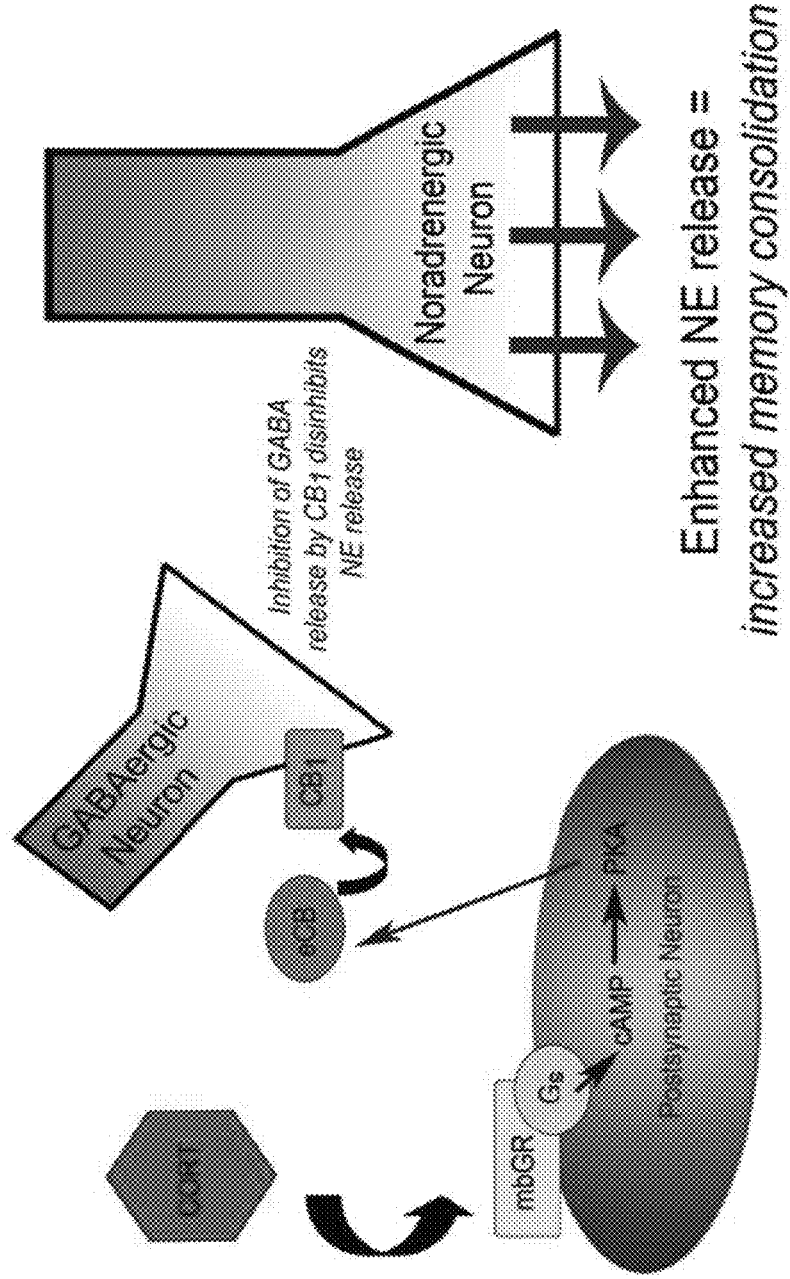

FIG. 16 is a schematic illustration of a proposed mechanism for memory consolidation in the basolateral nucleus of the amygdala (BLA). Corticosterone (CORT) binds to a yet-uncharacterized membrane-bound glucocorticoid receptor (mbGR) that activates the Gs-cAMP/PKA pathway to induce endocannabinoid (eCB) synthesis. Endocannabinoids are released into the synapse where they bind to CB1 receptors on GABAergic terminals inhibiting GABA release. This inhibition of GABA release disinhibits norepinephrine (NE) release and increases NE activation of post-synaptic β-adrenoreceptors, increasing the consolidation of emotionally-aversive memories.

Figure 17A:
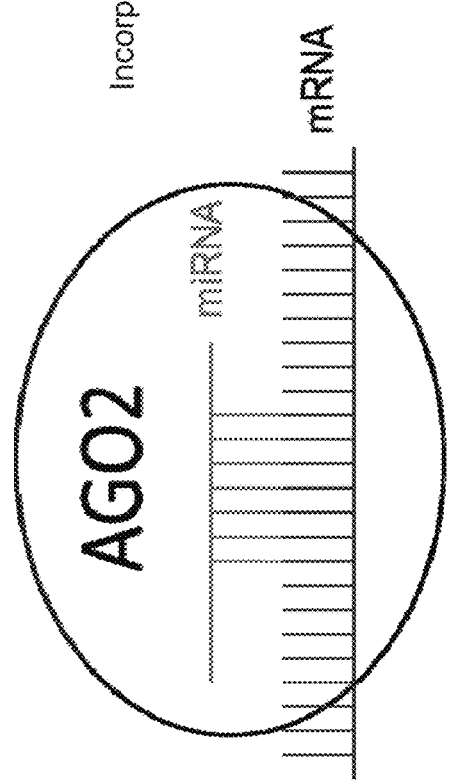
Figure 17B:
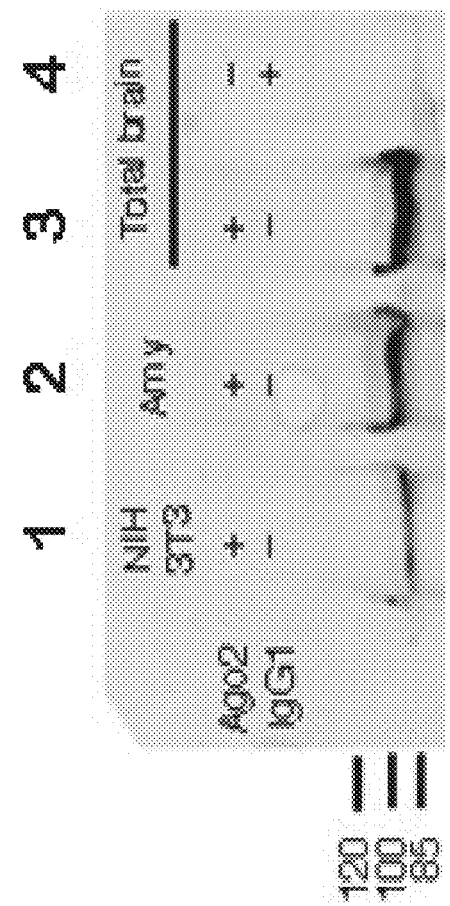

FIGS. 17A-17B illustrate Ago2 in the RISC complex. FIG. 17A is a schematic illustration of Ago2 in the RISC complex, mediating the interaction between the miRNA and the mRNA; FIG. 17B illustrates a western blot analysis performed with anti-Ago2 antibody. This IP was specific to the Ago2 protein as can be seen when comparing the total brain sample that was precipitated once with the Ago2 antibody and once with the IgG1 control. Of note, there was no detection of the Ago2 protein on the samples precipitated with the IgG1 control.

FIGS. 18A-18D depict a social avoidance test. Mice were placed in a maze for 3 minutes alone for habituation (FIG. 18A and FIG. 18B) and their movement was recorded and plotted. After 3 minutes a novel ICR mouse was placed in the chamber next to the examined mouse (FIG. 18C and FIG. 18D) and the movement of the examined mouse was recorded and plotted again.

Figure 19A:
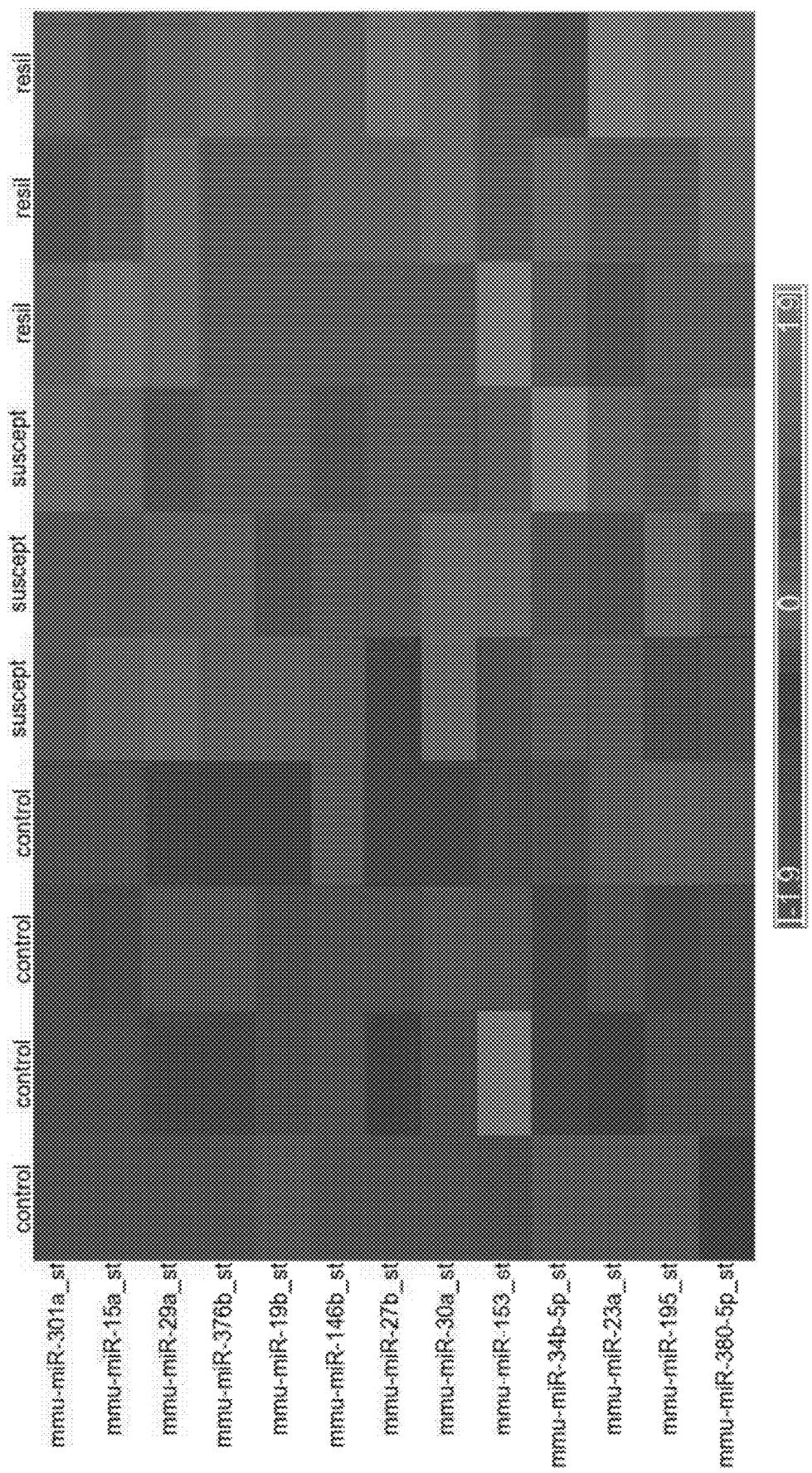

FIG. 19A depicts a heatmap illustration of selected miR-NAs up regulated in the arrays.

Figure 19B:
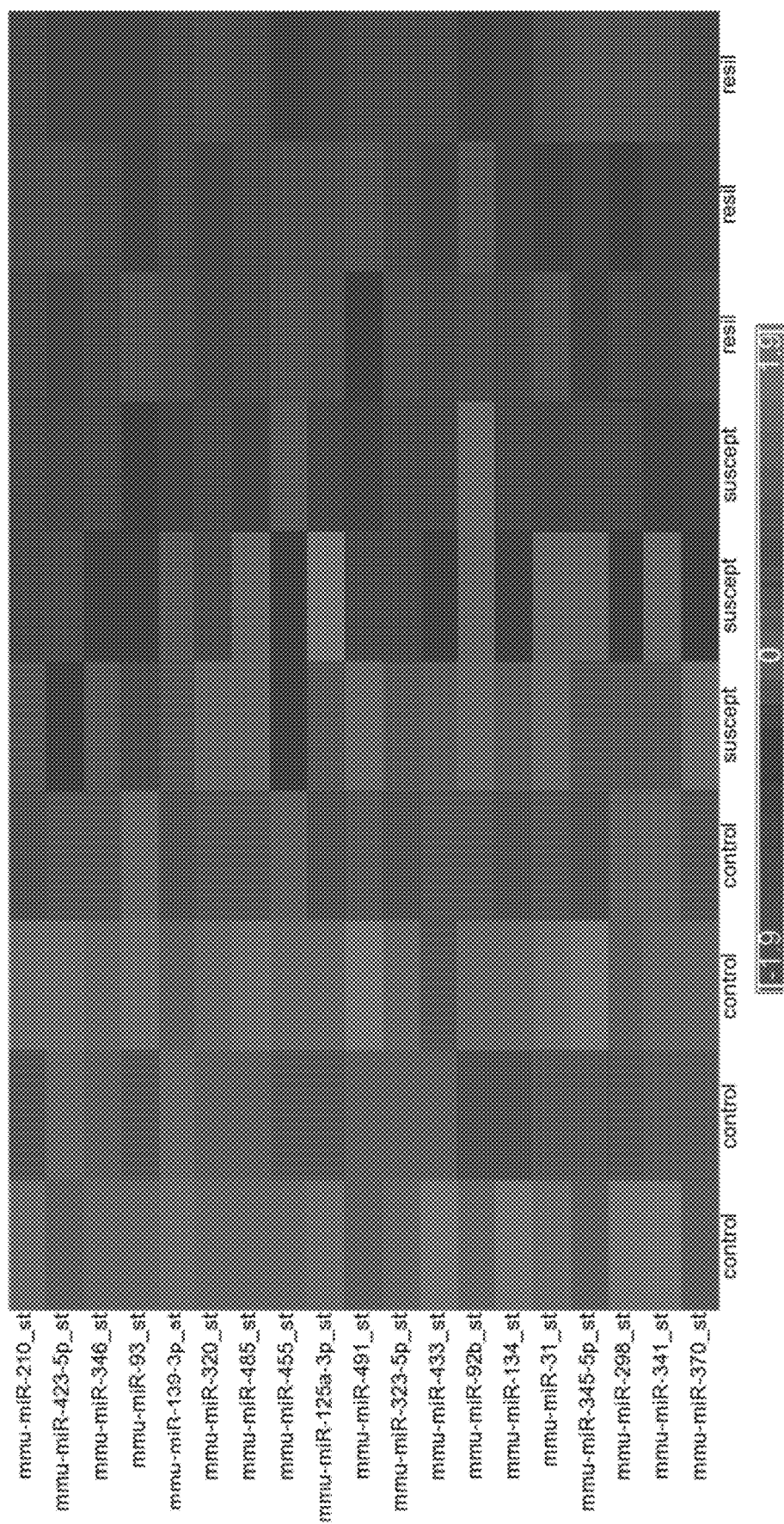

FIG. 19B depicts a heatmap illustration of selected miR-NAs down regulated in the arrays.

Figure 20A:
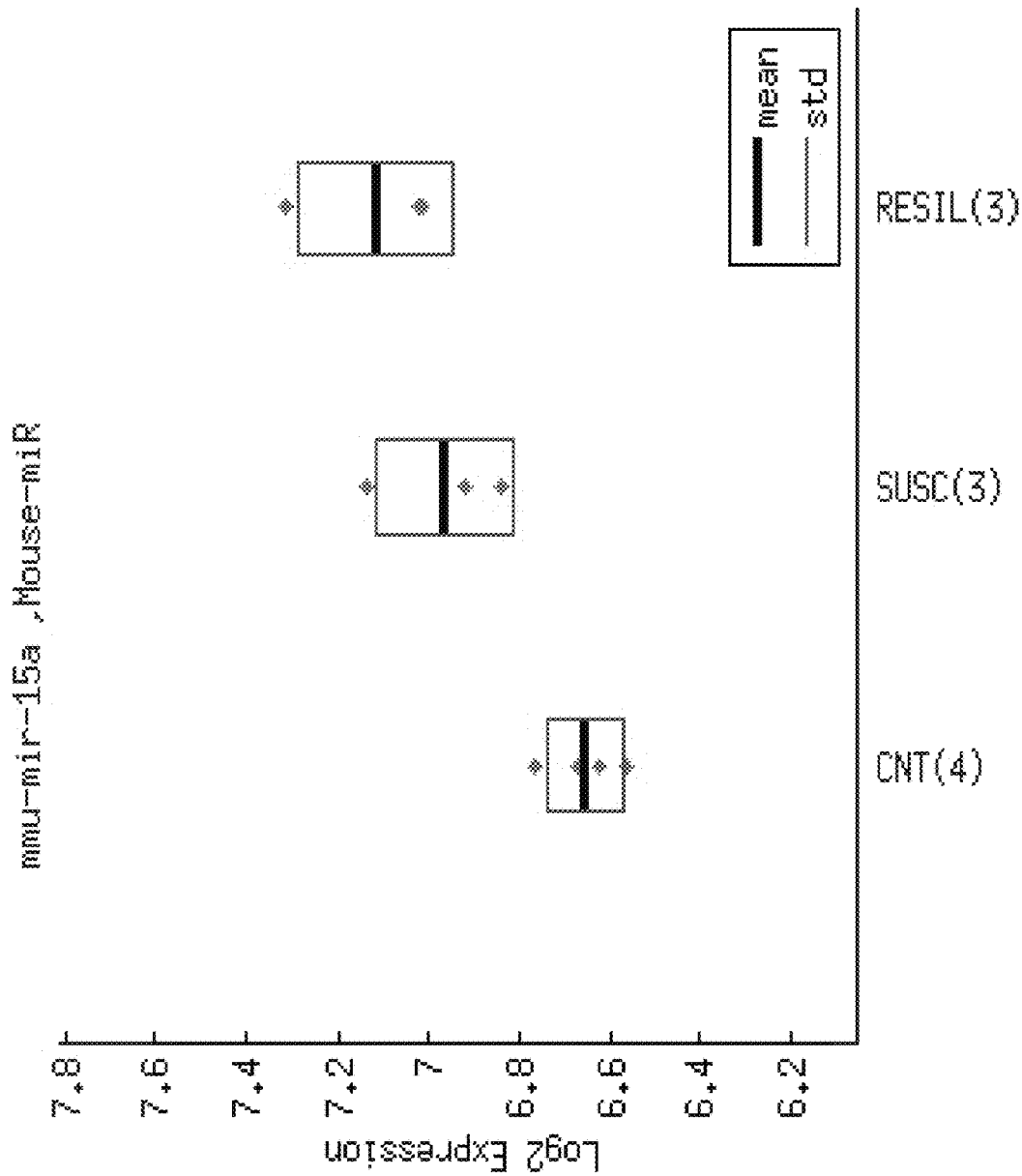
Figure 20B:
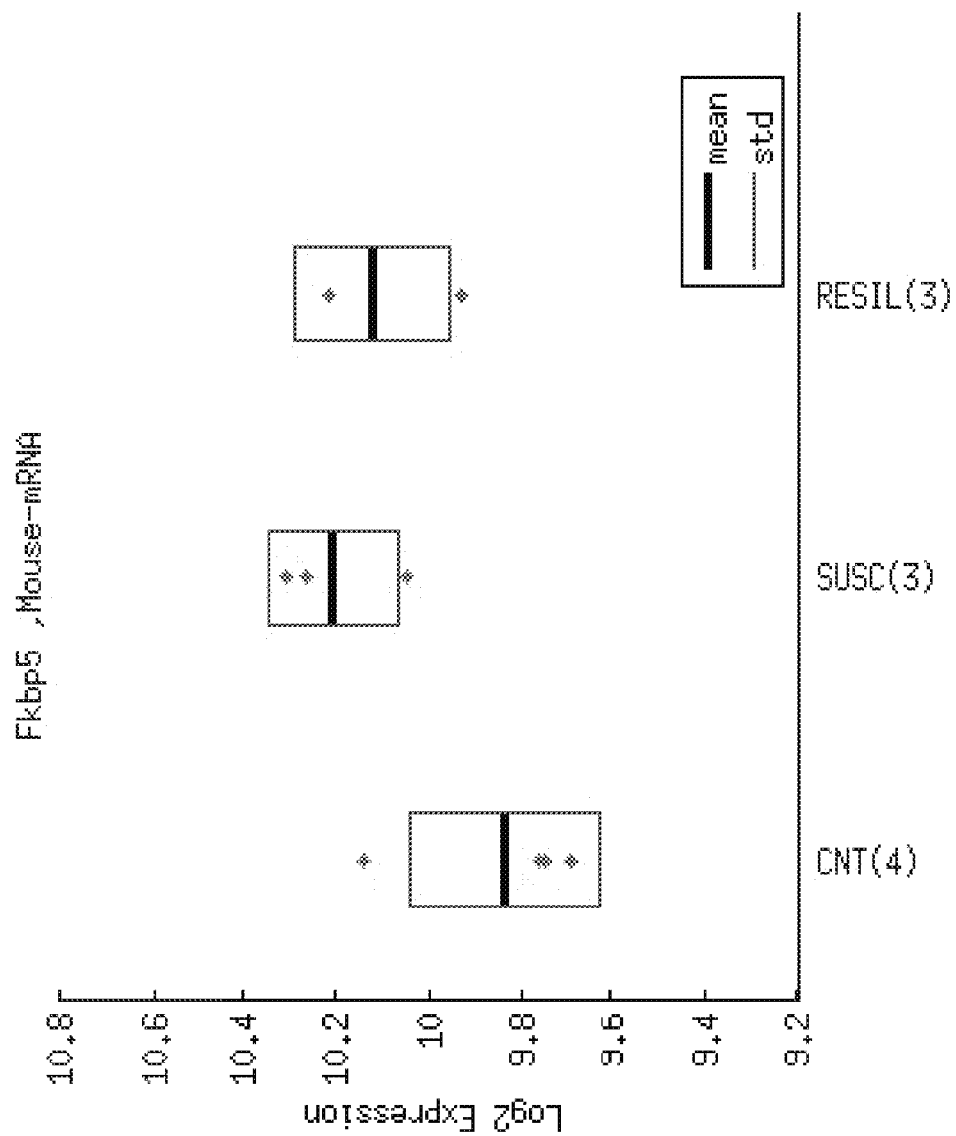

FIGS. 20A-20B depict a log 2 expression of miR-15a (FIG. 20A) and FKBP5 (FIG. 20B) from the microarray results. Each red dot refers to one repetition of an array. The control group (CNT) had 4 repetitions, the "Susceptible" group (SUSC) had 3 repetitions and the "Resilient" group (RESIL) had 3 repetitions. The black line showed the mean of the repetitions in each group.

FIG. 20C depicts a 3' UTR sequence of mouse FKBP5 (taken from targetscan(dot)org).

Figure 21A:
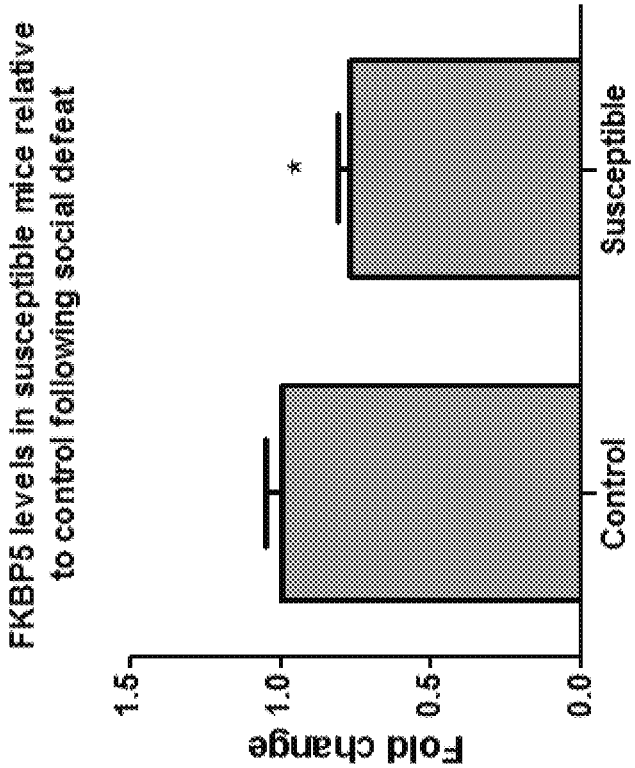
Figure 21B:
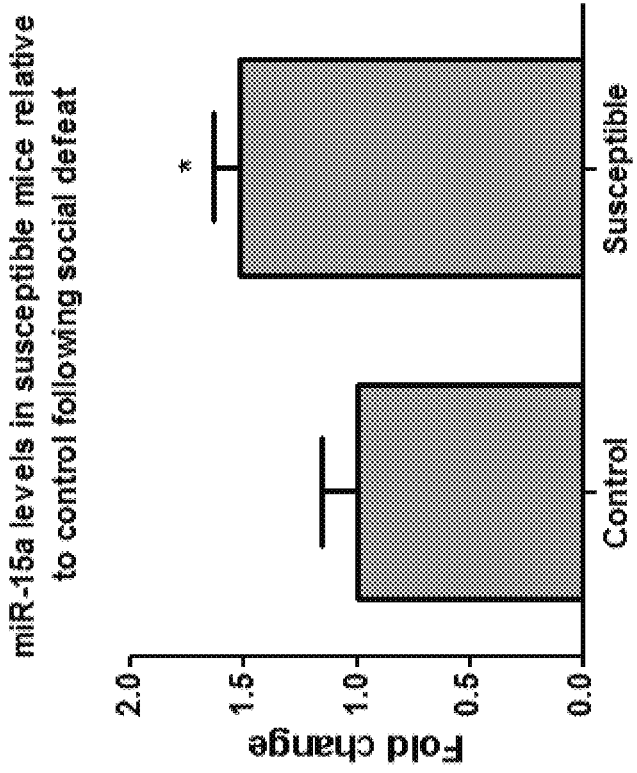

FIGS. 21A-21B depict the levels of amygdalar miR-15a (FIG. 21A) and FKBP5 (FIG. 21B) in "Susceptible" mice relative to control mice following social defeat. Of note, miR-15a levels were elevated in the amygdala of mice subjected to social defeat and characterized as "Susceptible" (FIG. 21A). FKBP5 levels were decreased in the amygdala of mice subjected to social defeat and characterized as "Susceptible" (FIG. 21B).

Figure 22:
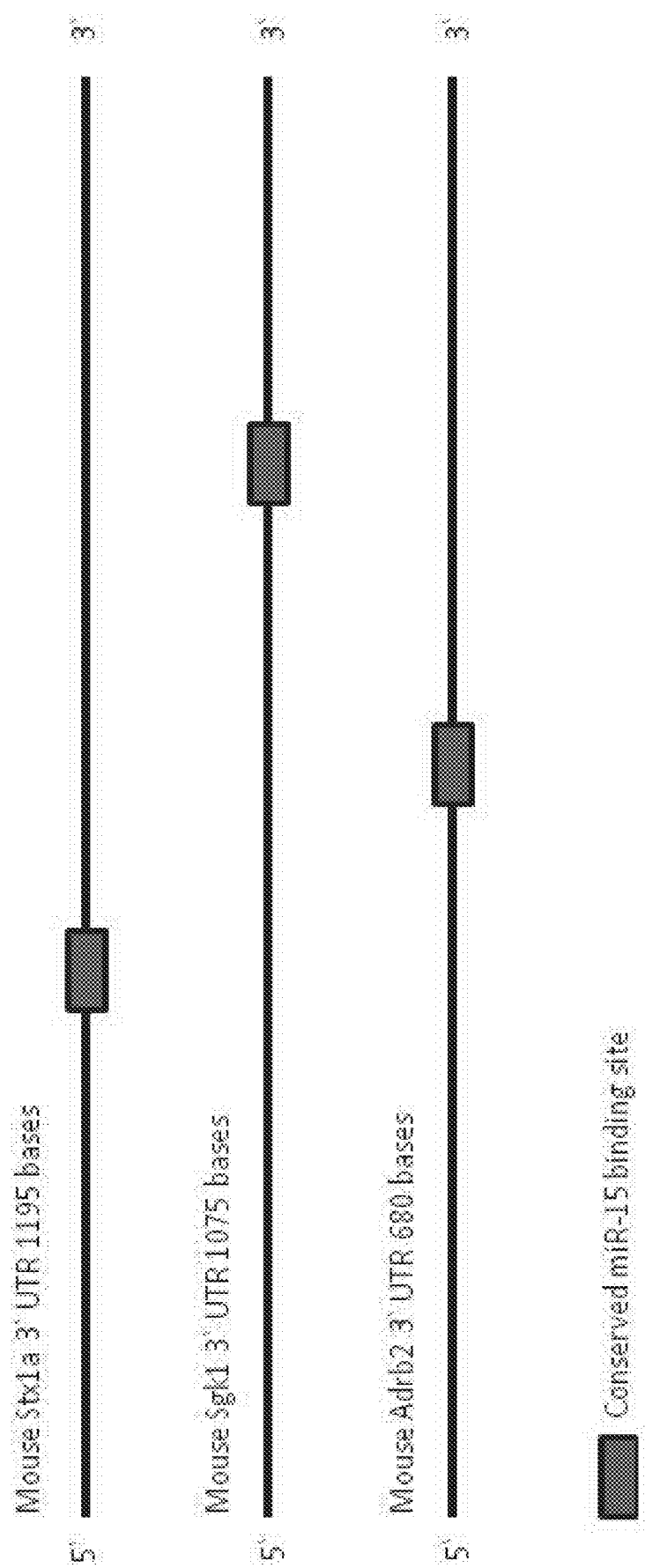

FIG. 22 is a schematic illustration of the 3'UTR of Stx1a, Sgk1 and Adrb2, each harboring a single miRNA-15 binding site.

Figure 23:
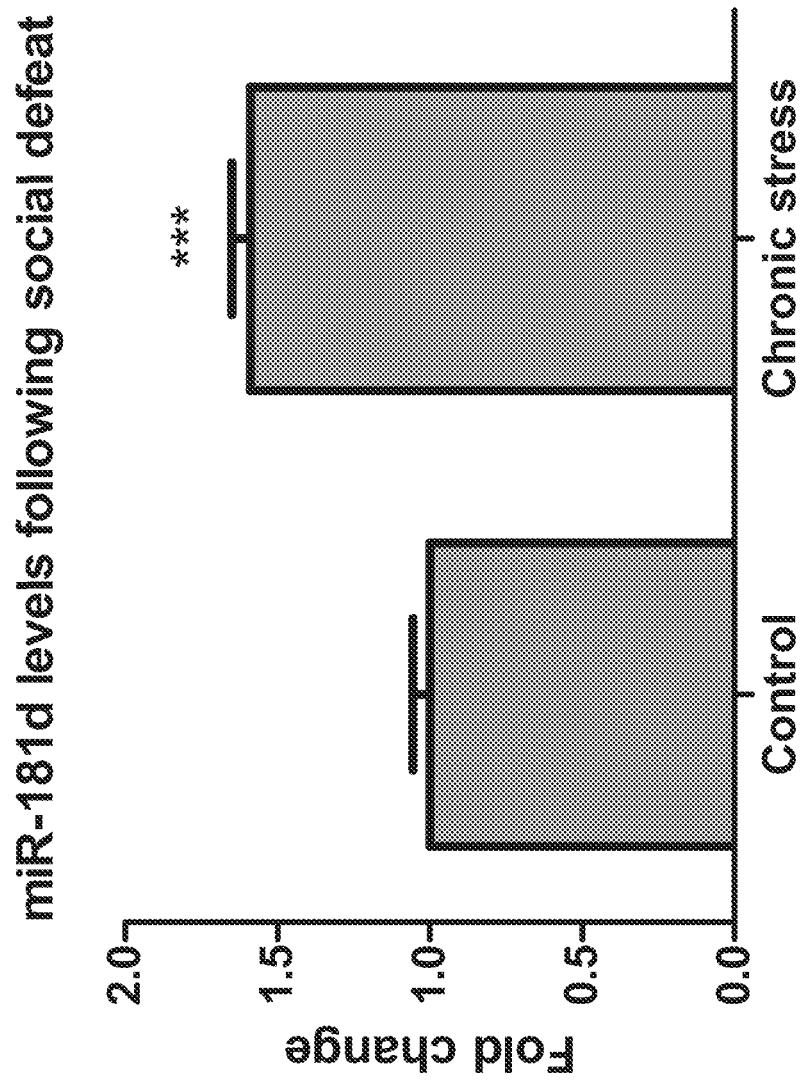

FIG. 23 depicts the levels of amygdalar miR-181 in mice subjected to social defeat relative to control mice. Of note, miR-181 levels were elevated in the amygdala of mice subjected to social defeat.

Figure 24:
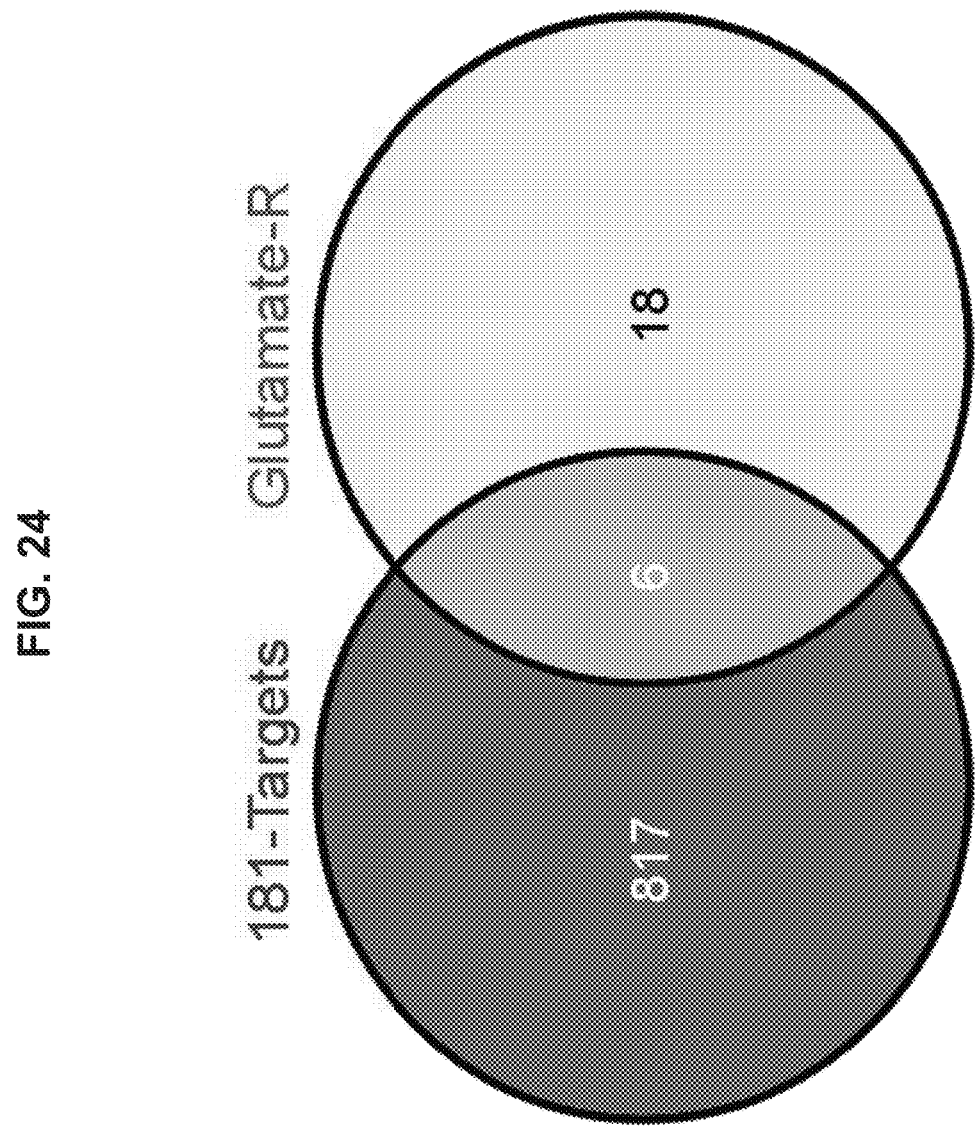

FIG. 24 depicts Van diagrams representing crossing bioinformatics predictions for miR-181 and glutamate receptors.

Figure 25:
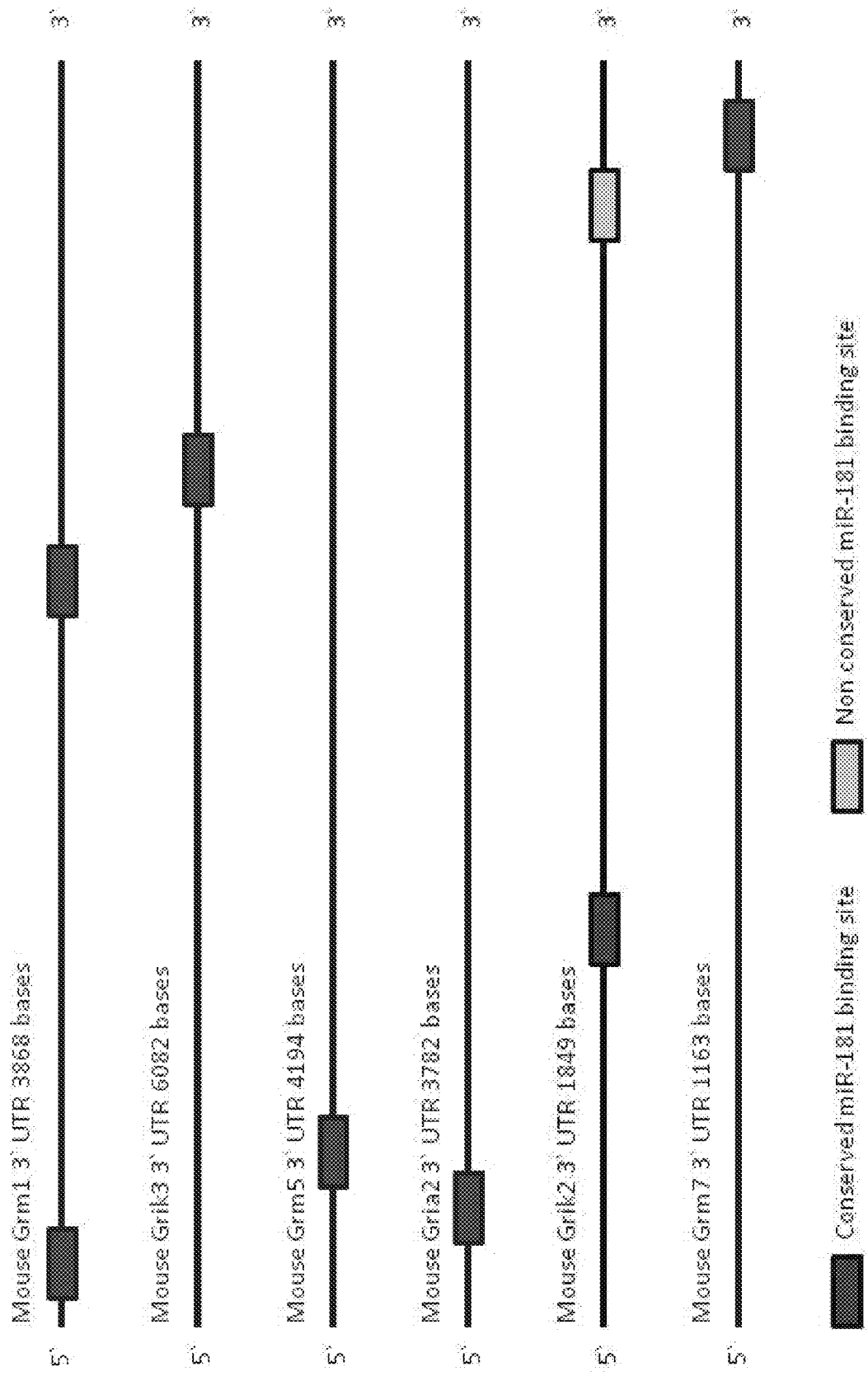

FIG. 25 is a schematic illustration of intact 3'UTR of 6 potential targets of miR-181.

Figure 26:
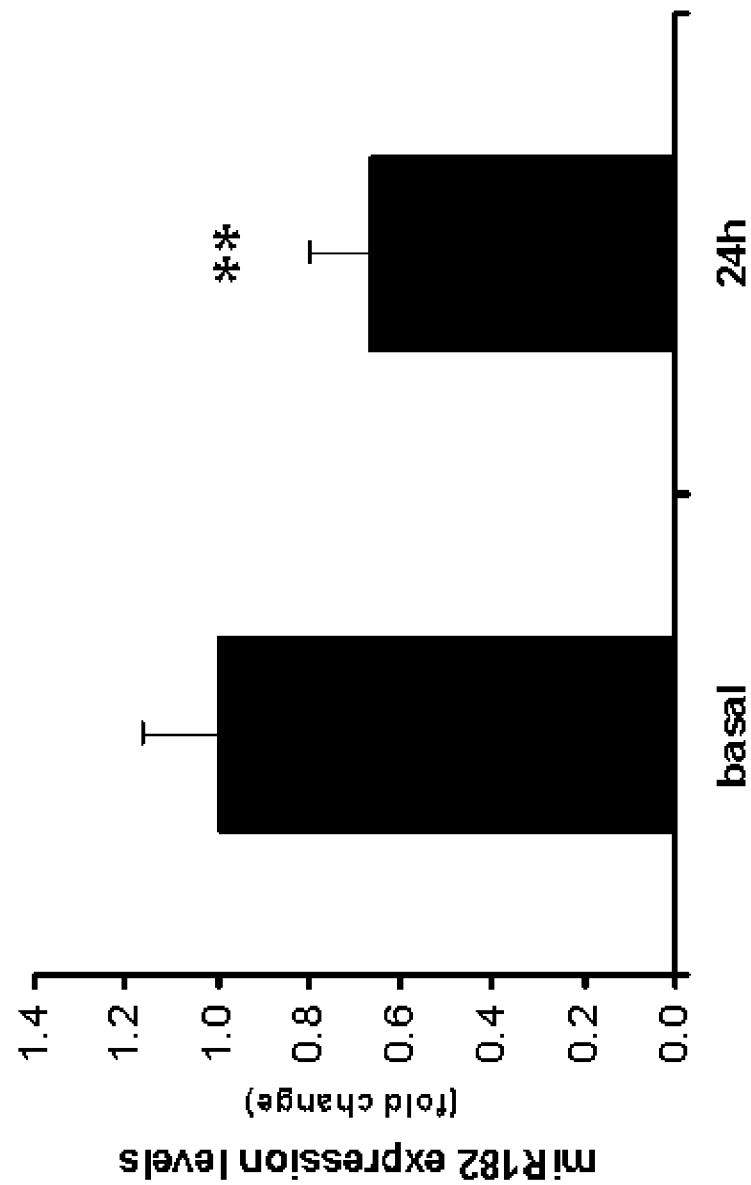

FIG. 26 depicts expression levels of miR182 in the raphe nucleus following stress. Of note, an acute 30 minute immobilization stress led to decreased expression levels of miR182 in the RN when tested 24 hours following the stress as measured by real time PCR. **=P<0.01; n=8 in each group.

FIGS. 27, 28 and 29 depict results of a luciferase reporter assay indicating that miR182 targets DSCAM, L1CAM and TSNAX 3'UTR. FIG. 27 illustrates data of luciferase assays depicting renila luciferase activity normalized to the activity of a co-transfected firefly luciferase reporter in N2a cells transfected with 3'UTR of the genes described and an empty vector, or a vector over-expressing a specific miR. Mutation in miR182 seed match in L1cam (FIG. 28) and Tsnax (FIG. 29) 3' UTRs blocked the represoric effect of miR182. Bars represent mean±s.e.m. *P<0.05, P<0.01, *P<0.001.

Figure 30A:
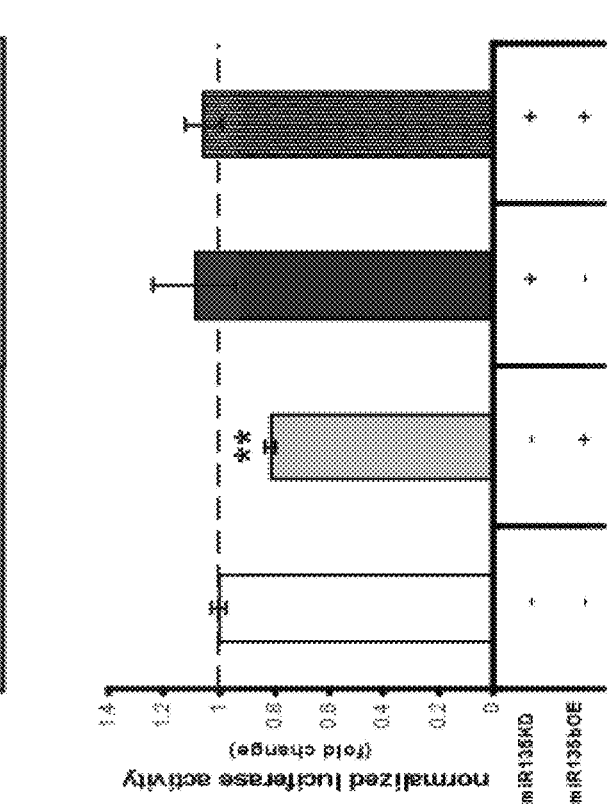
Figure 30B:
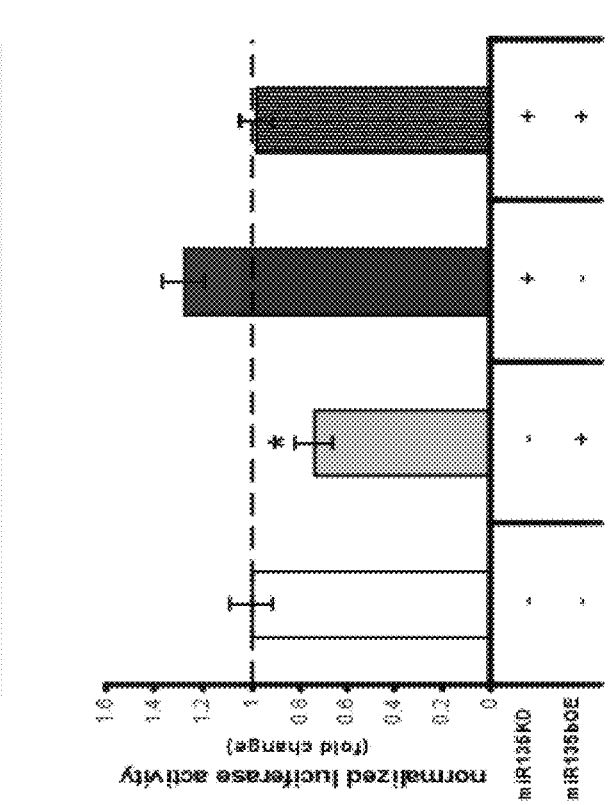

FIGS. 30A-30E depict validation of miR135 KD in vitro and in vivo. FIGS. 30A-30B illustrate results of a luciferase reporter assay indicating miR135 targeting of Htr1a (FIG. 30A) and slc6a4 (FIG. 30B) was blocked by the miR135b KD construct; FIG. 30C is a schematic illustration of miR135bKD and control viral vectors; and FIGS. 30D-30E are illustrations of a DRN injection site (FIG. 30D adopted from Paxinos), and FIG. 30E is a GFP staining of DRN infected with miR135 KD lentiviruses.

Figure 31B:
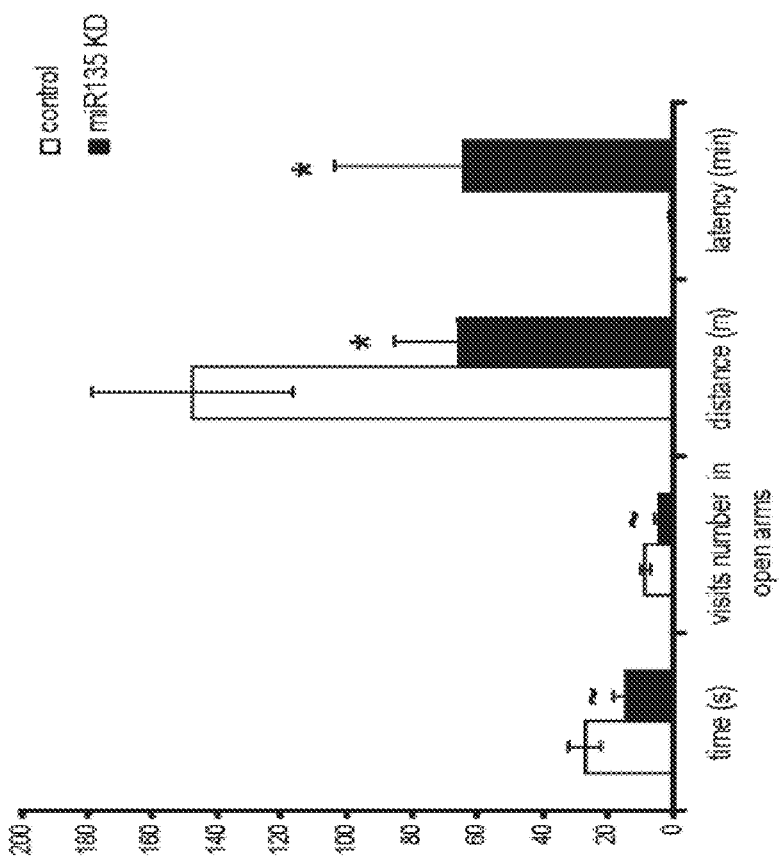
Figure 31A:
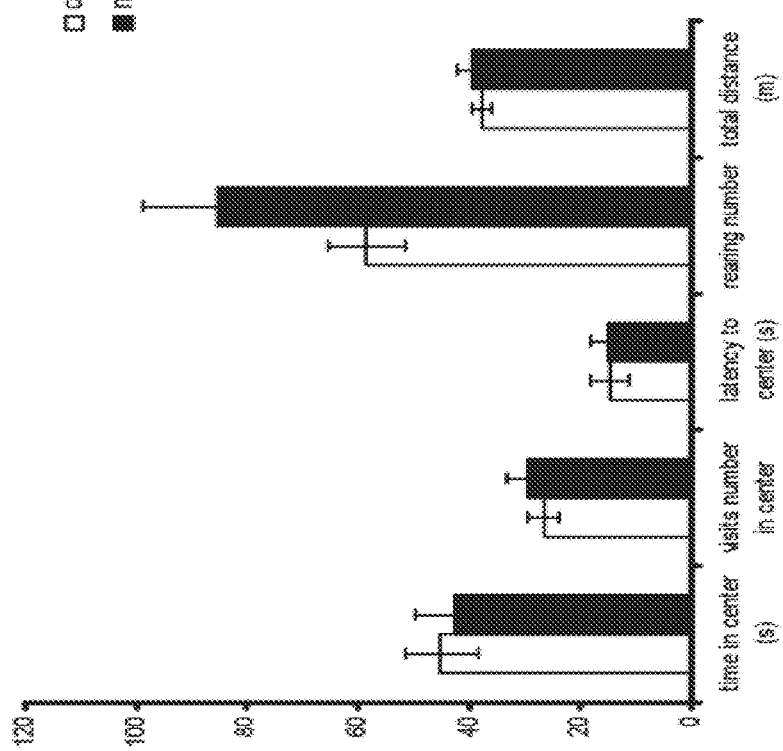
Figure 31G:
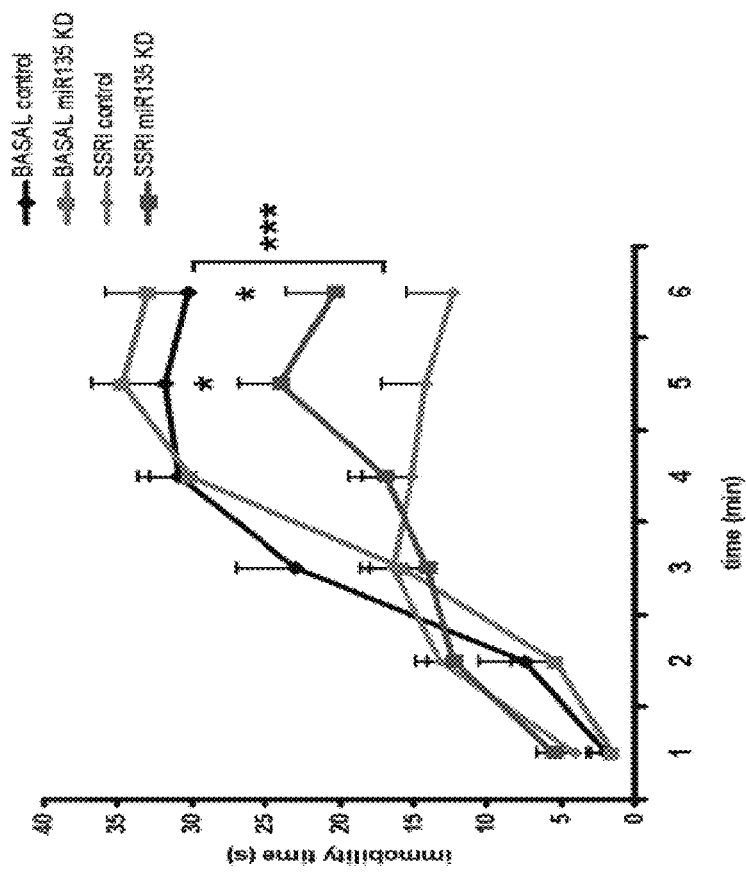
Figure 31F:
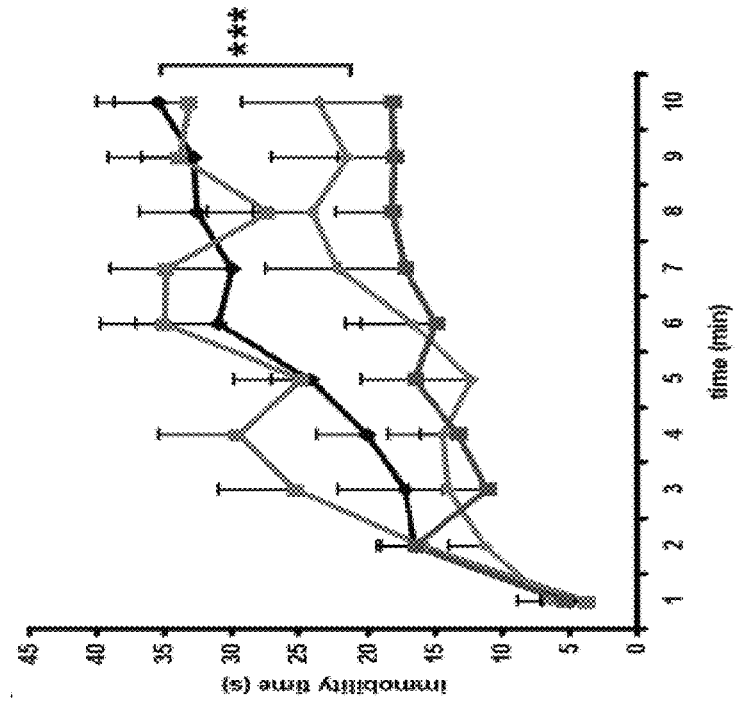

FIGS. 31A-31G depict increased anxiety-like behavior and attenuated response to SSRI in miR135KD mice. FIG. 31A illustrates that the behavior of miR135KD mice was similar to control mice in the open field test; FIG. 31B illustrates increased anxiety-like behavior in miR135KD mice compared to control mice in the elevated pulse maze; FIG. 31C illustrates that in the dark light transfer test miR135KD mice spent more time in the light chamber compared to control mice under basal stress conditions, but not following acute stress; FIG. 31D illustrates that miR135KD mice visited the light chamber more times compared to control mice, under basal stress conditions, but not following acute stress; FIG. 31E illustrates that miR135KD mice traveled less distance in the light chamber compared to control mice, under basal stress conditions, but not following acute stress; FIG. 31F illustrates no difference between miR135KD mice and control mice in tail suspension test both in basal conditions and following SSRI administration, yet reduction in immobility time was observed following SSRI treatment compared to basal condition in both groups (FIGS. 31F-31G). Immobility time was reduced by SSRI in both groups, however the reduction was attenuated in miR135KD mice compared to controls in the last 2 minutes of the test.~=p<0.1*=p<0.05;=p<0.01; *=p<0.001. n=10-11 in each group.

Figure 32:
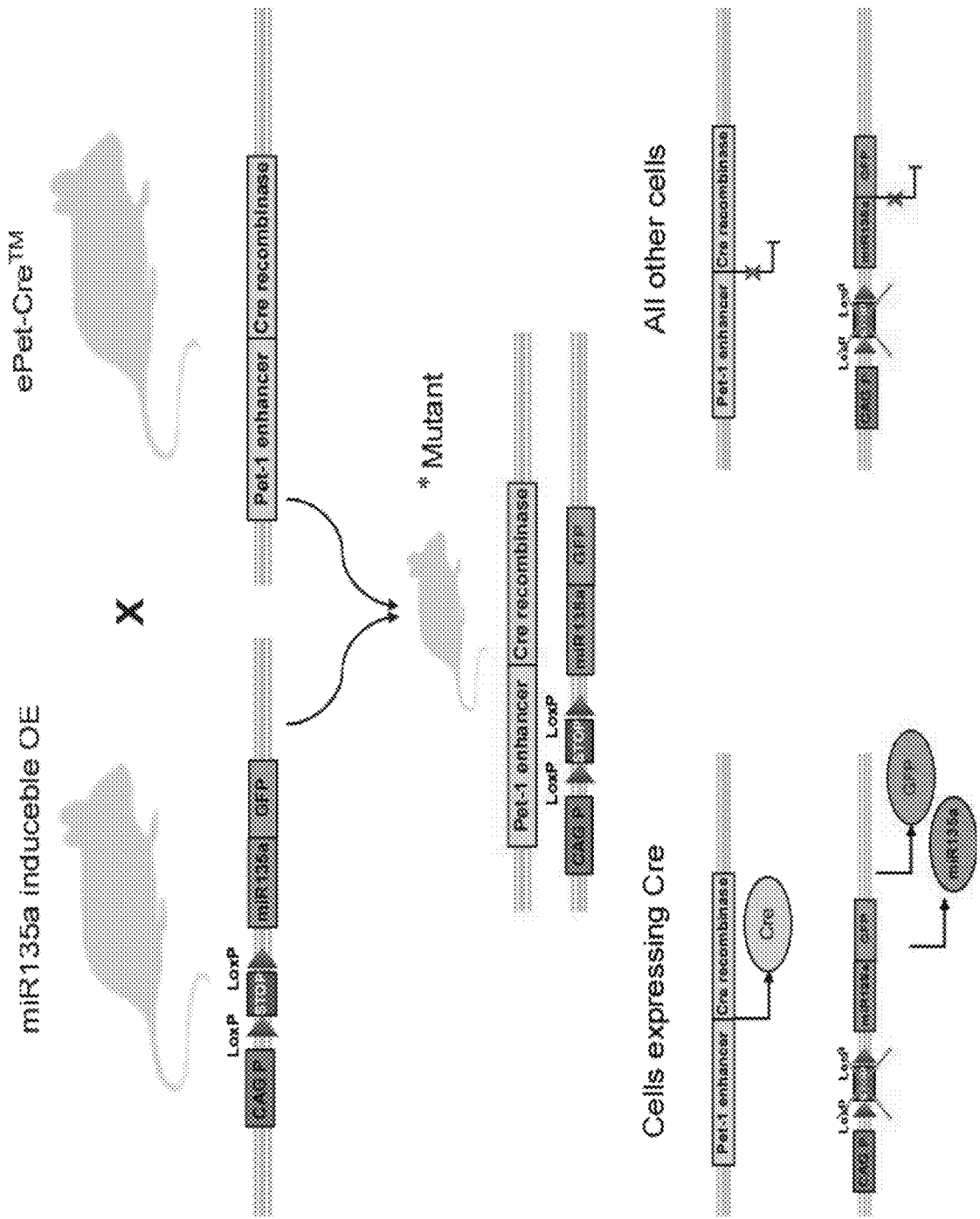

FIG. 32 is a schematic illustration of miR135 mice inducible overexpression system. Transgenic mice expressing floxed transactional stop before miR135a sequence and GFP reporter. Mutant transgenic mice express miR135a only in 5-HT ePet positive cells.

FIGS. 33A-33C depict validation of a mice line overexpressing miR135 in 5-HT neurons. FIG. 33A illustrates that miR135 was overexpressed in the RN of miR135OE mice compared to control mice. FIGS. 33B-33C illustrate that miR 135 target genes mRNA were downregulated in miR135OE mice RN, both Slc6a4 (FIG. 33B) and Htr1a (FIG. 33C). #=p<0.1*=p<0.05; n=4 in each group.

Figures 34D, 34E:
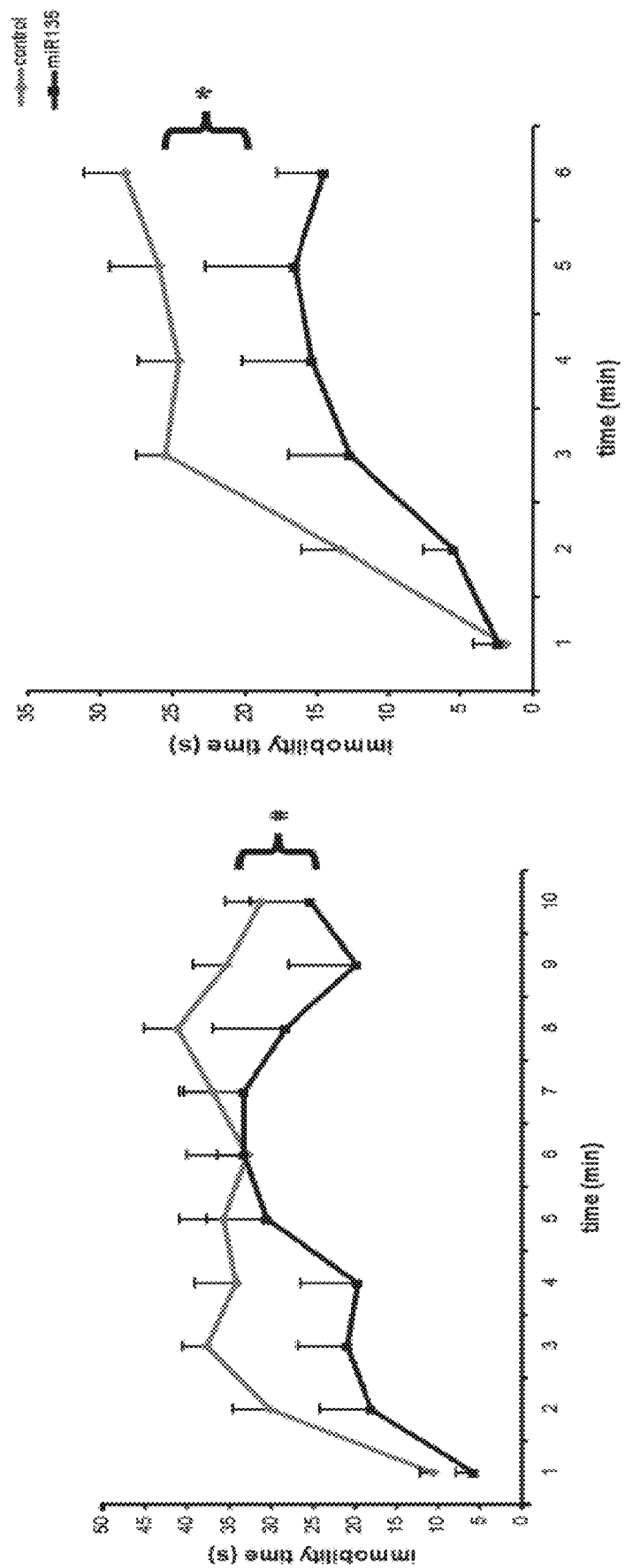

FIGS. 34A-34E depict decreased anxiety and depression-like behavior following social defeat in miR135OE mice. FIG. 34A shows that miR135OE mice have a decreased anxiety-like behavior in the open field test; FIG. 34B shows less anxiety like behaviors compared to control of miR135OE mice in a dark light transfer test; FIG. 34C shows decreased anxiety-like behavior compared to control in elevated pulse maze of miR135OE mice; FIG. 34D shows tendency towards decreased immobility time of miR135OE mice compared to controls in tail suspension test; and FIG. 34E shows reduced immobility time in miR135OE mice compared to controls in the forced swim test. #=p<0.1*=p<0.05;**=p<0.01 n=7-11 in each group.

FIGS. 35A-35D illustrate microRNA "fingerprint" of 5HT neurons. (FIG. 35A) Schematic illustration of the experimental design for determining 5HT neuronal microRNA "fingerprint". ePet-EYFP mouse embryo hindbrains were dissected and FACS sorted to 5HT-YFP positive and YFP negative cells. miR expression from the two populations was compared using the Agilent microRNA microarray; (FIGS. 35B-35D) Validation of cell phenotype by real time PCR indicating that YFP (FIG. 35B) and TPH2 (FIG. 35C) were significantly enriched in 5HT compared to non-5HT cells and that GAD67, a GABAergic marker, was significantly higher in non-5HT cells (FIG. 35D). Bars represent mean±s.e.m. ***P<0.001.

FIGS. 36A-36C illustrate evolutionary conservation of miR-135 variants. (FIGS. 36A-C) miR-135a-1 (FIG. 36A), miR-135a-2 (FIG. 36B) and miR-135b (FIG. 36C) are highly conserved through evolution while the mature miR sequences, highlighted in color, are almost perfectly conserved. Data modified form UCSC genome browser (Kent W J, 2002).

FIGS. 37A-37G illustrate that miR-135 is upregulated in adult mouse RN following antidepressant treatment. (FIG. 37A) Alignment between mature miR-135a and miR-135b indicating one nucleotide difference; (FIG. 37B) Expression levels of miR-135a and miR-135b in the mouse RN; (FIG. 37C) Expression profile of several miRs in adult mouse RN indicating miR-135a is approximately 5 times less abundant than miR-124, and 2.5 fold less than miR-16. Bars represent means±s.e.m; (FIG. 37D) Mice exposed to social defeat demonstrated increased social avoidance unless treated with chronic imipramine. Interaction ratio is calculated as time spent in the zone near the non-familiar mouse divided by the time spent in the same zone during habitation multiplied by 100. Bars represent means±s.e.m. *P<0.05; (FIGS. 37E and 37F) miR-135a levels were upregulated in the RN following chronic (FIG. 37E) or acute (FIG. 37F) imipramine administration and were unchanged following exposure to chronic social defeat protocol. Bars represent means±s.e.m. P<0.01; (FIG. 37G) SSRI and not NRI or saline, following either acute or chronically administration, caused a significant increase in miR-135a levels in the RN. Bars represent means±s.e.m. *P<0.001.

Figures 38A, 38B, 38C, 38D:
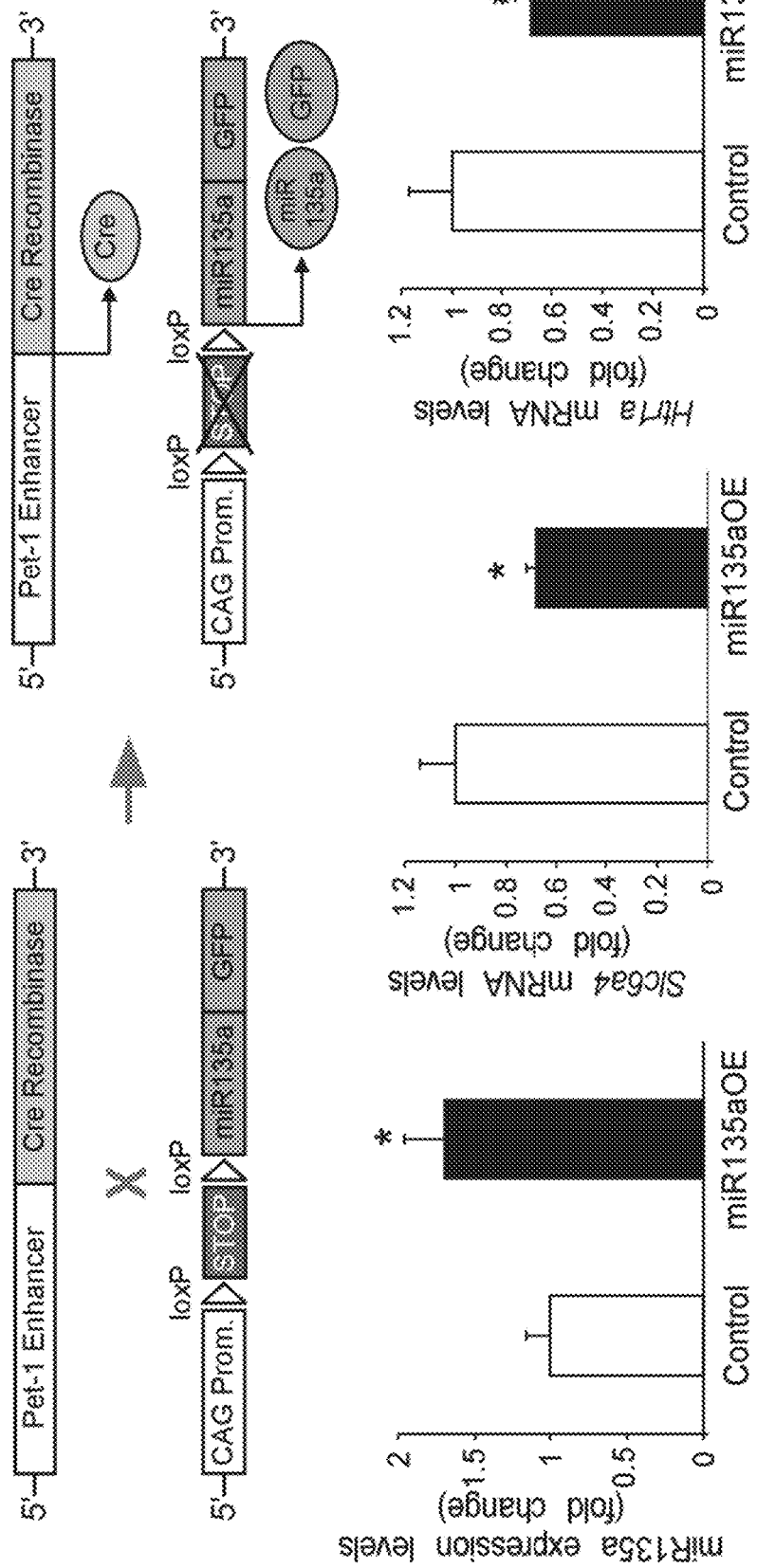

FIGS. 38A-38M illustrate that overexpression of miR-135 specifically in 5HT neurons cause behavioral resiliency to social defeat. (FIG. 38A) Schematic illustration of miR-135 conditional overexpression mouse model. Transgenic mice with floxed transcriptional STOP sequence upstream to miR-135a and GFP sequences were crossed with the ePet-Cre recombinase mice. Double transgenic mice overexpress miR-135a specifically in 5HT-positive cells. Littermate mice carrying only the transgene for miR-135a and not the ePet-Cre transgene served as controls; (FIG. 38B) miR-135a expression levels in the RN were upregulated by approximately 2 fold in miR-135 overexpressing (OE) mice compared to controls; (FIGS. 38C and 38D) miR-135 target genes, Slc6a4 (FIG. 38C) and Htr1a (FIG. 38D) mRNA were downregulated in miR-135OE mice compared to control littermates. Bars represent means±s.e.m. #P<0.1; *P<0.05; (FIGS. 38E-38G) In the dark-light transfer test miR-135OE mice and their control littermates were tested either under 'basal' stress conditions or following chronic social defeat. No differences were observed between the genotypes under 'basal' conditions, however, following chronic social defeat miR-135OE mice spent more time in light (FIG. 38E), visited the lit compartment more frequently (FIG. 38F) and traveled a longer distance in light (FIG. 38G); The behavioral performance of the miR-135OE mice did not significantly differ following the social defeat protocol. In contrast, control mice demonstrated significant increase in anxiety like-behaviors in all measured parameters of the dark-light test following social defeat. Bars represent means±s.e.m. *P<0.05, *P<0.001; (FIGS. 38H-38J) In the elevated plus-maze test, control mice that were exposed to social defeat spent less time (FIG. 38H), had a smaller number of visits (FIG. 38I) and traveled less distance (FIG. 38J) in the open arms, compared to control mice tested under 'basal' conditions. No significant differences between 'basal' and stress conditions were observed in the miR-135OE group. Bars represent means±s.e.m. P<0.01, *P<0.001; (FIGS. 38K and 38L) In the forced swim test no significant differences were observed between the groups when tested under 'basal' stress conditions (FIG. 38K), however, when tested following chronic social defeat miR-135OE mice demonstrated decreased immobility compared to control littermates (FIG. 38L). Line graphs represent means±s.e.m. *p<0.001; (FIG. 38M) No differences in locomotion activity were observed between the miR-135OE and control littermates as measured by total distance traveled in the open-field test. Bars represent means±s.e.m.

Figure 39A:
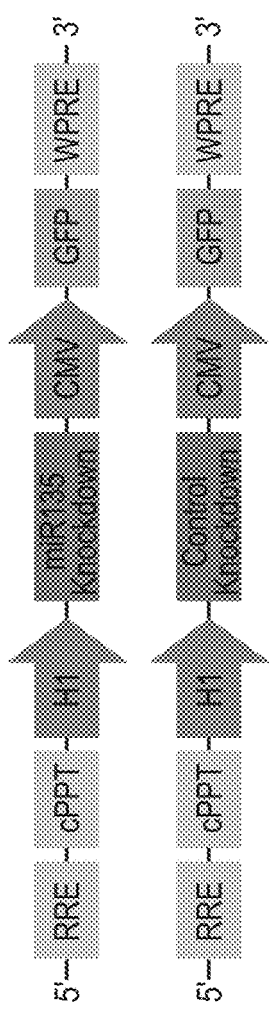
Figure 39B:
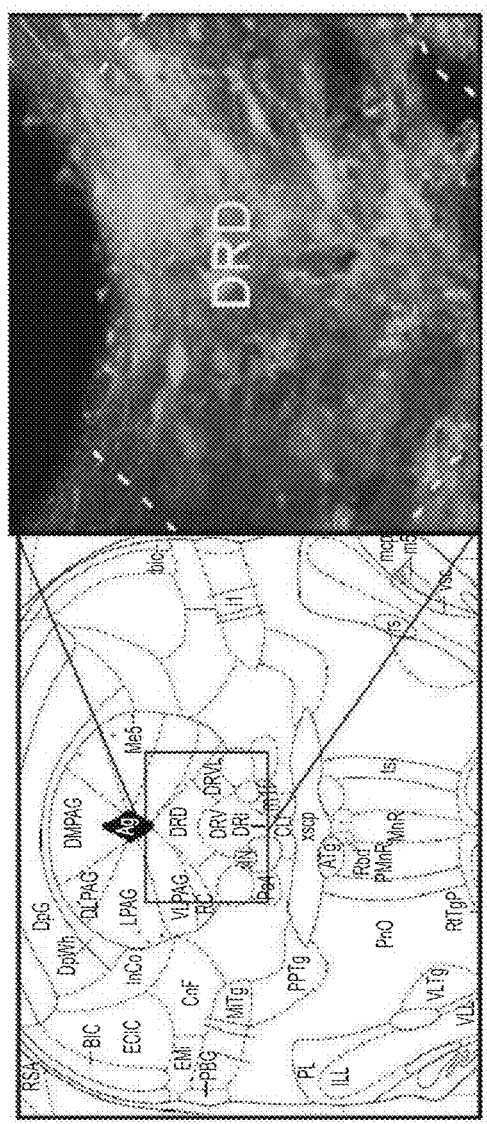

FIGS. 39A-39N illustrate that knockdown of miR-135 in the RN of adult mice caused increased anxiety-like behavior and attenuated response to antidepressants. (FIG. 39A) Schematic illustration of "miR-135 capture" structure; (FIG. 39B) Schematic illustration of miR-135 KD and control viral vectors; (FIG. 39C) miR-135 KD lentiviruses infection increased Htr1a and Slc6a4 mRNA expression levels in RN46a cells that endogenously express these genes and miR-135; (FIG. 39D) Brain section map showing the site of injection, adapted from the Paxinos and Franklin mouse brain atlas (Paxinos, 1997) (left panel) and GFP immunostaining in DRD of adult mice infected with miR-135KD lentiviruses; (FIGS. 39E-39H) In the dark light transfer test, miR-135KD mice spent less time (FIG. 39E) had fewer visits (FIG. 39F) and traveled less distance (FIGS. 39G and 39H) in the light compartment, compared to control KD injected mice. Bars represent means±s.e.m. *P<0.05; (FIGS. 39I-39L) In the elevated plus-maze test miR-135KD mice demonstrated tendency to spend less time (FIG. 39I) had fewer visits (FIG. 39J) and travel significantly less distance (FIGS. 39K and 39L) in the open arms. Bars represent means±s.e.m. #P<0.1, *P<0.05; (FIG. 39M) In the forced swim test, miR-135KD mice did not differ in their immobility time from control mice when tested under 'basal' conditions, however when tested 30 minutes following SSRI administration, miR-135KD mice demonstrated increased immobility time, indicating attenuated response to antidepressants. Bars represent means±s.e.m. *p<0.05;

***p<0.001; (FIG. 39N) No significant differences in locomotor activity between miR-135KD and control mice were observed as measured by total distance traveled in the open-field test. Bars represent means±s.e.m.

Figure 40A:
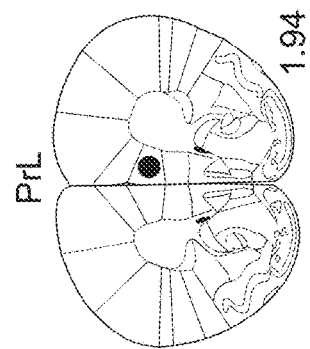
Figure 40B:
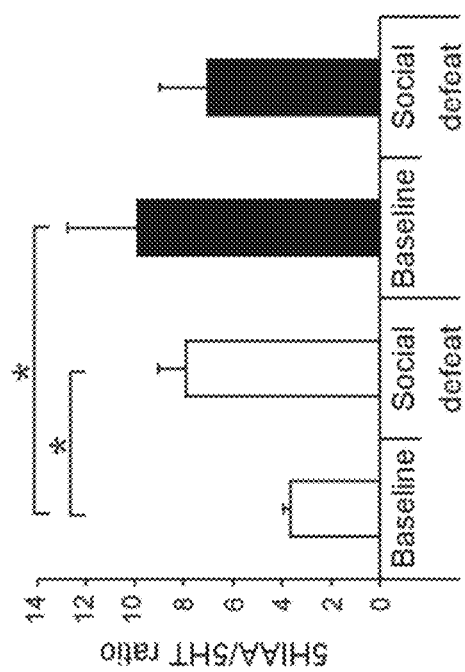
Figure 40C:
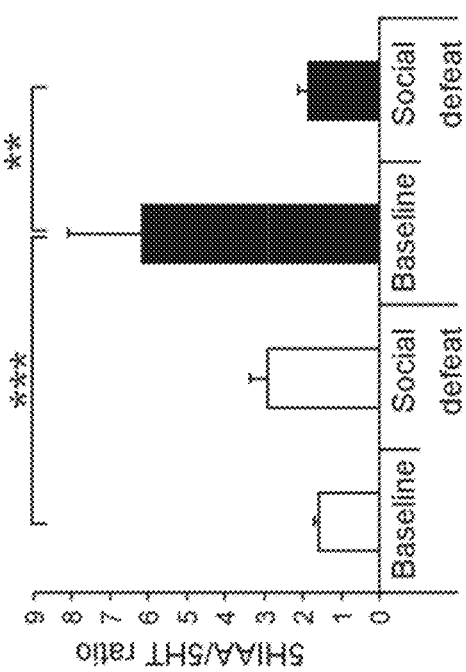
Figure 40D:
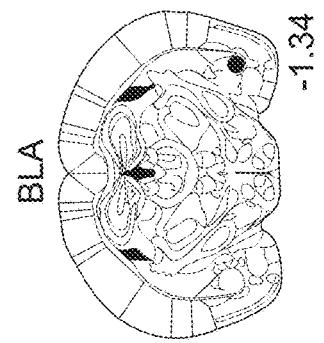
Figure 40E:
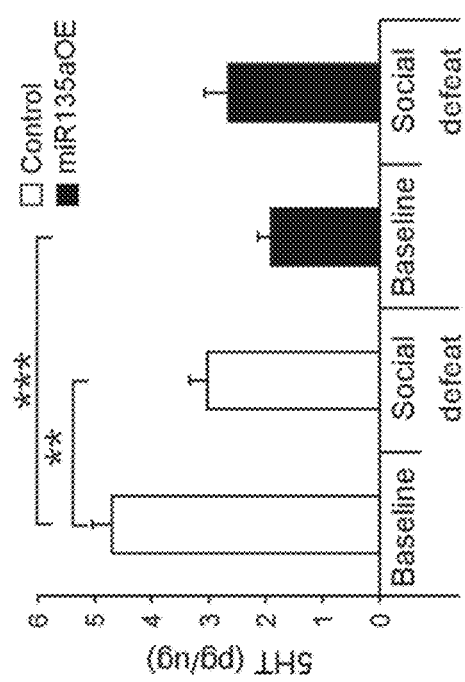
Figure 40F:
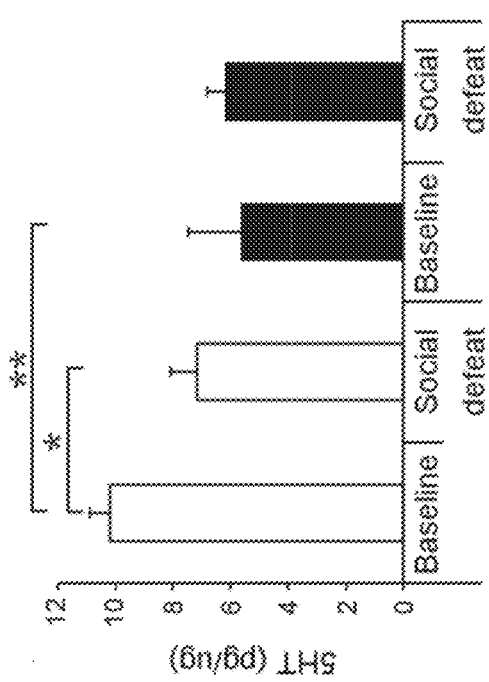
Figure 40O:
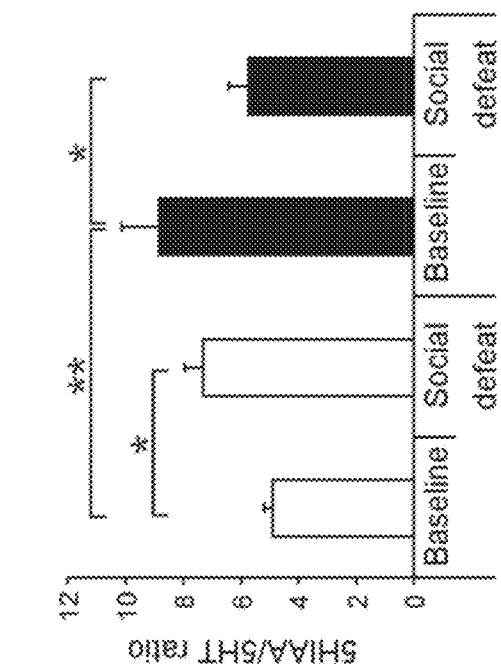
Figure 40N:
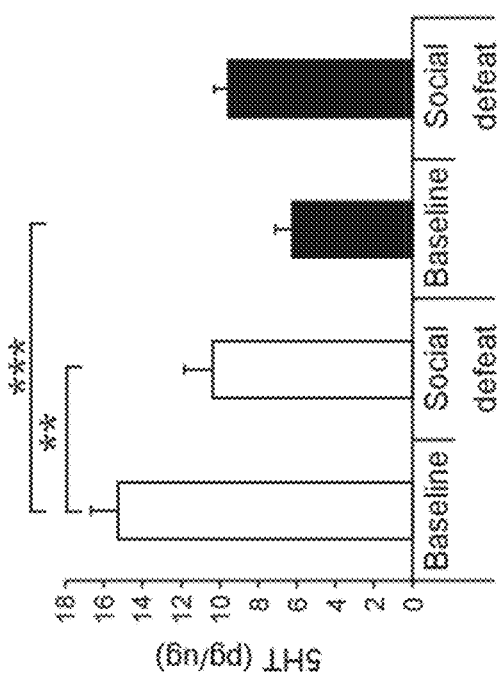
Figure 40M:
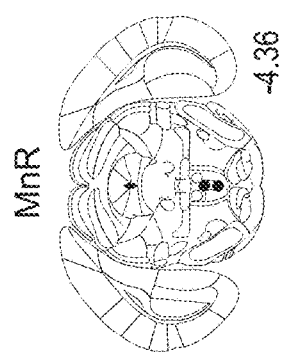

FIGS. 40A-40O illustrate that overexpression of miR-135 in 5HT neurons alters 5HT levels across the brain and blocks social defeat induced 5HT reduction. (FIGS. 40A, 40D, 40G, 40J, 40M) Schematic illustration of microdissection sites from miR-135OE 5HT and control mouse brains under basal conditions or following chronic social defeat. PrL—prelimbic cortex, BLA—basolateral amygdala, CA1V—hippocampus CA1 ventral, DRV—dorsal raphe nucleus, ventral part, MnR—median raphe nucleus. Section map adopted from (Paxinos, 1997); (FIGS. 40B, 40E, 40H, 40K, 40N) 5HT levels as measured by HPLC in different brain sites revealed decreased 5HT levels in miR-135OE mice compared to controls in basal stress conditions. Additionally, 5HT levels were downregulated in control mice exposed to social defeat compared to basal stress conditions, an effect not observed in miR-135OE 5HT mice; (FIGS. 40C, 40F, 40I, 40L, 40O) 5HT metabolism calculated as the ratio between the levels of the metabolite 5HIAA to 5HT levels was upregulated in miR-135OE 5HT mice compared to controls in basal stress conditions. Furthermore, 5HT metabolism was reduced in the BLA, CA1V, DRV and MnR in miR-135OE 5HT exposed to chronic social defeat compared to control mice from the same genotype. In the PrL, DRV and MnR 5HT metabolism was upregulated in control mice exposed to social defeat compared to basal conditions. Bars represent means ±s.e.m. *P<0.05, P<0.01, *P<0.001.

FIGS. 41A-41E illustrates lower levels of miR-135 in the blood of human depressed patients. (FIG. 41A) miR-135a levels in total blood of depressed human patients are robustly reduced compared to those of healthy controls; (FIG. 41B) miR-16 blood levels do not differ significantly between the groups. Bars represent means±s.e.m. ***P<0.001; (FIG. 41C) Depressed patients treated for 3 months with cognitive behavioral therapy (CBT) showed a significant increase in total blood miR-135a levels; (FIG. 41D) miR-16 levels were similar in all groups of patients. Bars represent means ±s.e.m. *P<0.05; (FIG. 41E) Schematic representation of a suggested model describing the involvement of miR-135 in regulating serotonergic synapse components under normal condition (upper panel), depression (middle panel) and antidepressant administration (lower panel).

FIGS. 42A-42L illustrate 5HT levels in RN structures of miR-135OE mice under 'basal' conditions and following chronic stress conditions. (FIGS. 42A, 42D, 42G, 42J) Schematic illustration of RN microdissection sites from miR-135OE 5HT and control mouse brains under basal conditions or following chronic social defeat. DRD—dorsal raphe nucleus, dorsal part, DRI—dorsal raphe nucleus, interfascicular part, DRVL—dorsal raphe nucleus, ventrolateral part, VLPAG—ventrolateral periaqueductal gray; DRC—dorsal raphe nucleus, caudal part. Section map adopted from (Paxinos G., 1997); (FIGS. 42B, 42E, 42H, 42K) 5HT levels in all the brain areas illustrated apart from the DRVL were decreased in miR-135OE-5HT mice compared to controls in basal stress conditions. Additionally, 5HT levels were decreased in control mice exposed to social defeat compared to basal conditions, an effect missing in the miR-135OE 5HT mice; (FIGS. 42C, 42F, 42I, 42L) 5HT metabolism calculated as the ratio between the levels of the metabolite 5HIAA to 5HT levels, was increased in miR-135OE 5HT mice compared to controls in basal stress conditions. Furthermore, 5HT metabolism was reduced in all the areas described in miR-135OE 5HT exposed to chronic social defeat compared to mice from the same genotype tested under basal conditions. Bars represent means±s.e.m. *P<0.05, P<0.01, *P<0.001.

FIGS. 43A-43L illustrate 5HT levels in brain structures of miR-135OE mice under 'basal' conditions and following chronic stress conditions. (FIGS. 43A, 43D, 43G, 43J) Schematic illustration of microdissection sites from miR-135OE 5HT and control mouse brains under basal conditions or following chronic social defeat. IL—infralimbic cortex, BNST—bed nucleus of stria terminalis, CeA—central amygdala, S—subiculum. Section map adopted from (Paxinos G., 1997); (FIGS. 43B, 43E, 43H, 43K) 5HT levels in all the brain areas illustrated were decreased in miR-135OE-5HT mice compared to controls in basal stress conditions. Additionally, 5HT levels were decreased in control mice exposed to social defeat compared to basal conditions, an effect missing in the miR-135OE 5HT mice; (FIGS. 43C, 43F, 43I, 43L) 5HT metabolism calculated as the ratio between the levels of the metabolite 5HIAA to 5HT levels was increased in miR-135OE 5HT mice compared to controls in basal stress conditions. Furthermore, 5HT metabolism was reduced in all the areas described in miR-135OE 5HT exposed to chronic social defeat compared to mice from the same genotype tested under basal conditions. Bars represent means±s.e.m. *P<0.05, P<0.01, *P<0.001.

FIG. 44 illustrates modifications to miR-135 oligonucleotides. 5'Ph illustrates a 5' phosphylation while bold underline illustrates a 2' O-methylation.

DESCRIPTION OF SPECIFIC EMBODIMENTS OF THE INVENTION

The present invention, in some embodiments thereof, relates to microRNAs and, more particularly, but not exclusively, to the use of same for disease, diagnosis, monitoring and treatment.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The link between dysregulated serotonergic activity and psychiatric disorders such as anxiety and depression has been previously established, yet the molecular mechanisms underlying these pathologies are not fully understood. MicroRNAs (miRs) are a subset of small RNA molecules that regulate gene expression post-transcriptionally and are abundant in the brain.

While reducing the present invention to practice, the present inventors have uncovered that specific microRNAs (miRs) are involved in regulation of serotonin (5HT) neuroglia related genes and are thus involved in modulating medical conditions associated with aberrant serotonin levels such as psychiatric disorders.

Figure 2E:
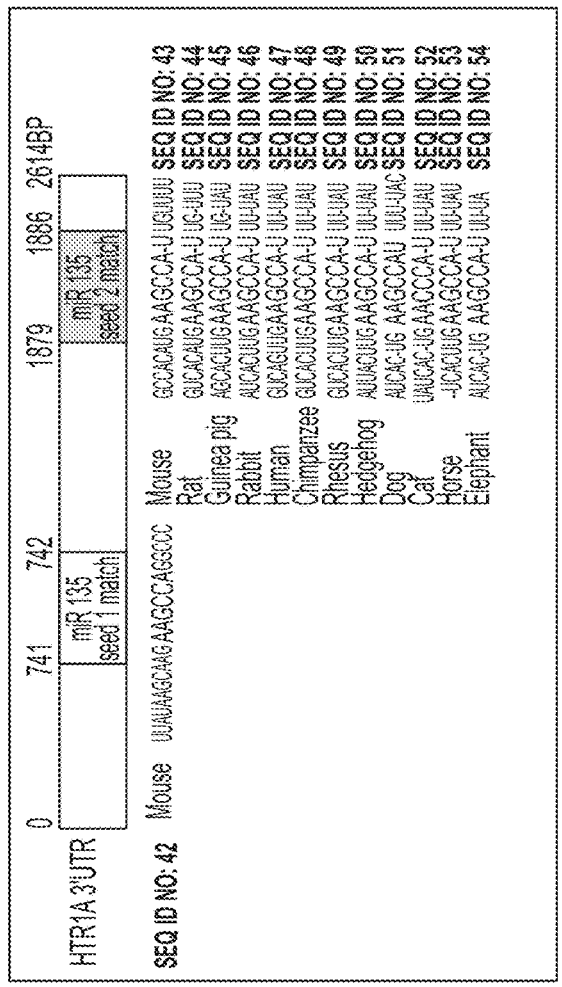
Figure 3A:
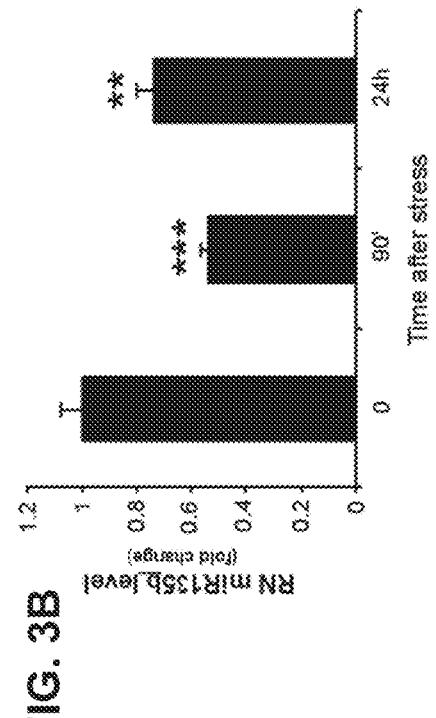
Figure 3B:
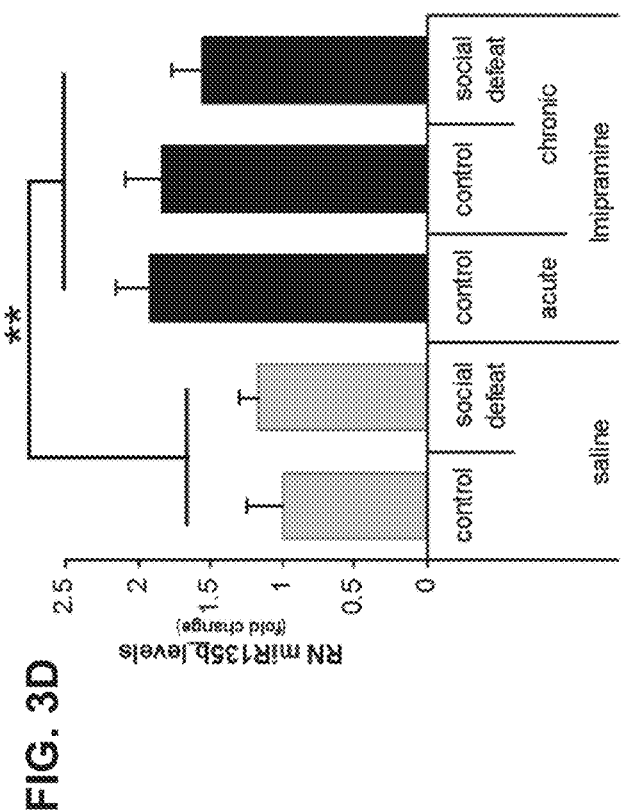
Figure 3C:
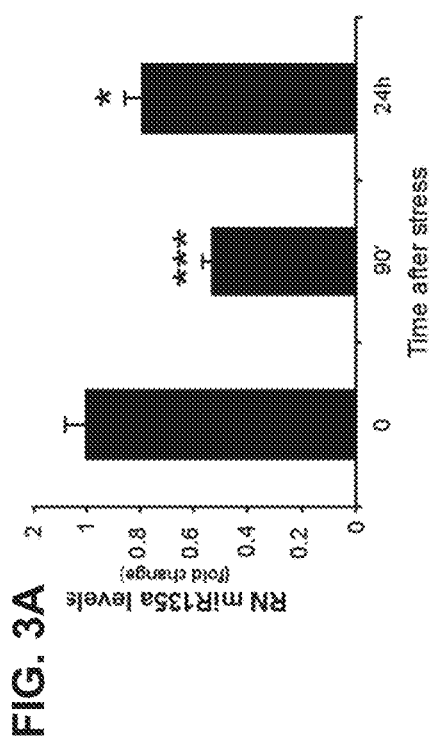
Figure 3D:
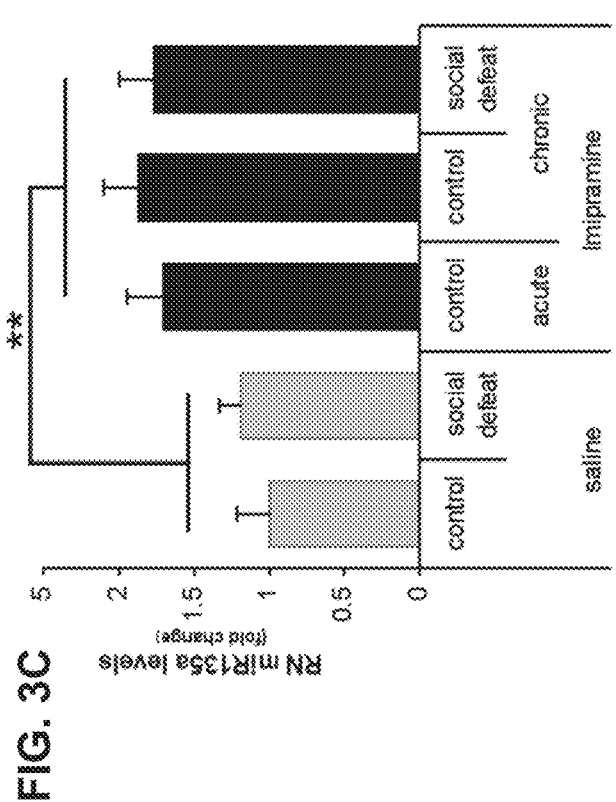
Figure 3F:
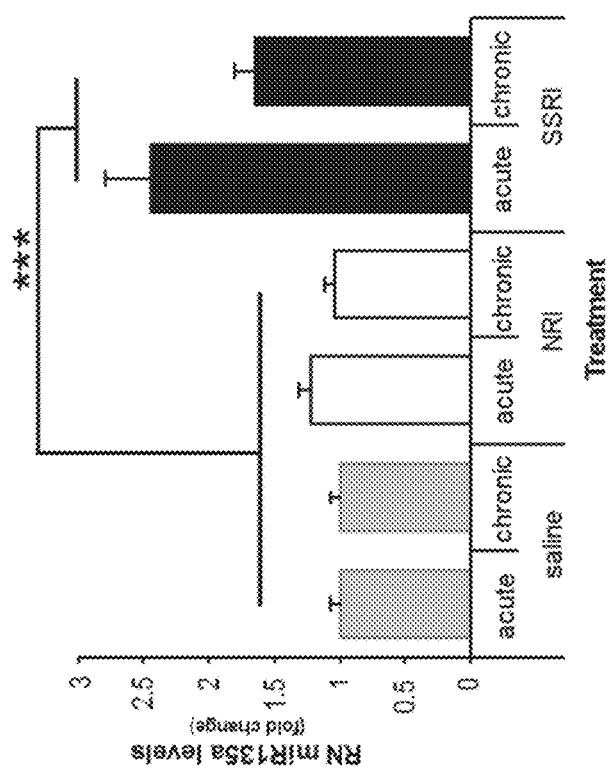
Figure 3E:
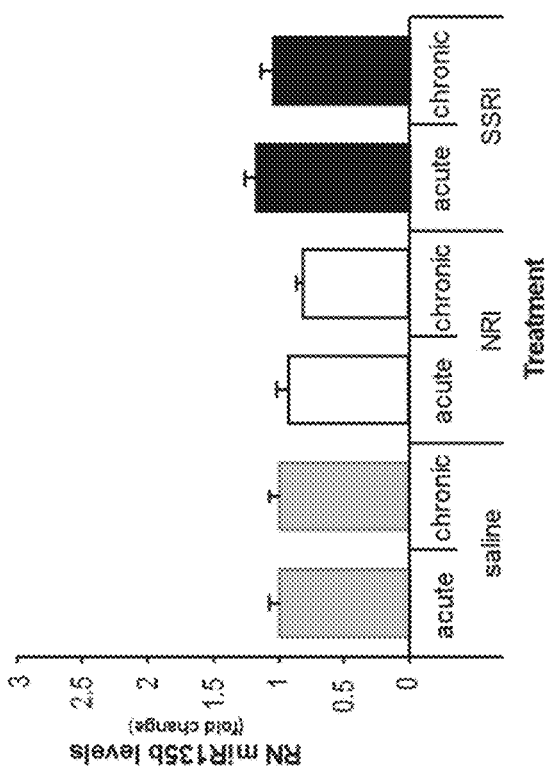
Figure 9:
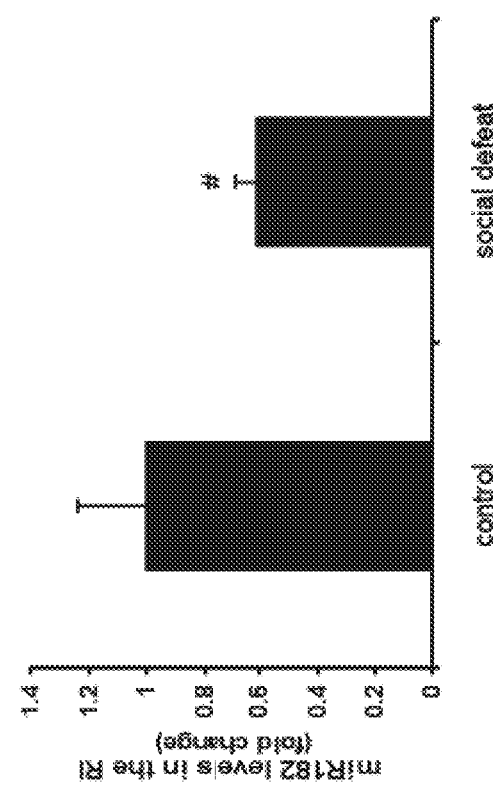
FIG. 9 is a graph illustrating real time PCR results of miR-182 expression levels in adult mice DRN indicating a trend for decreased expression following chronic social defeat. Data represents mean±SEM n=7 controls and 18 mice in social defeat group, #=p=0.1.

As is illustrated hereinbelow and in the Examples section which follows, the present inventors determined the miRs expression pattern in 5HT neurons, obtained from the raphe nucleus (RN) of 5HT reporter mice (ePET-YFP), using miRs microarray (see Tables 2A-B in the Examples section which follows). The unique miRs expression profile of serotonergic neurons obtained from the array was bioinformatically analyzed to identify miRs that putatively target key serotonergic related genes, such as serotonin transporter (Slc6a4, FIG. 1D), serotonin auto receptor (Htr1a, FIG. 1E), tryptophan hydroxylase 2 (Tph2, FIG. 1F) and monoamine hydroxylase (MaoA, FIG. 1G). miRNA targeting of the 3'UTRs for these genes were further tested in vitro illustrating specific miRs (e.g. miR-135) that specifically target and regulate the 5HT neuronal genes (see FIGS. 1H-1I and FIGS. 2C-2D). The present inventors have further illustrated that miR-135 expression levels are altered in the RN following acute stress (FIGS. 3A-3D) and following treatment with antidepressants (FIGS. 3E-3F). In vivo miR-135 over-expression in the RN of adult mice reduced depression-like behaviors following social defeat (FIGS. 4A-4H). Moreover, the present inventors have illustrated the activity of miR-182 as a regulator of neuronal activity (via direct repression of Htr1a, FIG. 8) and of psychopathological behavior (FIG. 9) and of miR-15 as regulator of stress response [via direct repression of CRH1R (FIGS. 7A-7B), FK506 binding protein 5 (FKBP5) (FIGS. 21A-21B) and Stx1a, Sgk1 and Adrb2 (FIG. 22)]. The present inventors have also illustrated the specific targeting of beta adrenergic receptor (Adrb1) and cannabinoid receptor 1 (CB1) by miR-19. miR-19 over-expression repressed Adrb1 (FIGS. 6A-6C) while knock-down of miR-19 enhanced Adrb1 expression (FIGS. 6D-6E). miR-19 over-expression also repressed CB1 (FIG. 14). The present inventors have also uncovered targets for miR-181. Specifically, the present inventors have illustrated that miR-181 specifically regulates glutamate receptors (FIGS. 24 and 25). Taken together, these results substantiate the use of miRNAs or sequences regulating same, such as miR-135, miR-335, miR-181, miR-182, miR-26, miR-27, miR-15 and miR-19, as therapeutic modalities.

While further reducing the present invention to practice, the present inventor has uncovered that miR135 can be used as a potent therapeutic agent for the treatment of bipolar disorder, which affects as much as 4% of people.

While further reducing the present invention to practice, the present inventors have uncovered that miR-135 is significantly down-regulated in the blood of human depressed patients (as compared to healthy controls) and is upregulated following improvement in the patients' psychiatric score. In fact, miR-135 was found to be an essential regulatory element responsible for maintaining intact serotonergic tone under normal conditions, and essential for the brain response to antidepressants (see schematic model in FIG. 41E).

Increased levels of miR-135 were found to repress both Slc6a4 and presynaptic Htr1a levels, causing an increase in 5HT in the synaptic cleft, which is associated with decreases in depressive symptoms. Further bioinformatic analysis conducted by the present inventors, predicted new targets for miR135 which are associated with neuropsychiatric disorders including bipolar affective disorder or lithium action. These targets may thus be used as targets for therapeutic intervention in neuropsychiatric disorders.

The present assay further provides a non-invasive test for both screening patients for psychiatric conditions and monitoring treatment. Together, these results place miR-135 as a pivotal tool for the diagnosis and management of psychiatric conditions such as mood disorders in which continuous monitoring of patients psychological balance is critical.

Thus, according to one aspect of the present invention there is provided a method of treating a medical condition in which an elevation of serotonin level is therapeutically beneficial in a subject in need thereof, the method comprising administering to or expressing in a cell of the subject an exogenous polynucleotide encoding at least one microRNA or a precursor thereof.

According to a specific embodiment, for treating a medical condition in which an elevation of serotonin level is therapeutically beneficial, the microRNA comprises miR-135, miR-335, miR-26 and miR-182.

According to one aspect of the present invention there is provided a method of treating a bipolar disorder in a subject in need thereof, the method comprising administering to the subject therapeutically effective amount of a miR-135, a precursor thereof or a nucleic acid molecule encoding the miR-135 or the precursor thereof, thereby treating the bipolar disorder.

According to another aspect of the present invention there is provided a method of treating a medical condition in which a low adrenaline or noradrenaline level is therapeutically beneficial in a subject in need thereof, the method comprising administering to or expressing in a cell of the subject an exogenous polynucleotide encoding a microRNA or a precursor thereof.

According to a specific embodiment, for treating a medical condition in which a low adrenaline or noradrenaline level is therapeutically beneficial, the microRNA comprises miR-19.

According to another aspect of the present invention there is provided a method of treating a medical condition in which a low corticotropin-releasing hormone (CRH) level is therapeutically beneficial in a subject in need thereof, the method comprising administering to or expressing in a cell of the subject an exogenous polynucleotide encoding a microRNA or a precursor thereof.

According to a specific embodiment, for treating a medical condition in which a low corticotropin-releasing hormone (CRH) level is therapeutically beneficial, the microRNA comprises miR-15.

According to another aspect of the present invention there is provided a method of treating a medical condition in which a low glutamate receptor level is therapeutically beneficial in a subject in need thereof, the method comprising administering to or expressing in a cell of the subject an exogenous polynucleotide encoding a microRNA or a precursor thereof.

According to a specific embodiment, for treating a medical condition in which a low glutamate receptor level is therapeutically beneficial, the microRNA comprises miR-181.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" or "subject in need thereof" includes mammals, such as human beings, male or female, at any age which suffers from the pathology or are at risk to develop the pathology.

As used herein the phrase "medical condition in which an elevation of serotonin level is therapeutically beneficial" refers to a disease or disorder in which increasing the level of serotonin can prevent an occurrence of a disease or medical symptoms associated therewith or halt disease progression or medical symptoms associated therewith (as further detailed hereinbelow).

As used herein, the term "serotonin" refers to the monoamine neurotransmitter [also referred to as 5-hydroxytryptamine (5-HT)]. Serotonin is set forth e.g. in CAS number 50-67-9.

According to one embodiment, there is provided a method of increasing a serotonin level in a synaptic cleft, the method comprising administering to or expressing in a neuroglia cell e.g., serotonergic neuron of the subject an exogenous polynucleotide encoding at least one microRNA or a precursor thereof.

As used herein, the term "synaptic cleft" refers to the area between two neurons through which electrical or chemical signals pass.

A "neuroglia cell" refers to a neuron or a glial cell (e.g., oligodendrocytes or astrocyte).

As used herein, the term "serotonergic neuron" refers to a neuron which secretes serotonin or is capable of serotonin reuptake (i.e. by serotonin transporters expressed on their cell surfaces).

The medical condition in which an elevation of serotonin level is therapeutically beneficial may comprise, for example, any mood disorder including depression, major depression, anxiety, stress, fatigue, impaired cognitive function, panic attack, compulsive behavior, addiction, social phobia, schizophrenia, sleep disorder, food related disorder (e.g. eating disorder), growth disorder and reproduction disorder. According to a specific embodiment, the medical condition in which an elevation of serotonin level is therapeutically beneficial comprises depression.

According to a specific embodiment, the medical condition in which an elevation of serotonin level is therapeutically beneficial comprises a bipolar disorder.

As used herein the term "bipolar disorder", also known as bipolar affective disorder, manic-depressive disorder, or manic depression, refers to the mental illness classified as a mood disorder. Typically, individuals with bipolar disorder experience one or more episodes of an abnormally elevated state, clinically referred to as mania. Mania may occur with different levels of severity. At milder levels of mania, or "hypomania", individuals may appear energetic, excitable, and may be highly productive. As mania becomes more severe, individuals begin to behave erratically and impulsively, often making poor decisions due to unrealistic ideas about the future, and may have great difficulty with sleep. At the most severe level, individuals may experience psychosis. The manic episodes typically alternate with episodes or symptoms of depression, or mixed episodes which present features of both mania and depression. Such episodes are normally separated by periods of normal state. Manic and depressive episodes may last from a few days to several months, but in some patients depression and mania may rapidly alternate, referred to as rapid cycling.

Bipolar disorder according to some embodiments of the present invention encompasses any type of bipolar disorder and any form and/or subform of bipolar disorder, including but not limited to, mania, acute mania, severe mania, hypomania, depression, moderate depression, dysthymia, severe depression, episodes of mania and/or depression, psychosis/psychotic symptoms (e.g. hallucinations, delusions), mixed bipolar state, bipolar I disorder, bipolar II disorder, rapid-cycling bipolar disorder, Cyclothymia and/or Bipolar Disorder Not Otherwise Specified (BD-NOS).

According to one embodiment, treating a bipolar disorder may be effected by administering to the subject a therapeutically effective amount of a miR-135, a precursor thereof or a nucleic acid molecule encoding the miR-135 or the precursor thereof.

According to one embodiment, treating a bipolar disorder may be further effected by administering to the subject a medicament for the treatment of a bipolar disorder.

Exemplary medicaments for the treatment of a bipolar disorder which may be used in accordance with the present teachings include, but are not limited to, lithium, antipsychotic medicaments and mood stabilizer medicaments as described in further detail below.

According to one embodiment, there is provided a use of a therapeutically effective amount of a miR-135, a precursor thereof or a nucleic acid molecule encoding the miR-135 or the precursor thereof for the manufacture of a medicament identified for treating a bipolar disease in a subject in need thereof.

Thus, according to one embodiment, when the medical condition is a mood disorder, e.g. bipolar disease, depression or anxiety, the microRNA is miR-135.

It will be appreciated that the mood disorder, e.g. bipolar disease, depression or anxiety, may not necessarily be related to serotonin.

According to one embodiment, there is provided a method of treating a medical condition in which an elevation of serotonin level is therapeutically beneficial in a subject in need thereof, the method comprising administering to the subject an agent capable of downregulating an activity or expression of a miR-135 target gene selected from the group consisting of adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (*Drosophila*) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GAB A-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt11); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3); and zinc finger, BED domain containing 4 (Zbed4).

According to a specific embodiment, the agent is not miR-135.

Agents which can be used in accordance with the present teachings (e.g., capable of downregulating an activity or expression of a miR-135 target gene) are described in detail below.

As used herein the phrase "medical condition in which a low adrenaline or noradrenaline level is therapeutically beneficial" refers to a disease or disorder in which decreasing the expression or activity of adrenaline or noradrenaline can prevent an occurrence of a disease or medical symptoms associated therewith or halt disease progression or medical symptoms associated therewith (as further detailed hereinbelow).

As used herein, the term "adrenaline" refers to the hormone and neurotransmitter (also known as epinephrine). Adrenaline is set forth e.g. in CAS number 51-43-4.

As used herein, the term "noradrenaline" refers to the catecholamine acting as a hormone and neurotransmitter (also known as norepinephrine). Noradrenaline is set forth e.g. in CAS numbers (1) 51-41-2 (1) and 138-65-8(d1).

The medical condition in which a low adrenaline or noradrenaline level is therapeutically beneficial may comprise, for example, stress-related disorder, anxiety, memory impairment, heart conditions (e.g. palpitations, tachycardia and arrhythmia), headaches, tremors, hypertension, and acute pulmonary edema.

As used herein the phrase "medical condition in which a low corticotropin-releasing hormone (CRH) level is therapeutically beneficial" refers to a disease or disorder in which decreasing the expression or activity of CRH can prevent an occurrence of a disease or medical symptoms associated therewith or halt disease progression or medical symptoms associated therewith (as further detailed hereinbelow).

As used herein, the term "corticotropin-releasing hormone (CRH)" refers to the polypeptide hormone and neurotransmitter (also known as corticotropin-releasing factor (CRF) or corticoliberin). CRH is set forth e.g. in NP_000747.1.

The medical condition in which a low CRH level is therapeutically beneficial may comprise, for example, stress, depression, anxiety, stress, fatigue, impaired cognitive function, panic attack, compulsive behavior, addiction, social phobia, sleep disorder, food related disorder, growth disorder, reproduction disorder and obesity.

As used herein the phrase "medical condition in which a low glutamate receptor level is therapeutically beneficial" refers to a disease or disorder in which decreasing the expression or activity of a glutamate receptor can prevent an occurrence of a disease or medical symptoms associated therewith or halt disease progression or medical symptoms associated therewith (as further detailed hereinbelow).

As used herein, the term "glutamate receptor" refers to a synaptic receptor typically located on the membranes of neuronal cells (e.g. Grm1, Grik3, Grm5, Gria2, Grik2 and Grm7). Glutamate receptor is set forth e.g. in NP_000822.2 [glutamate receptor ionotropic kainate 3 (Grik3)]; NP_000817.2, NP_001077088.1, NP_001077089.1 [glutamate receptor ionotropic AMPA 2 (Gria2)]; NP_001159719.1, NP_068775.1, NP_786944.1 [glutamate receptor ionotropic kainate 2 (Grik2)]; NP_000833.1, NP_001137303.1 [glutamate receptor metabotropic 5 (Grm5)]; NP_000835.1, NP_870989.1 [glutamate receptor metabotropic 7 (Grm7)]; NP_000829.2, NP_001107801.1 [glutamate receptor metabotropic 1 (Grm1)].

The medical condition in which a low glutamate receptor level is therapeutically beneficial may comprise, for example, seizures (e.g. epilepsy), Huntington's disease, Schizophrenia, Fragile X syndrome, generalized anxiety disorder and cancer (e.g. melanoma).

As used herein, the term "microRNA or a precursor thereof" refers to the microRNA (miRNA) molecules acting as post-transcriptional regulators. MicroRNAs are typically processed from pre-miR (pre-microRNA precursors). Pre-miRs are a set of precursor miRNA molecules transcribed by RNA polymerase III that are efficiently processed into functional miRNAs, e.g., upon transfection into cultured cells. A Pre-miR can be used to elicit specific miRNA activity in cell types that do not normally express this miRNA, thus addressing the function of its target by down regulating its expression in a "gain of (miRNA) function" experiment. Pre-miR designs exist to all of the known miRNAs listed in the miRNA Registry and can be readily designed for any research. The microRNAs may be administered to the cell per se or encoded from a precursor molecule ligated into a nucleic acid construct, as further described hereinbelow. According to one embodiment, this term encompasses any type of micoRNA including 5 prime (i.e. miR) or 3 prime (i.e. miR*) and their precursors.

As used herein, the term "miR-135 or a precursor thereof" is meant to encompass any type of miR-135 including miR-135a and miR-135b 5 prime (i.e. miR-135) or 3 prime (i.e. miR-135*) and their precursors. Exemplary precursor miR-135 include, but are not limited to, miR-135a-1 as set forth in Accession No. MI0000452, ENTREZGENE 406925 and SEQ ID NO: 58; miR-135a-2 as set forth in Accession No. MI0000453, ENTREZGENE: 406926 and SEQ ID NO: 59; and miR-135b as set forth in Accession No. MI0000810, ENTREZGENE: 442891 and SEQ ID NO: 60. Exemplary mature miR-135 include, but are not limited to, miR-135a as set forth in Accession No. MIMAT0000428 (SEQ ID NO: 61) and miR-135b as set forth in Accession No. MIMAT0000758 (SEQ ID NO: 62). Exemplary mature miR-135* include, but are not limited to, miR-135a* as set forth in Accession No. MIMAT0004595 (SEQ ID NO: 192) and miR-135b* as set forth in Accession No. MIMAT0004698 (SEQ ID NO: 193).

It will be appreciated that the microRNAs of the present teachings (e.g. miR-135) may bind, attach, regulate, process, interfere, augment, stabilize and/or destabilize any microRNA target. Such a target can be any molecule, including, but not limited to, DNA molecules, RNA molecules and polypeptides, such as but not limited to, serotonin related genes, such as the serotonin transporter (i.e. SERT or Slc6a4), the serotonin inhibitory receptor 1a (Htr1a), tryptophan hydroxylase 2 (Tph2) and monoamine hydroxylase (MaoA); adrenaline or noradrenaline receptors (adrenergic receptors such as Add); Adenylate cyclase type 1 (ADCY1); CRH receptors such as Crh1R; or any other molecules e.g. FK506 binding protein 5 (FKBP5), cannabinoid receptor 1 (CB1), Down Syndrome Cell Adhesion Molecule (Dscam), Translin-associated protein X (Tsnax) and Cell adhesion molecule L1 (L1cam); as well as other targets associated with stress-related neuropsychiatric disorders (e.g. bipolar disorder) including those listed in Table 1, below.

TABLE 1

Putative targets of miR-135 associated with stress-related neuropsychiatric disorders

| Human ortholog | Gene name |
|---|---|
| Adcyap1 | adenylate cyclase activating polypeptide 1 (also PACAP) |
| Adcyap1r1 | adenylate cyclase activating polypeptide 1 receptor 1 |
| Adra2a | adrenergic receptor, alpha 2a |
| Ank3 | ankyrin 3, epithelial |
| Arc | activity-regulated cytoskeleton-associated protein |
| Arhgap6 | Rho GTPase activating protein 6 |
| Atf3 | activating transcription factor 3 |
| Bace1 | beta-site APP cleaving enzyme 1 |
| Cacna1d | calcium channel, voltage-dependent, L type, alpha 1D subunit |
| Cadm3 | cell adhesion molecule 3 |
| Cplx1 | complexin 1 |
| Cplx2 | complexin 2 |
| Csmd1 | CUB and Sushi multiple domains 1 |
| Csnk1g1 | casein kinase 1, gamma 1 |
| Dcx | doublecortin |
| Diras2 | DIRAS family, GTP-binding RAS-like 2 |
| Dlg2 | discs, large homolog 2 (Drosophila) |
| Elk1 | ELK1, member of ETS oncogene family |
| Frk | fyn-related kinase |
| Fut9 | fucosyltransferase 9 (alpha (1,3) fucosyltransferase) |
| Gabrb2 | gamma-aminobutyric acid (GABA-A) receptor, subunit beta 2 |
| Gata3 | GATA binding protein 3 |
| Ghsr | growth hormone secretagogue receptor |
| Gpr3 | G protein-coupled receptor 3 |
| Gria3 | glutamate receptor, ionotropic, AMPA3 (alpha 3) |
| Grik3 | glutamate receptor, ionotropic, kainate 3 |
| Grk5 | G protein-coupled receptor kinase 5 |
| Gsk3b | glycogen synthase kinase 3 beta |
| Hcn1 | hyperpolarization activated cyclic nucleotide-gated potassium channel 1 |
| Hcn2 | hyperpolarization-activated, cyclic nucleotide-gated K+ 2 |
| Htr1a | 5-hydroxytryptamine (serotonin) receptor 1A |
| Impa1 | inositol (myo)-1(or 4)-monophosphatase 1 |
| Kalrn | kalirin, RhoGEF kinase |
| Kcnn3 | potassium intermediate/small conductance calcium-activated channel, subfamily N, member 3 |
| Kpna3 | karyopherin alpha 3 (importin alpha 4) |
| Myt1l | myelin transcription factor 1-like |
| Ncoa2 | nuclear receptor coactivator 2 |
| Ndrg4 | N-Myc Downstream-Regulated Gene 4 |
| Nos1ap | nitric oxide synthase 1 (neuronal) adaptor protein |
| Nr3c2 | nuclear receptor subfamily 3, group C, member 2 |
| Ntng1 | netrin G1 |
| Nucks1 | nuclear casein kinase and cyclin-dependent kinase substrate 1 |
| Pde1a | phosphodiesterase 1A, calmodulin-dependent |
| Pde4a | phosphodiesterase 4A, cAMP specific |
| Pde8b | phosphodiesterase 8B |
| Plcb1 | phospholipase C, beta 1 |
| Prlr | prolactin receptor |
| Rab1b | RAB1B, member RAS oncogene family |
| Rap2a | Ras-Related Protein Rap-2a |
| Rorb | Retinoid-Related Orphan Receptor Beta |

TABLE 1-continued

Putative targets of miR-135 associated with stress-related neuropsychiatric disorders

| Human ortholog | Gene name |
|---|---|
| Sirt1 | sirtuin 1 (silent mating type information regulation 2, homolog) 1 |
| Slc12a6 | solute carrier family 12, (potassium/chloride transporters) member 6 |
| Slc5a7 | solute carrier family 5 (choline transporter), member 7 |
| Slc6a4 | solute carrier family 6 (neurotransmitter transporter, serotonin), member 4 |
| Sp1 | trans-acting transcription factor 1 |
| Sv2b | synaptic vesicle glycoprotein 2 b |
| Syne1 | Synaptic nuclear envelope 1 (encodes nesprin-1) |
| Syt1 | synaptotagmin I |
| Syt2 | synaptotagmin II |
| Syt3 | synaptotagmin III |
| Tgfbr2 | transforming growth factor, beta receptor II |
| Thrb | thyroid hormone receptor, beta |
| Trpc6 | transient receptor potential cation channel, subfamily C, member 6 |
| Vamp2 | vesicle-associated membrane protein 2 |
| Wnt3 | wingless-related MMTV integration site 3 |
| Zbed4 | zinc finger, BED domain containing 4 |

It will be appreciated that the microRNAs of the present invention can be identified via various databases including for example the micro-RNA registry (www(dot)sanger(dot)ac(dot)uk/Software/Rfam/mirna/index(dot)shtml).

The methods of the present invention may be effected by administering to the subject a microRNA (e.g. miR-135) or an effector thereof or expressing in a cell of the subject an exogenous nucleic acid molecule (i.e. polynucleotide) encoding the microRNA (e.g. miR-135) or the precursor thereof. The term "polynucleotide" refers to a single-stranded or double-stranded oligomer or polymer of ribonucleic acid (RNA), deoxyribonucleic acid (DNA) or mimetics thereof. This term includes polynucleotides and/or oligonucleotides derived from naturally occurring nucleic acids molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions. Such modified or substituted oligonucleotides may be preferred over native forms because of desirable properties such as, for example, enhanced cellular uptake, enhanced affinity for nucleic acid target and increased stability in the presence of nucleases.

The length of the polynucleotide of the present invention is optionally of 100 nucleotides or less, optionally of 90 nucleotides or less, optionally 80 nucleotides or less, optionally 70 nucleotides or less, optionally 60 nucleotides or less, optionally 50 nucleotides or less, optionally 40 nucleotides or less, optionally 30 nucleotides or less, e.g., 29 nucleotides, 28 nucleotides, 27 nucleotides, 26 nucleotides, 25 nucleotides, 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, optionally between 12 and 24 nucleotides, optionally between 5-15, optionally, between 5-25, most preferably, about 20-25 nucleotides.

The polynucleotides (including oligonucleotides) designed according to the teachings of the present invention can be generated according to any oligonucleotide synthesis method known in the art, including both enzymatic syntheses and solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that a polynucleotide comprising an RNA molecule can be produced biologically using an expression vector as is further described hereinbelow. Alternatively, a polynucleotide comprising an RNA molecule can be chemically synthesized using naturally occurring nucleotides or variously modified nucleotides as described below.

According to one embodiment, the polynucleotide of the present invention is a modified polynucleotide. Polynucleotides can be modified using various methods known in the art.

Thus, the polynucleotides of the invention can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Chemical modifications are described in greater detail below.

According to one embodiment, the polynucleotides comprise a single modification. According to another embodiment, the polynucleotides comprise two, three, four, five or more modifications.

For example, the oligonucleotides or polynucleotides of the present invention may comprise heterocyclic nucleosides consisting of purines and the pyrimidines bases, bonded in a 3'-to-5' phosphodiester linkage.

Preferably used oligonucleotides or polynucleotides are those modified either in backbone (e.g. sugar-phosphate backbone), internucleoside linkages, or bases, as is broadly described hereinunder.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050 and 8,017,763; as well as in U.S. Pat. Applic. No. 20100222413, incorporated herein by reference.

According to one embodiment, the polynucleotide comprises a phosphorus-modified internucleotide linkage at the 5' or 3' end of the nucleotide sequence.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'; and boron phosphonate. Various salts, mixed salts, and free acid forms of the above modifications can also be used.

According to one embodiment, the modified polynucleotide comprises a phosphorothioate at the internucleotide linkage at the 5' or 3' end of the nucleotide sequence.

According to one embodiment, the modified polynucleotide comprises a boranophosphate at the internucleotide linkage at the 5' or 3' end of the nucleotide sequence.

According to one embodiment, the modified polynucleotide comprises a methyl phosphonate at the internucleotide linkage at the 5' or 3' end of the nucleotide sequence.

According to one embodiment, the modified polynucleotide comprises a phosphodiester at the internucleotide linkage at the 5' or 3' end of the nucleotide sequence.

According to one embodiment, the polynucleotide comprises a sugar modification (e.g. ribose modification).

According to one embodiment, the polynucleotide comprises a modification corresponding to position 2 of the ribose.

According to one embodiment, the modified polynucleotide comprises at least one 2'-modified nucleotide, e.g., a 2'-deoxy, 2'-fluoro, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-Fluoroarabinooligonucleotides (FANA), or 2'-O—N-methylacetamido (2'-O-NMA).

According to one embodiment, the modified polynucleotide comprises at least one 2'-O-methyl-modified nucleotide, and in some embodiments, all of the nucleotides of the modified polynucleotide include a 2'-O-methyl modification.

According to one embodiment, the modified polynucleotide comprises a modified internucleotide linkage and a sugar backbone modification.

According to one embodiment, the modified polynucleotide comprises a phosphorus-modified internucleotide linkage and a sugar backbone modification (e.g. 2'-modified nucleotide).

Exemplary modified miR-135 polynucleotides include, but are not limited to, SEQ ID NOs: 194-209.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

According to one embodiment, the polynucleotides of the invention can have a chemical modification on a nucleotide in an internal (i.e., non-terminal) region having noncomplementarity with the target nucleic acid. For example, a modified nucleotide can be incorporated into the region of a miRNA that forms a bulge. The modification can include a ligand attached to the miRNA, e.g., by a linker. The modification can, for example, improve pharmacokinetics or stability of the polynucleotide, or improve hybridization properties (e.g., hybridization thermodynamics) of the polynucleotide to a target nucleic acid.

In some embodiments, the orientation of a modification or ligand incorporated into or tethered to the bulge region of a polynucleotide is oriented to occupy the space in the bulge region. For example, the modification can include a modified base or sugar on the nucleic acid strand or a ligand that functions as an intercalator. These are preferably located in the bulge. The intercalator can be an aromatic, e.g., a polycyclic aromatic or heterocyclic aromatic compound. A polycyclic intercalator can have stacking capabilities, and can include systems with 2, 3, or 4 fused rings. In some embodiments, the orientation of a modification or ligand incorporated into or tethered to the bulge region of the polynucleotide is oriented to occupy the space in the bulge region. This orientation facilitates the improved hybridization properties or an otherwise desired characteristic of the polynucleotide.

In one embodiment, the polynucleotide can include an aminoglycoside ligand, which can cause the polynucleotide to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments the guanidine analog (the guanidinoglycoside) of an aminoglycoside ligand is tethered to a polynucleotide agent. In a guanidinoglycoside, the amine group on the amino acid is exchanged for a guanidine group. Attachment of a guanidine analog can enhance cell permeability of the polynucleotide.

A polynucleotide can be designed and synthesized to include a region of noncomplementarity (e.g., a region that is 3, 4, 5, or 6 nucleotides long) flanked by regions of sufficient complementarity to form a duplex (e.g., regions that are 7, 8, 9, 10, or 11 nucleotides long) with a target RNA.

For increased nuclease resistance and/or binding affinity to the target, the polynucleotides of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), e.g. inclusion of nucleic acid analogues in which the ribose ring is "locked" by a methylene bridge connecting the 2'-O atom and the 4'-C atom, ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to the target. The inclusion of pyranose sugars in the oligonucleotide backbone can also decrease endonucleolytic cleavage.

A polynucleotide can be further modified by including a 3' cationic group, or by inverting the nucleoside at the terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

The 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the polynucleotide includes a modification that improves targeting, e.g. a targeting modification described herein. Examples of modifications that target single-stranded oligonucleotide agents to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

The polynucleotide of the invention can be constructed using chemical synthesis and/or enzymatic ligation reactions using procedures known in the art. For example, the polynucleotide can be chemically synthesized using naturally occurring nucleotides or variously modified nucleotides designed to increase the biological stability of the molecules or to increase the physical stability of the duplex formed between the polynucleotide and target nucleic acids, e.g., phosphorothioate derivatives and acridine substituted nucleotides can be used.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and 0-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

According to one embodiment, the modified polynucleotide is further modified so as to be attached to a ligand that is selected to improve stability, distribution or cellular uptake of the agent, e.g., cholesterol.

Thus, the polynucleotide may be modified to include a non-nucleotide moiety, e.g., a cholesterol moiety. The non-nucleotide moiety (e.g. cholesterol moiety) can be attached, e.g., to the 3' or 5' end of the polynucleotide.

According to a specific embodiment, the miRNA polynucleotide of the present invention has a nucleic acid sequence as set forth in SEQ ID NOs: 58-94 (see Table 1A).

TABLE 1A miRNA polynucleotide sequences

| Sequence | miRNA |
|---|---|
| SEQ ID NOs: 77-80 | miR-15 |
| SEQ ID NOs: 72-76 | miR-19 |
| SEQ ID NOs: 65-69 | miR-26 |
| SEQ ID NOs: 81-84 | miR-27 |
| SEQ ID NOs: 58-62 | miR-135 |
| SEQ ID NOs: 85-94 | miR-181 |
| SEQ ID NOs: 70-71 | miR-182 |
| SEQ ID NOs: 63-64 | miR-335 |

As is mentioned hereinabove and is shown in the Examples section which follows, micro-RNAs are processed molecules derived from specific precursors (i.e., pre-miRNA), upregulation of a specific miRNA function can be effected using a specific miRNA precursor molecule.

According to a specific embodiment, the miR-135 comprises miR-135a or miR-135b.

According to a specific embodiment, the precursor miR-135 polynucleotide of the present invention has a nucleic acid sequence as set forth in SEQ ID NOs: 58-60.

According to a specific embodiment, the mature miR-135 polynucleotide of the present invention has a nucleic acid sequence as set forth in SEQ ID NOs: 61-62.

According to a specific embodiment, the mature miR-135* polynucleotide of the present invention has a nucleic acid sequence as set forth in SEQ ID NOs: 192-193.

Also contemplated are sequences homologous to the miRNAs and precursors thereof. The level of homology should be relatively high for the mature miRNA but more orders of freedom are allowed at the precursor level (e.g., at least 60%, 70%, 80%, 85%, 90%, 95% or more) as long as the sequence alterations are in the hair pin sequence and not in the nucleic acid segment corresponding to the mature miR.

Such precursor polynucleotide agents are typically administered to the target cells (e.g. neuroglia cells or cardiac cells) as part of an expression construct. In this case, the polynucleotide agent is ligated in a nucleic acid construct under the control of a cis-acting regulatory element (e.g. promoter) capable of directing an expression of the microRNA in the target cells (e.g. neuroglia cells or cardiac cells) in a constitutive or inducible manner.

Examples of microRNA polynucleotide agents of the present invention include, but are not limited to, miR-15 (e.g. GenBank accession no. NR_029485), miR-19 (e.g. GenBank accession no. NR_029489.1), miR-26 (e.g. GenBank accession nos. NR_029500 and NR_029499), miR-27 (e.g. GenBank accession no. NR_029501), miR-135 (e.g. GenBank accession nos. NR_029677.1, NR_029678.1, NR_029893.1), miR-335 (e.g. GenBank accession no. NR_029899.1), miR-181 (e.g. GenBank accession no. NR_029611.1) and miR-182 (e.g. GenBank accession no. NR_029614).

Such precursor polynucleotide agents are typically administered to the target cells (e.g. neuroglia cells, choroid plexus (CP) cells, stem cells or differentiated stem cells) as part of an expression construct. In this case, the polynucleotide agent is ligated in a nucleic acid construct under the control of a cis-acting regulatory element (e.g. promoter) capable of directing an expression of the microRNA in the target cells (e.g. neuroglia cells, CP cells, stem cells or differentiated stem cells) in a constitutive or inducible manner.

Examples of neuron cell specific promoters include, but are not limited to, neuron-specific enolase gene promoter, synapsin promoter, enhanced synapsin promoter, calcium calmodulin promoter and Thy1 promoter.

An exemplary neuroglia cell specific promoter includes glial fibrillary acidic protein (GFAP) promoter.

Examples of choroid plexus specific promoters include, but are not limited to a β splice variant of the type 2 corticotrophin releasing factor receptor (CRFR2β) promoter, a G protein-coupled receptor 125 (GPR125) promoter and a transthyretin promoter.

According to one embodiment, the promoter sequence (e.g. choroid plexus specific promoter) is placed 3' to the polynucleotide sequence (e.g. miR-135 polynucleotide sequence) on a nucleic acid construct such that expression thereof is constitutive, but tissue specific.

According to another embodiment, the choroid plexus specific promoter sequence is situated relative to the polynucleotide sequence (e.g. miR-135 polynucleotide sequence) on a nucleic acid construct such that expression thereof is tissue specific, but also may be controlled in an exogenously regulatable fashion.

In order to ensure that the polynucleotide of interest is expressed both specifically in cells of the choroid plexus and in an exogenously controllable fashion, a nucleic acid construct may be designed such that it comprises a polynucleotide encoding a transactivator under control of the choroid plexus specific promoter. The polynucleotide may be inserted in the same nucleic acid construct or in an additional construct under control of an inducible promoter. The transactivator in combination with an inducer act to regulate expression from the inducible promoter.

Inducible promoters suitable for use with the present invention are preferably response elements capable for directing transcription of the polynucleotide sequence. A suitable response element can be, for example, a tetracycline response element (such as described by Gossen and Bujard (Proc. Natl. Acad. Sci. USA 89:5547-551, 1992); an ectysone-inducible response element (No D et al., Proc Natl Acad Sci USA. 93:3346-3351, 1996) a metal-ion response element such as described by Mayo et al. (Cell. 29:99-108, 1982); Brinster et al. (Nature 296:39-42, 1982) and Searle et al. (Mol. Cell. Biol. 5:1480-1489, 1985); a heat shock response element such as described by Nouer et al. (in: Heat Shock Response, ed. Nouer, L., CRC, Boca Raton, Fla., pp 167-220, 1991); or a hormone response element such as described by Lee et al. (Nature 294:228-232, 1981); Hynes et al. (Proc. Natl. Acad. Sci. USA 78:2038-2042, 1981); Klock et al. (Nature 329:734-736, 1987); and Israel and Kaufman (Nucl. Acids Res. 17:2589-2604, 1989). Preferably the response element is an ectysone-inducible response element, more preferably the response element is a tetracycline response element.

Examples of cardiac cell specific promoters include, but are not limited to, cardiac NCX1 promoter and a-myosin heavy chain (αMHC) promoter.

The expression constructs of the present invention may also include additional sequences which render it suitable for replication and integration in eukaryotes (e.g., shuttle vectors). Typical cloning vectors contain transcription and translation initiation sequences (e.g., promoters, enhances) and transcription and translation terminators (e.g., polyadenylation signals). The expression constructs of the present invention can further include an enhancer, which can be adjacent or distant to the promoter sequence and can function in up regulating the transcription therefrom.

Enhancer elements can stimulate transcription up to 1,000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. See Gluzman, Y. and Shenk, T., eds. (1983). Enhancers and Eukaryotic Gene Expression, Cold Spring Harbor Press, Cold Spring Harbor, N.Y., which is incorporated herein by reference.

Polyadenylation sequences can also be added to the expression constructs of the present invention in order to increase the efficiency of expression of the detectable moiety. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression constructs of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression constructs of the present invention may or may not include a eukaryotic replicon. If a eukaryotic replicon is present, the vector is capable of amplification in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired nucleic acid.

The nucleic acid construct may be introduced into the target cells (e.g. neuroglia cells or cardiac cells) of the present invention using an appropriate gene delivery vehicle/method (transfection, transduction, etc.) and an appropriate expression system.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Stratgene, pTRES which is available from Clontech, and their derivatives.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Barr virus include pHEBO and p2O5. Other exemplary vectors include pMSG, pAV009/A$^+$, pMTO10/A+, pMAMneo-5 and baculovirus pDSVE.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpes-viral vectors.

Retroviral vectors represent a class of vectors particularly suitable for use with the present invention. Defective retroviruses are routinely used in transfer of genes into mammalian cells (for a review, see Miller, A. D. (1990). Blood 76, 271). A recombinant retrovirus comprising the polynucleotides of the present invention can be constructed using well-known molecular techniques. Portions of the retroviral genome can be removed to render the retrovirus replication machinery defective, and the replication-deficient retrovirus can then packaged into virions, which can be used to infect target cells through the use of a helper virus while employing standard techniques. Protocols for producing recombinant retroviruses and for infecting cells with viruses in vitro or in vivo can be found in, for example, Ausubel et al. (1994) Current Protocols in Molecular Biology (Greene Publishing Associates, Inc. & John Wiley & Sons, Inc.). Retroviruses have been used to introduce a variety of genes into many different cell types, including neuronal cells, epithelial cells, endothelial cells, lymphocytes, myoblasts, hepatocytes, and bone marrow cells.

According to one embodiment, a lentiviral vector, a type of retroviral vector, is used according to the present teachings. Lentiviral vectors are widely used as vectors due to their ability to integrate into the genome of non-dividing as well as dividing cells. The viral genome, in the form of RNA, is reverse-transcribed when the virus enters the cell to produce DNA, which is then inserted into the genome at a random position by the viral integrase enzyme. The vector (a provirus) remains in the genome and is passed on to the progeny of the cell when it divides. For safety reasons, lentiviral vectors never carry the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the ψ (psi) sequence. This sequence is used to package the genome into the virion.

A specific example of a suitable lentiviral vector for introducing and expressing the polynucleotide sequences of the present invention in neuroglia cells or cardiac cells is the lentivirus pLKO.1 vector.

Another suitable expression vector that may be used according to this aspect of the present invention is the adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues, and easy production of high titers (Russel, W. C. (2000) J Gen Virol 81, 57-63). The adenovirus DNA is transported to the nucleus, but does not integrate thereinto. Thus the risk of mutagenesis with adenoviral vectors is minimized, while short-term expression is particularly suitable for treating cancer cells. Adenoviral vectors used in experimental cancer treatments are described by Seth et al. (1999). "Adenoviral vectors for cancer gene therapy," pp. 103-120, P. Seth, ed., Adenoviruses: Basic Biology to Gene Therapy, Landes, Austin, Tex.).

A suitable viral expression vector may also be a chimeric adenovirus/retrovirus vector combining retroviral and adenoviral components. Such vectors may be more efficient than traditional expression vectors for transducing tumor cells (Pan et al. (2002). Cancer Letts 184, 179-188).

Various methods can be used to introduce the nucleic acid constructs of the present invention into mammalian cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

When introducing the expression constructs of the present invention into target cells (e.g. neuroglia cells or cardiac cells) by viral infection the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

In order to circumvent the blood brain barrier, the constructs of the present invention may be administered directly into the brain (via the ventricle), into the olfactory bulb (via an intranasal administration), via the spinal cord (e.g. by an epidural catheter) or by expression in the choroid plexus, as further detailed herein.

Alternatively, lipid-based systems may be used for the delivery of these constructs into the target cells (e.g. brain cells such as neuroglia cells) of the present invention.

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or negatively charged. For Mononuclear Phagocyte System (MPS) uptake, the liposomes can be hydrophobic since hydrophilic masking of the liposome membrane (e.g., by use of polyetheleneglycol-linked lipids and hydrophilic particles) may be less prone to MPS uptake. Optionally, the liposomes do not comprise sterically shielded lipids such as ganglioside-GM$_1$ and phosphatidylinositol since these lipids prevent MPS uptake.

The liposomes may be a single lipid layer or may be multilamellar. If the therapeutic agent is hydrophilic, its delivery may be further improved using large unilamellar vesicles because of their greater internal volume. Conversely, if the therapeutic agent is hydrophobic, its delivery may be further improved using multilamellar vesicles. Alternatively, the therapeutic agent (e.g. oligonucleotide) may not be able to penetrate the lipid bilayer and consequently would remain adsorbed to the liposome surface. In this case, increasing the surface area of the liposome may further improve delivery of the therapeutic agent. Suitable liposomes in accordance with the invention are non-toxic liposomes such as, for example, those prepared from phosphatidyl-choline phosphoglycerol, and cholesterol. The diameter of the liposomes used can range from 0.1-1.0 microns. However, other size ranges suitable for phagocytosis by phagocytic cells may also be used. For sizing liposomes, homogenization may be used, which relies on shearing energy to fragment large liposomes into smaller ones. Homogenizers which may be conveniently used include microfluidizers produced by Microfluidics of Boston, Mass. In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

Any method known in the art can be used to incorporate micro-RNA polynucleotide agent (miR-135 or the precursor thereof) into a liposome. For example, the micro-RNA polynucleotide agent (miR-135 or the precursor thereof) may be encapsulated within the liposome. Alternatively, it may be adsorbed on the liposome's surface. Other methods that may be used to incorporate a pharmaceutical agent into a liposome of the present invention are those described by Alfonso et al., [The science and practice of pharmacy, Mack Publishing, Easton Pa. 19$^{th}$ ed., (1995)] and those described by Kulkarni et al., [J. Microencapsul. 1995, 12 (3) 229-46].

The liposomes used in the methods of the present invention may cross the blood barriers. Thus, according to an embodiment the liposomes of the present invention do not comprise a blood barrier targeting polysaccharide (e.g. mannose) in their membrane portion. Optionally, the liposomes of the present invention do not comprise peptides in their membrane portion that target the liposomes to a receptor on a blood barrier. Examples of such peptides include but are not limited to transferrin, insulin, IGF-1, IGF-2 anti-transferrin receptor antibody, anti-insulin receptor antibody, anti-IGF-1 receptor antibody and anti-IGF-2 receptor antibody.

In order to determine liposomes that are especially suitable in accordance with the present invention a screening assay can be performed such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804.

Other non-lipid based vectors that can be used according to this aspect of the present invention include but are not limited to polylysine, dendrimers and Gagomers.

Regardless of the method or construct employed, there is provided an isolated cell comprising the nucleic acid construct encoding a microRNA, as detailed above.

As used herein the term "isolated" refers to at least partially separated from the natural environment e.g., the human body.

According to one embodiment, there is provided an isolated cell comprising a nucleic acid construct expressing at least one microRNA or a precursor thereof, wherein the microRNA is selected from the group consisting of miR-135, miR-335, miR-15, miR-19, miR-26, miR-27, miR-181 and miR-182 under a transcriptional control of a cis acting regulatory element.

According to a specific embodiment, there is provided an isolated neuroglia cell comprising a nucleic acid construct expressing at least one microRNA or a precursor thereof, wherein the microRNA is selected from the group consisting of miR-135, miR-335, miR-26 and miR-182 under a transcriptional control of a cis acting regulatory element.

According to a specific embodiment, there is provided an isolated cell comprising a nucleic acid construct expressing a miR-19 or a precursor thereof under a transcriptional control of a cis acting regulatory element.

According to a specific embodiment, there is provided an isolated cell comprising a nucleic acid construct expressing a miR-15 or a precursor thereof under a transcriptional control of a cis acting regulatory element.

According to a specific embodiment, the cell is a neuroglia cell or a cardiac cell.

According to a specific embodiment, the neuroglia cell is a neuron such as a serotonergic neuron.

The microRNAs or precursors thereof are to be provided to the cells i.e., target cells (e.g. neuroglia cells or cardiac cells) of the present invention in vivo (i.e., inside the organism or the subject) or ex vivo (e.g., in a tissue culture). In case the cells are treated ex vivo, the method preferably includes a step of administering such cells back to the individual (ex vivo cell therapy).

For ex vivo therapy, cells (e.g. neuroglia cells such as oligodendrocytes, CP cells, stem cells and/or differentiated stem cells) are preferably treated with the agent of the present invention (e.g., a microRNA, e.g. miR-135, or a precursor thereof or a polynucleotide encoding the microRNA e.g. miR-135, or a precursor thereof), following which they are administered to the subject in need thereof.

Administration of the ex vivo treated cells of the present invention can be effected using any suitable route of introduction, such as intravenous, intraperitoneal, intra-kidney, intra-gastrointestinal track, subcutaneous, transcutaneous, intramuscular, intracutaneous, intrathecal, epidural, and rectal. According to presently preferred embodiments, the ex vivo treated cells of the present invention may be introduced to the individual using intravenous, intra-kidney, intra-gastrointestinal track, and/or intraperitoneal administration.

The cells of the present invention (e.g. neuroglia cells such as oligodendrocytes, CP cells, stem cells, differentiated stem cells and/or cardiac cells) can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxy-cinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 μm. Such microcapsules can be further encapsulated with an additional 2-5 μm of ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 μm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

Examples of immunosuppressive agents which may be used in conjunction with the ex vivo treatment include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

For in vivo therapy, the agent (e.g., microRNA, e.g. miR-135, a precursor thereof or a polynucleotide encoding the microRNA or the precursor thereof) is administered to the subject per se or as part of a pharmaceutical composition. Preferably such compositions are formulated to allow passage through the blood brain barrier (BBB).

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Methods for drug delivery behind the BBB include intracerebral implantation (such as with needles) and convection-enhanced distribution. Mannitol can be used in bypassing the BBB. Likewise, mucosal (e.g., nasal) administration can be used to bypass the BBB.

The micro-RNA polynucleotide agents of the present invention can also be administered to an organism in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide accountable for the biological effect (e.g. miroRNA, e.g. miR-135, a precursor thereof, or a polynucleotide encoding the microRNA or the precursor thereof).

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. miroRNA) effective to prevent, alleviate or ameliorate symptoms of a disorder (e.g., mood disorder such as bipolar disease) or prolong the survival of the subject being treated.

According to an embodiment of the present invention, overexpression of miR-135 has an anti-depressant effect.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient plasma levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

It will be appreciated that animal models exist by which the agents of the present invention may be tested prior to human treatment. For example, animal models of depression, stress, anxiety such as learned helplessness model (LH), chronic mild stress (CMS) model, social defeat stress (SDS) model and maternal deprivation model and sleep deprivation model may be used. For example, animal models of bipolar disease include, for example, transgenic mice with neuron-specific expression of mutant Polg (D181A) [as taught by Kato et al., Neuroscience and Biobehavioral Reviews (2007) 6 (31):832-842, incorporated herein by reference], as well as the well established mania rat models of Amphetamine-induced hyperactivity [taught e.g. in U.S.

Pat. No. 6,555,585] and Ketamine-induced hyperactivity [taught e.g. in Ghedim et al., Journal of Psychiatric Research (2012) 46: 1569-1575], incorporated by reference, may be used.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that the therapeutic compositions of the invention may comprise, in addition to the micro-RNA (e.g. miR-135 or polynucleotide encoding same), other known medications for the treatment of depression, stress, anxiety, sleep deprivation, etc. such as, but not limited to, selective serotonin reuptake inhibitors (SSRIs), serotonin-norepinephrine reuptake inhibitors (SNRIs), noradrenergic and specific serotonergic antidepressants (NaSSAs), norepinephrine (noradrenaline) reuptake inhibitors (NRIs), norepinephrine-dopamine reuptake inhibitors, selective serotonin reuptake enhancers, norepinephrine-dopamine disinhibitors, tricyclic antidepressants (e.g. Imipramine), monoamine oxidase inhibitors (MAOIs). These medications may be included in the article of manufacture in a single or in separate packagings.

According to one embodiment, the therapeutic composition of the invention comprises, in addition to the micro-RNA (e.g. miR-135 or polynucleotide encoding same), a medicament for the treatment of a bipolar disorder. Any medicament or any combination of medicaments for the treatment of a bipolar disorder may be used in accordance with the present teachings, including but not limited to, lithium (e.g. Lithium carbonate, Lithium citrate, Lithium sulfate), antipsychotic medicaments (e.g. typical antipsychotics and atypical antipsychotics, as detailed below), mood stabilizer medicaments (e.g. Valproic acid (VPA, Valproate), minerals, anticonvulsants, antipsychotics) and anti-depressants.

Exemplary typical antipsychotic medicaments which may be used in accordance with the present teachings, include but are not limited to, Low potency medicaments: Chlorpromazine (Largactil, Thorazine), Chlorprothixene (Truxal), Thioridazine (Mellaril), Mesoridazine and Levomepromazine; Medium potency medicaments: Loxapine (Loxapac, Loxitane), Molindone (Moban), Perphenazine (Trilafon) and Thiothixene (Navane); High potency medicaments: Haloperidol (Haldol, Serenace), Fluphenazine (Prolixin), Droperidol, Zuclopenthixol (Clopixol), Flupentixol (Depixol), Prochlorperazine and Trifluoperazine (Stelazine). In addition, Prochlorperazine (Compazine, Buccastem, Stemetil) and Pimozide (Orap) may be used.

Exemplary atypical antipsychotic medicaments (also referred to as second generation antipsychotics) which may be used in accordance with the present teachings, include but are not limited to, Amisulpride (Solian), Aripiprazole (Abilify), Asenapine (Saphris), Blonanserin (Lonasen), Bitopertin (RG1678), Brexpiprazole (OPC-34712), Carpipramine (Prazinil), Clocapramine (Clofekton), Clozapine (Clozaril), Cariprazine (RGH-188), Iloperidone (Fanapt), Lurasidone (Latuda), LY2140023, Melperone (Buronil), Mosapramine (Cremin), Olanzapine (Zyprexa), Paliperidone (Invega), Perospirone (Lullan), Pimavanserin (ACP-103), Quetiapine (Seroquel), Remoxipride (Roxiam), Risperidone (Risperdal), Sertindole (Serdolect), Sulpiride (Sulpirid), Vabicaserin (SCA-136), Ziprasidone (Geodon), Zotepine (Nipolept) and Zicronapine (Lu 31-130).

Exemplary mood stabilizers which may be used in accordance with the present teachings, include but are not limited to, minerals (e.g. lithium); anticonvulsant mood stabilizers including Valproic acid (Depakine), divalproex sodium (Depakote), and sodium valproate (Depacon, Epilim), Lamotrigine (Lamictal), Carbamazepine (Tegretol), Oxcarbazepine (Trileptal), Topiramate (Topamax), Riluzole (Rilutek) and Gabapentin (Neurontin); antipsychotics (as described above); and food supplements (e.g. omega-3 fatty acids).

Exemplary anti-depressants which may be used in accordance with the present teachings, include but are not limited to, Selective serotonin reuptake inhibitors (SSRIs, such as Citalopram, Escitalopram, Fluoxetine, Fluvoxamine, Paroxetine and Sertraline); Serotonin-norepinephrine reuptake inhibitors (SNRIs, such as Desvenlafaxine, Duloxetine, Milnacipran and Venlafaxine); Noradrenergic and specific serotonergic antidepressants (such as Mianserin and Mirtazapine); Norepinephrine (noradrenaline) reuptake inhibitors (NRIs, such as Atomoxetine, Mazindol, Reboxetine and Viloxazine); Norepinephrine-dopamine reuptake inhibitors (such as Bupropion); Selective serotonin reuptake enhancers (such as Tianeptine); Norepinephrine-dopamine disinhibitors (NDDIs such as Agomelatine); Tricyclic antidepressants (including Tertiary amine tricyclic antidepressants and Secondary amine tricyclic antidepressants); and Monoamine oxidase inhibitor (MAOIs).

According to one embodiment, the anti-depressant drug comprises selective serotonin reuptake inhibitors (SSRI), tricyclic antidepressants and noradrenaline reuptake inhibitors (NRI).

According to a specific embodiment, the anti-depressant drug comprises selective serotonin reuptake inhibitors (SSRI).

It will be appreciated that additional non-pharmaceutical therapeutic strategies may be employed in combination with the present teachings, including but not limited to, clinical psychology, electroconvulsive therapy, involuntary commitment, light therapy, psychotherapy, transcranial magnetic stimulation and cognitive behavioral therapy.

The present inventors have shown that overexpression of miR-27 results in suppression of MaoA (see Example 1, hereinbelow), overexpression of miR-135 results in suppression of Slc6a4 (see Example 1, hereinbelow), overexpression of miR-135, miR-335, miR-26, miR-181 or miR-182 results in suppression of Htr1a (see Example 1, hereinbelow), overexpression of miR-19 results in suppression of Add (see Example 2, hereinbelow) and in suppression of CB1 (see Example 3B, hereinbelow), and that overexpression of miR-15 results in suppression of Crh1R (see Example 4, hereinbelow) and in suppression of FKBP5 (see Example 4B, hereinbelow).

Thus, according to one embodiment of the present invention, there is provided a method of regulating an expression of a serotonin transporter (Slc6a4) gene in a neuroglia cell, the method comprising modulating an activity or expression of a microRNA or a precursor thereof, wherein the microRNA is selected from the group consisting of miR-135 and miR-335.

As used herein, the term "serotonin transporter (Slc6a4)" refers to the monoamine transporter protein (also named SERT) involved in reuptake of serotonin from the synaptic cleft. An exemplary Slc6a4 is set forth in NP_001036.1.

According to another embodiment, there is provided a method of regulating an expression of a serotonin inhibitory receptor 1a (Htr1a) gene in a neuroglia cell, the method comprising modulating an activity or expression of a microRNA or a precursor thereof in the neuroglia cell, wherein the microRNA is selected from the group consisting of miR-135, miR-335, miR-181, miR-182 and miR-26.

As used herein, the term "serotonin inhibitory receptor 1a (Htr1a)" refers to the G protein-coupled receptor that functions as an autoreceptor in the presynaptic neuron and mediated inhibition of serotonin release. An exemplary Htr1a is set forth in NP_000515.2.

According to another embodiment, there is provided a method of regulating an expression of a monoamine hydroxylase (MaoA) gene in a neuroglia cell, the method comprising modulating an activity or expression of a miR-27 or a precursor thereof.

As used herein, the term "monoamine hydroxylase (MaoA)" refers to the enzyme that degrades amine neurotransmitters, such as dopamine, norepinephrine, and serotonin. An exemplary MaoA is set forth in NP_000231.1.

According to one embodiment of the present invention, there is provided a method of regulating an expression of a tryptophan hydroxylase 2 (Tph2) gene in a neuroglia cell, the method comprising modulating an activity or expression of a microRNA or a precursor thereof in the neuroglia cell, wherein the microRNA is selected from the group consisting of miR-181 and miR27.

As used herein, the term "tryptophan hydroxylase 2 (Tph2)" refers to the enzyme which catalyzes the first and rate limiting step in the biosynthesis of serotonin. In exemplary Tph2 is set forth in NP_NP_775489.2.

According to another embodiment, there is provided a method of regulating an expression of a beta adrenergic receptor 1 (Adrb1) gene in a neuroglia cell or cardiac cell, the method comprising modulating an activity or expression of a miR-19 or a precursor thereof.

As used herein, the term "beta adrenergic receptor 1 (Adrb1)" refers to the receptor that mediates the physiological effects of adrenaline and noradrenaline. An exemplary Adrb1 is set forth in NP_000675.1.

According to another embodiment, there is provided a method of regulating an expression of a beta 2 adrenergic receptor (Adrb2) gene in a neuroglia cell, the method comprising modulating an activity or expression of a miR-15 or a precursor thereof.

As used herein, the term "beta 2 adrenergic receptor (Adrb2)" refers to the receptor that is directly associated with the class C L-type calcium channel Ca(V)1.2. Adrb2 is set forth e.g. in NP_000015.1.

According to another embodiment, there is provided a method of regulating an expression of a CRH type 1 receptor gene in a neuroglia cell, the method comprising modulating an activity or expression of a miR-15 or a precursor thereof.

As used herein, the term "CRH type 1" refers to the receptor which binds corticotropin-releasing hormone (CRH). CRH type 1 is set forth e.g. in NP_001138618.1, NP_001138619.1, NP_001138620.1 and NP_004373.2.

According to another embodiment, there is provided a method of regulating an expression of a glutamate receptor gene in a neuroglia cell, the method comprising modulating an activity or expression of miR-181 or a precursor thereof.

According to another embodiment, the glutamate receptor gene comprises glutamate receptor metabotropic 1 (Grm1), glutamate receptor ionotropic kainate 3 (Grik3), glutamate receptor metabotropic 5 (Grm5), glutamate receptor ionotropic kainate 2 (Grik2) and glutamate receptor metabotropic 7 (Grm7), as described in further detail above.

According to another embodiment, there is provided a method of regulating an expression of a Down Syndrome Cell Adhesion Molecule (Dscam) gene in a neuroglia cell, the method comprising modulating an activity or expression of a miR-182 or a precursor thereof.

As used herein, the term "Down Syndrome Cell Adhesion Molecule (Dscam)" refers to the cell adhesion molecule that plays a role in neuronal self-avoidance. Dscam is set forth e.g. in NP_001380.2.

According to another embodiment, there is provided a method of regulating an expression of a Cell adhesion molecule L1 (L1cam) gene in a neuroglia cell, the method comprising modulating an activity or expression of a miR-182 or a precursor thereof.

As used herein, the term "Cell adhesion molecule L1 (L1cam)" refers to the neuronal cell adhesion molecule. L1cam is set forth e.g. in NP_000416.1, NP_001137435.1, NP_076493.1.

According to another embodiment, there is provided a method of regulating an expression of a Translin-associated protein X (Tsnax) gene in a neuroglia cell, the method comprising modulating an activity or expression of a miR-182 or a precursor thereof.

As used herein, the term "Translin-associated protein X (Tsnax)" refers to the protein which specifically interacts with translin. Tsnax is set forth e.g. in NP_005990.1.

According to another embodiment, there is provided a method of regulating an expression of a cannabinoid receptor 1 (CB1) gene in a neuroglia cell, the method comprising modulating an activity or expression of a miR-19 or a precursor thereof.

As used herein, the term "cannabinoid receptor 1 (CB1)" refers to the of cell membrane receptor (also known as CNR1). CB1 is set forth e.g. in NP_001153698.1, NP_001153730.1, NP_001153731.1, NP_057167.2, NP_149421.2.

According to another embodiment, there is provided a method of regulating an expression of a FK506 binding protein 5 (FKBP5) gene in a neuroglia cell, the method comprising modulating an activity or expression of a miR-15 or a precursor thereof.

As used herein, the term "FK506 binding protein 5 (FKBP5)" refers to the protein which specifically binds to the immunosuppressants FK506 and rapamycin. FKBP5 is set forth e.g. in NP_001139247.1, NP_001139248.1, NP_001139249.1, NP_004108.1.

According to another embodiment, there is provided a method of regulating an expression of a syntaxin 1a (Stx1a) gene in a neuroglia cell, the method comprising modulating an activity or expression of a miR-15 or a precursor thereof.

As used herein, the term "syntaxin 1a (Stx1a)" refers to the nervous system-specific protein. Stx1a is set forth e.g. in NP_001159375.1, NP_004594.1.

According to another embodiment, there is provided a method of regulating an expression of a serum/glucocorticoid regulated kinase (Sgk1) gene in a neuroglia cell, the method comprising modulating an activity or expression of a miR-15 or a precursor thereof.

As used herein, the term "serum/glucocorticoid regulated kinase (Sgk1)" refers to serine/threonine protein kinase. Sgk1 is set forth e.g. in NP_001137148.1, NP_001137149.1, NP_001137150.1, NP_005618.2.

The present teachings contemplate upregulating (i.e. increasing) or downregulating (i.e. decreasing) the expression levels of the aforementioned genes.

Downregulation of gene expression according to the present teachings is typically carried out by administering to or expressing in the target cells (e.g. neuroglia cell or cardiac cell) a microRNA polynucleotide (as depicted in further detail hereinabove).

According to a specific embodiment, when the regulating comprises downregulating the expression of the Slc6a4 gene, the modulating comprises upregulating the miR-135 and/or miR-335.

According to a specific embodiment, when the regulating comprises downregulating the expression of the Htr1a gene, the modulating comprises upregulating the miR-135, miR-335, miR-181, miR-182 and/or miR-26.

According to a specific embodiment, when the regulating comprises downregulating the expression of the MaoA gene, the modulating comprises upregulating the miR-27.

According to a specific embodiment, when the regulating comprises downregulating the expression of the Adrb1 gene, the modulating comprises upregulating the miR-19.

According to a specific embodiment, when the regulating comprises downregulating the expression of the CRH type 1 receptor gene, the modulating comprises upregulating the miR-15.

According to a specific embodiment, when the regulating comprises downregulating the expression of the CB1 gene, the modulating comprises upregulating the miR-19.

According to a specific embodiment, when the regulating comprises downregulating the expression of the FKBP5 gene, the modulating comprises upregulating the miR-15.

According to one embodiment, there is provided a method of downregulating an expression of a gene selected from the group consisting of adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (*Drosophila*) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt11); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3); and zinc finger, BED domain containing 4 (Zbed4) in a neuroglia cell, the method comprising: (a) upregulating an activity or expression of a miR-135 or a precursor thereof in the neuroglia cell; and (b) measuring an expression of the gene in the neuroglia cell, thereby downregulating the expression of the gene.

According to a specific embodiment, downregulating the expression of the gene is effected by upregulating an activity or expression of a microRNA or a precursor thereof which is not miR-135.

According to a specific embodiment, downregulating the expression of the miR-135 target gene is effected by administering to the subject an agent capable of downregulating an activity or expression of the mir-135 target gene.

Downregulation of a gene (e.g. miR-135 target gene) or gene product can be effected on the genomic and/or the transcript level using a variety of molecules which interfere with transcription and/or translation [e.g., RNA silencing agents (e.g., antisense, siRNA, shRNA, micro-RNA), Ribozyme, DNAzyme and a CRISPR system (e.g. CRISPR/Cas)], or on the protein level using e.g., antagonists, enzymes that cleave the polypeptide and the like.

Following is a list of agents capable of downregulating expression level and/or activity of a gene or gene product of some embodiments of the invention.

One example, of an agent capable of downregulating an activity of a polypeptide gene product is an antibody or antibody fragment capable of specifically binding the gene product (i.e. protein). Such inhibition is valuable for extracellular, cell surface or secreted polypeptides in particular. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Downregulation of a gene (e.g. miR-135 target gene) can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., target gene) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

The invention according to some embodiments thereof also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., a siRNA) may be connected to form a hairpin or stem-loop structure (e.g., a shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the target gene mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

Another agent capable of downregulating a gene (e.g. miR-135 target gene) is a DNAzyme molecule capable of specifically cleaving an mRNA transcript or DNA sequence of the target gene. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www(dot)asgt(dot)org). In another application, DNAzymes complementary to bcr-ab1 oncogenes were successful in inhibiting the oncogenes expression in leukemia cells, and lessening relapse rates in autologous bone marrow transplant in cases of CML and ALL.

Downregulation of a gene (e.g. miR-135 target gene) can also be effected by using an antisense polynucleotide capable of specifically hybridizing with an mRNA transcript encoding the gene.

Design of antisense molecules which can be used to efficiently downregulate a gene must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Another agent capable of downregulating a gene (e.g. miR-135 target gene) is a ribozyme molecule capable of specifically cleaving an mRNA transcript encoding a gene. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating a gene (e.g. miR-135 target gene) is a RNA-guided endonuclease technology e.g. CRISPR system.

As used herein, the term "CRISPR system" also known as Clustered Regularly Interspaced Short Palindromic Repeats refers collectively to transcripts and other elements involved in the expression of or directing the activity of CRISPR-associated genes, including sequences encoding a Cas gene (e.g. CRISPR-associated endonuclease 9), a tracr (trans-activating CRISPR) sequence (e.g. tracrRNA or an active partial tracrRNA), a tracr-mate sequence (encompassing a "direct repeat" and a tracrRNA-processed partial direct repeat) or a guide sequence (also referred to as a "spacer") including but not limited to a crRNA sequence or a sgRNA sequence (i.e. single guide RNA).

In some embodiments, one or more elements of a CRISPR system is derived from a type I, type II, or type III CRISPR system. In some embodiments, one or more elements of a CRISPR system (e.g. Cas) is derived from a particular organism comprising an endogenous CRISPR system, such as *Streptococcus pyogenes, Neisseria meningitides, Streptococcus thermophilus* or *Treponema denticola*.

In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence (i.e. guide RNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%. A target sequence may comprise any polynucleotide, such as DNA or RNA polynucleotides. In some embodiments, a target sequence is located in the nucleus or cytoplasm of a cell.

Thus, the CRISPR system comprises two distinct components, a guide RNA (gRNA) that hybridizes with the target sequence, and a nuclease (e.g. Type-II Cas9 protein), wherein the gRNA targets the target sequence and the nuclease (e.g. Cas9 protein) cleaves the target sequence or silences target genes. The guide RNA may comprise a combination of an endogenous bacterial crRNA and tracrRNA, i.e. the gRNA combines the targeting specificity of the crRNA with the scaffolding properties of the tracrRNA (required for Cas9 binding). Alternatively, the guide RNA may comprise a single guide RNA (sgRNA) capable of directly binding Cas.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. This results in disruption of the gene of interest (i.e. target sequence) e.g. via insertions or deletions.

According to one embodiment, the Cas protein (e.g. Cas9) has no nuclease activity (i.e. is catalytically inactive) and is said to be 'dead' (dCas9). Catalytically inactive Cas9 protein can be used in accordance with the present teachings to bind to DNA (based on guide RNA specificity), this typically results in blockage of RNA polymerase binding or elongation, leading to suppression of transcription. Thus, dCas9 can be used for transcription repression.

As mentioned, a tracrRNA sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracrRNA sequence to all or a portion of a tracr mate sequence that is operably linked to the guide sequence (e.g. crRNA).

In some embodiments, the tracr sequence has sufficient complementarity to a tracr mate sequence to hybridize and participate in formation of a CRISPR complex. As with the target sequence, a complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned.

Introducing CRISPR/Cas into a cell may be effected using one or more vectors driving expression of one or more elements of a CRISPR system such that expression of the elements of the CRISPR system direct formation of a CRISPR complex at one or more target sites. For example, a Cas enzyme, a guide sequence linked to a tracr-mate sequence, and a tracrRNA sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and one or more of the guide sequence, tracr mate sequence (optionally operably linked to the guide sequence), and a tracrRNA sequence embedded within one or more intron sequences (e.g. each in a different intron, two or more in at least one intron, or all in a single intron).

Alternatively, according to another embodiment of the present invention, upregulating gene expression is affected by administering to or expressing in the target cells (e.g. neuroglia cell or cardiac cell) an agent capable of down-regulating an expression of a microRNA.

Downregulation of microRNAs can be effected on the genomic and/or the transcript level using a variety of molecules which interfere with transcription and/or translation (e.g., RNA silencing agents, Ribozyme, DNAzyme and antisense), as discussed above.

Methods of downregulating microRNA expression are known in the art.

Nucleic acid agents that down-regulate miR activity include, but are not limited to, a target mimic, a micro-RNA resistant gene and a miRNA inhibitor.

The target mimic or micro-RNA resistant target is essentially complementary to the microRNA provided that one or more of following mismatches are allowed:

(a) a mismatch between the nucleotide at the 5' end of the microRNA and the corresponding nucleotide sequence in the target mimic or micro-RNA resistant target;

(b) a mismatch between any one of the nucleotides in position 1 to position 9 of the microRNA and the corresponding nucleotide sequence in the target mimic or micro-RNA resistant target; or (c) three mismatches between any one of the nucleotides in position 12 to position 21 of the microRNA and the corresponding nucleotide sequence in the target mimic or micro-RNA resistant target provided that there are no more than two consecutive mismatches.

The target mimic RNA is essentially similar to the target RNA modified to render it resistant to miRNA induced cleavage, e.g. by modifying the sequence thereof such that a variation is introduced in the nucleotide of the target sequence complementary to the nucleotides 10 or 11 of the miRNA resulting in a mismatch.

Alternatively, a microRNA-resistant target may be implemented. Thus, a silent mutation may be introduced in the microRNA binding site of the target gene so that the DNA and resulting RNA sequences are changed in a way that prevents microRNA binding, but the amino acid sequence of the protein is unchanged. Thus, a new sequence can be synthesized instead of the existing binding site, in which the DNA sequence is changed, resulting in lack of miRNA binding to its target.

According to a specific embodiment, the target mimic or micro-RNA resistant target is linked to the promoter naturally associated with the pre-miRNA recognizing the target gene and introduced into the cell. In this way, the miRNA target mimic or micro-RNA resistant target RNA will be expressed under the same circumstances as the miRNA and the target mimic or micro-RNA resistant target RNA will substitute for the non-target mimic/micro-RNA resistant target RNA degraded by the miRNA induced cleavage.

Non-functional miRNA alleles or miRNA resistant target genes may also be introduced by homologous recombination to substitute the miRNA encoding alleles or miRNA sensitive target genes.

Recombinant expression is effected by cloning the nucleic acid of interest (e.g., miRNA, target gene, silencing agent etc) into a nucleic acid expression construct under the expression of a suitable promoter.

In other embodiments of the invention, synthetic single stranded nucleic acids are used as miRNA inhibitors. A miRNA inhibitor is typically between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA.

In other embodiments of the invention, downregulation of microRNA can be effected using an antisense polynucleotide capable of specifically hybridizing with a microRNA or with a precursor thereof.

It will be appreciated that the microRNA antisense agents (e.g. anti-miRNA oligos) of the present invention may also comprise chemical modifications, molecular modifications and/or the addition of moieties, e.g. a cholesterol moiety (e.g. antagomirs).

The miRNA inhibitors may be contacted with the cells using transient transfection techniques miRNA inhibitors are commercially available from Companies such as Applied Biosystems.

Alternatively, the miRNA inhibitors may be part of an expression vector, as described herein above. In this case, cells may be transiently or stably transfected with the vector.

According to a specific embodiment, when the regulating comprises upregulating the expression of the Tph2 gene, the modulating comprises downregulating the miR-181 and/or miR-27.

According to another specific embodiment, there is provided a method of upregulating an expression of a gene selected from the group consisting of an adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3

(Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (*Drosophila*) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); glutamate receptor, ionotropic, kainate 3 (Grik3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), 5-hydroxytryptamine (serotonin) receptor 1A (Htr1a); inositol monophosphatase (IMPA1), kalirin, RhoGEF kinase (Kalrn); a potassium intermediate/small conductance calcium-activated channel, subfamily N, member 3 (KCNN3); karyopherin alpha 3 (importin alpha 4) (Kpna3); myelin transcription factor 1-like (Myt1l); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); solute carrier family 6 (neurotransmitter transporter, serotonin), member 4 (Slc6a4); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3) and zinc finger, BED domain containing 4 (Zbed4) in a neuroglia cell, the method comprising: (a) downregulating an activity or expression of a miR-135 or a precursor thereof in the neuroglia cell; and (b)

measuring an expression of the gene in the neuroglia cell, thereby upregulating the expression of the gene.

According to a specific embodiment, upregulating the expression of any of these genes is effected by a method other than downregulating an activity or expression of a microRNA (e.g. miR-135) or a precursor thereof. Thus, upregulating an activity or expression of a gene may be affected by overexpressing the gene or a target thereof.

According to one embodiment, downregulating the expression of a microRNA is effected by the use of a nucleic acid sequence which specifically binds and downregulates the expression of the microRNA. An exemplary nucleic acid sequence which may be used in accordance with the present invention may be purchased from any manufacturer, as for example, from Genecopoeia (miArrest, microRNA vector based inhibitors).

Thus, according to another embodiment, there is provide an isolated polynucleotide comprising a nucleic acid sequence for downregulating an expression of miR-181, miR-182, miR-26, miR-27, miR-135, miR-335, miR-15 and miR-19 or a precursor thereof.

Exemplary polynucleotides which may be used in accordance with the present invention to downregulate the expression of miR-181 include, but are not limited to, those set in SEQ ID NOs: 134-137 and SEQ ID NOs: 154-157.

Exemplary polynucleotides which may be used in accordance with the present invention to downregulate the expression of miR-182 include, but are not limited to, those set in SEQ ID NOs: 138-141 and SEQ ID NO: 147.

Exemplary polynucleotides which may be used in accordance with the present invention to downregulate the expression of miR-26 include, but are not limited to, those set in SEQ ID NOs: 126-129 and SEQ ID NOs: 145-146.

Exemplary polynucleotides which may be used in accordance with the present invention to downregulate the expression of miR-27 include, but are not limited to, those set in SEQ ID NOs: 130-133 and SEQ ID NOs: 152-153.

Exemplary polynucleotides which may be used in accordance with the present invention to downregulate the expression of miR-135 include, but are not limited to, those set in SEQ ID NOs: 110-113 and SEQ ID NOs: 142-143.

Exemplary polynucleotides which may be used in accordance with the present invention to downregulate the expression of miR-335 include, but are not limited to, those set in SEQ ID NOs: 114-117 and SEQ ID NO: 144.

Exemplary polynucleotides which may be used in accordance with the present invention to downregulate the expression of miR-15 include, but are not limited to, those set in SEQ ID NOs: 118-121 and SEQ ID NOs: 150-151.

Exemplary polynucleotides which may be used in accordance with the present invention to downregulate the expression of miR-19 include, but are not limited to, those set in SEQ ID NOs: 122-125 and SEQ ID NOs: 148-149.

Such nucleic acid sequences may be further comprised in an expression vector as described in further detail hereinabove.

The present invention further contemplates assessing the expression of the target gene (e.g. transcript or polypeptide) following downregulating or upregulating the microRNA level in the cell (e.g. neuroglia cell or cardiac cell).

Thus, the presence and/or level of a target gene (e.g. Slc6a4, Htr1a, MaoA, Adrb1, Adrb2, CRH type 1 receptor, CB1, FKBP5, Tph2, Grm1, Grik3, Grm5, Grik2, Grm7, Gria2, Dscam, L1cam, Tsnax, Sgk1, Stx1a, Adcyap1, Adcyap1r1, Adra2a, Ank3, Arc, Arhgap6, Atf3, Bace1, Cacna1d, Cadm3, Cplx1, Cplx2, Csmd1, Csnk1g1, Dcx, Diras2, Dlg2, Elk1, Frk, Fut9, Gabrb2, Gata3, Ghsr, Gpr3, Gria3, Grk5, Gsk3b, Hcn1, Hcn2, Impa1, Kalrn, Kcnn3, Kpna3, Myt1l, Ncoa2, Ndrg4, Nos1ap, Nr3c2, Ntng1, Nucks1, Pde1a, Pde4a, Pde8b, Plcb1, Prlr, Rab1b, Rap2a, Rorb, Sirt1, Slc12a6, Slc5a7, Sp1, Sv2b, Syne1, Syt1, Syt2, Syt3, Tgfbr2, Thrb, Trpc6, Vamp2, Wnt3 and/or Zbed4) nucleic acid sequence (e.g. transcript) can be determined using an isolated polynucleotide (e.g., a polynucleotide probe, an oligonucleotide probe/primer) capable of hybridizing to a target gene's nucleic acid sequence (e.g. Slc6a4 as set forth in e.g. NM 001045.4 or a portion thereof; Htr1a as set forth in e.g. NM_000524.3 or a portion thereof; MaoA as set forth in e.g. NM_000240.3 or NM_001270458.1 or a portion thereof; Adrb1 as set forth in e.g. NM_000684.2 or a portion thereof; Adrb2 as set forth in e.g. NM_000024.5 or a portion thereof; CRH type 1 receptor as set forth in e.g. NM_001145146.1, NM_001145147.1 or a portion thereof;

CB1 as set forth in e.g. NM_001160226.1, NM_033181.3 or a portion thereof; FKBP5 as set forth in e.g. NM_001145775.1, NM_001145777.1 or a portion thereof; Tph2 as set forth in e.g. NM_173353.3 or a portion thereof; Grm1 as set forth in e.g. NM_000838.3, NM_001114329.1 or a portion thereof; Grik3 as set forth in e.g. NM_000831.3 or a portion thereof; Grm5 as set forth in e.g. NM_000842.3, NM_001143831.2 or a portion thereof; Grik2 as set forth in e.g. NM_001166247.1, NM_021956.4 or a portion thereof; Grm7 as set forth in e.g. NM_000844.3, NM_181874.2 or a portion thereof; Gria2 as set forth in e.g. NM_000826.3, NM_001083619.1 or a portion thereof; Dscam as set forth in e.g. NM_001389.3 or a portion thereof; L1cam as set forth in e.g. NM_000425.3, NM_001143963.1, NM_024003.2 or a portion thereof; Tsnax as set forth in e.g. NM_005999.2 or a portion thereof; Sgk1 as set forth in e.g. NM_001143676.1, NM_001143677.1, NM_001143678.1 or a portion thereof and/or Stx1a as set forth in e.g. NM_001165903.1, NM_004603.3 or a portion thereof, Adcyap1 as set forth in e.g. NM_001117.4, NM_001099733.1 or a portion thereof, Adcyap1r1 as set forth in e.g. NM_001118.4, NM_001199635.1, NM_001199636.1, NM_001199637.1 or a portion thereof, Adra2a as set forth in e.g. NM_000681.3 or a portion thereof, ANK3 as set forth in e.g. NM_001149.3, NM_001204403.1, NM_001204404.1 or NM_020987.3, or a portion thereof, Arc as set forth in e.g. NM_015193.4 or a portion thereof, Arhgap6 as set forth in e.g. NM_001287242.1, NM_006125.2, NM_013423.2, NM_013427.2 or a portion thereof, Atf3 as set forth in e.g. NM_001030287.3, NM_001040619.2, NM_001206484.2, NM_001206486.2, NM_001206488.2, NM_001674.3 or a portion thereof, Bace1 as set forth in e.g. NM_001207048.1, NM_001207049.1, NM_012104.4, NM_138971.3, NM_138972.3, NM_138973.3 or a portion thereof, Cacna1d as set forth in e.g. NM_000720.3, NM_001128839.2, NM_001128840.2 or a portion thereof, Cadm3 as set forth in e.g. NM_001127173.1, NM_021189.3 or a portion thereof, Cplx1 as set forth in e.g. NM_006651.3 or a portion thereof, Cplx2 as set forth in e.g. NM_001008220.1, NM_006650.3 or a portion thereof, Csmd1 as set forth in e.g. NM_033225.5 or a portion thereof, Csnk1g1 as set forth in e.g. NM_022048.3 or a portion thereof, Dcx as set forth in e.g. NM_000555.3, NM_001195553.1, NM_178151.2, NM_178152.2, NM_178153.2 or a portion thereof, Diras2 as set forth in e.g. NM_017594.3 or a portion thereof, Dlg2 as set forth in e.g. NM_001142699.1, NM_001142700.1, NM_001142702.1, NM_001206769.1, NM_001364.3 or a portion thereof, Elk1 as set forth in e.g. NM_001114123.2, NM_001257168.1, NM_005229.4 or a portion thereof, Frk as set forth in e.g. NM_002031.2 or a portion thereof, Fut9 as set forth in e.g. NM_006581.3 or a portion thereof, Gabrb2 as set forth in e.g. NM_000813.2, NM_021911.2 or a portion thereof, Gata3 as set forth in e.g. NM_001002295.1, NM_002051.2 or a portion thereof, Ghsr as set forth in e.g. NM_004122.2, NM_198407.2 or a portion thereof, Gpr3 as set forth in e.g. NM_005281.3 or a portion thereof, GRIA3 as set forth in e.g. NM_000828.4, NM_001256743.1, NM_007325.4 or a portion thereof, Grk5 as set forth in e.g. NM_005308.2 or a portion thereof, GSK3B as set forth in e.g. NM_001146156.1, NM_002093.3 or a portion thereof, Hcn1 as set forth in e.g. NM_021072.3 or a portion thereof, Hcn2 as set forth in e.g. NM_001194.3 or a portion thereof, IMPA1 as set forth in e.g. NM_001144878.1, NM_001144879.1, NM_005536.3 or a portion thereof, Kalrn as set forth in e.g. NM_001024660.3, NM_003947.4, NM_007064.3, or a portion thereof, KCNN3 as set forth in e.g. NM_001204087.1, NM_002249.5, NM_170782.2 or a portion thereof, Kpna3 as set forth in e.g. NM_002267.3 or a portion thereof, Myt1l as set forth in e.g. NM_015025.2 or a portion thereof, Ncoa2 as set forth in e.g. NM_006540.2 or a portion thereof, Ndrg4 as set forth in e.g. NM_020465.3, NM_022910.3, NM_001130487.1, NM_001242836.1 or a portion thereof, NOS1AP as set forth in e.g. NM_001126060.1, NM_001164757.1, NM_014697.2 or a portion thereof, Nr3c2 as set forth in e.g. NM_000901.4, NM_001166104.1 or a portion thereof, Ntng1 as set forth in e.g. NM_001113226.1, NM_001113228.1, NM_014917.2 or a portion thereof, Nucks1 as set forth in e.g. NM_022731.4 or a portion thereof, Pde1a as set forth in e.g. NM_005019.4, NM_001003683.2, NM_001258312.1 or a portion thereof, Pde4a as set forth in e.g. NM_001111307.1, NM_001111308.1, NM_001111309.1 or a portion thereof, Pde8b as set forth in e.g. NM_003719.3, NM_001029851.2, NM_001029852.2 or a portion thereof, Plcb1 as set forth in e.g. NM_015192.3, NM_182734.2 or a portion thereof, Prlr as set forth in e.g. NM_000949.5, NM_001204315.1, NM_001204316.1 or a portion thereof, Rab1b as set forth in e.g. NM_030981.2 or a portion thereof, Rap2a as set forth in e.g. NM_021033.6 or a portion thereof, Rorb as set forth in e.g. NM_006914.3 or a portion thereof, Sirt1 as set forth in e.g. NM_001142498.1, NM_012238.4 or a portion thereof, Slc12a6 as set forth in e.g. NM_133647.1, NM_005135.2, NM_001042495.1 or a portion thereof, Slc5a7 as set forth in e.g. NM_021815.2 or a portion thereof, Sp1 as set forth in e.g. NM_138473.2, NM_003109.1, NM_001251825.1 or a portion thereof, Sv2b as set forth in e.g. NM_001167580.1, NM_014848.4 or a portion thereof, Syne1 as set forth in e.g. NM_033071.3, NM_182961.3 or a portion thereof, Syt1 as set forth in e.g. NM_001135805.1, NM_001135806.1, NM_005639.2 or a portion thereof, Syt2 as set forth in e.g. NM_001136504.1, NM_177402.4 or a portion thereof, Syt3 as set forth in e.g. NM_001160328.1, NM_001160329.1, NM_032298.2 or a portion thereof, Tgfbr2 as set forth in e.g. NM_001024847.2, NM_003242.5 or a portion thereof, Thrb as set forth in e.g. NM_000461.4, NM_001128176.2, NM_001128177.1, NM_001252634.1 or a portion thereof, Trpc6 as set forth in e.g. NM_004621.5 or a portion thereof, Vamp2 as set forth in e.g. NM_014232.2 or a portion thereof, Wnt3 as set forth in e.g. NM_030753.4 or a portion thereof and/or Zbed4 as set forth in e.g. NM_014838.2 or a portion thereof). Such a polynucleotide can be at any size, such as a short polynucleotide (e.g., of 15-200 bases), and intermediate polynucleotide (e.g., 200-2000 bases) or a long polynucleotide larger of 2000 bases.

The isolated polynucleotide probe used by the present invention can be any directly or indirectly labeled RNA molecule (e.g., RNA oligonucleotide, an in vitro transcribed RNA molecule), DNA molecule (e.g., oligonucleotide, cDNA molecule, genomic molecule) and/or an analogue thereof [e.g., peptide nucleic acid (PNA)] which is specific to the target gene RNA transcript of the present invention.

Oligonucleotides designed according to the teachings of the present invention can be generated according to any oligonucleotide synthesis method known in the art, as described in detail hereinabove.

The oligonucleotide of the present invention is of at least 17, at least 18, at least 19, at least 20, at least 22, at least 25, at least 30 or at least 40, bases specifically hybridizable with sequence alterations described hereinabove.

The oligonucleotides of the present invention may comprise heterocylic nucleosides consisting of purines and the pyrimidines bases, bonded in a 3' to 5' phosphodiester linkage.

Preferably used oligonucleotides are those modified in a backbone (e.g. sugar-phosphate backbone), internucleoside linkages and/or bases, as is broadly described hereinabove.

The isolated polynucleotide used by the present invention can be labeled either directly or indirectly using a tag or label molecule. Such labels can be, for example, fluorescent molecules (e.g., fluorescein or Texas Red), radioactive molecule (e.g., $^{32}$P-γ-ATP or $^{32}$P-α-ATP) and chromogenic substrates [e.g., Fast Red, BCIP/INT, available from (AB-CAM, Cambridge, Mass.)]. Direct labeling can be achieved by covalently conjugating a label molecule to the polynucleotide (e.g., using solid-phase synthesis) or by incorporation via polymerization (e.g., using an in vitro transcription reaction or random-primed labeling). Indirect labeling can be achieved by covalently conjugating or incorporating to the polynucleotide a non-labeled tag molecule (e.g., Digoxigenin or biotin) and subsequently subjecting the polynucleotide to a labeled molecule (e.g., anti-Digoxigenin antibody or streptavidin) capable of specifically recognizing the non-labeled tag.

The above-described polynucleotides can be employed in a variety of RNA detection methods such as Northern blot analysis, reverse-transcribed PCR (RT-PCR) [e.g., a semi-quantitative RT-PCR, quantitative RT-PCR using e.g., the Light Cycler™ (Roche)], RNA in situ hybridization (RNA-ISH), in situ RT-PCR stain [e.g., as described in Nuovo G J, et al. 1993, Intracellular localization of polymerase chain reaction (PCR)-amplified hepatitis C cDNA. Am J Surg Pathol. 17: 683-90, and Komminoth P, et al. 1994, Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract., 190: 1017-25] and oligonucleotide microarray analysis [e.g., using the Affymetrix microarray (Affymetrix®, Santa Clara, Calif.)].

The presence and/or level of the target gene (e.g. Slc6a4, Htr1a, MaoA, Adrb1, Adrb2, CRH type 1 receptor, CB1, FKBP5, Tph2, Grm1, Grik3, Grm5, Grik2, Grm7, Gria2, Dscam, L1cam, Tsnax, Sgk, 1 Stx1a, Adcyap1, Adcyap1r1, Adra2a, Ank3, Arc, Arhgap6, Atf3, Bace1, Cacna1d, Cadm3, Cplx1, Cplx2, Csmd1, Csnk1g1, Dcx, Diras2, Dlg2, Elk1, Frk, Fut9, Gabrb2, Gata3, Ghsr, Gpr3, Gria3, Grk5, Gsk3b, Hcn1, Hcn2, Impa1, Kalrn, Kcnn3, Kpna3, Myt11, Ncoa2, Ndrg4, Nos1ap, Nr3c2, Ntng1, Nucks1, Pde1a, Pde4a, Pde8b, Plcb1, Prlr, Rab1b, Rap2a, Rorb, Sirt1, Slc12a6, Slc5a7, Sp1, Sv2b, Syne1, Syt1, Syt2, Syt3, Tgfbr2, Thrb, Trpc6, Vamp2, Wnt3 and/or Zbed4) amino acid sequence (e.g. protein) can be determined using, for example, a specific antibody via the formation of an immunocomplex [i.e., a complex formed between the target gene antigen (an amino acid sequence) present in the biological sample and the specific antibody].

The immunocomplex of the present invention can be formed at a variety of temperatures, salt concentration and pH values which may vary depending on the method and the biological sample used and those of skills in the art are capable of adjusting the conditions suitable for the formation of each immunocomplex.

The term "antibody" as used in this invention includes intact molecules as well as functional fragments thereof, such as Fab, F(ab')2, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Exemplary antibodies which may be used in accordance with the present invention include e.g. anti-Slc6a4 antibody available e.g. from Abnova Corporation, Abgent and MBL International; anti-Htr1a antibody available e.g. from Novus Biologicals, Acris Antibodies GmbH and Abnova Corporation; anti-MaoA antibody available e.g. from Abnova Corporation, Proteintech Group, Inc. and Abgent; anti-Adrb1 antibody available e.g. from Biorbyt, Abgent and antibodies-online; anti-Adrb2 antibody available e.g. from Tocris Bioscience, Abnova Corporation and antibodies-online; anti-CRH type 1 receptor antibody available e.g. from MyBioSource(dot)com, Abcam and Novus Biologicals; anti-CB 1 antibody available e.g. from Santa Cruz Biotechnology, Inc. and Epitomics, Inc.; anti-FKBP5 antibody available e.g. from BD Biosciences and Abnova Corporation; anti-Tph2 antibody available e.g. from Novus Biologicals and Acris Antibodies GmbH; anti-Grm1 antibody available e.g. from Novus Biologicals and Biorbyt; anti-Grik3 antibody available e.g. from Acris Antibodies GmbH and Atlas Antibodies; anti-Grm5 antibody available e.g. from Biorbyt and Acris Antibodies GmbH; anti-Grik2 antibody available e.g. from Proteintech Group, Inc., Aviva Systems Biology and Abgent; anti-Grm7 antibody available e.g. from Acris Antibodies GmbH and antibodies-online; anti-Gria2 antibody available e.g. from Proteintech Group, Inc. and Abnova Corporation; anti-Dscam antibody available e.g. from Novus Biologicals and R&D Systems; anti-L1cam antibody available e.g. from GeneTex, Novus Biologicals and Acris Antibodies GmbH; anti-Tsnax antibody available e.g. from BD Biosciences and GenWay Biotech, Inc.; anti-Sgk1 antibody available e.g. from Epitomics, Inc. and Acris Antibodies GmbH; and/or anti-Stx1a antibody available e.g. from MBL International and Spring Bioscience.

Various methods can be used to detect the formation of the immunocomplex of the present invention and those of skills in the art are capable of determining which method is suitable for each immunocomplex and/or the type of cells used for diagnosis.

The specific antibody (e.g. anti-Slc6a4 antibody; anti-Htr1a antibody; anti-MaoA antibody; anti-Adrb1 antibody; anti-Adrb2 antibody; anti-CRH type 1 receptor antibody; anti-CB1 antibody; anti-FKBP5 antibody; anti-Tph2 antibody; anti-Grm1 antibody; anti-Grik3 antibody; anti-Grm5 antibody; anti-Grik2 antibody; anti-Grm7 antibody; anti-Gria2 antibody; anti-Dscam antibody; anti-L1cam antibody; anti-Tsnax antibody; anti-Sgk1 antibody and/or anti-Stx1a antibody) used in the immunocomplex of the present invention can be labeled using methods known in the art. It will be appreciated that the labeled antibodies can be either primary antibodies (i.e., which bind to the specific antigen, e.g., a target gene-specific antigen) or secondary antibodies (e.g., labeled goat anti rabbit antibodies, labeled mouse anti human antibody) which bind to the primary antibodies. The antibody can be directly conjugated to a label or can be conjugated to an enzyme.

Antibodies of the present invention can be fluorescently labeled (using a fluorescent dye conjugated to an antibody), radiolabeled (using radiolabeled e.g., $^{125}$I, antibodies), or conjugated to an enzyme (e.g., horseradish peroxidase or alkaline phosphatase) and used along with a chromogenic substrate to produce a colorimetric reaction. The chromogenic substrates utilized by the enzyme-conjugated antibodies of the present invention include, but are not limited to, AEC, Fast red, ELF-97 substrate [2-(5'-chloro-2-phosphoryloxyphenyl)-6-chloro-4(3H)-quinazolinone], p-nitrophenyl phosphate (PNPP), phenolphthalein diphosphate, and ELF 39-phosphate, BCIP/INT, Vector Red (VR), salmon and magenta phosphate (Avivi C., et al., 1994, J Histochem. Cytochem. 1994; 42: 551-4) for alkaline phosphatase enzyme and Nova Red, diaminobenzidine (DAB), Vector® SG substrate, luminol-based chemiluminescent substrate for the peroxidase enzyme. These enzymatic substrates are commercially available from Sigma (St Louis, Mo., USA), Molecular Probes Inc. (Eugene, Oreg., USA), Vector Laboratories Inc. (Burlingame, Calif., USA), Zymed Laboratories Inc. (San Francisco, Calif., USA), Dako Cytomation (Denmark).

Detection of the immunocomplex in a biological sample, such as blood sample or serum, which may contain soluble (e.g., secreted, shedded) target gene polypeptide can be performed using fluorescence activated cell sorting (FACS), enzyme linked immunosorbent assay (ELISA), Western blot and radio-immunoassay (RIA) analyses, immunoprecipitation (IP) or by a molecular weight-based approach.

For Western blot the proteins are extracted from a cell sample and are subjected to electrophoresis (e.g., SDS-PAGE) and blotting to a membrane (e.g., nylon or PVDF). The membrane is then interacted with a specific antibody (e.g. anti-Slc6a4 antibody; anti-Htr1a antibody; anti-MaoA antibody; anti-Adrb1 antibody; anti-Adrb2 antibody; anti-CRH type 1 receptor antibody; anti-CB1 antibody; anti-FKBP5 antibody; anti-Tph2 antibody; anti-Grm1 antibody; anti-Grik3 antibody; anti-Grm5 antibody; anti-Grik2 antibody; anti-Grm7 antibody; anti-Gria2 antibody; anti-Dscam antibody; anti-L1cam antibody; anti-Tsnax antibody; anti-Sgk1 antibody and/or anti-Stx1a antibody) which can be either directly labeled or further subjected to a secondary labeled antibody. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

In case the concentration of the antigen in the biological sample is low, detection of the antigen (target gene amino acid sequence) can be performed by immunoprecipitation (IP). For immunoprecipitation analysis the specific antibody (e.g. anti-Slc6a4 antibody; anti-Htr1a antibody; anti-MaoA antibody; anti-Adrb1 antibody; anti-Adrb2 antibody; anti-CRH type 1 receptor antibody; anti-CB1 antibody; anti-FKBP5 antibody; anti-Tph2 antibody; anti-Grm1 antibody; anti-Grik3 antibody; anti-Grm5 antibody; anti-Grik2 antibody; anti-Grm7 antibody; anti-Gria2 antibody; anti-Dscam antibody; anti-L1cam antibody; anti-Tsnax antibody; anti-Sgk1 antibody and/or anti-Stx1a antibody) may directly interact with a sample (e.g., cell lysate) including the target gene polypeptide and the formed complex can be further detected using a secondary antibody conjugated to beads (e.g., if the specific antibody is a mouse monoclonal antibody, the secondary antibody may be an anti-mouse antibody conjugated to e.g., Sepharose beads). The beads can be then precipitated by centrifugation, following which the precipitated proteins (e.g., target gene polypeptide and specific antibodies) can be detached from the beads (e.g., using denaturation at 95° C.) and further subjected to Western blot analysis using antibodies. Alternatively, the specific antibody and the beads-conjugated secondary antibody may be added to the biological sample containing the antigen (target gene polypeptide) to thereby form an immunocomplex. Alternatively, if the target gene polypeptide is a highly glycosilated protein, it can be also precipitated using a substrate capable of binding glycosilated polypeptides such Concavalin A (GE Healthcare Bio-Sciences, Uppsala, Sweden) which may be also conjugated to beads, followed by Western blot analysis specific antibodies as described above.

FACS analysis enables the detection of antigens present on cell membranes. Briefly, specific antibodies, as described above, are linked to fluorophores and detection is performed by means of a cell sorting machine which reads the wavelength of light emitted from each cell as it passes through a light beam. This method may employ two or more antibodies simultaneously.

The presence and/or level of target gene polypeptide can be also determined using ELISA. Briefly, a sample containing the target gene antigen is fixed to a surface such as a well of a microtiter plate. An antigen specific antibody (e.g. anti-Slc6a4 antibody; anti-Htr1a antibody; anti-MaoA antibody; anti-Adrb1 antibody; anti-Adrb2 antibody; anti-CRH type 1 receptor antibody; anti-CB1 antibody; anti-FKBP5 antibody; anti-Tph2 antibody; anti-Grm1 antibody; anti-Grik3 antibody; anti-Grm5 antibody; anti-Grik2 antibody; anti-Grm7 antibody; anti-Gria2 antibody; anti-Dscam antibody; anti-L1cam antibody; anti-Tsnax antibody; anti-Sgk1 antibody and/or anti-Stx1a antibody) coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

The presence and/or level of a target gene polypeptide can be also determined using radio-immunoassay (RIA). In one version, this method involves precipitation of the desired antigen (target gene polypeptide) with a specific antibody and radiolabeled antibody binding protein (e.g., protein A labeled with $I^{125}$) immobilized on a precipitable carrier such as agarose beads. The number of counts in the precipitated pellet is proportional to the amount of antigen.

In an alternate version of the RIA, a labeled antigen and an unlabelled antibody binding protein are employed. A sample containing an unknown amount of antigen is added in varying amounts. The decrease in precipitated counts from the labeled antigen is proportional to the amount of antigen in the added sample.

The presence and/or level of a target gene polypeptide can be also determined using molecular weight-based approach. Since the immunocomplex exhibits a higher molecular weight than its components, methods capable of detecting such a change in the molecular weight can be also employed. For example, the immunocomplex can be detected by a gel retardation assay. Briefly, a non-denaturing acrylamide gel is loaded with samples. A shift in the size (molecular weight) of the protein product as compared with its components is indicative of the presence of an immunocomplex. Such a shift to a higher molecular weight can be viewed using a non-specific protein staining such as silver stain or Commassie blue stain.

In situ detection of the target gene polypeptide in a biological sample such as a tissue section (e.g., paraffin embedded or cryosection) can be performed using immunological staining methods which detects the binding of antibodies on the cells in situ. Examples of immunological staining procedures include but are not limited to, fluorescently labeled immunohistochemistry (using a fluorescent dye conjugated to an antibody), radiolabeled immunohistochemistry (using radiolabeled e.g., $^{125}I$, antibodies), and immunocytochemistry [using an enzyme (e.g., horseradish peroxidase or alkaline phosphatase) and a chromogenic substrate to produce a colorimetric reaction]. It will be appreciated that the enzymes conjugated to antibodies can utilize various chromogenic substrates as described hereinabove.

Preferably, the immunological staining used by the present invention is immunohistochemistry and/or immunocytochemistry.

Immunological staining is preferably followed by counterstaining the cells using a dye, which binds to non-stained cell compartments. For example, if the labeled antibody binds to antigens present on the cell cytoplasm, a nuclear stain (e.g., Hematoxylin-Eosin stain) is an appropriate counterstaining.

According to one embodiment, the method comprises measuring an expression of the Tph2 gene following the downregulating of the miR-181 and/or the miR-27.

According to one embodiment, the method comprises measuring an expression of the Slc6a4 gene following upregulating the miR-135 and/or miR-335.

According to one embodiment, the method comprises measuring an expression of the Htr1a gene following upregulating the miR-135, miR-335, miR-181, miR-182 and/or miR-26.

According to one embodiment, the method comprises measuring an expression of the MaoA gene following upregulating the upregulating the miR-27.

According to one embodiment, the method comprises measuring an expression of the Adrb1 gene following upregulating the miR-19.

According to one embodiment, the method comprises measuring an expression of the CB1 gene following upregulating the CB1.

According to one embodiment, the method comprises measuring an expression of the CRH type 1 receptor gene following upregulating the miR-15.

According to one embodiment, the method comprises measuring an expression of the FKBP5 gene following upregulating the miR-15.

As mentioned hereinabove, the present inventors have further realized that the level of miR-135 is significantly down-regulated in blood samples of human subjects suffering from mood disorders including depression, anxiety, bipolar disorder and stress (as compared to healthy human subjects) and is upregulated in blood samples of human subjects being treated with an anti-depressant therapy (as compared to the same subject prior to initiation of treatment or untreated human subjects).

Thus, there is provided a method of diagnosing a mood disorder in a human subject in need thereof, the method comprising measuring an expression level of a miR-135 in a biological sample of the human subject, wherein a lower expression level of the miR-135 as compared to that in a biological sample of a healthy subject is indicative of the mood disorder.

Any mood disorder may be diagnosed in accordance with the present invention, including but not limited to, a bipolar disorder, a depression, a major depression, an anxiety, a stress, a fatigue, an impaired cognitive function, a panic attack, a compulsive behavior, an addiction, a social phobia, a schizophrenia, a sleep disorder and an eating disorder (e.g. Anorexia nervosa, Bulimia nervosa, Eating disorders not otherwise specified, Binge eating disorder (BED) or Pica eating disorder).

Measuring the expression level of miR-135 (e.g. miR-135a) is typically effected in a biological sample.

According to a specific embodiment, the term "biological sample" refers to body fluids such as fresh whole blood, fractionated whole blood, blood plasma, blood serum, cerebrospinal fluid (CSF), urine, lymph fluids, and various external secretions of the respiratory, intestinal and genitourinary tracts, tears, saliva, milk as well as white blood cells including mononuclear cells (e.g. lymphocytes, monocytes, dendritic cells).

Typically, whole blood and fractionated whole blood (i.e. blood sample fractionated, e.g. by centrifugation, into separate components) comprises all of the blood components including blood plasma, leukocytes, platelets and erythrocytes. Blood serum is the blood component that is neither a blood cell nor a clotting factor, it is the blood plasma with the fibrinogens removed. Serum includes proteins not used in blood clotting (coagulation) and the electrolytes, antibodies, antigens, hormones, and any exogenous substances (e.g., drugs and microorganisms). Furthermore, blood plasma comprises all of the components of the serum along with clotting factors.

According to a specific embodiment, the biological sample is a whole blood sample.

According to a specific embodiment, the biological sample is a serum or plasma sample.

According to a specific embodiment, the biological sample is a mononuclear cell sample).

According to a specific embodiment, the cell sample is devoid of erythrocytes.

According to a specific embodiment the biological sample is at least 90% white blood cells (e.g., at least 90% mononuclear cells).

Measuring an expression level of a miR-135 may be carried out by any method known to one of ordinary skill in the art, as for example, by northern blot analysis, RNase protection assay, and PCR (e.g. real-time PCR).

As mentioned, a lower expression level of the miR-135 as compared to that in a biological sample of a healthy human subject (i.e. a subject not being affected by a mood disorder) is indicative of the mood disorder.

According to one embodiment, a lower expression level of the miR-135 as compared to that in a biological sample of a healthy human subject is statistically significant.

The expression level of miR-135 in a human subject having a mood disorder may be lower by about 5%, 10%, 15%, 20%, 25%, 30%, 40%, 50%, 60%, 70%, 80%, 90% or 100% as compared to that of a healthy human subject.

Diagnosis can be further assessed and established using Gold-standard methods. Typically, at least one of a full patient medical history, physical assessment, and thorough evaluation of symptoms helps determine the disorder (mood disorder including depression or bipolar disorder). Standardized questionnaires can be helpful for diagnosis of depression, such as the Hamilton Rating Scale for Depression, and the Beck Depression Inventory.

Diagnosis of bipolar disorder can be further assessed using typical criteria. The most widely used criteria for diagnosing bipolar disorder are from the American Psychiatric Association's Diagnostic and Statistical Manual of Mental Disorders (e.g. version DSM-IV-TR), and the World Health Organization's International Statistical Classification of Diseases and Related Health Problems (e.g. ICD-10).

Furthermore, tests may be carried out to exclude medical illnesses such as hypo- or hyperthyroidism, metabolic disturbance, a systemic infection or chronic disease, and syphilis or HIV infection. An EEG may be used to exclude epilepsy, and a CT scan of the head to exclude brain lesions.

The present inventors have further shown that blood levels of miR-135 (e.g. miR-135a) are upregulated in human subjects following an antidepressant therapy (see Example 16 of the Examples section which follows).

Thus, according to another embodiment of the present invention, there is provided a method of monitoring treatment of an anti-depressant drug or a medicament for the treatment of a mood disorder (e.g. bipolar disorder), the method comprising: (a) treating a human subject in need thereof with an anti-depressant drug or a medicament for the treatment of a mood disorder; and (b) measuring an expression level of a miR-135 in a biological sample of the human subject prior to and following the treatment, wherein a higher expression level of the miR-135 following the treatment by the anti-depressant drug or the medicament for the treatment of the mood disorder as compared to the expression level of the miR-135 prior to the treatment by the anti-depressant drug or the medicament for the treatment of the mood disorder is indicative of the efficient treatment.

According to one embodiment, the method further comprises (c) treating the human subject when a higher expression level of the miR-135 is observed in step (b) to improve treatment.

The biological sample (e.g. fresh whole blood, fractionated whole blood, blood plasma or blood serum) is typically obtained from the human subject following to treatment with an anti-depressant drug or with a medicament for the treatment of a mood disorder, however, a blood sample may also be obtained from the subject prior to treatment for further comparison of miR-135 levels.

According to a specific embodiment, miR-135 comprises miR-135a.

As used herein, the term "anti-depressant drug" refers to any medication used to alleviate mood disorders, such as major depression and dysthymia, and anxiety disorders, such as social anxiety disorder. Exemplary anti-depressant drugs include, but are not limited to, Selective serotonin reuptake inhibitors (SSRIs, such as Citalopram, Escitalopram, Fluoxetine, Fluvoxamine, Paroxetine and Sertraline); Serotonin-norepinephrine reuptake inhibitors (SNRIs, such as Desvenlafaxine, Duloxetine, Milnacipran and Venlafaxine); Noradrenergic and specific serotonergic antidepressants (such as Mianserin and Mirtazapine); Norepinephrine (noradrenaline) reuptake inhibitors (NRIs, such as Atomoxetine, Mazindol, Reboxetine and Viloxazine); Norepinephrine-dopamine reuptake inhibitors (such as Bupropion); Selective serotonin reuptake enhancers (such as Tianeptine); Norepinephrine-dopamine disinhibitors (NDDIs such as Agomelatine); Tricyclic antidepressants (including Tertiary amine tricyclic antidepressants and Secondary amine tricyclic antidepressants); and Monoamine oxidase inhibitor (MAOIs).

According to one embodiment, the anti-depressant drug comprises selective serotonin reuptake inhibitors (SSRI), tricyclic antidepressants or noradrenaline reuptake inhibitors (NRI).

According to a specific embodiment, the anti-depressant drug comprises selective serotonin reuptake inhibitors (SSRI).

As used herein, the term "a medicament for the treatment of a mood disorder" refers to any medicament or any combination of medicaments used for the treatment of a mood disorder including bipolar disorder. Exemplary medicaments include, but not limited to, lithium (e.g. Lithium carbonate, Lithium citrate, Lithium sulfate), antipsychotic medicaments (e.g. typical antipsychotics and atypical antipsychotics, as detailed hereinabove) and mood stabilizer medicaments (e.g. Valproic acid (VPA, Valproate), minerals, anticonvulsants, antipsychotics, as detailed hereinabove).

Other treatment options which are encompassed by the present methods (alone or in combination with the above) include non-pharmaceutical therapeutic strategies, including but not limited to, clinical psychology, electroconvulsive therapy, involuntary commitment, light therapy, psychotherapy, transcranial magnetic stimulation and cognitive behavioral therapy.

An efficient anti-depressant/mood disorder treatment is determined when a significantly higher expression level of the miR-135 is obtained following to the treatment as compared to the miR-135 expression level prior to the treatment.

The expression level of miR-135 in a subject following treatment may be higher by about 5%, 10%, 15%, 20%, 25%, 30%, 40%, 50%, 60%, 70%, 80%, 90% or 100% as compared to that of the subject prior to the anti-depressant or mood disorder treatment.

Monitoring treatment may also be effected by assessing the patient's well being, and additionally or alternatively, by subjecting the subject to behavioral tests, MRI or any other method known to one of skill in the art.

It is expected that during the life of a patent maturing from this application many relevant inhibitors of miRNAs or alternatively miRNA modifications will be developed and the scope of the term microRNAs is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differential Expression of miRs in Serotonin Neurons

Materials and Experimental Procedures
5HT Neurons MicroRNA Microarray
Hindbrain cells from embryonic day 12 of ePET YFP mice were cultured and sorted to distinguish 5HT neurons from surrounding non-5HT neurons. Total RNA including the miRNA population was purified, labeled and hybridized on Agilent Mouse miRNA Microarray (Agilent Tech, Mississauga, ON, Canada) design number 021828 based on Sanger miRBase release 12.0 according to manufactures instructions. The microarrays were scanned and the data was extracted and processed using the Feature Extraction Software (Agilent Technologies). Following scanning, intensity output data of the GeneView.txt files was analyzed to quantify differential relative expression of microRNAs using the Partek® Genomics Suite (Partek Inc., St. Louis, Mo.). The data was log 2 transformed, quantile normalized and filtered according to the flag "gIsGeneDetected" in the GeneView file. Of 666 murine miRs, 198 remained for further analysis upon this filtering step. Differentially expressed miRs were then identified by using a threshold of a 1.5 fold change with significance according to ANOVA. Contrasts were calculated within the ANOVA test. The Benjamini and Hochberg correction was used for false-positive reduction (multiple testing correction).

Cloning of 3' UTRs into Psicheck2 Luciferase Expression Plasmid

3'UTR sequences of Slc6a4, Htr1a, MaoA and Tph2 were PCR amplified from mouse genomic DNA, or total brain cDNA. 3'UTR PCR fragments were ligated into pGEM-T easy vector (Promega) according to the manufacturer's guidelines, and further subcloned into a single NotI site at the 3' end of luciferase in the Psicheck2 reporter plasmid (Promega). Mutated 3' UTR sequences, lacking miR-135 seed sequences, were synthesized with primers overhangs across the seed match sequence. Cloning orientation was verified by diagnostic cuts and by sequencing.

Transfections and Luciferase Assay

HEK293T cells were grown on poly-L-lysine in 48-well format to a 70-85% confluence and transfected using Polyethyleneimine with the following plasmids: 5 ng of Psicheck2-3'UTR plasmid and 215 ng of over-expressing vector for a specific miRNA, or empty-miR-vec over-expression plasmids. 24 hours following transfection cells were lysed and luciferase reporters activity were assayed as previously described [Chen A. et al. Mol Endocrinol (2005) 19: 441-58]. *Renilla* luciferase values were normalized to control firefly luciferase levels (transcribed from the same vector but not affected by 3'UTR tested) and averaged across six well repetitions per condition.

Animals and Housing

Adult C57BL/6J male mice, 10 weeks old (Harlan, Jerusalem, Israel) were housed in a temperature-controlled room (22±1° C.) on a reverse 12 hour light/dark cycle. Food and water were available ad libitum. All experimental protocols were approved by the Institutional Animal Care and Use Committee of The Weizmann Institute of Science.

Acute Immobilization Stress Paradigms

Adult mice were introduced into a 50 ml ventilated tube for 30 minutes during their dark cycle.

Chronic Social Defeat

Mice were subjected to a social defeat protocol as previously described [Krishnan V. et al. Cell (2007) 131: 391-404]. Briefly, the mice were placed in a home cage of an aggressive ICR mouse and they physically interacted for five minutes. During this time, the ICR mouse attacked the intruder mouse and the intruder displayed subordinate posturing. A perforated clear plexiglass dividers were then placed between the animals and the mice remained in the same cage for 24 hours to allow sensory contact. The procedure was then repeated with an unfamiliar ICR mouse for each of the next 10 days.

Antidepressant Treatment

Mice received i.p. injection of tricyclic-Imipramine, or SSRI-Fluoxetine, or NRI-Reboxetine (20 mg/kg in saline) or saline. Chronic injections were carried out for 18-21 consecutive days, and an acute injection was performed 24 hours prior to brain microdissections.

Microdissection of the Raphe Nucleus and Plasma Collections

Brain samples were taken from mice raphe nucleus (RN) after removing the brain and placing it on acryl brain matrix (Stoelting). Slices were taken using standard razor blades (GEM) based on designated anatomical markers. Blunted 14G syringes were used to extract the RN region from 3 mm slices removed from the matrix. Additionally, trunk blood was collected in EDTA containing tubes to avoid coagulation. After centrifugation in 3,500 g for 30 minutes at 4° C., plasma was separated and kept at −70° C. until RNA purification.

microRNA Purification and Quantitative RT-PCR Expression Analysis mRNAs, including microRNAs, were isolated from sorted neurons, frozen brain punches and plasma using miRNeasy mini kit (Qiagen) according to the manufacturer instructions, and treated using miScript Reverse transcription kit miRNA to generate cDNA. cDNA samples were then analyzed using SYBR®Green PCR kit (Qiagen) according to the manufacturer's guidelines in AB 7500 thermocycler (Applied Biosystems). Specific primers for each miR were used together with the commercial universal primer, while U6 snRNA was used as internal control.

TABLE 1B

Primers sequences used for real time PCR

| SEQ ID NO. | Primer sequence | Gene |
|---|---|---|
| 1 | TATGGCTTTTTATTCCTATGTGA | miR135a |
| 2 | TATGGCTTTTCATTCCTATGTGA | miR135b |
| 3 | TTTGTTCGTTCGGCTCGCGTGA | miR375 |
| 4 | GATGACACGCAAATTCGTGAA | U6 |
| 5 | TAAGGCACGCGGTGAATGCC | miR124 |

TABLE 1C

Primers sequences used for molecular cloning

| Primer Sequence | Orientation | Product size | Gene | |
|---|---|---|---|---|
| AGTTCTGCCGCTGATGATG (SEQ ID NO: 6) | sense | 2600$^{with\ 2}$ | Htr1a 3' UTR | 1 |
| GCACAAATGGAGAGTCTGATTAAA (SEQ ID NO: 7) | antisense | | Htr1a 3' UTR | 2 |
| TGCCTTTAATGCAAAACAGC (SEQ ID NO: 8) | sense | 2000$^{with\ 4}$ | MaoA 3'UTR | 3 |
| CCAAGTTTACAACCATCAAGCA (SEQ ID NO: 9) | antisense | | MaoA 3'UTR | 4 |
| ATCCGCATGAATGCTGTGTA (SEQ ID NO: 10) | sense | 760$^{with\ 6}$ | Slc6a4 3UTR | 5 |
| GTGGGTGGTGGAAGAGACAC (SEQ ID NO: 11) | antisense | | Slc6a4 3UTR | 6 |
| CCTACACGCAGAGCATTGAA (SEQ ID NO: 12) | sense | 870$^{with\ 8}$ | Tph2 3' UTR | 7 |
| ACATCCCTGTGGGATTTGAG (SEQ ID NO: 13) | antisense | | Tph2 3' UTR | 8 |
| TGTCTTGCTTATATTTTCTCAGTAG (SEQ ID NO: 14) | sense | 320$^{with\ 6}$ | Slc6a4 3UTR mutated | 9 |
| GAAAATATAAGCAAGACATCCCTGTT (SEQ ID NO: 15) | antisense | 440$^{with\ 5}$ | Slc6a4 3UTR mutated | 10 |
| AAAGATCCCTTTCCCCAATG (SEQ ID NO: 16) | sense | 1400$^{with\ 12}$ | Htr1a 3' UTR short | 11 |
| CAGTGCGTCTTCTCCACAGA (SEQ ID NO: 17) | antisense | | Htr1a 3' UTR short | 12 |
| ATAAGCAAGGGCCCAAAAGGAAGA (SEQ ID NO: 18) | sense | 1300$^{with\ 12}$ | Htr1a 3' UTR mutated seed 1 | 13 |
| TTTTGGGCCCTTGCTTATAAGTCC (SEQ ID NO: 19) | antisense | 120$^{with\ 11}$ | Htr1a 3' UTR mutated seed 1 | 14 |
| CTGCCCTGCCACATGTGTTTTTAT (SEQ ID NO: 20) | sense | 170$^{with\ 12}$ | Htr1a 3' UTR mutated seed 2 | 15 |
| TAACAAATAAAAACACATGTGGCA (SEQ ID NO: 21) | antisense | 1260$^{with\ 11}$ | Htr1a 3' UTR mutated seed 2 | 16 |
| ACCGGTCATATGATTCCCCAGTTTCCTGCTTT (SEQ ID NO: 22) | sense | 199$^{with\ 18}$ | Pre-mmu-miR135b | 17 |
| ACCGGTCCTCTGTGGCTGGTCCTTAG (SEQ ID NO: 23) | antisense | | Pre-mmu-miR135b | 18 |

Cloning of miR135b Over Expression Viral Vector

Pre-miR-135b was amplified by PCR from mouse genomic DNA with primers adding restriction enzyme AgeI sites and then was inSlc6a4ed to pGEM-T Easy vector (Promega, Madison, Wis.). After sequencing of pGEM-T Easy and digestion of both pGEM-T Easy and pEGFP vector (Clontech laboratories Inc., Mountain View, Calif.) with the AgeI, the premature miR-135b sequence was ligated to the pEGFP vector to construct the expression plasmid pEGFP-miR-135b. Afterwards, pEGFP-miR-135b was cut by BamHI and B srGI in parallel to cutting pCSC-E/Syn-eGFP plasmid with the same enzymes, and the miR-135b-eGFP sequence was ligated to pCSC-E/Syn to construct pCSC-eSNY-pre-miR-135b-eGFP plasmid which was confirmed by restriction endonuclease analysis and DNA sequencing.

Production of Lentiviral Vectors

Recombinant lentiviruses were produced by transient transfection in HEK293T cells, as previously described [Naldini L et al., Proc Natl Acad Sci USA (1996) 93:11382-8]. Briefly, infectious lentiviruses were harvested at 48 and 72 hours post-transfection, filtered through 0.45 pin-pore cellulose acetate filters and concentrated by ultracentrifugation.

Intracerebral Injections of Lentiviruses

To provide precision control over the stereotaxic surgery and site of lentiviral delivery, inventors used a computer-guided stereotaxic instrument and a motorized nanoinjector (Angle Two™ Stereotaxic Instrument, myNeurolab). As previously described [Singer O. et al. Nat Neurosci (2005). 8, 1343-9] mice were placed on a stereotaxic apparatus under general anesthesia, and coordinates were determined as defined by the Franklin and Paxinos atlas. The lentiviral preparation was delivered using a Hamilton syringe connected to the motorized nanoinjector system and solution injected at a rate of 0.2 µl every 1 min. Following two weeks recovery period, mice were subjected to behavioral and physiological studies and afterwards anesthetized and perfused with phosphate buffered 4% paraformaldehyde. The fixed brains were serially sectioned to 30µ slices in order to confirm the preciseness of the injection site, using immunohistochemistry.

Immunohistochemistry

The procedure used for immunohistochemistry was carried out as previously described [Chen A et al. J Neurosci (2006) 26: 5500-10]. For GFP immunostaining, inventors used biotinylated anti GFP antibody raised in rabbit as primary antibody (Abcam, Cambridge, UK), and streptavidin conjugated Cy2 as secondary antibody (Jackson Immunoresearch Laboratories Inc, West Grove, Pa., USA).

Behavioral Assessments

All behavioral assessments were performed during the dark phase following habituation to the test room for 2 hours prior each test.

Tail Suspension Test

The tail suspension test was performed in the TSE Tail Suspension Monitor (TSE Systems, Bad Homburg, Germany). Each mouse was taped by the tip of its tail, and suspended from the force sensor for 10 minutes. Time spent immobile and time spent struggling were calculated and recorded by the software based on pre-set thresholds.

Modified Forced Swim Test

The tail suspension test was performed as previously described [Krishnan V and Nestler E J, Nature (2008) 455: 894-902]. In short, the apparatus used was a plastic bucket, 18 cm of diameter, filled with 25° C. water to a depth of 15 cm. Each mouse was placed in the center of the bucket to initiate a 6 minutes video recorded test session. The duration of time spent immobile during the 2-6 minute of testing was automatically scored using EtoVision XT (Noldus, Wageningen, Netherlands).

Locomotor Activity

To control for the possibility of behavioral effects originating from differences in ambulatory movement, locomotor activity of mice was examined over a 48 hours period, which proceeded a few days of habituation. Mice were single housed in specialized home cages and locomotion was measured using the InfraMot system (TSE Systems, Bad Hamburg, Germany).

Statistical Analysis

Data were expressed as means+/−SEM. To test for statistical significance, student's t test was used in cases where only two groups were compared, such as between microarray validation qPCR. One way ANOVAs was used to compare between multiple groups such as between the different treatments in the luciferase assay. Two way ANOVAs was used in the cases of 2 independent variable, such as the SSRI NRI injection, both in acute and chronic durations. Post hoc t tests were used when necessary to reveal statistical significance. Differences between groups were considered significant when P<0.05.

Results

Figure 1A:
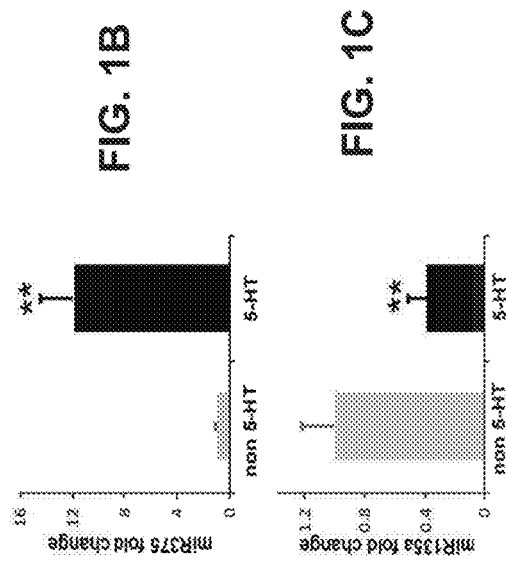
Figure 1B:
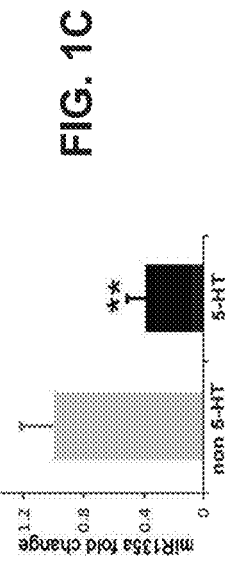
Figure 1C:
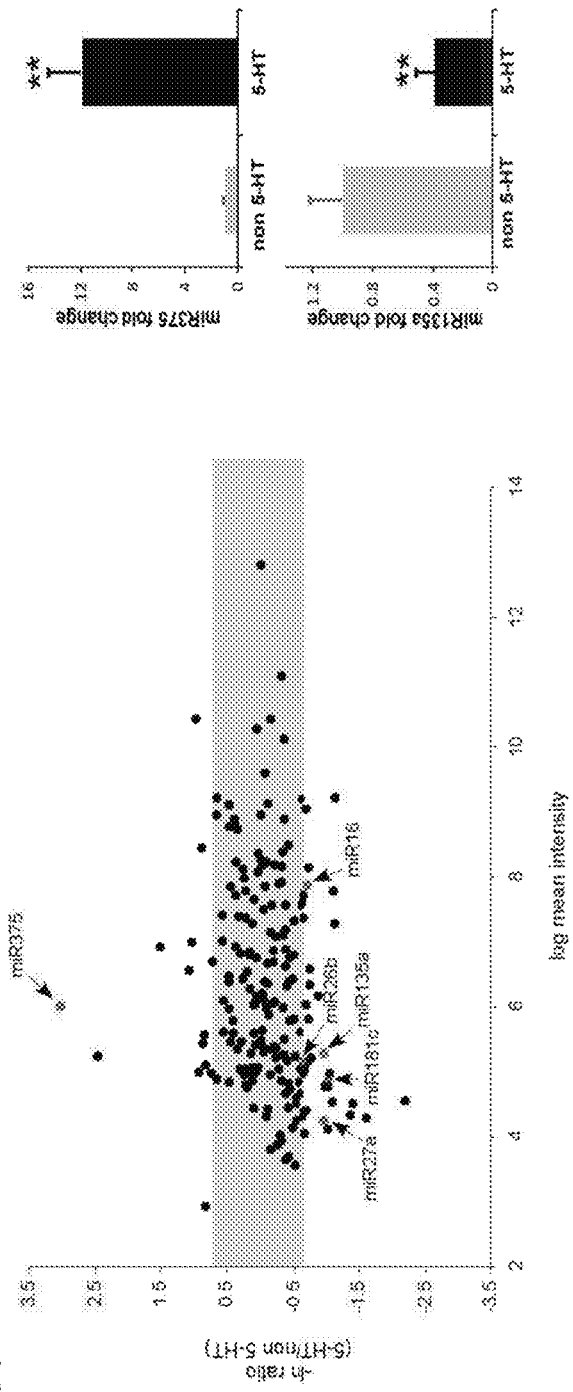
Figure 1D:
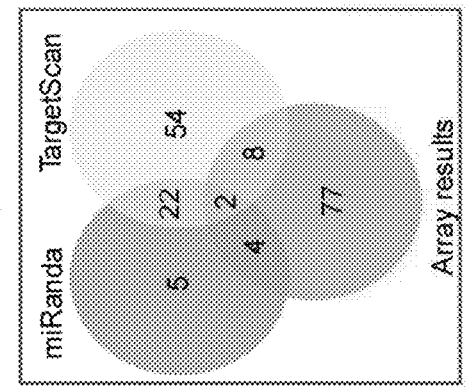
Figure 1E:
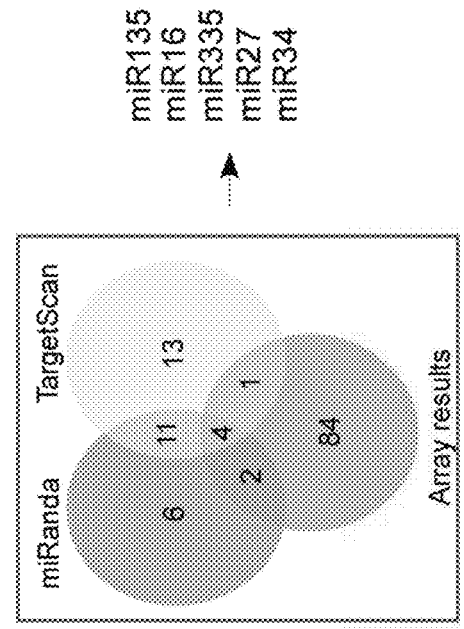
Figure 1F:
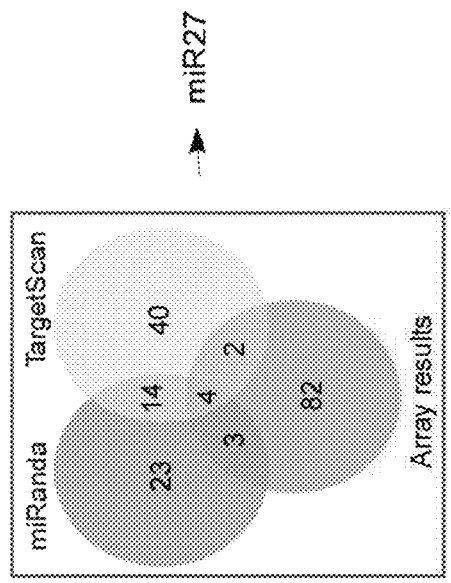
Figure 1G:
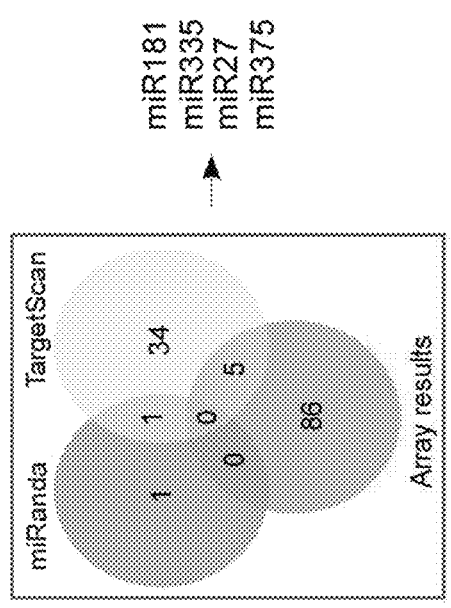
Figure 1H:
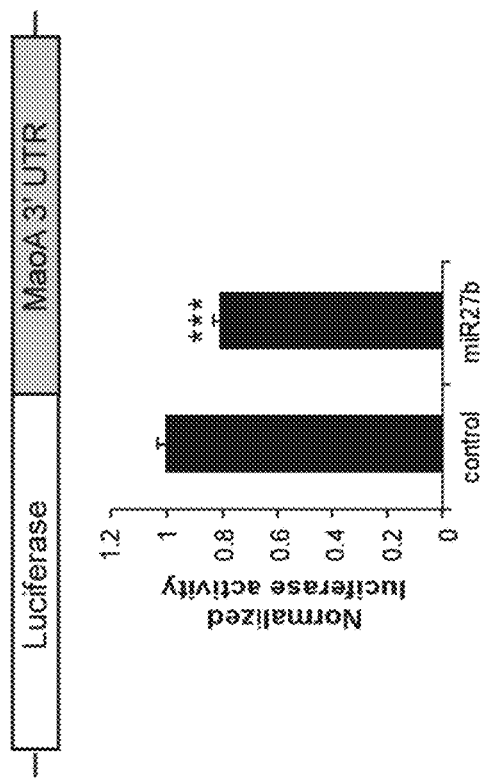
Figure 1I:
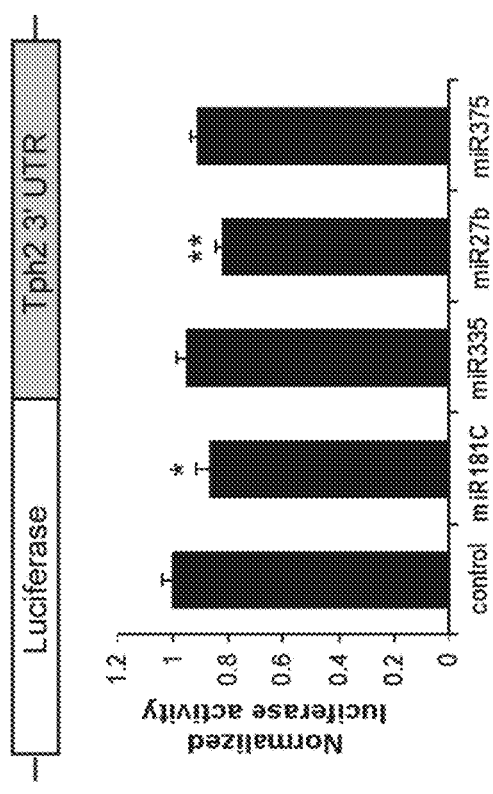

5HT neurons were isolated from the RN of ePET YFP embryos, and their miR expression profile was compared to non-5HT neurons, obtained from the same nucleus, using miR microarray (FIG. 1A). Fourteen miRs were found to be upregulated and twenty-seven downregulated by more than 2 fold in 5HT neurons compared to the non-5HT neurons (see Tables 2A-B, below). Representative validation of array results was performed using real time PCR for miRs upregulated in 5HT neurons such as miR-375 (P=0.0071; FIG. 1B) and downregulated such as miR-135a (P=0.0075; FIG. 1C). In order to further study the role of miRs as modulators of 5HT neurons, extensive bioinformatic analysis was performed in a hypothesis driven manner. Targeting prediction of known serotonin related genes that have been previously demonstrated to be associated with psychopathologies, were crossed with the microarray results. The following four protein coding target genes expressed in 5HT neurons in the RN were chosen for testing: serotonin transporter, responsible for 5HT reuptake (also known as SERT or Slc6a4); serotonin inhibitory receptor 1a (also known as Htr1a); tryptophan hydroxylase 2 (Tph2), the rate limiting enzyme of 5HT synthesis in the brain; and monoamine hydroxylase (MaoA), which deactivates 5HT. MicroRNA targeting predictions for these genes was performed using two different web-based algorithms: Target Scan [www(dot)targetscan (dot)org] and Miranda [www(dot)microrna(dot)org] and were crossed with the list of 91 miRs altered by at least ±1.5 in the 5HT neurons miRs array, compared to non-5RH cells. Based on the miRs array data and the bioinformatic analysis, eight miRs were chosen for further in vitro studies (FIG. 1D-G).

TABLE 2A

List of miRs upregulated in 5HT neurons compared to non-serotonergic (by more than 2 fold).

| Fold change | microRNA name |
|---|---|
| 20.72 | mmu-miR-375 |
| 11.73 | mmu-miR-376c |
| 4.44 | mmu-miR-7a |
| 2.87 | mmu-miR-137 |
| 2.79 | mghv-miR-M1-2 |

TABLE 2A-continued

List of miRs upregulated in 5HT neurons compared to non-serotonergic (by more than 2 fold).

| Fold change | microRNA name |
| --- | --- |
| 2.61 | mmu-miR-709 |
| 2.51 | mmu-miR-291b-5p |
| 2.40 | mmu-miR-1224 |
| 2.37 | mmu-miR-1892 |
| 2.31 | mmu-miR-702 |
| 2.25 | mmu-miR-139-3p |
| 2.24 | mmu-miR-762 |
| 2.10 | mmu-miR-671-5p |
| 2.04 | mmu-miR-483* |

TABLE 2B

List of miRs downregulated in 5HT neurons compared to non-serotonergic (by more than 2 fold).

| Fold change | microRNA name |
| --- | --- |
| −5.10 | mmu-miR-691 |
| −4.11 | mmu-miR-4661 |
| −3.95 | mmu-miR-17 |
| −3.18 | mmu-miR-376b |
| −3.13 | mmu-miR-124 |
| −3.08 | mmu-miR-218 |
| −2.99 | mmu-miR-128 |
| −2.92 | mmu-miR-140* |
| −2.86 | mmu-miR-148a |
| −2.86 | mmu-miR-340-5p |
| −2.82 | mmu-miR-181c |
| −2.72 | mmu-miR-210 |
| −2.69 | mmu-miR-135a |
| −2.66 | mmu-miR-27a |
| −2.45 | mmu-miR-452 |
| −2.20 | mmu-miR-370 |
| −2.19 | mmu-miR-300 |
| −2.17 | mmu-miR-376a |
| −2.13 | mmu-miR-127 |
| −2.12 | mmu-miR-15b |
| −2.07 | mmu-miR-101a |
| −2.06 | mmu-miR-16 |
| −2.05 | mmu-miR-324-5p |
| −2.05 | mmu-miR-434-5p |
| −2.03 | mmu-miR-92a |
| −2.00 | mmu-miR-669i |

Figure 2F:
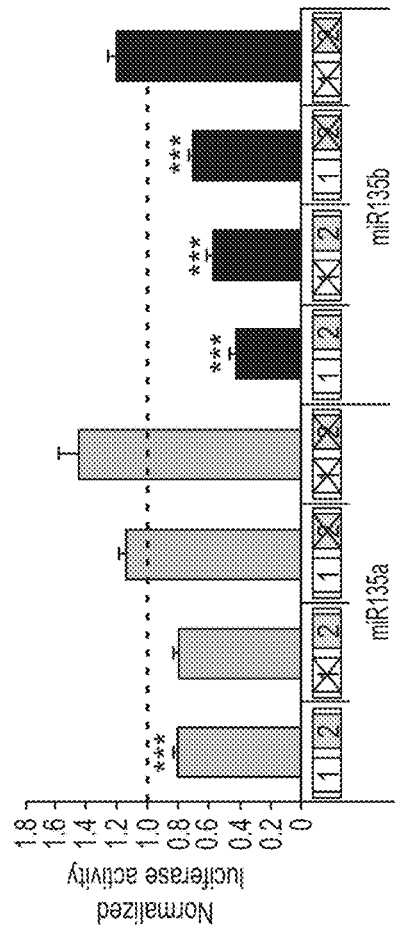
Figure 2G:
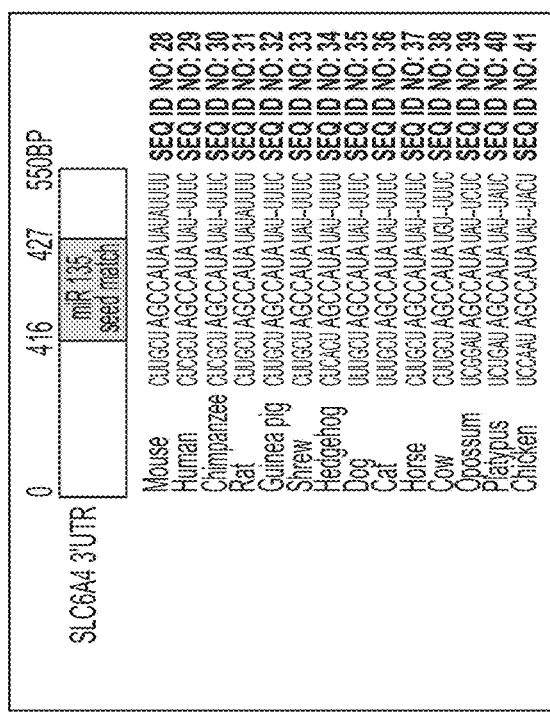
Figure 2H:
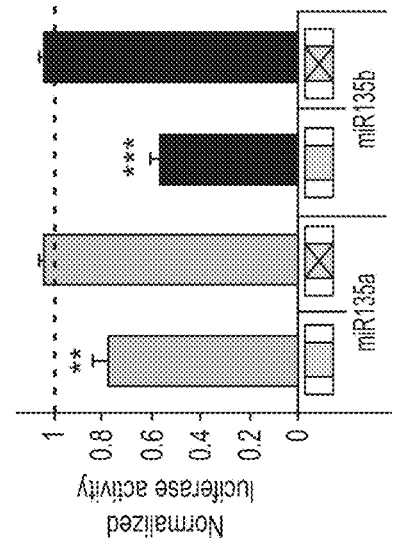

In vitro luciferase assays were performed to test the miR-target interactions between the 3'UTR of the tested 5HT related gene and the miRs predicted to putatively target it. Inventors found that Tph2 3'UTR was mildly repressed (by approximately 20%) by miR-27b (P=0.0051) and miR-181C (P=0.0305, FIG. 1H) and MaoA 3'UTR was also repressed by miR-27b (P=0.0008, FIG. 1I). miR-135 targeting of Slc6a4 3'UTR (FIGS. 2A and 2C) and Htr1a 3'UTR (FIGS. 2B and 2D) resulted in robust repression of translation of these transcripts. While miR-135a lead to approximately 30% repression to Slc6a4 (P=0.014) and Htr1a (P<0.0001), miR-135b caused approximately 50% repression to Slc6a4 (P=0.0002) and Htr1a (P<0.0001). Additionally significant repression of Htr1a 3'UTR was generated by miR-335 (P<0.0001), miR-181c (P=0.0029) and miR-26a (P<0.0001, FIG. 2D). Further genomic approach bioinformatic analysis revealed a strong conservation of miR-135 seed match in the slc6a4 3'UTR (FIG. 2E) and in one out of the two identified seed matches in the Htr1a 3'UTR (FIG. 2F). Mutation studies in the 3'UTR of the Slc6a4 transcript, which removed the miR seed match of miR-135, revealed that both miR-135a and miR-135b targeting of Slc6a4 was mediated via its seed match sequence. The repression induced by the miR-135 was fully blocked by the mutation in Slc6a4 3'UTR (FIG. 2G). Mutating the Htr1a miR-135 seed matches individually or both revealed that miR-135a was repressing Htr1a 3'UTR via the distal and not the proximal seed match while miR-135b act via both predicted sites (FIG. 2H).

Inventors further tested the regulation of RN-miR-135 expression in vivo following different environmental challenges or pharmacological treatments. Following manipulation of the mice (i.e. acute immobilization stress) RN was removed, RNA was extracted and miR-135 levels were tested using real time PCR. Since 5HT levels are known to be alerted by acute stress, inventors tested miR-135 levels in different time points after acute restraint stress, and found that both miR-135a and miR-135b were downregulated 90 minutes following acute stress (P<0.0001). The reduced levels of these miRs still remained 24 hours after stress, compared to control mice (P=0.0357 for miR-135a, FIG. 3A; P=0.0055 for miR-135b, FIG. 3B). Furthermore, since 5HT neuronal functions and Slc6a4 and Htr1a expression levels are known to be strongly affected in depressed patients and following anti-depressants medications, inventors tested the levels of the two miR variants in mice exposed to environmental model for induction of depression-like behaviors (chronic social defeat model) and to the tricyclic antidepressant, Imipramine. Interestingly, chronic social defeat stress did not alter miR-135 levels in the raphe nucleus, however, Imipramine administered acutely or chronically, both in stressed and non stressed mice, increased miR-135a (P=0.003; FIG. 3C) and miR-135b (P=0.0093; FIG. 3D) expression levels in the RN. Since Imipramine is not a specific 5HT reuptake inhibitor, inventors further tested the affect of both acute and chronic selective serotonin reuptake inhibitors (SSRI), Fluoxetine, and the noradrenaline reuptake inhibitors (NRI), Reboxetine, and found a robust increase in miR-135a levels following both acute and chronic SSRI treatment (P<0.0001, FIG. 3E), and not in miR-135b levels in the RN (FIG. 3F).

Figure 4B:
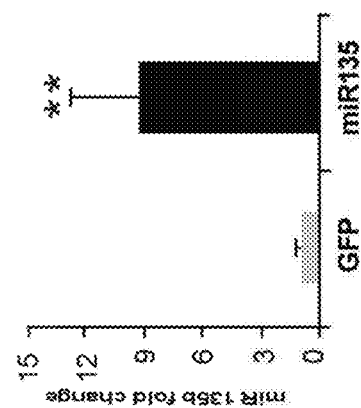
Figure 4A:

To further explore the importance of miR-135 levels in the whole animal context inventors manipulated miR-135 levels in vivo specifically in the RN of adult mice and tested its effects on the mice depression-like behaviors. To this end, inventors constructed recombinant lentiviruses over-expressing miR-135b specifically in neurons using the enhanced synapsin promoter, which also co-expressed the GFP reporter (see materials and experimental procedures section above and FIG. 4A). Inventors tested the lentiviruses in vivo by injecting them into the RN of adult mice, and compared miR-135b levels in RN to control lentiviruses injected mice. Real time PCR analysis of miR-135b levels revealed a 10 fold induction compared to control lentiviruses injected mice (P=0.0032, FIG. 4B). Adult mice injected with miR-135b over-expression were exposed to chronic social defeat, to initiate depression-like behaviors, and were subsequently tested behaviorally. Following behavioral testing, mice were perfused and brains were analyzed for location of injection site (FIGS. 4C-4D). RN miR-135 over-expressing mice demonstrated reduced immobility time in the forced swim (P=0.0088 in minute 3 and P=0.00330 for minute 4; FIG. 4E) and in the tail suspension tests (P=0.07356 in the last 5 min of the test, FIG. 4F) without any observed change in their home cage locomotion (FIGS. 4G-4H), suggesting an antidepressant effect for miR-135 over-expression.

Taken together, the present inventors determined the specific miRs expression fingerprint of the RN serotonergic and non-serotonergic neurons. The present inventors crossed this unique data set with bioinformatics prediction for miRs targeting of 5HT related genes. The present inventors tested in vitro the targeting prediction for Tph2, MaoA, Slc6a4 and Htr1a using 3'UTR's luciferase assays and in mutation studies and reveled, among other miR-target interactions, a strong inhibitory effect for miR-135 both on 516a4 and Htr1a 3'UTR. Finally, the present inventors demonstrated that site-specific over-expression of miR-135 in the adult mice RN leads to decreased depression-like behaviors following social defeat.

Example 2 miR-19 Specifically Targets Type One Beta Adrenergic Receptor (Adrb1)

Materials and Experimental Procedures
Cloning of 3' UTRs into Psicheck2 Luciferase Expression Plasmid
3'UTR sequence of ADRb1 was PCR amplified from mouse genomic DNA. Mutated 3' UTR sequences, lacking all four miR-19 seed matches, was synthesized by Epoch Biolabs, Inc. (TX, USA). 3'UTR PCR fragments were ligated into pGEM-T easy vector (Promega) according to the manufacturer's guidelines, and further subcloned into a single NotI site at the 3' end of luciferase in the Psicheck2 reporter plasmid (Promega). Cloning orientation was verified by diagnostic cuts and by sequencing.

Transfections and Luciferase Assay
HEK293T cells or HT22 neuronal cells were grown on poly-L-lysine in 48-well format to a 70-85% confluence and transfected using Polyethyleneimine with the following plasmids: Psicheck2-3'UTR plasmid, pre-mmu-miR-19b over-expression in pEGFP plasmid or pEGFP plasmid alone (clontech), miR-19b knockdown (KD) plasmid (Genecopoeia) or control-KD plasmid (Genecopoeia). 24 hours following transfection cells were lysed and luciferase reporters activity were assayed as previously described [Chen A. et al. Mol Endocrinol (2005) 19: 441-58]. *Renilla* luciferase values were normalized to control firefly luciferase levels (transcribed from the same vector but not affected by 3'UTR tested) and averaged across six well repetitions per condition.

Results
Bioinformatic analysis for stress related genes with a distinct, evolutionary conserved miRNA target sequences that contain several repeats in their 3'UTR revealed miR-19 as a strong candidate for the targeting of type one beta adrenergic receptor (Adrb1), with three strongly conserved and one less conserved miR-19 seed match on Adrb1 3'UTR. Adrb1 is an adrenergic receptor that is expressed in various regions of the brain including the amygdala, hippocampus and paraventricular nucleus (PVN). Amygdalar Adrb1 was previously described as affecting anxiety-like behavior [Fu A et al., Brain Res (2008) 1211: 85-92; Rudoy C A and Van Bockstaele E J, Prog Neuropsychopharmacol Biol Psychiatry (2007) 31: 1119-29] and fear memory [Roozendaal B et al., J Neurosci (2004) 24: 8161-9; Roozendaal B et al., Neuroscience (2006) 138: 901-10]. Intriguingly, Adrb1 was found on CRF positive cells of the amygdala and is a G-protein coupled receptor (GPCR) that exert its effect via Gs further activating adenylate cyclase (AC). There are 10 known genes encoding for AC, namely ADCY1-10. Three of these (ADCY1, ADCY7 and ADCY9) were bioinformatically predicted to be targeted by miR-19. ADCY1 has a brain-specific expression and it was previously shown that over-expression of same in the mouse forebrain enhances recognition memory and LTP [Wang H et al., Nat Neurosci (2004) 7: 635-42].

Figure 5:
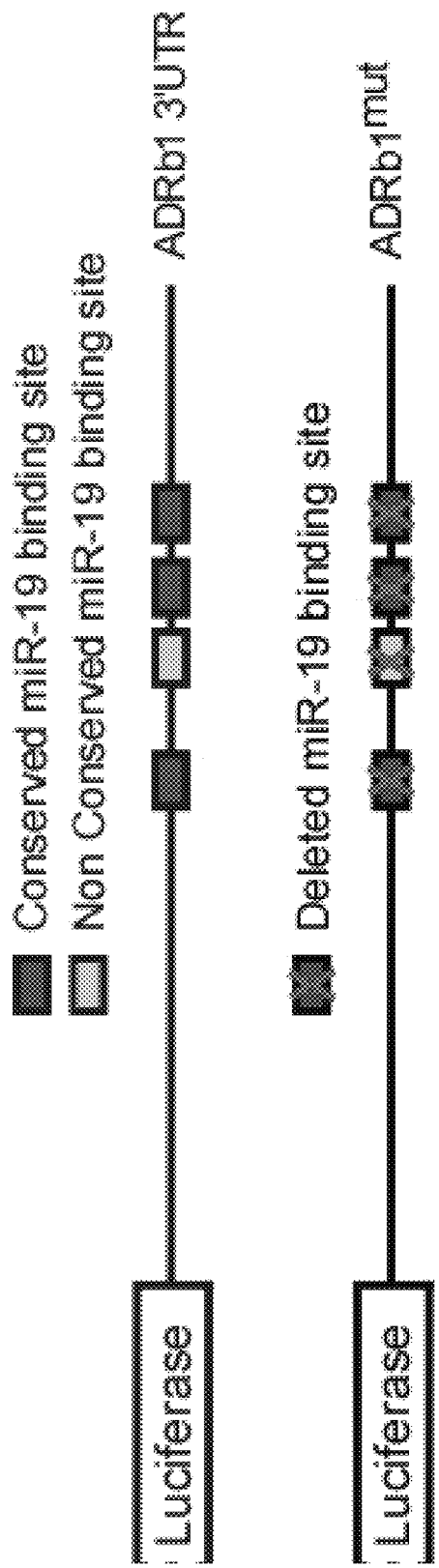

In order to investigate whether miR-19 indeed regulates Adrb1 or ADCY1 expression through its presumed target sequences on Adrb1-3'UTR or ADCY1-3'UTR, an intact, or mutated forms of Adrb1-3'UTR (FIG. 5) or ADCY1-3'UTR were cloned downstream of the luciferase gene in the Psicheck2 expression plasmid. In the mutated form of ADRb1-3'UTR all 4 seed matches for miR-19b were absent (FIG. 5). In the mutated form of the partial ADCY1-3'UTR, only the conserved seed-match (out of 3) was absent.

Luciferase assay was used to determine the nature of interaction between miR-19 and Adrb1-3'UTR and also between miR-19 and ADCY1-3'UTR. In HT22 cells, that endogenously express low levels of miR-19, no difference was found between luciferase levels controlled by either intact or mutated form of ADRb1-3'UTR (FIG. 6A). However, when miR-19b was over-expressed in HT22 cells, luciferase levels were significantly (approximately 2 fold) lower when driven by the intact form relative to the mutated form of ADRb1-3'UTR (in addition to a general, seemingly non-specific reduction in normalized luciferase expression) (FIG. 6B). In HEK293T cells that endogenously express high levels of miR-19b, luciferase expression levels regulated by ADRb1-3'UTR were 2-4 times lower than those expressed when regulated by the mutated form of ADRb1-3'UTR (FIG. 6C).

MiRs knockdown (KD) system was used in order to manipulate miR-19 levels in HEK293T cells. Namely, (1) miRCURY LNA KD probes (Exiqon, MA, USA FIG. 6D), and (2) plasmid based knockdown sequence miArrest (Genecopoeia, Rockville, Md., USA, FIG. 6E). LNA-Anti-miR-19b enhanced luciferase levels expressed when regulated under ADRb1-3'UTR at about 20% relative to control scrambled KD probe and had no effect on the mutated form of ADRb1-3'UTR (FIG. 6D). Whereas, plasmid based miR-19b KD, caused up to 2 fold enhancement in luciferase expression regulated by the intact form of ADRb1-3'UTR relative to Control KD sequence (FIG. 6E). No full rescue of luciferase levels relative to that driven by the mutant form of ADRb1-3'UTR was achieved. This may be explained either by miR-19b specificity of the probe/genomic sequence (spearing miR-19a regulation), the high miR-19 levels in HEK293T cells that may be difficult to fully down-regulate, or the effect of other possible miRNAs expressed in HEK293T cells that may bind to the same seed-match sequences on ADRb1-3'UTR.

Example 3A

MiR-19a and MiR-19b are Upregulated in the PFC and Amygdala Following Chronic Stress Materials and Experimental Procedures
Animals and Housing
miR 17~92 flx/flx Mice [Ventura A et al, Cell (2008) 875-86:(5)132; 7], are crossbred with CamKIIa-Cre mice [Dragatsis I et al Genesis. (2000) 26(2):133-5]. Transgenic Mice or Adult C57BL/6J male mice are housed in a temperature-controlled room (22±1° C.) on a reverse 12 hour light/dark cycle. Food and water available ad libitum. All experimental protocols were approved by the Institutional Animal Care and Use Committee of The Weizmann Institute of Science.

Generating Lentiviruses for miR-19b Manipulation in Adult Brain

MiR-19b KD sequence was cloned into a lentiviral plasmid following the RNA polymerase III-H1 promoter. In addition, Pre-miR-19b sequence was cloned following a neuronal specific promoter (Enhanced synapsin, ESyn) in a lentiviral plasmid. Lentiviruses are generated for both in-vivo miR-19b-KD and Pre-miR-19b-overexpression (OE) experiments. These lentiviruses are used to manipulate miR-19b levels in target regions where miR-19 levels are found to be altered following a behavioral/pharmacological challenge.

Generating Mice Lacking miR-19 in the Forebrain

In order to generate mice lacking miR-19 in the forebrain, inventors are breading mice carrying the gene encoding for Cre recombinase under the CamKIIa promoter, with mice carrying a conditional form of the miRs cluster miR17~92. MiR-19 family includes miR-19a and miR-19b. In the mouse genome miR-19b has two identical copies, miR-19b-1 and miR-19b-2. MiR19a and miR-19b-1 are located on the same miRNA cluster, namely miR17~92, whereas miR-19b-2 is located at a different genomic locus, miR106a~363. The latter seems to have little or no expression in mouse tissues and therefore the knockout of miR17~92 cluster is expected to be enough to enable a profound effect on miR-19a and miR-19b expression levels in the forebrain.

Behavioral/Pharmacological Challenges

Mice lacking miR-17~92 cluster in the forebrain, or mice where miR-19 was specifically manipulated (overexpressed or down-regulated (KD) in specific brain regions) will be examined for expression levels of ADRb1, ADCY1 and other transcripts and gene products. These animals will be also tested for anxiety like behavior, locomotor activity and memory performance. Furthermore, the levels of expression of miR-19a and miR-19b are examined in different regions of interest (E.G the hippocampus, amygdala and forebrain) following an acute and chronic systemic treatment with the Noradrenaline reuptake inhibitor Reboxetine in WT mice.

Results

The physiological link between miRNA-19 and Adrb1 was studied by assessing the level of miR-19a/b in the prefrontal cortex (PFC) of mice that were injected with Reboxetine, a noradrenalin reuptake inhibitor (NRI), either acutely or chronically (FIGS. 12A-12D). As shown in FIGS. 12A-12D, miR-19 a/b levels were down regulated following acute administration of Reboxetine (FIGS. 12A-12B) and upregulated following chronic administration of Reboxetine (FIGS. 12C-12D).

Next, the levels of miR-19 were assessed following stress by measuring the levels of miR-19 a and b in the PFC and amygdale of mice subjected to social defeat protocol (FIGS. 13A-13D). As shown in FIGS. 13A-13D, the levels of miR-19 a and b increased both in the PFC and amygdala following chronic stress. These results illustrate the involvement of miR-19 in the regulation of the central stress response.

Example 3B miRNA-19 and Cannabinoid Receptor 1 (CB1)

Materials and Experimental Procedures
Animals and Housing
As described in Example 3A, above.
Generating Lentiviruses for miRNA-19b Manipulation in Adult Brain
As described in Example 3A, above.
Results CB1 is one of the most abundantly expressed GPCRs in the brain and is particularly enriched in the cortex, amygdala, hippocampus, basal ganglia, and cerebellum (FIGS. 15A-15B) [Herkenham M. et al., The Journal of neuroscience: the official journal of the Society for Neuroscience (1991) 11:563-583; Mackie, K. Handbook of experimental pharmacology (2005) 299-325]. CB1 receptors are highly expressed on axons and axon terminals, where they are well positioned to modulate neurotransmission. Inventors found that CB1 contains 2 seed sites that are compatible with miRNA-19.

A luciferase assay was used to determine the nature of interaction between miRNA-19 and CB1-3'UTR. When miRNA-19b was over-expressed in HT22 cells along with the 3'UTR of CB1, luciferase levels were significantly (50%) lower when compared to GFP over expressed with the same 3'UTR (FIG. 14), supporting a possible role for miR-19 in the regulation of CB1 levels. Additional mutation experiments are performed to verify the role of the predicted miR-19 seed sequence to the observed regulation (as described for Adrb1 above).

Interestingly, previous studies have convincingly demonstrated that the consolidation of aversive memories is facilitated by cross-talk between glucocorticoids, noradrenergic and cannabinoid signaling in the basolateral nucleus of the amygdala (BLA) [Roozendaal, B. et al. Neurobiology of learning and memory (2006) 86:249-255]. A model proposed by Hill and McEwen [Hill M. N. and McEwen B. S. Proc of the Nat Acad of Sci of the USA (2009) 106:4579-4580] shows a possible mechanism of action in the BLA for memory consolidation (FIG. 16).

As shown in the present results, MiRNA-19 appears to regulate both Adrb1 and CB1 in vitro. Over-expression and knockdown of miR-19 using e.g. lentiviruses delivered specifically to the BLA where it may alter the levels of Adrb1 and CB1, are carried out as well as tests examining the mice's performance in learning and memory paradigms such as fear conditioning with and without exposure to stressful challenges.

Example 3C

Identification of Differentially Expressed miRNAs in Mice Subjected to Chronic Stress Materials and Experimental Procedures
Immunoprecipitation of Ago2 Protein Pools of 3 amygdalae from 3 animals that are part of the same group ("Susceptible", "Resilient" or Control) were homogenized in NP40 buffer which was supplemented with RNase inhibitor, protease inhibitor and phosphates inhibitor. The samples were maintained on constant agitation for 2 hours at 4° C. Samples were then centrifuged for 20 min at 12,000 rpm at 4° C. in a micro centrifuge, the supernatant was placed in a fresh tube kept on ice and the pellet was discarded. Magnetic protein G beads (Dynabeads, Invitrogen) were incubated with the Ago2 monoclonal antibody (WAKO) with rotation at room temperature for 10 minutes. After several washes the samples were added to the Ago2 coated protein G beads and incubated over night at 4° C. under agitation. The following day the beads were washed 3 times with PBS. For RNA purification the beads were homogenized in RLT buffer (RNeasy kit, miRNA supplementary protocol). For western blot analysis the beads were boiled in sample buffer to release the protein from the beads.

RNA Purification and Microarray

RNA from the Ago2 immunoprecipitation samples was isolated using the RNeasy plus kit (Qiagen) following Qiagen supplementary Protocol 1: Purification of total RNA containing miRNA. RNA for all other purposes was isolated from frozen brain punches using miRNeasy mini kit (Qiagen) according to the manufacturer recommendation, and RNA integrity was evaluated using the Agilent 2100 bioanalyzer. RNA derived from tissues of stressed mice following Ago2 immunoprecipitation was further analyzed on Affymetrix miRNA 2.0 arrays (enriched RNA protocol) and Affymetrix Mouse Gene 1.0 ST array.

Results

In order to identify and study differentially expressed miRNAs isolated from the amygdala of mice subjected to chronic stress paradigm and/or associated with "Resilient" or "Susceptible" behavioral phenotype, the social defeat protocol was used (see Methods section).

In order to identify a genuine connection between miRNAs and their target gene's 3' UTR following the social defeat paradigm, an immunoprecipitation (IP) of the Ago2 complex was performed and the population of miRNAs and mRNAs co-precipitated was analyzed. When a mature miRNA was formed it was incorporated to the RISC complex. While in the RISC complex, Ago2 facilitates the interaction between a specific miRNA and its target mRNA 3' UTR [Meister G. et al., Molecular cell (2004) 15:185-197] (FIG. 17A).

In order to verify that the Ago2 complex can indeed be precipitated with its bound RNA, the IP was performed on the amygdala of naive mice. The IP was performed using protein G magnetic beads which were reacted with monoclonal Ago2 antibody. As shown in FIG. 17B, a specific Ago2 band was precipitated from an extract of NIH 3T3 cells (FIG. 17B, lane 1) or from an extract of amygdala tissue (FIG. 17B, lane 2).

To demonstrate the specificity of the IP, a total brain sample was divided into two, where one was precipitated with anti Ago2 and the other with a control IgG1 nonspecific antibody. A specific Ago2 band was present only in the Ago2 precipitate (FIG. 17B, lanes 3, 4).

Therefore, by pulling down the Ago2 complex and analyzing the miRNA as well as the mRNA populations in the precipitated material there was a greater chance to discover a correct connection between a given miRNA and its targeted mRNA 3' UTR in specific brain regions.

Isolation of Ago 2 Associated RNA from Mice Amygdala Subjected to Social Defeat Paradigm Next, based on the specific results of the Ago2 IP experiment, the same strategy was implemented in order to reveal potential differences in miRNA and their target mRNAs in the brain of mice that were subjected to social defeat protocol.

After 10 days of the social defeat paradigm, mice were categorized into 3 groups: Control, "Susceptible" and "Resilient". A mouse was characterized as "Susceptible" when it exhibited social avoidance when it encountered a new mouse from the same strain that attacked him during the social defeat paradigm. A mouse was characterized as "Resilient" if it does not avoid the new aggressive mouse and interacts with it. Most of the mice subjected to social defeat typically exhibit social avoidance and therefore would be classified as "Susceptible". Approximately only 10-20% of the mice in an experiment are expected to be "Resilient". Shown below is an example of the social avoidance test conducted.

Figure 18A:
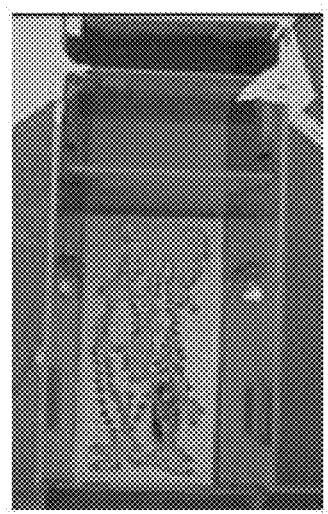
Figure 18B:
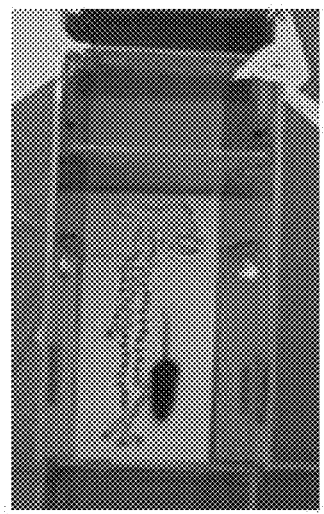
Figure 18C:
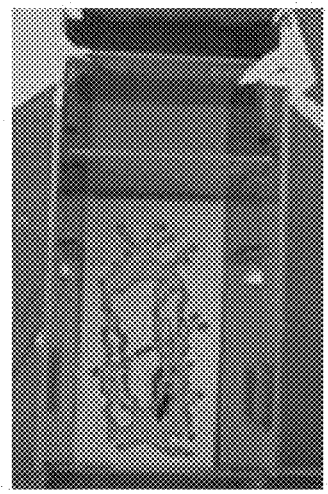
Figure 18D:
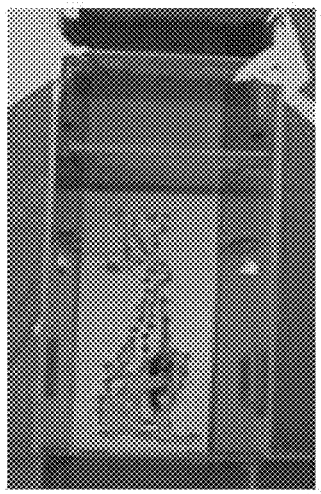

As demonstrated in FIG. 18A, the mouse was placed alone in the social maze for 3 minutes for habituation. The camera tracked the mouse movements throughout the maze. In FIG. 18C, the same mouse was exposed to a novel ICR mouse that was placed beyond a divider. The camera tracked the mouse in the farthest corner of the arena distant from the location of the novel mouse. This response was considered as social avoidance and therefore this mouse was classified as "Susceptible". In contrast, in FIG. 18B and FIG. 18D the mouse did not exhibit social avoidance and therefore was classified as "Resilient".

Forty mice underwent the social defeat paradigm and forty mice served as control. Following the social avoidance test 9 "Resilient" mice, 9 "Susceptible" mice and 12 control mice were selected for brain microdissection. Brain samples were collected 8 days after the social avoidance test from the amygdala, BNST, PFC, dorsal raphe and hippocampus along with trunk blood.

Pools of 3 amygdala punches obtained from 3 different mice were combined and the immunoprecipitation with anti Ago2 was performed. Following the IP, RNA was extracted from the precipitated material. After the pulling of 3 amygdalae from each group there were 3 RNA samples from the "Resilient" mice, 3 RNA samples from the "Susceptible" mice and 4 RNA samples from the control mice—a total of 10 RNA samples. Each sample was tested in a mouse ST microarray as well as in miRNA array (both Affymetrix). Genes and miRNAs that were up or down regulated in each of the 2 groups: "Susceptible" or "Resilient" relative to the control group, were examined. If an interaction between a certain miRNA and a target gene takes place inventors expected for an opposite correlation in their total levels. However, mRNA present in the RISC complex (precipitated with the anti Ago2) were expected to be in high levels because they have not yet been fragmented, therefore while looking at the array data inventors examined miRNAs and potential mRNA targets that were both either elevated or down regulated relative to the control sample because this was an indication that they interacted in the RISC complex.

Microarray Results

Table 3, hereinbelow, illustrated the preliminary array results analyzed using conventional filters.

TABLE 3

List of amygdalar miRNAs up regulated (Table 3A) or down regulated (Table 3B) following IP with Ago2.

(Table 3A)

| Upregulated | Fold-Change Susceptible | Fold-Change Resilient |
| --- | --- | --- |
| mmu-miR-301a_st | 1.96 | 2.11 |
| mmu-miR-15a_st | 1.66 | 1.87 |
| mmu-miR-29a_st | 1.42 | 1.82 |
| mmu-miR-19b_st | 1.97 | 2.34 |
| mmu-miR-146b_st | 1.55 | 1.94 |
| mmu-miR-181d_st | 1.54 | 1.64 |
| mmu-miR-146a_st | 1.41 | 1.60 |
| mmu-miR-27b_st | 1.45 | 1.91 |

TABLE 3-continued

List of amygdalar miRNAs up regulated (Table 3A) or down regulated (Table 3B) following IP with Ago2.

| | | |
|---|---|---|
| mmu-miR-20a_st | 1.57 | 1.52 |
| mmu-miR-30a_st | 1.34 | 1.65 |
| mmu-miR-100_st | 1.41 | 1.55 |
| mmu-miR-153_st | 1.44 | 1.92 |
| mmu-miR-194_st | 1.57 | 1.78 |
| mmu-miR-30c_st | 1.40 | 1.66 |
| mmu-miR-23a_st | 1.51 | 1.70 |
| mmu-miR-106a_st | 1.62 | 1.61 |
| mmu-miR-30b_st | 1.43 | 1.70 |
| mmu-miR-195_st | 1.59 | 1.98 |
| mmu-miR-30e_st | 1.36 | 1.56 |
| mmu-miR-126-3p_st | 1.58 | 1.76 |
| mmu-let-7i_st | 1.49 | 1.57 |
| mmu-miR-434-5p_st | 1.30 | 1.55 |
| mmu-miR-376b_st | 1.64 | 1.99 |
| mmu-miR-495_st | 1.45 | 1.82 |
| mmu-miR-369-5p_st | 1.60 | 1.77 |
| mmu-miR-421_st | 1.71 | 1.53 |
| mmu-miR-543_st | 1.52 | 1.69 |
| mmu-miR-410_st | 1.44 | 1.76 |
| mmu-miR-34b-5p_st | 2.18 | 1.53 |

(Table 3B)

| Downregulated | Fold-Change Susceptible | Fold-Change Resilient |
|---|---|---|
| mmu-miR-210_st | −1.59 | −2.13 |
| mmu-miR-298_st | −1.75 | −2.08 |
| mmu-miR-423-5p_st | −1.68 | −1.94 |
| mmu-miR-346_st | −1.74 | −1.96 |
| mmu-miR-139-3p_st | −1.71 | −2.13 |
| mmu-miR-320_st | −1.74 | −2.03 |
| mmu-miR-485_st | −1.53 | −1.88 |
| mmu-miR-491_st | −1.53 | −2.01 |
| mmu-miR-31_st | −1.30 | −1.53 |
| mmu-miR-92b_st | −1.20 | −1.53 |
| mmu-miR-93_st | −1.36 | −1.50 |
| mmu-miR-125a-3p_st | −1.32 | −1.55 |
| mmu-miR-134_st | −1.47 | −1.63 |
| mmu-miR-323-5p_st | −1.43 | −1.76 |
| mmu-miR-345-5p_st | −1.30 | −1.62 |
| mmu-miR-341_st | −1.36 | −1.89 |
| mmu-miR-370_st | −1.33 | −2.04 |
| mmu-miR-433_st | −1.49 | −1.75 |
| mmu-miR-455_st | −1.40 | −1.61 |

*For both Tables 3A-B, the data was presented as fold change for "Susceptible" or "Resilient" mice compared with Control. Values in bold are significantly altered.

Several miRNAs, which have been significantly upregulated in the "Susceptible" and "Resilient" groups of mice, have been selected and illustrated in a heatmap (see FIGS. 19A-19B).

Gene Expression Array (mRNA)

TABLE 4

List of amygdalar mRNAs up regulated following IP with Ago2.

| Upregulated | Fold-Change Susceptible | Fold-Change Resilient |
|---|---|---|
| Tnrc18 | 1.36 | 1.23 |
| Ifi30 | 1.34 | 1.21 |
| Adamts9 | 1.79 | 1.52 |
| Fkbp5 | 1.35 | 1.26 |
| Adh1 | 1.42 | 1.05 |
| Pxdn | 1.32 | 1.19 |
| Impdh2 | 1.41 | 1.02 |
| Pdzd2 | 1.31 | 1.31 |
| Csmd3 | 1.33 | 1.44 |
| Usf1 | 1.33 | 1.20 |
| A2m | 1.71 | 1.09 |
| Ccnd3 | 1.34 | 1.10 |
| Rrh | 1.33 | 1.02 |

TABLE 4-continued

List of amygdalar mRNAs up regulated following IP with Ago2.

| Upregulated | Fold-Change Susceptible | Fold-Change Resilient |
|---|---|---|
| Wfikkn2 | 1.40 | 1.07 |
| Fras1 | 1.48 | 1.34 |
| Notch2 | 1.50 | 1.22 |
| Fam38a | 1.33 | 1.18 |
| Hist1h3f | 1.31 | 1.19 |
| Fam167a | 1.31 | 1.05 |
| Calml4 | 1.68 | 1.11 |
| Tspan4 | 1.30 | 1.21 |
| Dnahc6 | 1.38 | 1.07 |
| Jag2 | 1.31 | 1.19 |
| Shank2 | 1.60 | 1.42 |
| Dock6 | 1.33 | 1.10 |
| Mamdc2 | 1.30 | 1.20 |
| Sgms2 | 1.39 | 1.13 |
| Iqub | 1.51 | 1.11 |
| Ubxn11 | 1.36 | 1.06 |
| Wfdc2 | 1.53 | 1.11 |
| Spef2 | 1.33 | 1.16 |
| Fggy | 1.31 | 1.14 |
| Pcolce2 | 1.37 | 1.16 |
| Thbs1 | 1.32 | 1.13 |
| Dnahc7b | 1.40 | 1.13 |
| Nt5dc2 | 1.41 | 1.12 |
| Slc4a2 | 1.34 | 1.07 |
| Adamts17 | 1.40 | 1.35 |
| Plscr2 | 1.34 | 1.21 |
| Clic6 | 1.43 | 1.13 |
| St6galnac2 | 1.38 | 1.08 |
| Amigo2 | 1.33 | 1.06 |
| Trio | 1.33 | 1.15 |
| Lamb1-1 | 1.35 | 1.20 |
| Sema3b | 1.40 | 1.01 |
| Fap | 1.39 | 1.10 |
| Frem1 | 1.51 | 1.20 |
| Pon1 | 1.34 | 1.03 |
| Plin4 | 1.43 | 1.24 |
| Steap1 | 1.36 | 1.10 |
| Rdh5 | 1.52 | 1.13 |
| Cldn2 | 1.56 | 1.11 |
| Frrs1 | 1.37 | 1.10 |
| Spef2 | 1.36 | 1.07 |
| Slco1a5 | 1.31 | 1.13 |
| Ltc4s | 1.35 | 1.17 |
| Mfsd7c | 1.37 | 1.14 |
| Acss3 | 1.32 | 1.16 |
| Hif3a | 1.36 | 1.17 |
| Serpinb8 | 1.40 | 1.18 |
| Pcolce | 1.36 | 1.16 |
| Dnmt3a | 1.20 | 1.19 |
| GILZ (Tsc22d3) | 1.19 | 1.15 |
| Sdk2 | 1.29 | 1.36 |
| Prg4 | 1.16 | 1.72 |
| Fbn1 | 1.24 | 1.10 |
| Slitrk6 | 1.11 | 1.28 |
| Plxna1 | 1.30 | 1.16 |
| Plxnb2 | 1.25 | 1.10 |
| Sema4b | 1.29 | 1.14 |

* Data is presented as fold change for "Susceptible" or "Resilient" mice compared with Control. Values in bold are significantly altered.

TABLE 5

List of amygdalar mRNAs down regulated following IP with Ago2.

| Downregulated | Fold-Change Susceptible | Fold-Change Resilient |
|---|---|---|
| Cyp2d10 | −1.22 | −1.34 |
| Lonrf1 | −1.32 | −1.31 |
| Btnl5 | −1.64 | −1.54 |
| B2m | −1.33 | −1.20 |
| Tekt5 | −1.36 | −1.10 |

TABLE 5-continued

List of amygdalar mRNAs down regulated following IP with Ago2.

| Downregulated | Fold-Change Susceptible | Fold-Change Resilient |
| --- | --- | --- |
| Prp2 | −1.51 | −1.02 |
| Krtap5-1 | −1.34 | −1.10 |
| Krtap5-4 | −1.33 | −1.10 |
| Klhl38 | −1.38 | −1.07 |
| Th | −1.42 | −1.03 |
| Pcsk9 | −1.33 | −1.20 |
| Dnahc3 | −1.39 | −1.22 |
| Sgpp2 | −1.37 | −1.03 |
| Opalin | −1.49 | −1.28 |

Several potential miRNAs and their putative targets in the brain are analyzed.

Example 4A miR-15a and miR-15b as Regulators of the Stress Response

Materials and Experimental Procedures

Total RNA Extraction

Amygdala tissue was dissected 90 minutes following acute stress procedure. Total RNA was isolated using miRNeasy kit (Qiagen) in order to preserve miRNAs. Frozen brain punches were transferred into lysis buffer and immediately homogenized. Neuronal primary cultures or N2a cell cultures were lysed in-well, on ice. Further processing was done according to the manufacturer's recommendation. RNA extracts were stored at −80° C. until use.

miRNA Array miRNA differential expression was assayed by Agilent (Agilent, Santa Clara, Calif., USA) or Affymetrix (Affymetrix, Santa Clara, Calif., USA) miRNA microarrays, according to the manufacturer's instructions. For the assessment of miRNA differential expression using the Agilent array, 100 ng total RNA per sample (3 control samples and two acute stress samples) were each labeled and hybridized according to the manufacturer's instructions. Arrays were scanned using an Agilent microarray scanner. The data was extracted using the Agilent Feature Extraction software v9 and analyzed using Partek® Genomics Suite (Partek Inc., St. Louis, Mo., USA). Data from the GeneView.txt files were subject to log transformation and quantile normalization. For the assessment of miRNA differential expression using the Affymetrix array, 1 µg total RNA per sample (two control samples and two acute stress samples) were each labeled and hybridized according to the manufacturer's instructions. Arrays were scanned using an Affymetrix microarray scanner. The data was extracted using the Affymetrix scanner software and normalized using the default parameters of the Affymetrix miRNAQCtool software (background adjustment, quantile normalization, log transformation and threshold determination). The normalized data from the four files were imported into Partek Genomics software. Genes not presented in any of the microarrays were filtered out. Due to the difference in miRNA distribution, different log ratio cutoffs (corresponding to about 1 standard error for each array) were chosen for each array: 0.2 for Agilent and 0.4 for Affymetrix. miRNAs with log ratios greater than the cutoff were compared between arrays and the common miRNAs are reported.

Cloning of 3' UTRs into Psicheck2 Luciferase Expression Plasmid

3'UTR sequence of CRFR1 was PCR amplified from mouse genomic DNA. 3'UTR PCR fragments were ligated into pGEM-T easy vector (Promega) according to the manufacturer's guidelines, and further subcloned into a single NotI site at the 3' end of luciferase in the Psicheck2 reporter plasmid (Promega). Cloning orientation was verified by diagnostic cuts and by sequencing.

Transfections and Luciferase Assay

HEK293T cells were grown on poly-L-lysine in 48-well format to a 70-85% confluence and transfected using Polyethyleneimine with the following plasmids: Psicheck2-3'UTR plasmid, pre-mmu-miR-15 over-expression in pEGFP plasmid or pEGFP plasmid alone (clontech). 24 hours following transfection, cells were lysed and luciferase reporters activity were assayed as previously described [Chen A. et al. Mol Endocrinol (2005) 19: 441-58]. Renilla luciferase values were normalized to control firefly luciferase levels (transcribed from the same vector but not affected by 3'UTR tested) and averaged across six well repetitions per condition.

Figure 7A:
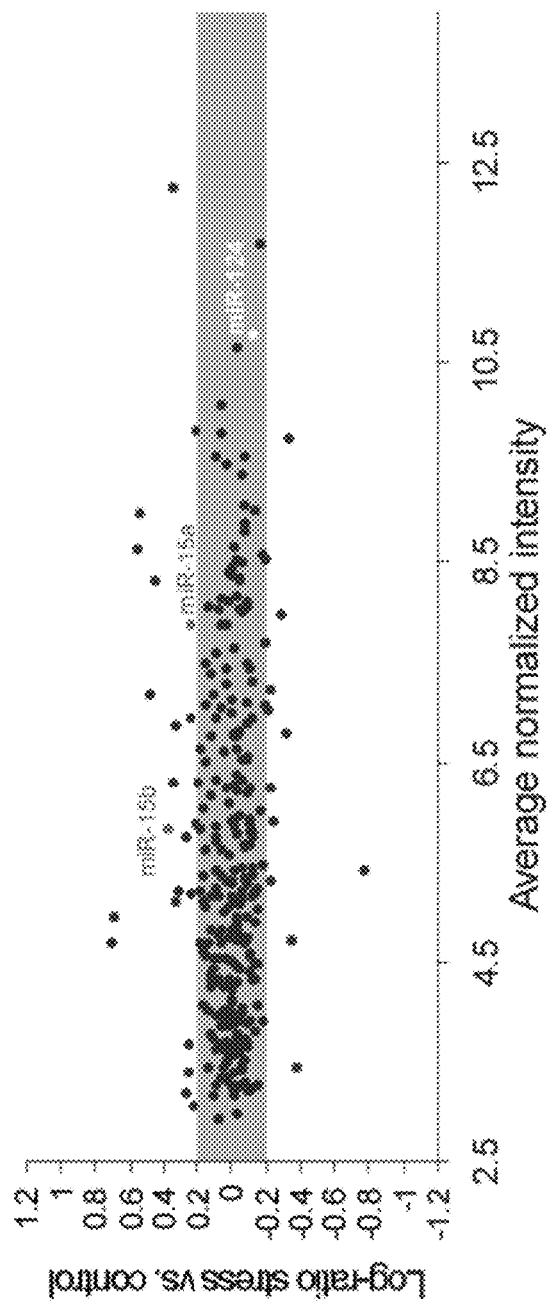
Figure 7B:
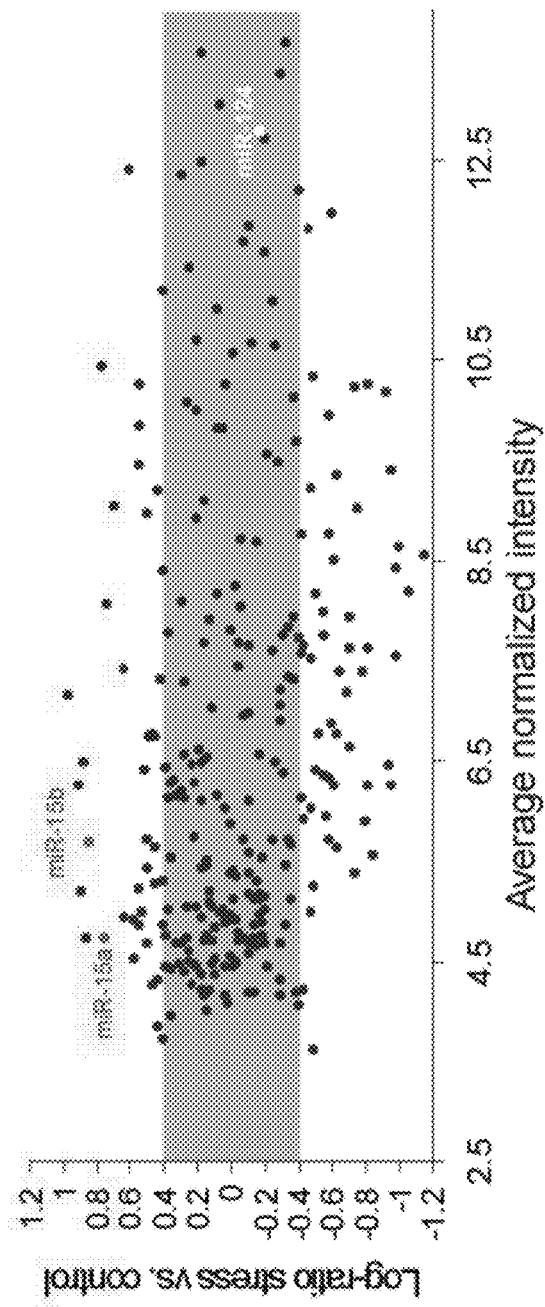
Figures 7C, 7D:
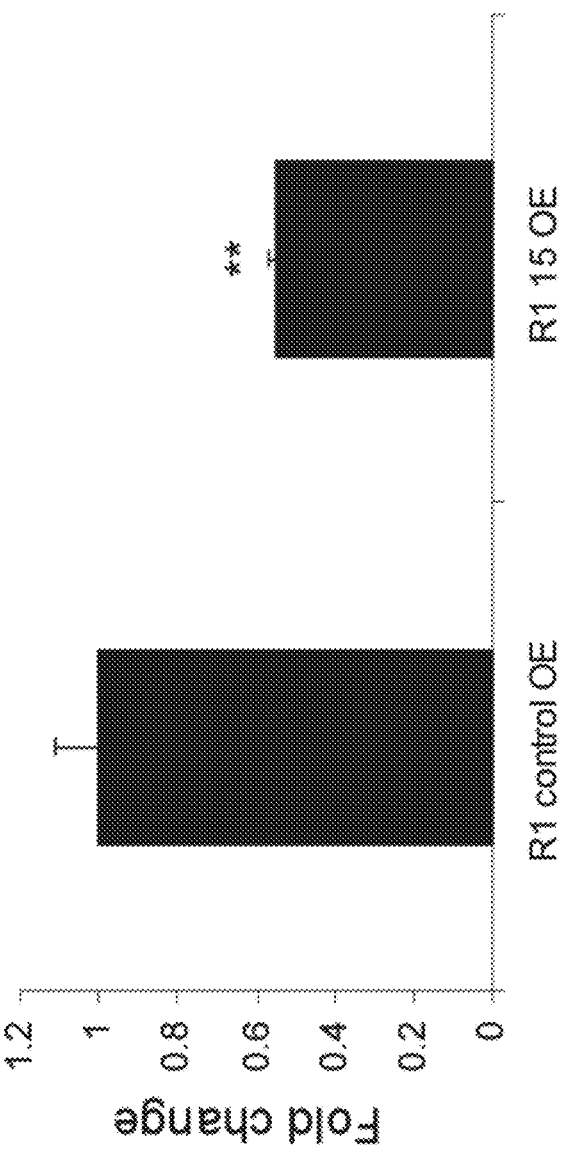

Results miR-15a and miR-15b emerged as up regulated 90 minutes following acute restraint stress (FIG. 7A-7B). Both miR-15a and miR-15b were bioinformatically predicted to target CRFR1-3'UTR (FIG. 7C). In-Vitro overexpression of miR-15b in HEK293T cells significantly reduced the levels of luciferase expression controlled by CRFR1-3'UTR (FIG. 7D).

Example 4B

The Effect of miR15 on FKBP5

Materials and Experimental Procedures

As illustrated in Example 4A, hereinabove.

Results

According to the array results, miR-15a and FK506 binding protein 5 (also known as FKBP5) were both up regulated in the "Susceptible" and "Resilient" mice relative to the control group (FIGS. 20A-20B), suggesting their up regulation in the RISC complex as a result of chronic stress.

Genetic studies have identified a role for FKBP5 in posttraumatic stress disorder, depression and anxiety. For example, single nucleotide polymorphisms (SNPs) in FKBP5 have been found to interact with childhood trauma to predict severity of adult posttraumatic stress disorder (PTSD) [Binder, E. B. et al., Nature genetics (2004) 36:1319-1325]. These findings suggest that individuals with these SNPs who are abused as children are more susceptible to PTSD as adults. FKBP5 has also been found to be less expressed in individuals with current PTSD [Yehuda, R. et al., Biological psychiatry (2009) 66:708-711]. The FKBP5 gene has been found to have multiple polyadenylation sites and is statistically associated with a higher rate of depressive disorders [Binder et al. supra].

Further analysis of the 3' UTR of FKBP5 revealed that it has one conserved seed match sequence to miR-15 (FIG. 20C).

If indeed miR-15a regulates FKBP5 mRNA, it was expected that while both miR-15a and FKBP5 would be up regulated in the Ago-2 precipitate (as shown by the microarray results, FIG. 20B), the total levels of either mRNA or protein of FKBP5 in the amygdala sample would be decreased.

In order to examine whether the interaction between miR-15a and FKBP5 takes place in the amygdale, a real time PCR analysis on total RNA sample obtained from the amygdala of "Susceptible" and control mice was performed. As shown in FIGS. 21A-21B, miR-15a levels were increased in total RNA extract taken from susceptible mice whereas FKBP5 levels were decreased. These results indicated that miR-15a represses FKBP5 levels in the amygdala following chronic stress condition.

Cloning the intact and mutated 3' UTR forms of FKBP5 for luciferase assay analysis are performed in order to find whether a direct interaction between miR-15a and FKBP5 occurs in vitro.

In addition to FKBP5, miR-15 can potentially regulate a number of genes that are involved in the stress response including Stx1a (syntaxin 1a), Sgk1 (serum/glucocorticoid regulated kinase) and Adrb2 (FIG. 22).

Example 4C miR-181 Regulates Glutamate Receptors

Materials and Experimental Procedures

Cloning of 3' UTRs into Psicheck2 Luciferase Expression Plasmid

3'UTR sequences of Grm1, Grik3, Grm5, Grik2 and Grm7 were PCR amplified from mouse genomic DNA. 3'UTR PCR fragments were ligated into either pGEM-T easy vector (Promega) or pJET12 vector (Fermentas) according to the manufacturer's guidelines, and further subcloned into a single NotI or XhoI site at the 3' end of luciferase in the Psicheck2 reporter plasmid (Promega). Cloning orientation was verified by diagnostic cuts and by sequencing.

Chronic Social Defeat

Mice were subjected to a social defeat protocol as previously described [Krishnan V. et al. Cell (2007) 131: 391-404]. Briefly, the mice were placed in a home cage of an aggressive ICR mouse where they physically interacted for five minutes. During this time, the ICR mouse attacked the intruder mouse and the intruder displayed subordinate posturing. Perforated clear plexiglass dividers were then placed between the animals and the mice remained in the same cage for 24 hours to allow sensory contact. The procedure was then repeated with an unfamiliar ICR mouse for each of the next 10 days.

Results miR-181d levels were significantly increased in mice suffering from chronic stress (FIG. 23). In an attempt to find interactions between miR-181 and potential mRNA targets, Inventors discovered that miR-181 can potentially regulate many types of glutamate receptors. In general, glutamate receptors can be divided into two groups, lonotropic glutamate receptors (iGluRs), which form the ion channel pore that activates when glutamate binds to the receptor, and Metabotropic glutamate receptors (mGluRs), which indirectly activate ion channels on the plasma membrane through a signaling cascade that involves G proteins.

Of the many specific subtypes of glutamate receptors, it is customary to refer to primary subtypes by a chemical which binds to it more selectively than glutamate. The research, though, is ongoing, as subtypes are identified and chemical affinities measured. Several compounds are routinely used in glutamate receptor research and associated with receptor subtypes:

TABLE 6

Glutamate receptors categorized into subgroups

| Name | Type |
| --- | --- |
| NMDA receptor | Ionotropic |
| Kainate receptor | |
| AMPA receptor | |
| mGluR | Metabotropic |

As illustrated in FIGS. 24 and 25, out of all the conserved predicted targets of miR-181, there are 6 glutamate receptors (Grm1, Grik3, Grm5, Gria2, Grik2 and Grm7).

It has been shown previously that miR-181a controls Gria2 surface expression in hippocampal neurons [Saba. R. et al., Molecular and Cellular Biology (2012) 32(3):619-32]. Luciferase assays are being performed in order to verify the miRNA-mRNA interaction. Furthermore, a conditional miR-181 KO mice line are crossed with a specific cre line thereby obtaining a deletion of miR-181 in specific brain nuclei.

Example 5A

MiR-182 a Fine Tuner of Normal Neuronal Activity and of Psychopathological Behavior Materials and Experimental Procedures Cloning of 3' UTRs into Psicheck2 Luciferase Expression Plasmid 3'UTR sequence of Htr1a was PCR amplified from mouse genomic DNA. 3'UTR PCR fragments were ligated into pGEM-T easy vector (Promega) according to the manufacturer's guidelines, and further subcloned into a single NotI site at the 3' end of luciferase in the Psicheck2 reporter plasmid (Promega). Cloning orientation was verified by diagnostic cuts and by sequencing.

Transfections and Luciferase Assay

HEK293T cells were grown on poly-L-lysine in 48-well format to a 70-85% confluence and transfected using Polyethyleneimine with the following plasmids: Psicheck2-3'UTR plasmid, pre-mmu-miR-182 over-expression in pEGFP plasmid or pEGFP plasmid alone (clontech). 24 hours following transfection cells were lysed and luciferase reporters activity were assayed as previously described [Chen A. et al. Mol Endocrinol (2005) 19: 441-58]. Renilla luciferase values were normalized to control firefly luciferase levels (transcribed from the same vector but not affected by 3'UTR tested) and averaged across six well repetitions per condition.

Chronic Social Defeat

Mice were subjected to a social defeat protocol as previously described [Krishnan V. et al. Cell (2007) 131: 391-404]. Briefly, the mice were placed in a home cage of an aggressive ICR mouse and they physically interacted for five minutes. During this time, the ICR mouse attacked the intruder mouse and the intruder displayed subordinate posturing. Perforated clear plexiglass dividers were then placed between the animals and the mice remained in the same cage for 24 hours to allow sensory contact. The procedure was then repeated with an unfamiliar ICR mouse for each of the next 10 days.

Microdissection of the Raphe Nucleus and Plasma Collections

Brain samples were taken from mice raphe nucleus (RN) after removing the brain and placing it on acryl brain matrix (Stoelting). Slices were taken using standard razor blades (GEM) based on designated anatomical markers. Blunted 14G syringes were used to extract the RN region from 3 mm slices removed from the matrix.

microRNA Purification and Quantitative RT-PCR Expression Analysis mRNAs, including microRNAs, were isolated from sorted neurons, frozen brain punches and plasma using miRNeasy mini kit (Qiagen) according to the manufacturer instructions, and treated using miScript Reverse transcription kit miRNA to generate cDNA. cDNA samples were then analyzed using SYBR®Green PCR kit (Qiagen) according to the manufacturer's guidelines in AB 7500 thermocycler (Applied Biosystems). Specific primers for each miR were used together with the commercial universal primer, while U6 snRNA was used as internal control.

Cloning of miR182 Over Expression Viral Vector

Pre-miR-182 was amplified by PCR from mouse genomic DNA with primers adding restriction enzyme AgeI sites and then was inSlc6a4ed to pGEM-T Easy vector (Promega, Madison, Wis.). After sequencing of pGEM-T Easy and digestion of both pGEM-T Easy and pEGFP vector (Clontech laboratories Inc., Mountain View, Calif.) with the AgeI, the premature miR-182 sequence was ligated to the pEGFP vector to construct the expression plasmid pEGFP-miR-182. Afterwards, pEGFP-miR-182 was cut by BamHI and B srGI in parallel to cutting pCSC-E/Syn-eGFP plasmid with the same enzymes, and the miR-182-eGFP sequence was ligated to pCSC-E/Syn to construct pCSC-eSNY-pre-miR-182-eGFP plasmid which was confirmed by restriction endonuclease analysis and DNA sequencing.

Production of Lentiviral Vectors

Recombinant lentiviruses were produced by transient transfection in HEK293T cells, as previously described [Naldini L et al., Proc Natl Acad Sci USA (1996) 93:11382-8]. Briefly, infectious lentiviruses were harvested at 48 and 72 hours post-transfection, filtered through 0.45 pin-pore cellulose acetate filters and concentrated by ultracentrifugation.

Results

To date miR-182 was reported mainly in cancer related studies such as human lung adenocarcinoma cells, glioma, breast cancer, bladder cancer, melanoma and DNA repair. Additionally, miR-182 was found to be involved in developmental processes such as inner ear and retinal development, and in the immune system in activation of T lymphocytes, and in lupus disease. In the nerves system mi-R182 was implied in sensory organ-specific rat dorsal root ganglia, and as a circadian clock modulator, while a correlation between genetic variants of pre-miR-182 were found in major depression patients [Saus E et al., Hum Mol Genet. (2010) 19(20):4017-25]. Additionally, miR-182 was listed among other 12 miRs as down-regulated in resilient to learned helpless behaviors male rats prefrontal cortex [Smalheiser N R et al., Int J Neuropsychopharmacol. (2011) 1-11].

Figure 8:
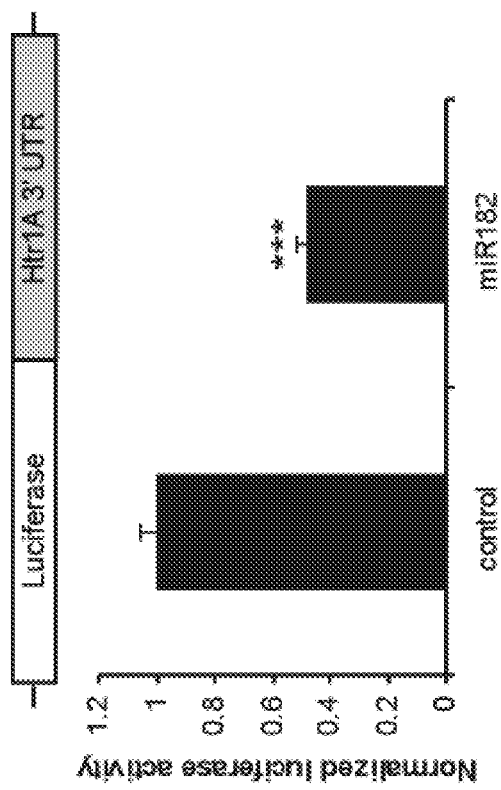
FIG. 8 is a graph illustrating luciferase reporter assay results indicating that miR-182 probably targets Htr1a 3'UTR. Luciferase assays data depicts renilla luciferase activity normalized to the activity of a co-transfected firefly luciferase reporter in HEK293 cells transfected with 3'UTR of the gene described and an empty vector, or a vector over-expressing a specific miR.

Bioinformatical analysis of Htr1a 3'UTR performed as part of the 5HT miRs microarray analysis implied a possible targeting of this gene by miR-182. Therefore, inventors performed in vitro testing via a luciferase assay, which revealed a strong repression of Ht1a 3'UTR by miR-182 (FIG. 8). Two conserved seed matches sequence for miR-182 appeared in Htr1a mouse 3' UTR.

Regulation studies indicated a strong tendency of down-regulation of miR-182 expression levels in the RN of adult male mice exposed to chronic social defeat compared to controls (FIG. 9) suggesting involvement of miR-182 in the molecular response to environmental stimulus known to induced depression-like behaviors.

Further bioinformatics analysis generating targeting predictions for miR-182 in two databases revealed a long list of potential targets, including genes related to neuronal activity both in normal and in pathological conditions (FIG. 10).

In order to further test miR-182 in vitro for identification of specific miR target interactions, and to reveal miR-182 role in regulation of normal and pathological behaviors in vivo, plasmid and lentiviral systems for manipulation of miR-182 were developed. Neuronal specific over-expression lentiviruses were manufactures (FIG. 11A) and tested in vitro in the neuronal cell line N2a. These results demonstrated increased miR-182 levels in cells infected with miR-182 over-expression lentiviruses compared to control (FIG. 11B). Knockdown plasmid sequence specific for miR-182 named miArrest (Genecopoeia, Rockville, Md., USA, FIG. 11C) was purchased and sub-cloned to viral constructs (FIG. 11C). These systems are tested in cell culture and by site specific injection to adult mice brains.

Null mice for miR-182 are developed in order to investigate the miRs role in retina development. Recently, inventors obtained breeding pairs for this line, and upon a generation a colony, miR-182 KO and their WT liter mates are being phenotyped behaviorally and physiologically.

Example 6

Regulation of miR182 Expression Levels by Acute Stress

Materials and Experimental Procedures

As described in Example 5A, hereinabove

Results

The effect of acute stress on miR182 level was examined. As illustrated in FIG. 26, acute immobilization stress led to decreased miR182 expression levels in mice raphe nucleus (RN) 24 hours following induction of stress (P<0.01). miR182 demonstrated reduced expression levels in the raphe nucleus both following acute and chronic stress, suggesting it has a role in modulation the molecular responses to stress in the raphe nucleus, possibly by effecting its target gene Ht1a modulating 5-HT levels in the synapse.

miR-Target Interaction Assay for miR182 Predicted Target Genes

Using a luciferase assay, eleven predicted target genes of miR182, chosen after extensive bioinformatics, were examined (FIG. 27). 3'UTRs of the target genes were tested in vitro to check if miR182 has a represoric effect as measured by the activity of the conjugated reporter gene luciferase. Out of the eleven genes tested three genes: Dscam (Down Syndrome Cell Adhesion Molecule), L1cam (Cell adhesion molecule L1) and Tsnax (Translin-associated protein X) had demonstrated represoric effect by miR182 as in luciferase assay (FIG. 27). When testing the 3'UTR of the listed above target gene of miR182 a conserved seed match sequence for miR182 was observed both in Tsnax, L1cam and Dscam, suggesting this miR-target interaction had a functional role (data not shown).

Next, the direct repressoric effect of miR182 on these three genes was verified. Therefore, the 3'UTRs was mutated to remove miR182 seed match sequence and compared the regular 3'UTRs to the mutated one in vitro by luciferase assays. miR182 repressoric effect on L1cam 3'UTR was abolished when mutated its seed match sequence (FIG. 28), and similarly the effect of miR182 on Tsnax was abolished in the mutated 3'UTR (FIG. 29) indicating miR182 targeted this gene directly. Similar verification for Dscam and Htr1a with mutated 3'UTR are performed.

A mice model lacking miR182 is used to study the interaction between miR182 and its target genes in vivo. Inventors are examining the behavioral phenotype of miR182KO mice in tests for social behavior, learning and memory, and schizophrenia-like behaviors.

Example 7

Establishment of miR135 Knockdown System;
Cloning, Lentiviruses Generation and In Vitro and In Vivo Validations Materials and Experimental Procedures
Cloning of miR135 KD Viral Vector miR135b KD plasmid pEZX-H1-miR135KD-CMV-mCherry and control pEZX-H1-control KD-CMV-mCherry were purchased from GeneCopeia (USA). H1 promoter and the KD sequence were amplified using primers with flanking NheI site and ligated to pGEM-T Easy. After sequencing of pGEM-T Easy and digestion of both pGEM-T Easy and p156- pRRL-CMV-GFP with the NheI site, H1-KD miR and nicked p156 were ligated to generate p156-pRRL-H1-miR135bKD-CMV-GFP and p156-pRRL-H1-control KD-CMV-GFP.

Results

To evaluate the effect of decreased miR135 levels in RN on mice 5-HT-related behaviors, a plasmid based miR135b inhibitor was utilized and its efficiently was tested in a luciferase assay. In this assay, HEK293T cells were co-transected with miR135OE, miR135KD and 3'UTR plasmids, and the ability of miR135bKD plasmid to block the repressing effect of miR135 on Slc6a4 and Htr1a 3' UTR was tested. miR135b repressoric effect of Htr1a 3'UTR was blocked by miR135KD plasmid (FIG. 30A). Similarly, miR135b effect on Slac6a4 3'UTR was blocked by miR135KD (FIG. 30B). These results indicate that miR135KD plasmid indeed blocks the biological activity of miR135.

miR135KD sequence and a control sequence were sub-cloned to a viral vector (FIG. 30C) and lentiviruses expressing the different knockdown (KD) sequence were generated. In order to test the lentiviruses' ability to infect brain tissue, mice RN were infected with either one of the lentiviruses. Indeed, infection caused expression of GFP (FIGS. 30D-30E) demonstrating the ability of miR135bKD lentiviruses to infect brain tis sue.

Example 8

Behavioral Effects of miR135 Knock Down in Adult Mice RN

Materials and Experimental Procedures
Behavioral Assessments

Mice were behaviorally characterized by using tests for anxiety and depression-like behaviors as described in Example 6 above.

Results

Following the in vitro and in vivo validation of miR135KD lentiviruses, they were used to manipulate miR135 levels in the RN and to test their effect on mice behavior. Adult mice were injected either with miR135KD lentiviruses, or KD control lentiviruses to RN and following recovery period were tested for anxiety and depression-like behaviors. Since miR135 represses negative regulators of 5-HT, we expected miR135KD to lead to decrease 5-HT levels in the synapse and by that to increased anxiety and depression-like behaviors.

In the open field test no differences were observed between the groups (FIG. 31A), however in the elevated pulse maze test, miR135KD mice demonstrated higher anxiety-like behavior by demonstrating a tendency to spend less time in the open arms (P=0.0644) and to visit less times in the open arms (P=0.0572 FIG. 31B). Additionally miR135KD mice walked significantly less distance in the open arms (P=0.0433) and had a longer tendency to visit in open arms (P=0.0124 FIG. 31B). Similarly, in the dark light test performed under basal stress conditions, miR135KD mice demonstrated a significant increased anxiety-like behavior compared to the controls by spending less time in the light (P=0.0454 FIG. 31C), visiting less times in the light chamber (P=0.0107 FIG. 31D) and walking a smaller distance in the light chamber (P=0.0402 s FIG. 31E). The results illustrated a decrease in miR135 levels 40 min and 24 hours after acute stress (FIG. 30A-30B), therefore, the present theory was that stressed miR135KD mice would not differ from their controls in anxiety-like behaviors when tested following acute stress, since the control mice would also have a decreased miR135 levels due to the stress. Indeed, there was no difference between the groups when re-tested in the dark light transfer test in any of the parameters, both when tested 40 minutes or 24 hours after acute stress (FIG. 31C-31E).

Depression-like behaviors of miR135KD were tested both under basal conditions and following pharmacological manipulation. Since miR135 levels were showed to increase in the RN following SSRI administration (FIG. 31E), the speculation was that the reduction of miR135 levels may lead to reduced response to SSRI. In the tail suspension test performed both in basal levels and after SSRI administration, there was no difference between miR135b KD mice and control KD mice in immobility time (FIG. 31F), and the expected decrease in immobility time due to SSRI treatment was observed (P<0.0008). However, in the forced swim test, additionally to the main effect for SSRI injection (P<0.0001), miR135KD mice injected with SSRI were more immobile in the last 2 minutes of the test compared to control KD mice (P=0.0141 5 minute, P=0.0404 6 minute; FIG. 31G suggesting attenuation of SSRI antidepressant effects by reducing miR135 levels in the RN. This result implies that miR135 is part of the endogenous alternation leading to behavioral changes caused by SSRI.

Example 9 miR135 Overexpression in 5-HT Neurons

Materials and Experimental Procedures

Mice over expressing miR135a in 5-HT neurons were compared to their littermates controls both in expression levels of miR135 and its target genes and behaviorally.

Results

The effects of manipulating miR135 levels specifically in 5-HT neurons in the RN of mice was tested for anxiety and depression-like behaviors. For that purpose, a genetic system was developed using the Cre-loxP system. Specifically, the 5-HT specificity was obtained using the ePet Cre mice expressing Cre recombinase specifically in the 5-HT RN positive neurons and miR135 overexpression was performed by crossing the 5-HT-specific Cre line (ePet Cre) with transgenic mouse line with conditional overexpression for miR135a (FIG. 32).

miR135 expression level in the RN of mice overexpressing miR135 specifically in 5-HT neurons (miR135OE) was tested by real time PCR for miR135 and compared to control mice, positive for the miR135 conditional overexpression allele but negative for ePet CRE. miR135OE mice demonstrated near to 2 fold overexpression compared to control mice (FIG. 33A; P<0.05). Overexpression levels of miR135 were similar to levels measured in the RN of mice following SSRI administration, suggesting this mice line was a good model for studying miR135 antidepressant characteristics. Additionally, miR135 target gene mRNA, Slc6a4 (FIG. 33B; P<0.05) and Htr1a (FIG. 33C; P<0.1) were downregulated in the RN of miR135OE mice compared to control demonstrating in vivo repression by miR135 of its target genes.

In order to test miR135 overexpression specifically in 5-HT neurons, miR135OE mice and their littermates controls were exposed to chronic social defeat paradigm, a procedure know to induce depression and anxiety-like behaviors, and subsequently were tested for anxiety and depression-like behaviors.

miR135OE mice demonstrated increased anxiety-like behaviors following social defeat compared to control liter mates. In the open field, a tendency for increased anxiety was observed in miR135OE mice time and visit number to the center (P<0.1, FIG. 34A). While in the dark light transfer test miR 135OE mice spent more time in light (P<0.05, FIG. 34B) and spent less time in the light chamber (P<0.01, FIG. 34B). Similar results were observed in the elevated pulse maze (P<0.05, FIG. 34B) while miR135OE mice spent more time in the open arms (P<0.05, FIG. 34C) and traveled larger distance in the open arms (P<0.05, FIG. 34C).

Depression-like behaviors of miR135OE mice following social defeat were lower than of the control litter mates. A tendency towards decreased immobility time of the miR135OE mice compared to controls was observed in the tail suspension test (P<0.1, FIG. 34D), along with a significant decreased immobility time in the forces swim test (P<0.05, FIG. 34E).

Materials and Experimental Procedures for Mir-135 Section

MicroRNA Microarray of 5HT Neurons

Hindbrain cells from embryonic day 12 of ePet-EYFP mice were FACS sorted to distinguish 5HT YFP-positive neurons from surrounding non-5HT YFP-negative cells as previously described (Wylie et al., 2010). Total RNA, including the miRNA population, with 3 biological repeats from each cell type was purified, labeled and hybridized on Agilent Mouse miRNA Microarray (Agilent Tech, Mississauga, ON, Canada) design number 021828 based on Sanger miRBase release 12.0 according to the manufactures instructions. The microarrays were scanned and the data were extracted and processed using the Feature Extraction Software (Agilent Technologies). Following scanning, intensity output data of the GeneView.txt files were analyzed to quantify differential relative expression of microRNAs using the Partek® Genomics Suite (Partek Inc., St. Louis, Mo.). The data were log 2 transformed, quantile normalized and filtered according to the flag "gIsGeneDetected" in the GeneView file. Of 666 murine miRs, 198 remained for further analysis after this filtering step. Differentially expressed miRs were then identified using a threshold of a 1.5 fold change.

Cloning of Target Transcripts 3' UTRs into psiCHEK-2 Luciferase Expression Plasmid 3' UTRs sequences of Slc6a4 and Htr1a were PCR amplified from mouse genomic DNA. 3'UTRs PCR fragments were ligated into pGEM-T easy vector (Promega) according to the manufacturer's guidelines, and further sub-cloned into a single NotI site at the 3' end of luciferase in the psiCHEK-2 reporter plasmid (Promega). Mutated 3' UTR sequences, lacking miR-135 seed sequences, were synthesized with primer overhangs across the seed match sequence. Cloning orientation was verified by diagnostic cuts and sequencing.

TABLE 7

Oligonucleotide primers used for cloning

| | Gene | Product size | Orientation | Primer Sequence |
|---|---|---|---|---|
| 1 | Slc6a4 3'UTR | 760 $^{with\ 2}$ | sense | ATCCGCATGAATGCTGTGTA (SEQ ID NO: 10) |
| 2 | Slc6a4 3'UTR | | antisense | GTGGGTGGTGGAAGAGACAC (SEQ ID NO: 11) |
| 3 | Htr1a 3' UTR | 2600 $^{with\ 4}$ | sense | AGTTCTGCCGCTGATGATG (SEQ ID NO: 6) |
| 4 | Htr1a 3' UTR | | antisense | GCACAAATGGAGAGTCTGATTAAA (SEQ ID NO: 7) |
| 5 | Slc6a4 3'UTR mutated | 320 $^{with\ 2}$ | sense | TGTCTTGCTTATATTTTCTCAGTAG (SEQ ID NO: 14) |
| 6 | Slc6a4 3'UTR mutated | 440 $^{with\ 1}$ | antisense | GAAAATATAAGCAAGACATCCCTGTT (SEQ ID NO: 15) |
| 7 | Htr1a 3' UTR short | 1400 $^{with\ 8}$ | sense | AAAGATCCCTTTCCCCAATG (SEQ ID NO: 16) |

TABLE 7-continued

Oligonucleotide primers used for cloning

| | Gene | Product size | Orientation | Primer Sequence |
|---|---|---|---|---|
| 8 | Htr1a 3' UTR short | | antisense | CAGTGCGTCTTCTCCACAGA (SEQ ID NO: 17) |
| 9 | Htr1a 3' UTR mutated seed 1 | 1300 with 8 | sense | ATAAGCAAGGGCCCAAAAGGAAGA (SEQ ID NO: 18) |
| 10 | Htr1a 3' UTR mutated seed 1 | 120 with 7 | antisense | TTTTGGGCCCTTGCTTATAAGTCC (SEQ ID NO: 19) |
| 11 | Htr1a 3' UTR mutated seed 2 | 170 with 8 | sense | CTGCCCTGCCACATGTGTTTTAT (SEQ ID NO: 20) |

Transfections and Luciferase Assays

HEK293T cells were grown on poly-L-lysine in a tissue culture plate to 70-85% confluence and transfected using polyethyleneimine with the following plasmids: psiCHECK-2 plasmid containing the wild type or mutated 3' UTR and the overexpressing vector for a specific miRNA (miR-135a as set forth in SEQ ID NO: 210 or miR-135b as set forth in SEQ ID NO: 211), or empty overexpression plasmids. Twenty-four hours following transfection cells were lysed and luciferase reporter activities were assayed as previously described (Kuperman et al., 2011). Renilla luciferase values were normalized to control firefly luciferase levels, transcribed from the same vector but not affected by 3' UTR, then tested and averaged across six repetitions per condition.

Animals and Housing

Adult C57BL/6 male mice (Harlan, Jerusalem, Israel) were used for the in vivo lentiviral experiments. ePet-Cre mice expressing Cre recombinase specifically in serotonergic neurons were used as previously described (Scott et al., 2005). Transgenic mice carrying a conditional cassette for miR-135 overexpression were also used. Mice were housed in a temperature-controlled room (22±1° C.) on a reverse 12 h light/dark cycle. Food and water were available ad libitum. All experimental protocols were performed on male mice and were approved by the Institutional Animal Care and Use Committee of The Weizmann Institute of Science.

Amphetamine-Induced Hyperactivity Rat Model

In these experiments rats are equally divided into 4 treatment groups. Rats are pretreated with miR-135, lithium, valproate, or saline (control) and then half of the rats in each group are administered amphetamine (0.5 mg/kg subcutaneously (s.c.)) and the other half is given saline (s.c.).

Alternatively, the rats are first administered amphetamine (0.5 mg/kg subcutaneously (s.c.)) or saline (s.c.) followed by treatment with miR-135, lithium, valproate, or saline (control).

Ten minutes later all rats are placed in the activity meter and the activities of rats pretreated or treated with miR-135 are compared to non treated rats (control group) and to rats pretreated or treated with lithium or with valproate. One week later the procedure is repeated.

Ketamine-Induced Hyperactivity Rat Model

In these experiments rats are equally divided into 4 treatment groups: control, lithium, valproate and miR-135 treated rats and are treated as follows:

Rats are pretreated (for 14 days) with miR-135, lithium (47.5 mg/kg, i.p., twice a day), valproate (200 mg/kg, i.p., twice a day), or with saline (i.p., twice a day) as a control. Between days 8 and 14, these rats are treated with ketamine (25 mg/kg, i.p.) or saline.

In a reversal protocol, rats are administered ketamine (25 mg/kg, i.p.) or saline first followed by administration of miR-135, lithium, valproate, or saline for 7 days. Then, rat activity is monitored as discussed herein.

Chronic Social Defeat

Mice were subjected to a social defeat protocol as previously described (Elliott et al., 2010). Briefly, mice were placed in a home cage of an aggressive ICR mouse where they physically interacted for five minutes. During this time, the ICR mouse attacked the intruder mouse and the intruder displayed subordinate posturing. Perforated clear Plexiglas dividers were then placed between the animals and the mice remained in the same cage for 24 hours to allow sensory contact. The procedure was then repeated with an unfamiliar ICR mouse for 10 consecutive days.

Antidepressant Treatment

Mice received i.p. injection of the tricyclic, imipramine, the SSRI, fluoxetine, or the NRI, reboxetine (20 mg/kg in saline), or saline. Chronic injections were carried out for 18-21 consecutive days, and acute injection was performed 24 hours prior to brain microdissection. For behavioral testing, mice were injected with 20 mg/kg SSRI i.p. 30 minutes prior to the test.

Brain Microdissection

Brain samples were taken from mice raphe nuclei (RN) using an acryl brain matrix (Stoelting). Slices were taken using standard razor blades based on designated anatomical markers. Blunted 14G syringes were used to extract the raphe region from 2 mm slices and the tissue was kept at −70° C. until RNA purification.

microRNA Purification and Quantitative Real Time PCR Expression Analysis mRNAs including microRNAs were isolated using miRNeasy mini kit (Qiagen) according to the manufacturer instructions, and treated using miScript Reverse transcription kit to generate cDNA. Samples were then analyzed using SYBR®Green PCR kit (Qiagen) according to the manufacturer's guidelines in AB 7500 thermocycler (Applied Biosystems). Specific primers for each miR were used together with the commercial universal primer, while U6 snRNA was used as an internal control. For mRNA quantification specific primers were designed for each transcript using the software "primer express 2" and expression was tested using real time PCR as previously described (Haramati et al., 2011).

TABLE 8

Oligonucleotide primers used for microRNA real time PCR

| Gene | Primer sequence |
|---|---|
| miR-135a | TATGGCTTTTTATTCCTATGTGA (SEQ ID NO: 1) |
| miR-135b | TATGGCTTTTCATTCCTATGTGA (SEQ ID NO: 2) |
| miR-375 | TTTGTTCGTTCGGCTCGCGTGA (SEQ ID NO: 3) |
| U6 | GATGACACGCAAATTCGTGAA (SEQ ID NO: 4) |
| miR-124 | TAAGGCACGCGGTGAATGCC (SEQ ID NO: 5) |
| miR-16 | TAGCAGCACGTAAATATTGGCG (SEQ ID NO: 158) |

TABLE 9

Oligonucleotide primers used for mRNA real time PCR

| Gene | Sense Primer | Antisense Primer |
|---|---|---|
| Slc6a4 | GGGTTTGGATAGTACGTTCGCA (SEQ ID NO: 159) | CATACGCCCCTCCTGATGTC (SEQ ID NO: 160) |
| Htr1a | GTGCACCATCAGCAAGGACC (SEQ ID NO: 161) | GCGCCGAAAGTGGAGTAGAT (SEQ ID NO: 162) |
| Tph2 | AGTATTTTGTGGATGTGGCCATG (SE QID NO: 163) | TGGGAATGGGCTGACCATATT (SEQ ID NO: 164) |
| YFP | CATGCCCGAAGGCTACGT (SEQ ID NO: 165) | CGATGCCCTTCAGCTCGAT (SEQ ID NO: 166) |
| GAD-67 | TCATGTCCCGGAAGCACC (SEQ ID NO: 167) | AATTGGCCCTTTCTATGCCG (SEQ ID NO: 168) |

Cloning of miR-135 Knockdown Lentiviral Constructs, Production of Lentiviruses and In Vitro Verifications miR-135 knockdown (KD) plasmid pEZX-H1-miR-135KD-CMV-mCherry and control pEZX-H1-control KD-CMV-mCherry were purchased from GeneCopeia (USA). H1 promoter and the KD sequence were amplified using primers containing NheI flanking site and were ligated to pGEM-T Easy vector. The H1-135 KD fragment was subcloned into the p156-pRRL-CMV-GFP lentiviral construct using the NheI restriction site resulting in p156-pRRL-H1-miR-135bKD-CMV-GFP and p156-pRRLH1-control KD-CMV-GFP lentiviral constructs, which were further confirmed by DNA sequencing. Recombinant lentiviruses were produced by transient transfection in HEK293T cells, as described previously (Tiscornia et al., 2006). Briefly, infectious lentiviruses were harvested at 48 and 72 hours post-transfection, filtered through 0.45 µm-pore cellulose acetate filters and concentrated by ultracentrifugation. For miR-135 KD efficiency verification rat raphe cell line (RN46A) were infected with either miR-135 KD or control KD lentiviruses, and 48 later mRNA were harvested and expression levels of Htr1a and Slc6a4 were tested using real time PCR.

Intracerebral Injections of Lentiviruses

For stereotaxic surgery and lentiviral delivery, computer-guided a stereotaxic instrument and a motorized nanoinjector were used (Angle Two™ Stereotaxic Instrument, myNeurolab) as previously described (Lebow et al., 2012). Mice were placed on a stereotaxic apparatus under general anesthesia, and the lentiviral preparation was delivered to coordinates determined as defined by the Franklin and Paxinos atlas to the DR: ML 0 mm; AP—4.6 mm; DV—3.9 mm in 300 tilt. Injections were performed at a rate of 0.2 µl/1 min. Following two weeks recovery period, mice were subjected to behavioral and physiological studies. Following phenotyping, mice were anesthetized and perfused with phosphate buffered 4% paraformaldehyde. The fixed brains were serially sectioned to 30 mm slices in order to confirm the location of the injection site, using immunohistochemistry.

Immunohistochemistry

The procedure used for immunohistochemistry is as described previously (Regev et al., 2011). For GFP immunostaining, biotinylated anti-GFP antibody was used raised in goat as primary antibody (Abcam, Cambridge, UK), and streptavidin conjugated Cy2 as secondary antibody (Jackson Immunoresearch Laboratories Inc, West Grove, Pa., USA).

Behavioral Assessments

All behavioral assessments were performed during the dark phase following habituation to the test room for 2 hours before each test. Mice were tested for anxiety-like behavior using the elevated plus-maze, dark-light transfer and open-field tests, and for depression-like behavior using the forced swim test.

Open-field test: The open-field test was performed in a 50×50×22 cm white box, lit to 120 lux. The mice were placed in the box for 10 minutes. Mice locomotion in the box was quantified using a video tracking system (VideoMot2; TSE Systems, Bad Hamburg, Germany).

Dark-light transfer test: The dark-light transfer test apparatus consisted of a polyvinyl chloride box divided into a black dark compartment (14×27×26 cm) and a connected white 1200 lx illuminated light compartment (30×27×26 cm). During the 5 minute test, time spent in the light compartment, distance traveled in light, and number of light-dark transitions were quantified with a video tracking system (VideoMot2; TSE Systems, Bad Hamburg, Germany).

Elevated plus-maze test: This test apparatus has the shape of a plus sign and contains 2 barrier walls and 2 lit (6 lux) open arms. During the 5 minute test, number of entries, distance traveled and the time spent in the open arms was automatically scored using a video tracking system (VideoMot2; TSE Systems, Bad Hamburg, Germany).

Modified forced swim test: The forced swim test was performed as previously described (Krishnan et al., 2007). The apparatus is a plastic bucket, with a diameter of 18 cm, filled with 25° C. water to a depth of 15 cm. Each mouse was placed in the center of the bucket to initiate a 6 minutes video recorded test session. The duration of time spent immobile in the 3-6 minutes of the test was automatically scored using EthoVision XT (Noldus, Wageningen, Netherlands).

Social avoidance test: In the social avoidance test, mice were placed in a 15 cm×35 cm arena with a small 15 cm×8 cm neighboring chamber separated by a divider with small open slits allowing full sensory contact. The tested mice were allowed to habituate to the arena for three minutes, and then an unfamiliar ICR mouse was placed in the neighboring chamber for another three minutes. Time spent near the divider was quantified using video tracking by Ethovision software (Noldus, Wageningen, Netherlands). Interaction ratio was calculated by dividing the time the mice spent in a defined area near the unfamiliar ICR to the time the mice spent in the same area during habitation, and multiplied by 100.

Microdissections, Sample Preparation and HPLC-ED Analysis of 5HT and 5-HIAA Concentrations Microdissections were performed as previously described (Neufeld-Cohen et al., 2010a) using the Palkovits microdissection technique (Palkovitz, 1988). Coronal brain sections (300 μm) were taken using a Leica CM1950 cryostat (North Central Instruments, USA). The sections were mounted onto glass slides and microdissected on a cold plate at −10° C. under a stereomicroscope using microdissection needles with varying inner diameters. Microdissections were each put in a tube containing 100 μL of acetate buffer (3.0 g/L sodium acetate, 4.3 mL/L glacial acetic acid; pH adjusted to 5.0). Next, samples were homogenized and centrifuged at 4° C. and 13,000 rpm for 3 min. The pellet was reconstituted with 175 μL of 0.2 M NaOH for protein content, and 50 μL of the supernatant was used for detection of 5HT and 5-hydroxyindoleacetic acid (HIAA) using high performance liquid chromatography with electrochemical detection (HPLC-ED) as previously described (Evans et al., 2008). Samples were placed in an ESA model 542 autosampler injecting the samples into the HPLC chromatographic system (ESA, Chelmsford, Mass., USA). The HPLC system also consisted of an ESA Model 582 Solvent Delivery Module to pump the mobile phase (9.53 g/L potassium dihydrogen orthophosphate dihydrate, 300 mg/L octanesulphonic acid, 35 mg/L EDTA, 920 mL/L HPLC grade H2O and 80 mL/L HPLC grade methanol; pH adjusted to 3.4 using orthophosphoric acid) through the chromatographic system. The stationary phase, where chromatographic separation occurred, consisted of an integrated precolumn/column system (Ultrasphere-XL 3 μm Octyl Guard Cartridge, 5/70×4.6 mm; MAC-MOD Analytical, USA). Electrochemical detection was accomplished using an ESA Model 5200A Coulochem II detector with dual potentiostats connected to an ESA 5021 Conditioning Cell with the electrode potential set at 0 mV and an ESA 5014B Microdialysis Cell with the channel 1 and channel 2 electrode potentials set at 25 mV and 250 mV, respectively. For each run, the average peak heights of known concentrations of 5HT and 5-HIAA were determined manually using chromatography analysis software (EZChrom Elite for Windows, Version 2.8; Agilent Technologies, USA) and used to calculate the concentration of the unknown samples. Tissue concentrations of 5HT and 5-HIAA were standardized to the amount of protein.

Human Sample Studies

Case-Control study: Eleven male patients diagnosed with major depression (N=9) or bipolar disorder (N=2) and twelve healthy male controls were selected from a study described in detail in (Menke et al., 2012). Briefly, patients were recruited from the Max-Planck Institute of Psychiatry and blood draws for RNA were performed within the first five days of in-patient admission for a depressive syndrome. The mean HRDS score at admission was 24.3 (SD: 5.3 and range 17-32). Controls were screened for the absence of lifetime psychiatric disorders using the Composite International Diagnostic Interview (CIDI) (Wittchen H U, 1999) and for absence of current psychiatric symptoms using the HRDS. Whole blood was collected using a PAXgene (PreAnalytiX GmbH, Hombrechtikon, Switzerland) whole blood RNA collection tube after 2 hours of fasting at 6 pm. Total RNA was isolated from PAXgene whole blood samples using the PAXgene Blood RNA Kit with the Qiagen method for column purification of nucleic acids (PreAnalytiX GmbH, Hombrechtikon, Switzerland). The quality, concentration and purity of the RNA was assessed using an Agilent 2100 Bioanalyzer (Agilent Technologies, USA) and 260 nm UV absorption (Nanophotometer, Germany).

Cognitive behavioral therapy (CBT): Patients for this analysis were derived from a randomized clinical trial designed to identify neuroimaging and other biological predictors of remission to cognitive behavioral therapy (CBT). All patients provided written informed consent prior to participation in the study. The study was conducted in accordance with the Declaration of Helsinki and its amendments, and approved by Emory's Institutional Review Board. The study design is described in detail in (Dunlop et al., 2012). Briefly, eligible participants were adult outpatients between 18 and 60 years of age who met the *Diagnostic and Statistical Manual of Mental Disorders, Fourth Edition* (*DSM-IV*) criteria for a primary diagnosis of MDD without psychotic features. Patients received 16 sessions of CBT. The CBT provided followed a standardized protocol (Beck et al., 1979). All patients were assessed for symptom change weekly for the first 6 weeks using the Hamilton Depression Rating Scale (HRDS) and then every other week for the remaining six weeks. All patients had an HRDS score of 15 or greater at randomization. From this study, 12 patients who had blood drawn for RNA at baseline, week 2 (N=16) and week 12 were selected. No current drug treatment was allowed at the baseline blood draw. 75% of patients were women, and 87% of European Ancestry. The mean age in the CBT group was 42.4 (SD: 9.6) years. Whole blood was collected into Tempus RNA tubes (Applied Biosystems) and extracted using the Tempus Spin RNA Isolation Reagent kit (Applied Biosystems). RNA quality and quantity were measured using the Agilent 2100 Bioanalyzer (Agilent Technologies, Palo Alto, Calif., USA) and photometric methods (Nanophotometer, Implen, Munich, Germany), respectively.

Statistical Analysis

Data was expressed as means+/−SEM. To test for statistical significance, Student's t test was used in cases were only two groups were compared, such as for the microarray real time PCR data validation. One way ANOVA was used for comparison between multiple groups such as between the different treatments in the luciferase assay. Two way ANOVA was used in cases of two independent variables, such as the SSRI or NRI injections both in acute or chronic administration. Repeated measure analysis was used when needed. Post hoc t tests were used when necessary to reveal statistical significance. Statistical analysis was performed using Jmp7 software, and differences between groups were considered significant when p<0.05.

Example 10 microRNA "Fingerprint" of 5HT Neurons

5HT neurons were isolated from the RN of ePet-EYFP embryos, and their miR expression profile was compared to non-5HT cells, obtained from the same brain area, using miR microarray (FIG. 35A). Cell sorting validation was performed by comparing the mRNA expression levels of relevant marker genes. YFP, the fluorescent marker for the ePET-positive neurons was significantly enriched in the 5HT population (FIG. 35B), tryptophan hydroxylase 2 (TPH2), a key enzyme in the production of 5HT, was robustly expressed in the 5HT cells (FIG. 35C) and glutamate decarboxylase 67 (GAD67), the enzyme catalyzing synthesis of GABA, a common non-5HT neurotransmitter in the RN, was abundant in the non-5HT cells (FIG. 35D). The miR "fingerprint" obtained from the microarray (FIG. 1A) contained fourteen (Table 10, below) and twenty-seven (Table 11, below) miRs that were expressed 2-fold more or less, respectively, in 5HT neurons compared to the non-5HT neurons. Representative validation of the array results was performed using real time PCR for miRs highly expressed in 5HT neurons such as miR-375 (FIG. 1B), and for miRs expressed at lower levels in 5HT neurons such as miR-135a (FIG. 1C).

TABLE 10

MicroRNA microarray results - list of microRNAs expressed at least two-fold higher in 5HT neurons compared to non-5HT cells of the mouse RN

| microRNA name | Fold change |
| --- | --- |
| mmu-miR-375 | 20.72 |
| mmu-miR-376c | 11.73 |
| mmu-miR-7a | 4.44 |
| mmu-miR-137 | 2.87 |
| mghv-miR-M1-2 | 2.79 |
| mmu-miR-709 | 2.61 |
| mmu-miR-291b-5p | 2.51 |
| mmu-miR-1224 | 2.40 |
| mmu-miR-1892 | 2.37 |
| mmu-miR-702 | 2.31 |
| mmu-miR-139-3p | 2.25 |
| mmu-miR-762 | 2.24 |
| mmu-miR-671-5p | 2.10 |
| mmu-miR-483* | 2.04 |

TABLE 11

MicroRNA microarray results - list of microRNAs expressed at least two-fold lower in 5HT neurons compared to non-5HT cells of the mouse RN

| microRNA name | Fold change |
| --- | --- |
| mmu-miR-691 | −5.10 |
| mmu-miR-4661 | −4.11 |
| mmu-miR-17 | −3.95 |
| mmu-miR-376b | −3.18 |
| mmu-miR-124 | −3.13 |
| mmu-miR-218 | −3.08 |
| mmu-miR-128 | −2.99 |
| mmu-miR-140* | −2.92 |
| mmu-miR-148a | −2.86 |
| mmu-miR-340-5p | −2.86 |
| mmu-miR-181c | −2.82 |
| mmu-miR-210 | −2.72 |
| mmu-miR-135a | −2.69 |
| mmu-miR-27a | −2.66 |
| mmu-miR-452 | −2.45 |
| mmu-miR-370 | −2.20 |
| mmu-miR-300 | −2.19 |
| mmu-miR-376a | −2.17 |
| mmu-miR-127 | −2.13 |
| mmu-miR-15b | −2.12 |
| mmu-miR-101a | −2.07 |
| mmu-miR-16 | −2.06 |
| mmu-miR-324-5p | −2.05 |
| mmu-miR-434-5p | −2.05 |
| mmu-miR-92a | −2.03 |
| mmu-miR-669i | −2.00 |

In order to further study the potential role of miRs as modulators of 5HT neurons, extensive bioinformatic analysis was performed in a hypothesis-driven manner. Targeting prediction of known 5HT-related genes expressed in serotonergic neurons that have been previously demonstrated to be associated with psychopathologies, were bioinformatically crossed with the microarray results. miR targeting predictions for these genes were performed using two different web-based algorithms: Target Scan (www(dot)targetscan(dot)org) and MiRanda (www(dot)microrna(dot)org) and were crossed with the list of 91 miRs altered by at least ±1.5 fold in the 5HT neuron miR array, compared to non-5HT cells. Two protein coding target genes expressed in 5HT neurons in the RN were selected: the serotonin transporter, responsible for 5HT reuptake (also known as SERT or Slc6a4) and serotonin inhibitory receptor 1a (also known as Htr1a). Based on the miR array data and the bioinformatic analysis, seven miRs were chosen for further in vitro validation (FIGS. 1D-1E).

Example 11 miR-135 Targets Htr1a and Slc6a4 Transcripts

In vitro luciferase assays were performed to test the miR-target interaction between the 3'UTR of the tested 5HT-related genes and the miRs predicted to putatively target these transcripts. miR-135 targeting of Slc6a4 3'UTR (FIGS. 2A, 2C) and Htr1a 3'UTR (FIGS. 2B, 2D) resulted in robust repression of translation of these transcripts. Additionally, significant repression of Htr1a 3'UTR was mediated by miR-335, miR-181c and miR-26a (FIG. 2D). Due to the strong effect of miR-135 on both Htr1a and Slc6a4 the present studies further focused on this miR-target interaction. Further bioinformatic analysis revealed that miR-135 has 3 highly conserved variants, miR-135α-1, miR-135α-2 and miR-135b (FIG. 36A-36C). In addition, miR-135 seed match sequences in the Slc6a4 3'UTR is highly conserved (FIG. 2E), and in one out of the two seed matches in the Htr1a 3'UTR strong conservation was observed (FIG. 2F). Mutation studies on the 3'UTR of the Slc6a4 transcript, in which the miR-135 seed match sequence was removed, revealed that both miR-135a and miR-135b targeting of Slc6a4 was mediated via its seed match sequence, since the repression induced by the miR-135 was fully blocked by the mutation in Slc6a4 3'UTR (FIG. 2G). Mutating the Htr1a miR-135 seed matches, individually or together, revealed that miR-135a represses Htr1a 3'UTR via the distal and not the proximal seed match while miR-135b acts via both predicted sites (FIG. 2H).

Example 12

RN-miR-135 Levels are Upregulated by Antidepressants

Figures 37A, 37B, 37C:
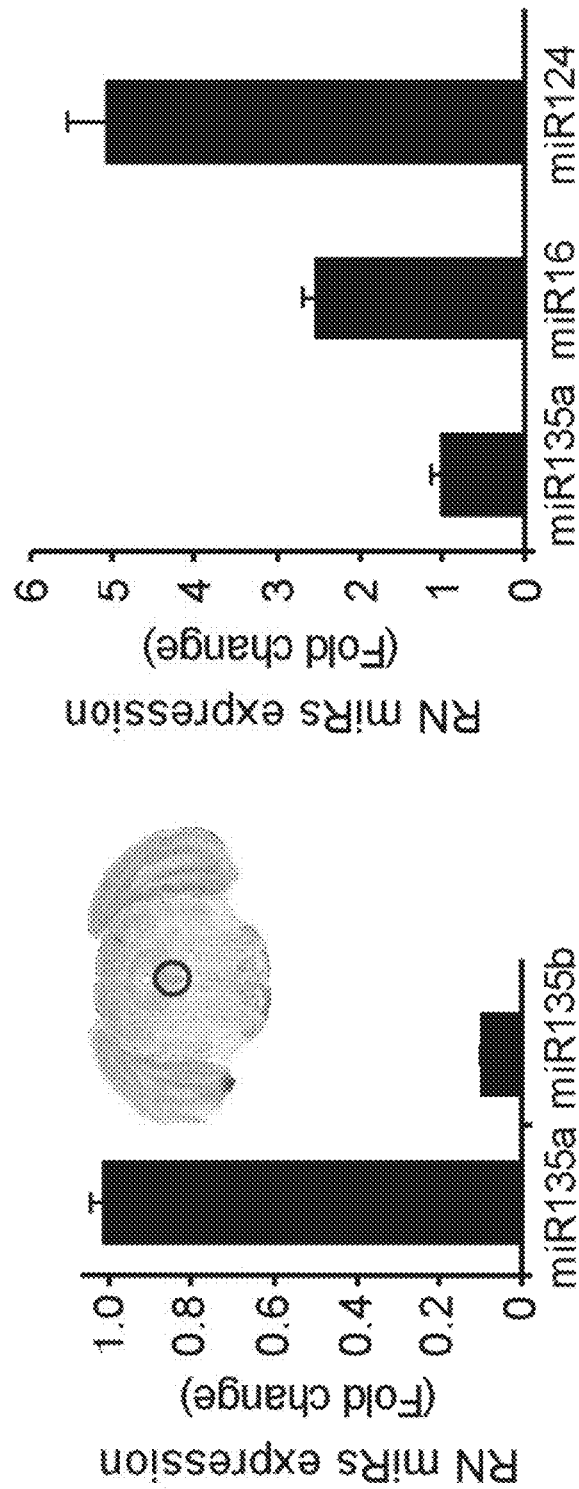

Since both Htr1a (Savitz et al., 2009) and Slc6a4 (Murphy et al., 2008) have been previously associated with depression and antidepressant cellular machinery, the present inventor sought to examine the regulation of miR-135 expression in response to antidepressant treatment. The mature miR-135a and miR-135b differ by only one nucleotide (FIG. 37A), yet are differentially expressed in the RN as observed in real time PCR results conducted on cDNA obtained from microdissected RN of adult wild type mice (FIG. 37B). miR 135b was expressed approximately 10 fold less than miR-135a, while the later is relatively highly expressed, only 5-fold less than miR-124, the most abundant miR in the brain and 2.5 fold less than miR-16 that was previously shown to have a role in controlling 5HT functions (FIG. 37C). Considering miR-135a is expressed at higher levels in the RN than miR-135b, and was also the variant differently altered in the 5HT microarray, the present inventor focused on regulation studies on this form. Next, the levels of miR-135a was tested in mice exposed to a chronic social defeat model (an environmental model used for the induction of depression-like behaviors) and to chronic treatment with the tricyclic antidepressant imipramine.

Figure 37D:
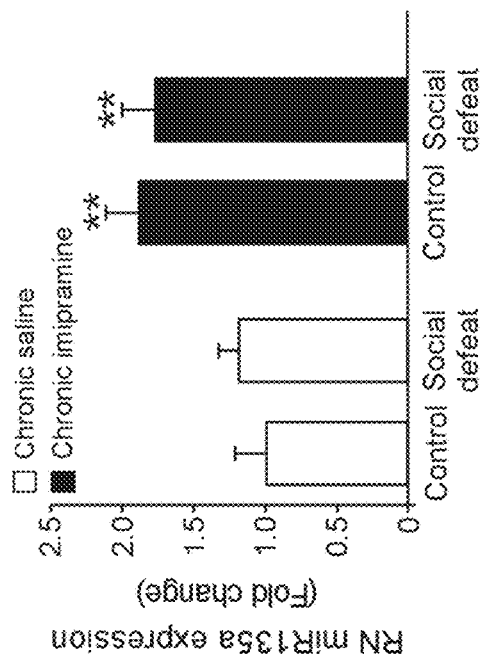
Figure 37E:
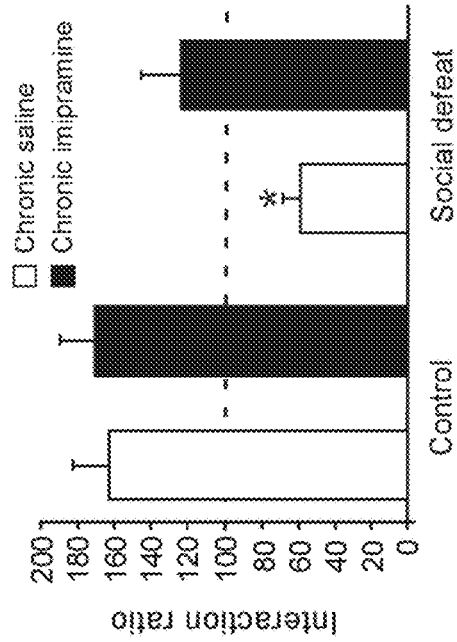
Figure 37F:
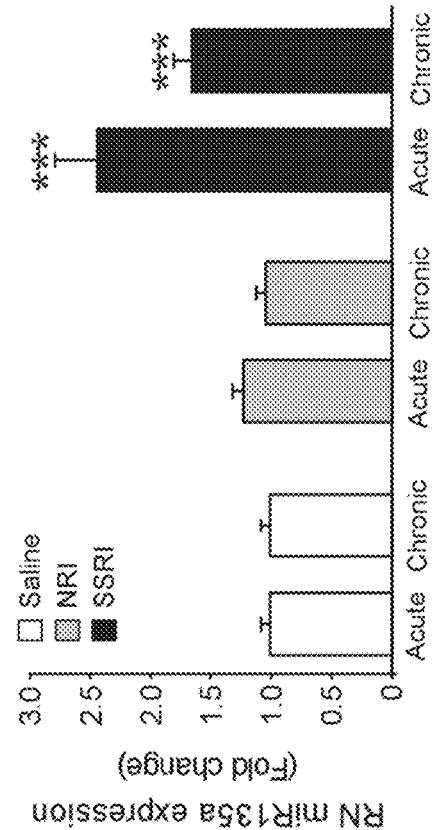
Figure 37G:
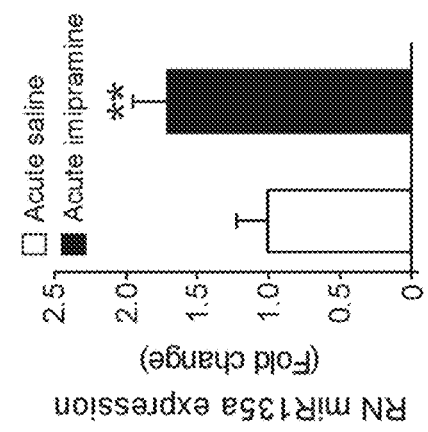

Using the social avoidance test, it was verified that social defeat can cause social avoidance and antidepressant administration can reverse this (FIG. 37D). Indeed, only mice exposed to social defeat and injected with saline and not those who received imipramine developed social avoidance as implied by an interaction ratio lower that 100% (FIG. 37D). Interestingly, chronic social defeat stress did not alter miR-135a levels in the RN, however, imipramine administered chronically (FIG. 37E) or acutely (FIG. 37F), both in stressed and non-stressed mice, significantly increased miR-135a expression levels in the RN. Since imipramine is not a specific 5HT reuptake inhibitor, the effects of both acute and chronic administration of the selective serotonin reuptake inhibitor (SSRI), fluoxetine, and the noradrenaline reuptake inhibitor (NRI), reboxetine, was further tested, a robust increase in miR-135a levels in the RN following both acute and chronic SSRI treatment was found, yet no differences were observed following the NRI treatment (FIG. 37G).

Example 13 miR-135 Overexpression Specifically in 5HT Neurons Reduces Anxiety and Depression-Like Behaviors Following Social Defeat To further explore the role of 5HT-miR-135 in vivo, a mouse model was established that specifically overexpresses miR-135 in 5HT neurons of the RN (miR-135OE). Mice expressing Cre recombinase specifically in the RN 5HT-positive neurons (ePet-Cre) were crossbred with a transgenic mouse line carrying a conditional miR-135a cassette (FIG. 38A). As controls, mice positive for the miR-135 overexpression transgene and negative for the ePet-Cre were used. miR-135a expression level in the RN of mice over expressing miR-135a specifically in 5HT neurons was tested by real time PCR, and was demonstrated to be overexpressed by approximately 2-fold compared to control mice (FIG. 38B). Overexpression levels of miR-135 in this mouse model were similar to those measured in the RN of mice following SSRI administration. Additionally, the levels of miR-135 target transcripts Slc6a4 (FIG. 38C) and Htr1a (FIG. 38D) were reduced in the RN of miR-135OE mice compared to control mice, demonstrating in vivo repression of miR-135 target genes.

The miR-135OE and their littermate controls were behaviorally characterized in tests for anxiety and depression-like behaviors, either under 'basal' conditions or following the chronic social defeat protocol. Under 'basal' conditions no differences were observed between miR-135OE and control mice in tests for anxiety and depression-like behaviors (FIGS. 38E-38J, left bars and 38K). However, miR-135OE mice demonstrated a significant resiliency to the effects of chronic social defeat. In the dark-light transfer test miR-135OE mice exposed to social defeat spent more time in light (FIG. 38E), visited the lit compartment more frequently (FIG. 38F) and traveled longer distance in light (FIG. 38G) relative to control mice. The behavioral performance of the miR-135OE mice did not significantly differ following the social defeat protocol. In contrast, control mice demonstrated significant increases in anxiety like-behaviors in all measured parameters of the dark-light test following social defeat (FIGS. 38E-38G). Similar results were observed in the elevated plus-maze test as control mice that were exposed to social defeat spent less time (FIG. 38H), had fewer visits (FIG. 38I) and traveled less distance (FIG. 38J) in the open arms compared to miR-135OE mice tested under the same conditions. No significant differences between 'basal' and stress conditions were observed in the miR-135OE group. Similar results were observed in tests assessing depression-like behaviors. While no differences were observed under 'basal' conditions (FIG. 38K), when tested following chronic social defeat, miR-135OE mice exhibited significantly less immobility time in the forced swim test compared to controls (FIG. 38L), which is interpreted as decreased depression-like behavior. These differences could not account for changes in locomotor activity since the distance traveled in the open-field was similar in both genotypes (FIG. 38M). Taken together, overexpression of miR-135 specifically in 5HT neurons protected against the adverse effect of chronic stress on anxiety and depression-like behaviors.

Example 14

Figure 39C:
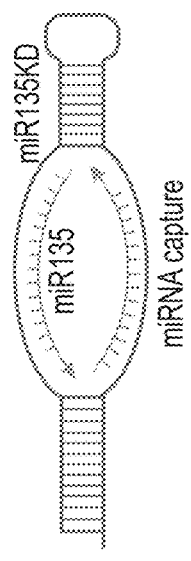

Knockdown of miR-135 in Adult Mice RN Increased Anxiety Like-Behaviors and Decreased the Response to Antidepressants To determine the importance of miR-135 endogenous levels in mediating depression-like behaviors in response to antidepressant treatment and anxiety-like behaviors under 'basal' conditions, a lentiviral-based system was established to specifically knockdown (KD) the endogenous levels of miR-135 in the RN of wild-type mice. Expression plasmid containing a miR-135 inhibitor (miRNA capture, FIG. 39A) or control sequence were subcloned into a lentiviral construct containing the H1 promoter and the GFP reporter (FIG. 39B) to allow constitutive expression of the miR-135 capture sequence. The efficiency of the lentiviruses, produced from these constructs, to suppress the expression of the target genes Htr1a and Slc6a4 was tested in vitro by infecting RN46A cells, which endogenously expressing both Htr1a, Slc6a4 and miR-135. RN46A cell infected with miR-135 KD lentiviruses expressed significantly higher levels of Htr1a and Slc6a4 mRNA as tested by real time PCR compared to cells infected by the KD control lentiviruses (FIG. 39C).

Figure 39D:
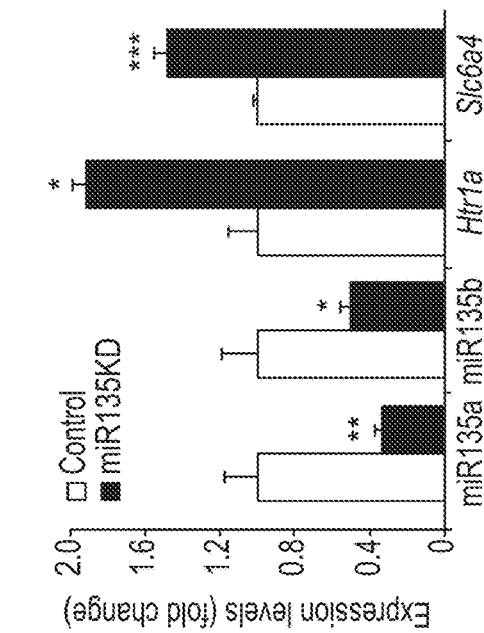

Wild-type adult mice RN were infected with either miR-135KD or control lentiviruses, and following a recovery period mice behaviors were assessed using tests for anxiety and depression-like behaviors. Infection accuracy was subsequently verified using GFP immunohistochemistry (FIG. 39D). In the dark-light transfer test the miR-135KD mice demonstrated a significant increase in anxiety-like behavior compared to control-injected mice (FIGS. 39E-39H). The miR-135 KD mice spent less time (FIG. 39E), visited less (FIG. 39F) and walked shorter distances in the lit compartment (FIG. 39G). Similarly, in the elevated plus-maze test the miR-135 KD mice demonstrated increased anxiety-like behaviors compared to control-injected mice. The miR-135 KD mice showed a tendency to spend less time (FIG. 39I), visit less (FIG. 39J) and travel significantly less distance (FIG. 39K) in the open arms of the maze (FIGS. 39I-39L).

Depression-like behaviors of the miR-135 KD mice were tested both under 'basal' conditions and following SSRI treatment. In the forced swim test no differences were observed between the groups under 'basal' conditions (FIG. 39M). However, following SSRI administration, miR-135 KD mice were significantly more immobile compared to control-injected mice (FIG. 39M), suggesting an important role for endogenous RN-miR-135 levels in mediating SSRI-induced antidepressant effects. Reduced levels of miR-135 in the RN did not affect the locomotor activity of these mice (FIG. 39N).

Example 15 miR-135 Overexpression Altered 5HT Levels and Metabolism

To evaluate whether changes in miR-135 levels are also reflected in the tissue concentrations of central 5HT and its turnover, the RN subdivisions were microdissected and the brain regions innervated by these areas from the miR-135 OE mouse model and control littermates. FIGS. 40A-40O, FIGS. 42A-42L and FIGS. 43A-43L depict tissue concentrations of 5HT and the 5HT metabolism (5HIAA/5HT ratio) in these mice under 'basal' conditions and following the social defeat protocol.

Tissue concentrations of 5HT and the 5HT metabolism within an anxiety and depression-related neural circuit were influenced by the miR-135 genotype, as well as the social defeat manipulation miR-135 OE decreased tissue 5HT concentrations, and increased serotonin metabolism, a pattern consistent with increased serotonin turnover, in brain regions implicated in regulation of anxiety-related behavior and stress resilience, such as the prelimbic cortex (PrL), infralimbic cortex (IL), basolateral amygdala (BLA), CA1 region of the ventral hippocampus (CA1V), subiculum (S), bed nucleus of the stria terminalis (BNST), central nucleus of the amygdala (CeA), dorsal, ventral, caudal and interfascicular parts of the dorsal raphe nucleus (DRD, DRV, DRC, DRI), and median raphe nucleus (MnR) (FIGS. 40A-40O, FIGS. 42A-42L and FIGS. 43A-43L). These results are in line with miR-135 OE decrease of Htr1a and Slc6a4 expression (FIGS. 38C-38D) under 'basal' conditions, effects that would be expected to result in increased serotonergic neuronal firing rates and serotonergic signaling, respectively.

Social defeat decreased tissue 5HT concentrations and increased 5HT metabolism in anxiety-related brain regions in control mice, a pattern consistent with increased serotonin turnover, including the PrL and BNST (FIGS. 40A-40O and FIGS. 42A-42L), persistent with previous studies demonstrating social defeat-induced activation of anxiety-related subsets of serotonergic neurons in the DRD and DRC. These effects of social defeat were prevented in miR-135OE mice, suggesting a mechanistic explanation to the behavioral resiliency to chronic stress observed in these mice.

Example 16 miR-135a Levels in the Blood are Downregulated in Depressed Patients and Upregulated by Therapy Since circulating miRs levels were shown to correlate with disease states, the present inventor tested whether blood miR-135 levels are altered in depressed human patients. Relative levels of miR-135a and miR-16 were tested in two sets of human blood samples. One compared depressed patients to matched healthy controls, the other changes in miRNA levels over time within depressed patient receiving 3 months of cognitive behavioral therapy (CBT). miR-135a levels were robustly reduced in currently depressed patients (mean Hamilton Depression Rating Scale (HRDDS)=24.3 (SD: 5.3), i.e. with moderate to severe depressive symptoms) compared to controls (FIG. 41A), while no significant changes in miR-16 were observed (FIG. 41B). Comparing miR-135a blood levels in depressed patients prior to and three months following treatment revealed a significant increase in miR-135a levels following CBT (FIG. 41C). No effect was observed in the same blood samples for miR-16 levels (FIG. 41D). These results suggest miR-135a levels in human blood as a possible biomarker for depression state and response to treatment.

Example 17

Anti-Bipolar Effect of miR-135 in Amphetamine-Induced Hyperactivity Rat Model

To evaluate the anti-bipolar effect of miR-135 preclinically, an in vivo amphetamine-induced hyperactivity model of mania in rats is used which is relevant to the manic phase of bipolar disorder. This model focuses on an induced increase in the activity level of the animal (hyperactivity) as a parallel to the hyperactivity of the manic patient. The reversal of the induced hyperactivity in rodents, by pretreatment with a drug indicates the possible efficacy of this drug in the treatment of human mania. The most consistent finding with lithium (the standard drug for mania) is the reduction in rearing. Rearing is followed in the models by observing the vertical activity of the animals.

Accordingly, pretreatment of rats with miR-135 prior to amphetamine-induced hyperactivity is being tested for the treatment of bipolar disease. Moreover, treatment of rats with miR-135 following amphetamine-induced hyperactivity is being tested for the treatment of bipolar disease.

Rats are housed under a 12 hr light/dark cycle and behavioral testing is conducted in the light phase. Specifically, rat activities are followed in an activity meter (Elvicom, Israel) based on 2 levels laser beams and equipped with a computerized system that can count the vertical movements of rats (rearing). Activities are recorded for 30 min for each session, and the resultant appropriate movement is reported per 30 min.

The activities of rats pretreated or treated with miR-135 are compared to non treated rats (control group) and to rats pretreated or treated with the standard drugs for mania, i.e. lithium or valproate. Rats are followed before and after being challenged with amphetamine. The statistical analyses are conducted using a two way ANOVA.

Example 18

Anti-Bipolar Effect of miR-135 in Ketamine-Induced Mania Rat Model

To evaluate the anti-bipolar effect of miR-135 preclinically, an in vivo ketamine-induced hyperactivity model of mania in rats is used. Ketamine induces hyperlocomotion of treated rats, which can be monitored as discussed above.

Rats are pretreated (for 14 days) with miR-135 or with the standard drugs for mania, i.e. lithium (47.5 mg/kg, i.p., twice a day) or valproate (200 mg/kg, i.p., twice a day), or with saline (i.p., twice a day) as a control. Between days 8 and 14, these rats are treated with ketamine (25 mg/kg, i.p.) or saline.

In a reversal protocol, rats first receive ketamine (25 mg/kg, i.p.) or saline followed by administration of miR-135, lithium, valproate, or saline for 7 days.

The activities of rats pretreated or treated with miR-135 are compared to non treated rats (control group) and to rats pretreated or treated with the standard drugs for mania, i.e. lithium or valproate. Rats are followed before and after being challenged with ketamine. The statistical analyses are conducted using a two way ANOVA.

Discussion

In the current study the role of specific miR was elucidated in regulating central 5HT system activity, under 'basal' and challenged conditions. The unique "fingerprint" of miR expression was determined in serotonergic neurons and several 5HT-linked target genes were bioinformatically identified. In-vitro luciferase assays and mutation studies revealed a strong repressive effect for miR-135 on both Slc6a4 and Htr1a transcripts. Intriguingly, miR-135 levels in the RN were robustly upregulated following acute or chronic SSRI administration. Genetically modified mice models, expressing higher or lower levels of miR-135 demonstrated major alternations in anxiety and depression-like behaviors, 5HT levels and metabolism, and behavioral response to antidepressant treatment. Finally, miR-135 levels in blood of depressed human patients and response to treatment were presented.

The use of the ePet-EYFP mouse model for the isolation of 5HT and non-5HT cells from the mouse RN allowed to determine for the first time the specific miR profile of serotonergic neurons. While this approach was successful and informative, yet, in order to efficiently sort the 5HT positive neurons from the mouse RN embryonic and not adult brain tissue was used, which means that at least part of the miRs presented in the 5HT miRs profile may be relevant to developmental processes and not adult 5HT neuronal functions. Nevertheless, serotonergic signaling during specific developmental periods is known to affect adult anxiety phenotypes (Gross et al., 2002). Interestingly, miR-375, commonly associated with pancreatic beta cell differentiation, was robustly expressed in 5HT neurons compared to control, supporting the suggested common developmental path of these tissues.

Bioinformatic analysis suggested several putative miR-target interactions between the serotonin receptor 1A (Htr1a) and the serotonin transporter (SERT or Slc6a4) 3'UTRs and miRs differentially expressed in the 5HT microarray. Htr1a and Slc6a4 have been shown to play a major role in the serotonergic system function, in depression and anxiety disorders, and in the response to antidepressants (Savitz et al., 2009) and (Murphy et al., 2008). Htr1a is an inhibitory G protein-coupled receptor that is expressed as an autoreceptor on 5HT producing cells and post-synaptically across the brain of 5HT projection sites. Stimulation of Htr1a autoreceptors inhibits serotonergic neuronal firing and the release of serotonin in nerve terminals and has been postulated to be one of the causes for the therapeutic lag that is commonly reported for most serotonergic antidepressants such as SSRIs. Slc6a4 is a plasma membrane transporter that terminates serotonin action by recycling it from the synaptic cleft into presynaptic neurons, in a sodium-dependent manner. Slc6a4 is the direct target of most commonly used antidepressants, either the former generation of tricyclic antidepressants that inhibit different monoamine reuptake transporter activities including Slc6a4, or the more specific SSRIs. Decreased activity of both Slc6a4 and the presynaptic Htr1a would be expected to increase 5HT levels in the synapse, which are consistent with antidepressant action and decreases in depressive symptoms. Luciferase assays confirmed miR-135 variants as significant repressors of both Slc6a4 and Htr1a transcripts. Mutation studies further demonstrated the importance of miR-135 seed binding sites in the Htr1a and Slc6a4 3'UTRs in mediating the observed miR-135 repressive effects. Single nucleotide polymorphisms (SNPs) in the 3'UTR of human Slc6a4 and Htr1a, previously reported for these genes (Piva et al., 2010), are not within miR-135 seed match sequences.

miR-135 was previously reported to be mainly involved in cancer-related pathologies and developmental processes. miR-135 was demonstrated to target the adenomatous polyposis coli gene and as a consequence to promote colorectal cancer, to modify chemotherapy resistance, and to regulate JAK2 in classic Hodgkin lymphoma. The role of miR-135 in developmental processes was demonstrated in megakaryocytopoiesis, porcine brain development, and mineralization in osteogenic differentiation by regulating Smad5, a key transducer of the BMP2 osteogenic signal. Additionally, miR-135 was suggested to be involved in regulating blood pressure by suppressing NR3C2 and to have a potential role in heart failure.

Several microRNA screening studies have reported that microRNA levels in various adult rodents or rat brain structures are affected by a range of behavioral and pharmacological manipulations (Kye et al., 2011). Stressful challenges were shown to alter miR expression in different brain sites using different paradigms (Smalheiser et al., 2011). The present inventor has recently demonstrated the involvement of miR-34 in the regulation of anxiety-like behaviors (Haramati et al., 2011), while miR-22, miR-138-2, miR-148a, and miR-488 were associated with panic disorder (Muinos-Gimeno et al., 2011). Studies using mice, presented in the current manuscript, revealed a clear upregulation of miR-135 following antidepressant administration. Further comparison of SSRI and NRI antidepressants demonstrated an SSRI- and not NRI-specific effect, further suggesting a role for miR-135 in the biology of 5HT neurons. While chronic stress is associated with increased susceptibility for the development of depression, surprisingly, chronic stress conditions did not affect miR-135 levels in the RN. Chronic SSRI treatment was reported to promote reduction in Slc6a4 and Htr1a protein levels but not mRNA [Slc6a4 (Benmansour et al., 2002), Htr1a (Savitz et al., 2009)] suggesting the possible involvement of a post-transcriptional mechanism in mediating SSRI activity. miR-16 was shown to target Slc6a4 and to have a role in antidepressant response (Baudry et al., 2010), while lithium administration was shown to alter miRs expression (Creson et al., 2011). An association was found between variants in miR-182 (Saus et al., 2010) and miR-30e (Xu et al., 2010b) in major depression patients, and miRs expression was altered in the prefrontal cortex of patients with suicidal depression (Smalheiser et al., 2012). Additionally, miR448 was shown to control expression of several 5HT receptors as part of adipose tissue development, and polymorphism in serotonin receptor 1B moderates the regulation by miR96 and associates with aggressive behaviors (Jensen et al., 2009). Finally, the miR510 targeting site of serotonin receptor-type 3E was shown to play a role in irritable bowel syndrome.

Antidepressant treatment was reported to activate the cAMP signal transduction pathway and to promote CREB binding to CRE sites. Promoter analysis of miR-135 5' flanking regions identified several putative CRE sites, suggesting a potential mechanism for the observed miR-135 upregulation by SSRI. Taken together, upregulation of miR-135 expression levels in the RN following antidepressant administration, along with the results demonstrating miR-135 targeting of Htr1a and Slc6a4, suggests that miR-135 is an endogenous antidepressant.

To further support a role for miR-135 as an endogenous antidepressant, a series of experiments were conducted in which miR-135 levels were manipulated in vivo and the effects on animal behavior was assessed. The transgenic mouse model that overexpresses miR-135 specifically in 5HT neurons, in levels equivalent to those observed following antidepressant treatment, showed a strong protective effect from the adverse behavioral effects of chronic social defeat. These results resembled the effect observed when Htr1a (Bortolozzi et al., 2012) or Slc6a4 (Thakker et al., 2005) were knocked down using siRNA approaches, showing reduced depression-like behaviors, or when Htr1a autoreceptor levels were increased using an elegant transgenic mice model, leading to elevation in anxiety and depression-like behaviors and reduced response to antidepressants (Richardson-Jones et al., 2010). In contrast, the developmental knockout mouse models for Htr1a (Savitz et al., 2009) and Slc6a4 (Holmes et al., 2003) showed paradoxical increases in anxiety and depression-like behaviors, which were suggested to be mediated by developmental compensatory changes. In addition to Htr1a and Slc6a4, it is also likely that miR-135a affects other genes in serotonin neurons that may possibly contribute to the observed phenotypes.

Using a complementary approach, the levels of miR-135 were knocked down specifically in the RN of adult wild-type mice using lentiviruses and behavior in mice was assessed under 'basal' (unstressed) conditions and following SSRI administration. In contrast to the behaviors observed by the mice that overexpress miR-135, reduced levels of this miR caused a robust increase in anxiety-like behavior and attenuated response to antidepressants. These results support an important role for miR-135 in maintaining intact responses to challenge under 'basal' conditions and its essential role in the mechanism of antidepressant action. These findings are in agreement with the published literature, which shows that higher levels of Htr1a are associated with increased behavioral despair and blunted responses to antidepressants (Richardson-Jones et al., 2010). Furthermore, polymorphism in the human Htr1a gene was associated with higher Htr1a autoreceptor binding and increased anxiety and depression (Fakra et al., 2009). In contrast, lower expression levels of Slc6a4, due to a shorter promoter variant, were reported to be associated with increased anxiety and depression and reduced responses to antidepressants (Homberg and Lesch, 2011).

Further support for a role of miR-135 in 5HT circuits emerged from the HPLC data indicating a robust alteration in 5HT levels and its metabolism across the brain of the miR-135OE mice model. 5HT levels were lower, while 5HT metabolism was higher, in the miR-135OE mice compared to controls under 'basal' stress conditions both in sub-nuclei of the raphe where 5HT is synthesized, and in the projection sites important for controlling anxiety and depression-like behaviors. This pattern of change in 5HT levels and 5HT metabolism is consistent with increased serotonergic neuronal firing and increased serotonergic signaling in miR-135OE mice. These differences could be a result of compensatory changes associated with the overexpression of miR-135 from development through adulthood. However, despite the low 'basal' 5HT levels, the mice demonstrate normal behaviors under 'basal' conditions, probably due to more active 5HT system as can be depicted by their higher 5HT metabolism at 'basal' conditions. Conceivably, lower expression levels of Slc6a4 and Htr1a that function as inhibitors of 5HT secretion in the RN enable the mice to function normally with lower levels of 5HT. Interestingly, chronic stress caused a decrease in 5HT levels accompanied by an increase in 5HT metabolism in some brain areas of control mice as expected, while in the miR-135OE mice these effects were not observed. These changes may provide a mechanistic explanation for the behavioral resiliency to chronic stress observed in the miR-135OE mice.

The possible use of circulating miRs as a non-invasive biomarker for pathological conditions is a rising field, which is promoted by relatively high levels and stability of miRs in the circulation. While little is known about the role and origin of the extracellular miRs, circulating miRs have been associated with pathophysiological states, such as different types of cancer, heart diseases, oxidative liver injury, sepsis, pregnancy and more. In the current study, the levels of miR-135 in the total blood of depressed patients were determined and a robust decrease in miR-135 levels in the blood of depressed patients, compared to match controls, was observed. These findings are in line with previous data from animal models indicating miR-135 to be an endogenous antidepressant, and suggest miR-135 as a possible biomarker for depression state and possibly for response to treatment.

Figure 41E:
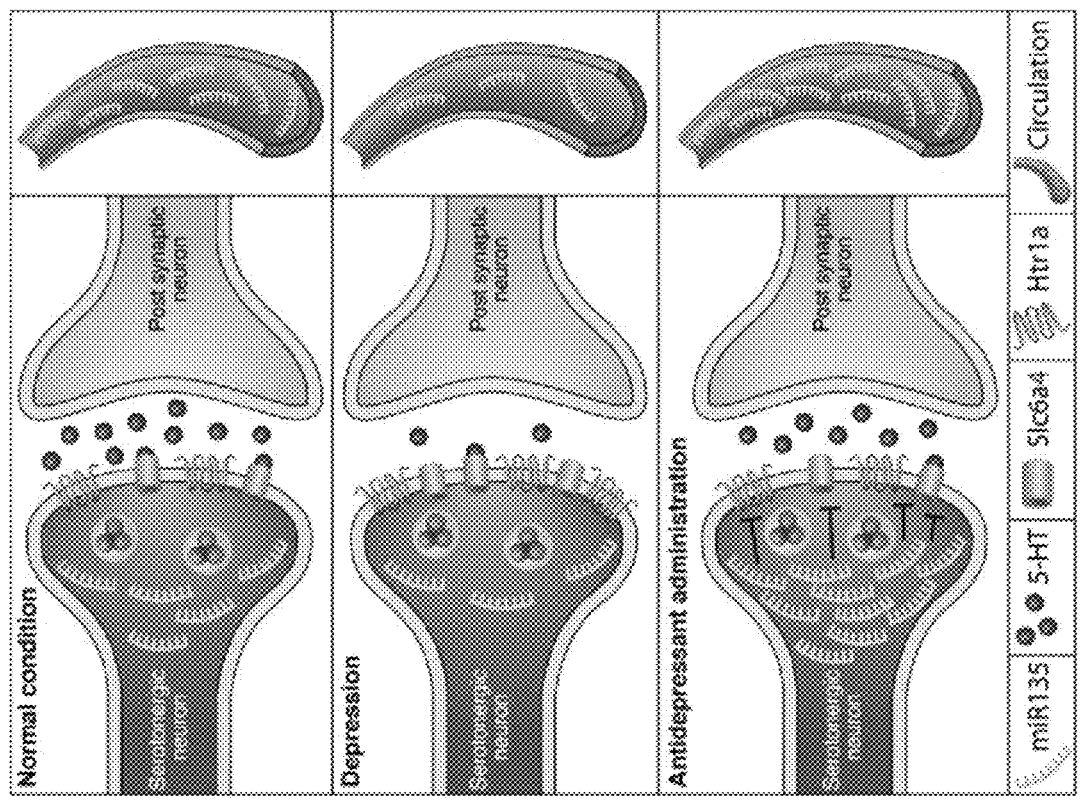
Figure 43A:
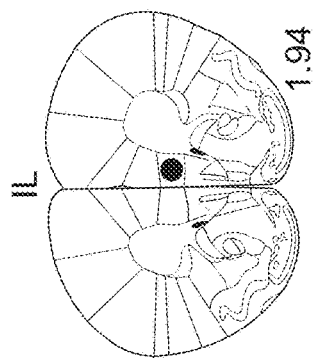
Figure 43B:
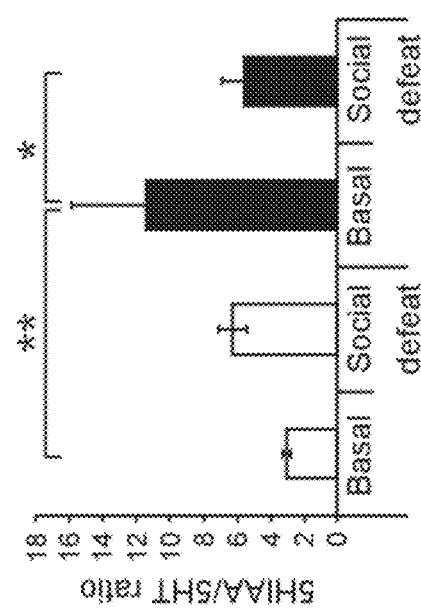
Figure 43C:
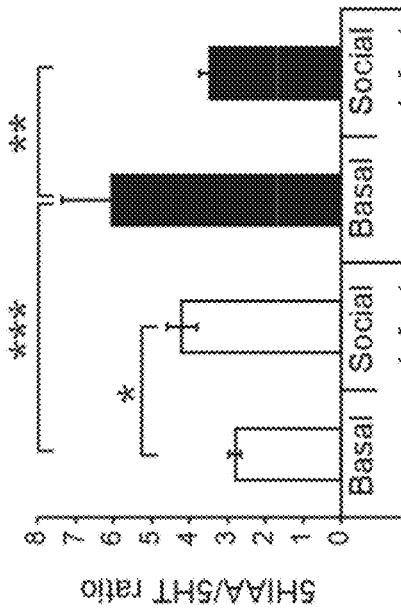
Figure 43D:
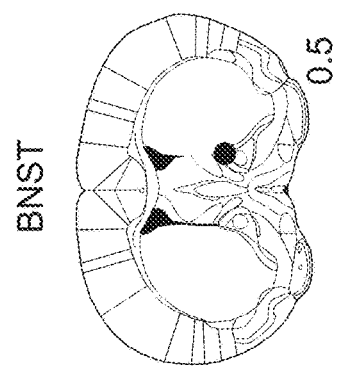
Figure 43E:
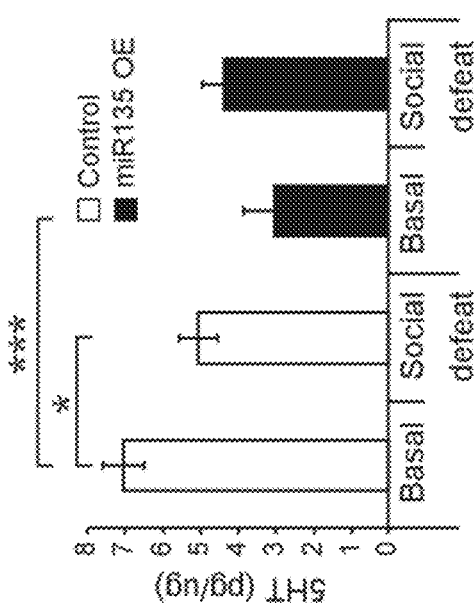
Figure 43F:
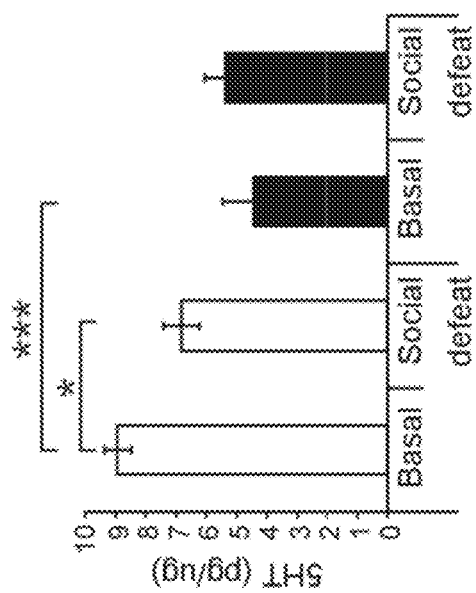
Figure 43G:
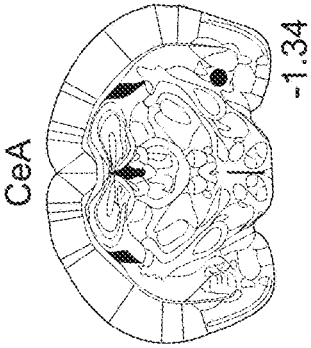
Figure 43H:
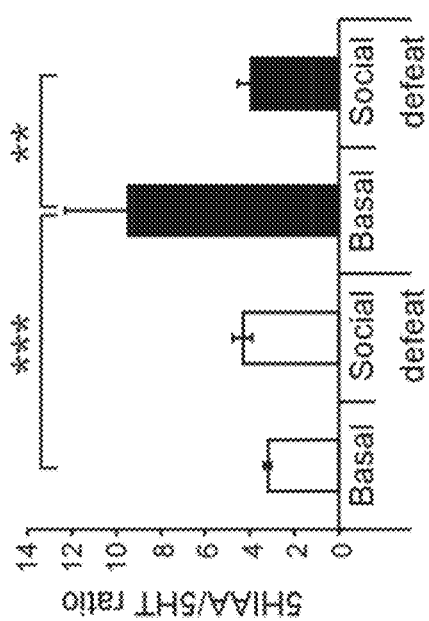
Figure 43I:
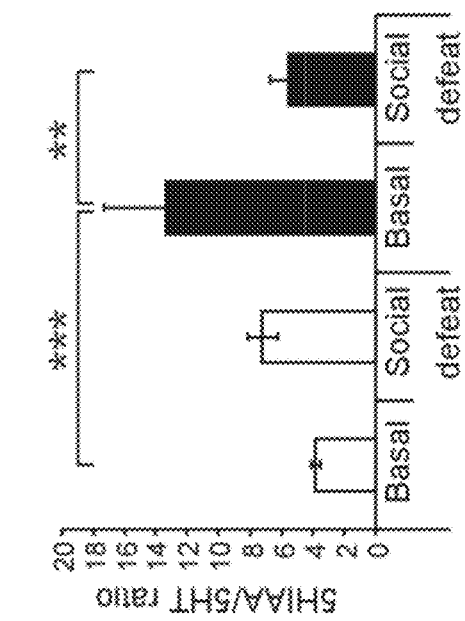
Figure 43J:
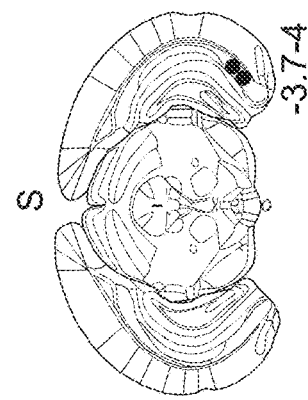
Figure 43K:
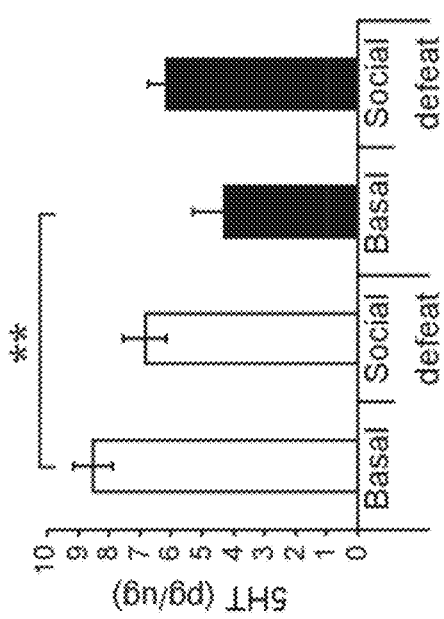
Figure 43L:
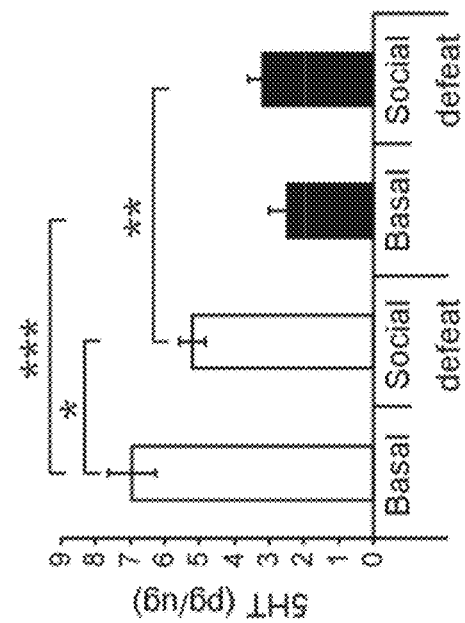

To conclude, the present inventor proposes that miR-135, expressed by 5HT neurons, is an essential regulatory element responsible for maintaining intact serotonergic tone under normal conditions, and essential for the brain response to antidepressants (see schematic model in FIG. 41E). Increased levels of miR-135 repress both Slc6a4 and pre-synaptic Htr1a levels, causing an increase in 5HT in the synaptic cleft, which is associated with decreases in depressive symptoms.

Further bioinformatic analysis conducted by the present inventors, predicted the following miR135 targets to be associated with stress-related neuropsychiatric disorders including bipolar affective disorder or lithium action: adenylate cyclase activating polypeptide 1 (Adcyap1 or PACAP); adenylate cyclase activating polypeptide 1 receptor 1 (Adcyap1r1); adrenergic receptor, alpha 2a (Adra2a); an ankyrin 3 (ANK3); activity-regulated cytoskeleton-associated protein (Arc); Rho GTPase activating protein 6 (Arhgap6); activating transcription factor 3 (Atf3); beta-site APP cleaving enzyme 1 (Bace1); calcium channel, voltage-dependent, L type, alpha 1D subunit (Cacna1d); cell adhesion molecule 3 (Cadm3); complexin 1 (Cplx1); complexin 2 (Cplx2); CUB and Sushi multiple domains 1 (Csmd1); casein kinase 1, gamma 1 (Csnk1g1); doublecortin (Dcx); DIRAS family, GTP-binding RAS-like 2 (Diras2); discs, large homolog 2 (*Drosophila*) (Dlg2); ELK1, member of ETS oncogene family (Elk1); fyn-related kinase (Frk); fucosyltransferase 9 (alpha (1,3) fucosyltransferase) (Fut9); gamma-aminobutyric acid (GABA-A) receptor, subunit beta 2 (Gabrb2); GATA binding protein 3 (Gata3); growth hormone secretagogue receptor (Ghsr); G protein-coupled receptor 3 (Gpr3); a glutamate receptor, ionotropic AMPA3 (alpha 3) (GRIA3); G protein-coupled receptor kinase 5 (Grk5); a glycogen synthase kinase-3beta (GSK3B); hyperpolarization activated cyclic nucleotide-gated potassium channel 1 (Hcn1), hyperpolarization-activated, cyclic nucleotide-gated K+2 (Hcn2), inositol monophosphatase (IMPA1), kalirin, RhoGEF kinase (Kahn); a potassium intermediate/small conductance calcium-activated channel, subfamily N, member 3 (KCNN3); karyopherin alpha 3 (importin alpha 4) (Kpna3); myelin transcription factor 1-like (Myt1l); nuclear receptor coactivator 2 (Ncoa2); N-Myc Downstream-Regulated Gene 4 (Ndrg4); a nitric oxide synthase 1 (neuronal) adaptor protein (NOS1AP); nuclear receptor subfamily 3, group C, member 2 (Nr3c2); netrin G1 (Ntng1); nuclear casein kinase and cyclin-dependent kinase substrate 1 (Nucks1); phosphodiesterase 1A, calmodulin-dependent (Pde1a); phosphodiesterase 4A, cAMP specific (Pde4a); phosphodiesterase 8B (Pde8b); phospholipase C, beta 1 (Plcb1); prolactin receptor (Prlr); RAB1B, member RAS oncogene family (Rab1b); Ras-Related Protein Rap-2a (Rap2a); Retinoid-Related Orphan Receptor Beta (Rorb); sirtuin 1 (silent mating type information regulation 2, homolog) 1 (Sirt1); solute carrier family 12, (potassium/chloride transporters) member 6 (Slc12a6); solute carrier family 5 (choline transporter), member 7 (Slc5a7); trans-acting transcription factor 1 (Sp1); synaptic vesicle glycoprotein 2 b (Sv2b); Synaptic nuclear envelope 1 (encodes nesprin-1) (Syne1); synaptotagmin I (Syt1); synaptotagmin II (Syt2); synaptotagmin III (Syt3); transforming growth factor, beta receptor II (Tgfbr2); thyroid hormone receptor, beta (Thrb); transient receptor potential cation channel, subfamily C, member 6 (Trpc6); vesicle-associated membrane protein 2 (Vamp2); wingless-related MMTV integration site 3 (Wnt3) and zinc finger, BED domain containing 4 (Zbed4).

Together, these data suggest that miR-135a may play a critical role in the pathophysiology of bipolar affective disorder, its treatment and diagnosis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Baldwin, D. S., Anderson, I. M., Nutt, D. J., Bandelow, B., Bond, A., Davidson, J. R., den Boer, J. A., Fineberg, N. A., Knapp, M., Scott, J., and Wittchen, H. U. (2005). Evidence-based guidelines for the pharmacological treatment of anxiety disorders: recommendations from the British Association for Psychopharmacology. J Psychopharmacol 19, 567-596.

Baudry, A., Mouillet-Richard, S., Schneider, B., Launay, J. M., and Kellermann, O. (2010). miR-16 targets the serotonin transporter: a new facet for adaptive responses to antidepressants. Science 329, 1537-1541.

Beck A. T., Rush., A. J., and B. F. Shaw (1979). Cognitive therapy of depression. Guilford Press, New York.

Benmansour, S., Owens, W. A., Cecchi, M., Morilak, D. A., and Frazer, A. (2002). Serotonin clearance in vivo is altered to a greater extent by antidepressant-induced downregulation of the serotonin transporter than by acute blockade of this transporter. J Neurosci 22, 6766-6772.

Bortolozzi, A., Castane, A., Semakova, J., Santana, N., Alvarado, G., Cortes, R., Ferres-Coy, A., Fernandez, G., Carmona, M. C., Toth, M., et al. (2012). Selective siRNA-mediated suppression of 5-HT1A autoreceptors evokes strong anti-depressant like effects. Mol Psychiatry 17, 612-623.

Creson, T. K., Austin, D. R., Shaltiel, G., McCammon, J., Wess, J., Manji, H. K., and Chen, G. (2011). Lithium treatment attenuates muscarinic M(1) receptor dysfunction. Bipolar Disord 13, 238-249.

Deneris, E. S., and Wyler, S. C. (2012). Serotonergic transcriptional networks and potential importance to mental health. Nat Neurosci 15, 519-527.

Dunlop, B. W., Kelley, M. E., Mletzko, T. C., Velasquez, C. M., Craighead, W. E., and Mayberg, H. S. (2012). Depression beliefs, treatment preference, and outcomes in a randomized trial for major depressive disorder. J Psychiatr Res 46, 375-381.

Elliott, E., Ezra-Nevo, G., Regev, L., Neufeld-Cohen, A., and Chen, A. (2010). Resilience to social stress coincides with functional DNA methylation of the Crf gene in adult mice. Nat Neurosci 13, 1351-1353.

Evans, A. K., Reinders, N., Ashford, K. A., Christie, I. N., Wakerley, J. B., and Lowry, C. A. (2008). Evidence for serotonin synthesis-dependent regulation of in vitro neuronal firing rates in the midbrain raphe complex. Eur J Pharmacol 590, 136-149.

Fakra, E., Hyde, L. W., Gorka, A., Fisher, P. M., Munoz, K. E., Kimak, M., Halder, I., Ferrell, R. E., Manuck, S. B., and Hariri, A. R. (2009). Effects of HTR1A C(-1019)G on amygdala reactivity and trait anxiety. Arch Gen Psychiatry 66, 33-40.

Gross, C., Zhuang, X., Stark, K., Ramboz, S., Oosting, R., Kirby, L., Santarelli, L., Beck, S., and Hen, R. (2002).

Serotonin1A receptor acts during development to establish normal anxiety-like behaviour in the adult. Nature 416, 396-400.

Haramati, S., Navon, I., Issler, O., Ezra-Nevo, G., Gil, S., Zwang, R., Hornstein, E., and Chen, A. (2011). MicroRNA as repressors of stress-induced anxiety: the case of amygdalar miR-34. J Neurosci 31, 14191-14203.

Holmes, A., Murphy, D. L., and Crawley, J. N. (2003). Abnormal behavioral phenotypes of serotonin transporter knockout mice: parallels with human anxiety and depression. Biol Psychiatry 54, 953-959.

Homberg, J. R., and Lesch, K. P. (2011). Looking on the bright side of serotonin transporter gene variation. Biol Psychiatry 69, 513-519.

Jensen, K. P., Covault, J., Conner, T. S., Tennen, H., Kranzler, H. R., and Furneaux, H. M. (2009). A common polymorphism in serotonin receptor 1B mRNA moderates regulation by miR-96 and associates with aggressive human behaviors. Mol Psychiatry 14, 381-389.

Kent W J, S. C., Furey T S, Roskin K M, Pringle T H, Zahler A M, Haussler D (2002). The human genome browser at UCSC. Genome Res 12, 996-1006.

Krishnan, V., Han, M. H., Graham, D. L., Berton, O., Renthal, W., Russo, S. J., Laplant, Q., Graham, A., Lutter, M., Lagace, D. C., et al. (2007). Molecular adaptations underlying susceptibility and resistance to social defeat in brain reward regions. Cell 131, 391-404.

Krishnan, V., and Nestler, E. J. (2008). The molecular neurobiology of depression. Nature 455, 894-902.

Kuperman, Y., Issler, O., Vaughan, J., Bilezikjian, L., Vale, W., and Chen, A. (2011). Expression and regulation of corticotropin-releasing factor receptor type 2beta in developing and mature mouse skeletal muscle. Mol Endocrinol 25, 157-169.

Kye, M. J., Neveu, P., Lee, Y. S., Zhou, M., Steen, J. A., Sahin, M., Kosik, K. S., and Silva, A. J. (2011). NMDA mediated contextual conditioning changes miRNA expression. PLoS One 6, e24682.

Lebow, M., Neufeld-Cohen, A., Kuperman, Y., Tsoory, M., Gil, S., and Chen, A. (2012). Susceptibility to PTSD-like behavior is mediated by corticotropin-releasing factor receptor type 2 levels in the bed nucleus of the stria terminalis. J Neurosci 32, 6906-6916.

Meltzer, H. Y., and Maes, M. (1995). Effects of ipsapirone on plasma cortisol and body temperature in major depression. Biol Psychiatry 38, 450-457.

Menke, A., Arloth, J., Putz, B., Weber, P., Klengel, T., Mehta, D., Gonik, M., Rex-Haffner, M., Rubel, J., Uhr, M., et al. (2012). Dexamethasone stimulated gene expression in peripheral blood is a sensitive marker for glucocorticoid receptor resistance in depressed patients. Neuropsychopharmacology 37, 1455-1464.

Michelsen, K. A., Schmitz, C., and Steinbusch, H. W. (2007). Brain Res Rev. Moncrieff, J., and Kirsch, I. (2005). Efficacy of antidepressants in adults. Bmj 331, 155-157.

Muinos-Gimeno, M., Espinosa-Parrilla, Y., Guidi, M., Kagerbauer, B., Sipila, T., Maron, E., Pettai, K., Kananen, L., Navines, R., Martin-Santos, R., et al. (2011). Human microRNAs miR-22, miR-138-2, miR-148a, and miR-488 are associated with panic disorder and regulate several anxiety candidate genes and related pathways. Biol Psychiatry 69, 526-533.

Murphy, D. L., Fox, M. A., Timpano, K. R., Moya, P. R., Ren-Patterson, R., Andrews, A. M., Holmes, A., Lesch, K. P., and Wendland, J. R. (2008). How the serotonin story is being rewritten by new gene-based discoveries principally related to SLC6A4, the serotonin transporter gene, which functions to influence all cellular serotonin systems. Neuropharmacology 55, 932-960.

Neufeld-Cohen, A., Evans, A. K., Getselter, D., Spyroglou, A., Hill, A., Gil, S., Tsoory, M., Beuschlein, F., Lowry, C. A., Vale, W., and Chen, A. (2010a). Urocortin-1 and -2 double-deficient mice show robust anxiolytic phenotype and modified serotonergic activity in anxiety circuits. Mol Psychiatry 15, 426-441, 339.

O'Connor, R. M., Dinan, T. G., and Cryan, J. F. (2012). Little things on which happiness depends: microRNAs as novel therapeutic targets for the treatment of anxiety and depression. Mol Psychiatry 17, 359-376.

Ohta, Y., Kosaka, Y., Kishimoto, N., Wang, J., Smith, S. B., Honig, G., Kim, H., Gasa, R. M., Neubauer, N., Liou, A., et al. (2011). Convergence of the insulin and serotonin programs in the pancreatic beta-cell. Diabetes 60, 3208-3216.

Palkovitz, M., and Brownstein, M. (1988). Maps and Guide to Microdissection of the Rat Brain. New York: Elsevier.

Paxinos G., F. K. J. (1997). The Mouse Brain in Stereotaxic Coordinates. Academic Press.

Piva, F., Giulietti, M., Nardi, B., Bellantuono, C., and Principato, G. (2010). An improved in silico selection of phenotype affecting polymorphisms in SLC6A4, HTR1A and HTR2A genes. Hum Psychopharmacol 25, 153-161.

Regev, L., Neufeld-Cohen, A., Tsoory, M., Kuperman, Y., Getselter, D., Gil, S., and Chen, A. (2011). Prolonged and site-specific over-expression of corticotrophin releasing factor reveals differential roles for extended amygdala nuclei in emotional regulation. Mol Psychiatry 16, 714-728.

Richardson-Jones, J. W., Craige, C. P., Guiard, B. P., Stephen, A., Metzger, K. L., Kung, H. F., Gardier, A. M., Dranovsky, A., David, D. J., Beck, S. G., et al. (2010). 5-HT1A autoreceptor levels determine vulnerability to stress and response to antidepressants. Neuron 65, 40-52.

Saus, E., Soria, V., Escaramis, G., Vivarelli, F., Crespo, J. M., Kagerbauer, B., Menchon, J. M., Urretavizcaya, M., Gratacos, M., and Estivill, X. (2010). Genetic variants and abnormal processing of pre-miR-182, a circadian clock modulator, in major depression patients with late insomnia. Hum Mol Genet 19, 4017-4025.

Savitz, J., Lucki, I., and Drevets, W. C. (2009). 5-HT(1A) receptor function in major depressive disorder. Prog Neurobiol 88, 17-31.

Scott, M. M., Wylie, C. J., Lerch, J. K., Murphy, R., Lobur, K., Herlitze, S., Jiang, W., Conlon, R. A., Strowbridge, B. W., and Deneris, E. S. (2005). A genetic approach to access serotonin neurons for in vivo and in vitro studies. Proc Natl Acad Sci USA 102, 16472-16477.

Smalheiser, N. R., Lugli, G., Rizavi, H. S., Torvik, V. I., Turecki, G., and Dwivedi, Y. (2012). MicroRNA expression is down-regulated and reorganized in prefrontal cortex of depressed suicide subjects. PLoS One 7, e33201.

Smalheiser, N. R., Lugli, G., Rizavi, H. S., Zhang, H., Torvik, V. I., Pandey, G. N., Davis, J. M., and Dwivedi, Y. (2011). MicroRNA expression in rat brain exposed to repeated inescapable shock: differential alterations in learned helplessness vs. nonlearned helplessness. Int J Neuropsychopharmacol, 1-11.

Thakker, D. R., Natt, F., Husken, D., van der Putten, H., Maier, R., Hoyer, D., and Cryan, J. F. (2005). siRNA-mediated knockdown of the serotonin transporter in the adult mouse brain. Mol Psychiatry 10, 782-789, 714.

Tiscornia, G., Singer, O., and Verma, I. M. (2006). Production and purification of lentiviral vectors. Nat Protoc 1, 241-245.

Wittchen H U, H. M., Gander F, Pfister H, Storz S, estiin T B, (1999). Screening for mental disorders: performance of the Composite International Diagnostic—Screener (CID-S). International Journal of Methods in Psychiatric Research 8, 59-70.

Wylie, C. J., Hendricks, T. J., Zhang, B., Wang, L., Lu, P., Leahy, P., Fox, S., Maeno, H., and Deneris, E. S. (2010). Distinct transcriptomes define rostral and caudal serotonin neurons. J Neurosci 30, 670-684.

Xu, B., Karayiorgou, M., and Gogos, J. A. (2010a). MicroRNAs in psychiatric and neurodevelopmental disorders. Brain Res 1338, 78-88.

Xu, Y., Liu, H., Li, F., Sun, N., Ren, Y., Liu, Z., Cao, X., Wang, Y., Liu, P., and Zhang, K. (2010b). A polymorphism in the microRNA-30e precursor associated with major depressive disorder risk and P300 waveform. J Affect Disord 127, 332-336.

What is claimed is:

1. A method of diagnosing and treating a mood disorder in a human subject in need thereof, the method comprising:
   (i) measuring an expression level of a miR-135 in a biological sample of the human subject, wherein a lower expression level of said miR-135 as compared to that in a biological sample of a healthy human subject is indicative of the mood disorder; and
   (ii) treating the human subject with an anti-depressant drug or a medicament for the treatment of a mood disorder when a lower expression level of said miR-135 is indicative of the mood disorder.

2. The method of claim 1, wherein said anti-depressant drug is selected from the group consisting of selective serotonin reuptake inhibitors (SSRI), tricyclic antidepressants and noradrenaline reuptake inhibitors (NRI).

3. The method of claim 1, wherein said medicament for said treatment of said mood disorder is selected from the group consisting of a lithium, an antipsychotic medicament and a mood stabilizer medicament.

4. The method of claim 1, wherein said biological sample is selected from the group consisting of a whole blood, a serum, a plasma and white blood cells.

5. The method of claim 1, further comprising obtaining a biological sample from said human subject prior to said measuring.

6. The method of claim 1, wherein said mood disorder is selected from the group consisting of a bipolar disorder, a depression, a major depression, an anxiety, a stress, a fatigue, an impaired cognitive function, a panic attack, a compulsive behavior, an addiction, a social phobia, a schizophrenia, a sleep disorder and an eating disorder.

7. The method of claim 1, wherein said miR-135 is selected from the group consisting of miR-135a or miR-135b.

8. The method of claim 1, wherein said miR-135 is as set forth in SEQ ID NO: 58-62.

9. The method of claim 1, wherein said miR-135 comprises miR-135* as set forth in SEQ ID NO: 192-193.

* * * * *

SEQUENCE LISTING

```
<160> NUMBER OF SEQ ID NOS: 213

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
tatggctttt tattcctatg tga                                              23

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
tatggctttt cattcctatg tga                                              23

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
tttgttcgtt cggctcgcgt ga                                               22

<210> SEQ ID NO 4
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 4
gatgacacgc aaattcgtga a                                                21

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
taaggcacgc ggtgaatgcc                                                  20

<210> SEQ ID NO 6
<211> LENGTH: 19
<212> TYPE: DNA
```

```
<213> ORGANISM: Artificial sequence
<220> FEATURE:
<223> OTHER INFORMATION: Single strand DNA oligonucleotide

<400> SEQUENCE: 6
agttctgccg ctgatgatg                                          19

<210> SEQ ID NO 7
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 7
gcacaaatgg agagtctgat taaa                                    24

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
tgcctttaat gcaaaacagc                                         20

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
ccaagtttac aaccatcaag ca                                      22

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
atccgcatga atgctgtgta                                         20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gtgggtggtg gaagagacac                                         20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
cctacacgca gagcattgaa                                         20
```

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
acatccctgt gggatttgag                                              20

<210> SEQ ID NO 14
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 14
tgtcttgctt atattttctc agtag                                        25

<210> SEQ ID NO 15
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
gaaaatataa gcaagacatc cctgtt                                       26

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
aaagatccct ttccccaatg                                              20

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
cagtgcgtct tctccacaga                                              20

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 18
ataagcaagg gcccaaaagg aaga                                         24

<210> SEQ ID NO 19
<211> LENGTH: 24
<212> TYPE: DNA
<213> ORGANISM: Artificial sequence
<220> FEATURE:

<223> OTHER INFORMATION: Single strand DNA oligonucleotide

<400> SEQUENCE: 19
ttttgggccc ttgcttataa gtcc                                                24

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
ctgccctgcc acatgtgttt ttat                                                24

<210> SEQ ID NO 21
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 21
taacaaataa aaacacatgt ggca                                                24

<210> SEQ ID NO 22
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 22
accggtcata tgattcccca gtttcctgct tt                                       32

<210> SEQ ID NO 23
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 23
accggtcctc tgtggctggt ccttag                                              26

<210> SEQ ID NO 24
<211> LENGTH: 23
<212> TYPE: RNA
<213> ORGANISM: Mus musculus

<400> SEQUENCE: 24
aguguauccu uauuuucgg uau                                                  23

<210> SEQ ID NO 25
<211> LENGTH: 23
<212> TYPE: RNA
<213> ORGANISM: Mus musculus

<400> SEQUENCE: 25
acagggaugu cuugcuagcc aua                                                 23

<210> SEQ ID NO 26
<211> LENGTH: 23
<212> TYPE: RNA
<213> ORGANISM: Mus musculus

```
<400> SEQUENCE: 26
aguguauccu uacuuuucgg uau                                           23

<210> SEQ ID NO 27
<211> LENGTH: 23
<212> TYPE: RNA
<213> ORGANISM: Mus musculus

<400> SEQUENCE: 27
cugcccugcc acaugaagcc auu                                           23

<210> SEQ ID NO 28
<211> LENGTH: 21
<212> TYPE: RNA
<213> ORGANISM: Mus musculus

<400> SEQUENCE: 28
cuugcuagcc auauauauuu u                                             21

<210> SEQ ID NO 29
<211> LENGTH: 20
<212> TYPE: RNA
<213> ORGANISM: Homo sapiens

<400> SEQUENCE: 29
uuucuauagc cauacucgcu                                               20

<210> SEQ ID NO 30
<211> LENGTH: 20
<212> TYPE: RNA
<213> ORGANISM: Pan troglodytes

<400> SEQUENCE: 30
cucgcuagcc auauauuuuc                                               20

<210> SEQ ID NO 31
<211> LENGTH: 21
<212> TYPE: RNA
<213> ORGANISM: Rattus norvegicus

<400> SEQUENCE: 31
agccauacuu gcuuauauuu u                                             21

<210> SEQ ID NO 32
<211> LENGTH: 20
<212> TYPE: RNA
<213> ORGANISM: Cavia porcellus

<400> SEQUENCE: 32
cuugcuagcc auauauuuuc                                               20

<210> SEQ ID NO 33
<211> LENGTH: 20
<212> TYPE: RNA
<213> ORGANISM: Suncus murinus

<400> SEQUENCE: 33
cuugcuagcc auauauuuuc                                               20

<210> SEQ ID NO 34
<211> LENGTH: 20
<212> TYPE: RNA
```

```
<213> ORGANISM: Atelerix albiventris

<400> SEQUENCE: 34
cucacuagcc auauauuuuu                                              20

<210> SEQ ID NO 35
<211> LENGTH: 20
<212> TYPE: RNA
<213> ORGANISM: Canis lupus familiaris

<400> SEQUENCE: 35
uuugcuagcc auauauuuuc                                              20

<210> SEQ ID NO 36
<211> LENGTH: 20
<212> TYPE: RNA
<213> ORGANISM: Felis catus

<400> SEQUENCE: 36
uuugcuagcc auauauuuuc                                              20

<210> SEQ ID NO 37
<211> LENGTH: 20
<212> TYPE: RNA
<213> ORGANISM: Equus caballus

<400> SEQUENCE: 37
cuugcuagcc auauauuuuc                                              20

<210> SEQ ID NO 38
<211> LENGTH: 19
<212> TYPE: RNA
<213> ORGANISM: Bos taurus

<400> SEQUENCE: 38
cuugcuagcc auauguuuu                                               19

<210> SEQ ID NO 39
<211> LENGTH: 20
<212> TYPE: RNA
<213> ORGANISM: Monodelphis domestica

<400> SEQUENCE: 39
ucggauagcc auauauucuc                                              20

<210> SEQ ID NO 40
<211> LENGTH: 20
<212> TYPE: RNA
<213> ORGANISM: Ornithorhynchus anatinus

<400> SEQUENCE: 40
ucugauagcc auauauuauc                                              20

<210> SEQ ID NO 41
<211> LENGTH: 20
<212> TYPE: RNA
<213> ORGANISM: Gallus gallus

<400> SEQUENCE: 41
uccaauagcc auauauuacu                                              20

<210> SEQ ID NO 42
<211> LENGTH: 22
```

```
<212> TYPE: RNA
<213> ORGANISM: Mus musculus

<400> SEQUENCE: 42
uuauaagcaa gaagccaggc cc                                           22

<210> SEQ ID NO 43
<211> LENGTH: 21
<212> TYPE: RNA
<213> ORGANISM: Mus musculus

<400> SEQUENCE: 43
gccacaugaa gccauguuuu u                                            21

<210> SEQ ID NO 44
<211> LENGTH: 20
<212> TYPE: RNA
<213> ORGANISM: Rattus norvegicus

<400> SEQUENCE: 44
gucacaugaa gccauuguuu                                              20

<210> SEQ ID NO 45
<211> LENGTH: 20
<212> TYPE: RNA
<213> ORGANISM: Cavia porcellus

<400> SEQUENCE: 45
agcacuugaa gccauuguau                                              20

<210> SEQ ID NO 46
<211> LENGTH: 20
<212> TYPE: RNA
<213> ORGANISM: Oryctolagus cuniculus

<400> SEQUENCE: 46
aucacuugaa gccauuuuau                                              20

<210> SEQ ID NO 47
<211> LENGTH: 20
<212> TYPE: RNA
<213> ORGANISM: Homo sapiens

<400> SEQUENCE: 47
gucaguugaa gccauuuuau                                              20

<210> SEQ ID NO 48
<211> LENGTH: 20
<212> TYPE: RNA
<213> ORGANISM: Pan troglodytes

<400> SEQUENCE: 48
gucacuugaa gccauuuuau                                              20

<210> SEQ ID NO 49
<211> LENGTH: 19
<212> TYPE: RNA
<213> ORGANISM: Macaca mulatta

<400> SEQUENCE: 49
gucacuugaa gccauuuau                                               19

<210> SEQ ID NO 50
```

```
<211> LENGTH: 20
<212> TYPE: RNA
<213> ORGANISM: Atelerix albiventris

<400> SEQUENCE: 50
auuacuugaa gccauuuuau                                                      20

<210> SEQ ID NO 51
<211> LENGTH: 19
<212> TYPE: RNA
<213> ORGANISM: Canis lupus familiaris

<400> SEQUENCE: 51
aucacugagc cauuuuuac                                                       19

<210> SEQ ID NO 52
<211> LENGTH: 20
<212> TYPE: RNA
<213> ORGANISM: Felis catus

<400> SEQUENCE: 52
uaucacugaa gccauuuuau                                                      20

<210> SEQ ID NO 53
<211> LENGTH: 19
<212> TYPE: RNA
<213> ORGANISM: Equus caballus

<400> SEQUENCE: 53
ucacuugaag ccauuuuau                                                       19

<210> SEQ ID NO 54
<211> LENGTH: 18
<212> TYPE: RNA
<213> ORGANISM: Loxodonta africana

<400> SEQUENCE: 54
aucacugaag ccauuuua                                                        18

<210> SEQ ID NO 55
<211> LENGTH: 23
<212> TYPE: RNA
<213> ORGANISM: Mus musculus

<400> SEQUENCE: 55
uggaaagccc ugccuugcug cuu                                                  23

<210> SEQ ID NO 56
<211> LENGTH: 22
<212> TYPE: RNA
<213> ORGANISM: Mus musculus

<400> SEQUENCE: 56
guguuuggua auacacgacg au                                                   22

<210> SEQ ID NO 57
<211> LENGTH: 22
<212> TYPE: RNA
<213> ORGANISM: Mus musculus

<400> SEQUENCE: 57
acauuuggua cuacacgacg au                                                   22
```

```
<210> SEQ ID NO 58
<211> LENGTH: 90
<212> TYPE: RNA
<213> ORGANISM: Homo sapiens

<400> SEQUENCE: 58
aggccucgcu guucucuaug gcuuuuuauu ccuaugugau ucuacugcuc acucauauag      60
ggauuggagc cguggcgcac ggcggggaca                                      90

<210> SEQ ID NO 59
<211> LENGTH: 100
<212> TYPE: RNA
<213> ORGANISM: Homo sapiens

<400> SEQUENCE: 59
agauaaauuc acucuagugc uuuauggcuu uuuauuccua ugugauagua auaaagucuc      60
auguagggau ggaagccaug aaauacauug ugaaaaauca                          100

<210> SEQ ID NO 60
<211> LENGTH: 97
<212> TYPE: RNA
<213> ORGANISM: Homo sapiens

<400> SEQUENCE: 60
cacucugcug uggccuaugg cuuuucauuc cuaugugauu gcugucccaa acucauguag      60
ggcuaaaagc caugggcuac agugaggggc gagcucc                              97

<210> SEQ ID NO 61
<211> LENGTH: 23
<212> TYPE: RNA
<213> ORGANISM: Homo sapiens

<400> SEQUENCE: 61
uauggcuuuu uauuccuaug uga                                             23

<210> SEQ ID NO 62
<211> LENGTH: 23
<212> TYPE: RNA
<213> ORGANISM: Homo sapiens

<400> SEQUENCE: 62
uauggcuuuu cauuccuaug uga                                             23

<210> SEQ ID NO 63
<211> LENGTH: 94
<212> TYPE: RNA
<213> ORGANISM: Homo sapiens

<400> SEQUENCE: 63
uguuuugagc gggggucaag agcaauaacg aaaaauguuu gucauaaacc guuuuucauu      60
auugcuccug accucucuc auuugcuaua uuca                                  94

<210> SEQ ID NO 64
<211> LENGTH: 23
<212> TYPE: RNA
<213> ORGANISM: Homo sapiens

<400> SEQUENCE: 64
ucaagagcaa uaacgaaaaa ugu                                             23

<210> SEQ ID NO 65
```

```
<211> LENGTH: 77
<212> TYPE: RNA
<213> ORGANISM: Homo sapiens

<400> SEQUENCE: 65
guggccucgu ucaaguaauc caggauaggc ugugcagguc ccaaugggcc uauucuuggu    60
uacuugcacg gggacgc                                                  77

<210> SEQ ID NO 66
<211> LENGTH: 84
<212> TYPE: RNA
<213> ORGANISM: Homo sapiens

<400> SEQUENCE: 66
ggcuguggcu ggauucaagu aauccaggau aggcuguuuc caucugugag gccuauucuu    60
gauuacuugu uucuggaggc agcu                                          84

<210> SEQ ID NO 67
<211> LENGTH: 77
<212> TYPE: RNA
<213> ORGANISM: Homo sapiens

<400> SEQUENCE: 67
ccgggaccca guucaaguaa uucaggauag guugugugcu guccagccug uucuccauua    60
cuuggcucgg ggaccgg                                                  77

<210> SEQ ID NO 68
<211> LENGTH: 22
<212> TYPE: RNA
<213> ORGANISM: Homo sapiens

<400> SEQUENCE: 68
uucaaguaau ccaggauagg cu                                            22

<210> SEQ ID NO 69
<211> LENGTH: 21
<212> TYPE: RNA
<213> ORGANISM: Homo sapiens

<400> SEQUENCE: 69
uucaaguaau ucaggauagg u                                             21

<210> SEQ ID NO 70
<211> LENGTH: 110
<212> TYPE: RNA
<213> ORGANISM: Homo sapiens

<400> SEQUENCE: 70
gagcugcuug ccucccccccg uuuuuggcaa ugguagaacu cacacuggug agguaacagg    60
auccgguggu ucuagacuug ccaacuaugg ggcgaggacu cagccggcac              110

<210> SEQ ID NO 71
<211> LENGTH: 25
<212> TYPE: RNA
<213> ORGANISM: Homo sapiens

<400> SEQUENCE: 71
uuuggcaaug guagaacuca caccg                                         25

<210> SEQ ID NO 72
<211> LENGTH: 82
```

```
<212> TYPE: RNA
<213> ORGANISM: Homo sapiens

<400> SEQUENCE: 72 gcagccucu guuaguuug cauaguugca cuacaagaag aauguaguug ugcaaaucua    60
ugcaaaacug augguggccu gc                                          82

<210> SEQ ID NO 73
<211> LENGTH: 87
<212> TYPE: RNA
<213> ORGANISM: Homo sapiens

<400> SEQUENCE: 73
cacuguucua ugguuaguuu ugcagguuug cauccagcug ugugauauuc ugcugugcaa    60
auccaugcaa aacugacugu gguagug                                       87

<210> SEQ ID NO 74
<211> LENGTH: 96
<212> TYPE: RNA
<213> ORGANISM: Homo sapiens

<400> SEQUENCE: 74
acauugcuac uuacaauuag uuuugcaggu uugcauuuca gcguauauau guauauguggg    60 cugugcaaau ccaugcaaaa cugauuguga uaaugu                              96

<210> SEQ ID NO 75
<211> LENGTH: 23
<212> TYPE: RNA
<213> ORGANISM: Homo sapiens

<400> SEQUENCE: 75
ugugcaaauc uaugcaaaac uga                                           23

<210> SEQ ID NO 76
<211> LENGTH: 23
<212> TYPE: RNA
<213> ORGANISM: Homo sapiens

<400> SEQUENCE: 76
ugugcaaauc caugcaaaac uga                                           23

<210> SEQ ID NO 77
<211> LENGTH: 83
<212> TYPE: RNA
<213> ORGANISM: Homo sapiens

<400> SEQUENCE: 77
ccuuggagua aaguagcagc acauaauggu uuuggauuu ugaaaaggug caggccauau     60
ugugcugccu caaaaauaca agg                                           83

<210> SEQ ID NO 78
<211> LENGTH: 98
<212> TYPE: RNA
<213> ORGANISM: Homo sapiens

<400> SEQUENCE: 78
uugaggccuu aaaguacugu agcagcacau cauggunuac augcuacagu caagaugcga    60
aucauuauuu gcugcucuag aaauuuaagg aaauucau                           98

<210> SEQ ID NO 79
```

```
<211> LENGTH: 22
<212> TYPE: RNA
<213> ORGANISM: Homo sapiens

<400> SEQUENCE: 79
uagcagcaca uaauguuug ug                                                   22

<210> SEQ ID NO 80
<211> LENGTH: 22
<212> TYPE: RNA
<213> ORGANISM: Homo sapiens

<400> SEQUENCE: 80
uagcagcaca ucaugguuua ca                                                  22

<210> SEQ ID NO 81
<211> LENGTH: 78
<212> TYPE: RNA
<213> ORGANISM: Homo sapiens

<400> SEQUENCE: 81
cugaggagca gggcuuagcu gcuugugagc agguccaca ccaagucgug uucacagugg          60
cuaaguuccg cccccccag                                                      78

<210> SEQ ID NO 82
<211> LENGTH: 97
<212> TYPE: RNA
<213> ORGANISM: Homo sapiens

<400> SEQUENCE: 82
accucucuaa caaggugcag agcuuagcug auuggugaac agugauuggu uccgcuuug          60 uucacagugg cuaaguucug caccugaaga aaggug                                   97

<210> SEQ ID NO 83
<211> LENGTH: 21
<212> TYPE: RNA
<213> ORGANISM: Homo sapiens

<400> SEQUENCE: 83
uucacagugg cuaaguuccg c                                                   21

<210> SEQ ID NO 84
<211> LENGTH: 21
<212> TYPE: RNA
<213> ORGANISM: Homo sapiens

<400> SEQUENCE: 84
uucacagugg cuaaguucug c                                                   21

<210> SEQ ID NO 85
<211> LENGTH: 110
<212> TYPE: RNA
<213> ORGANISM: Homo sapiens

<400> SEQUENCE: 85
ugaguuuuga gguugcuuca gugaacauuc aacgcugucg gugaguuugg aauuaaaauc         60
aaaaccaucg accguugauu guacccuaug gcuaaccauc aucuacucca                    110

<210> SEQ ID NO 86
<211> LENGTH: 110
<212> TYPE: RNA
<213> ORGANISM: Homo sapiens
```

```
<400> SEQUENCE: 86
agaagggcua ucaggccagc uucagagga cuccaaggaa cauucaacgc ugucggugag      60
uuugggauuu gaaaaaacca cugaccguug acuguaccuu gggguccuua               110

<210> SEQ ID NO 87
<211> LENGTH: 110
<212> TYPE: RNA
<213> ORGANISM: Homo sapiens

<400> SEQUENCE: 87
ccugugcaga gauuauuuuu uaaaaggucu caaucaacau ucauugcugu cgguggguug     60 aacuguggg acaagcucac ugaacaauga augcaacugu ggccccgcuu                110

<210> SEQ ID NO 88
<211> LENGTH: 89
<212> TYPE: RNA
<213> ORGANISM: Homo sapiens

<400> SEQUENCE: 88
cugauggcug cacucaacau ucauugcugu cgguggguuu gagucugaau caacucacug     60
aucaaugaau gcaaacugcg gaccaaaca                                       89

<210> SEQ ID NO 89
<211> LENGTH: 110
<212> TYPE: RNA
<213> ORGANISM: Homo sapiens

<400> SEQUENCE: 89
cggaaaauuu gccaagggui uggggggaaca uucaaccugu cggugaguuu gggcagcuca    60
ggcaaaccau cgaccguuga guggacccug aggccuggaa uugccauccu                110

<210> SEQ ID NO 90
<211> LENGTH: 137
<212> TYPE: RNA
<213> ORGANISM: Homo sapiens

<400> SEQUENCE: 90
gucccccucc cuaggccaca gccgaggucu caaucaacau ucauuguugu cgguggguug     60
ugaggacuga ggccagaccc accggggau gaaugucacu uggcugggc cagacacggc      120 uuaagggggaa ugggggac                                                  137

<210> SEQ ID NO 91
<211> LENGTH: 23
<212> TYPE: RNA
<213> ORGANISM: Homo sapiens

<400> SEQUENCE: 91
aacauucaac gcugucggug agu                                             23

<210> SEQ ID NO 92
<211> LENGTH: 23
<212> TYPE: RNA
<213> ORGANISM: Homo sapiens

<400> SEQUENCE: 92 aacaucauu gcugucggug ggu                                              23

<210> SEQ ID NO 93
```

```
<211> LENGTH: 22
<212> TYPE: RNA
<213> ORGANISM: Homo sapiens

<400> SEQUENCE: 93
aacauucaac cugucgguga gu                                              22

<210> SEQ ID NO 94
<211> LENGTH: 23
<212> TYPE: RNA
<213> ORGANISM: Homo sapiens

<400> SEQUENCE: 94
aacauucauu guugucggug ggu                                             23

<210> SEQ ID NO 95
<211> LENGTH: 25
<212> TYPE: RNA
<213> ORGANISM: Mus musculus

<400> SEQUENCE: 95
ugaccaccug cugcugcggg ggggu                                           25

<210> SEQ ID NO 96
<211> LENGTH: 26
<212> TYPE: RNA
<213> ORGANISM: Oryctolagus cuniculus

<400> SEQUENCE: 96
cagccacccu gcugcugccc aguggg                                          26

<210> SEQ ID NO 97
<211> LENGTH: 26
<212> TYPE: RNA
<213> ORGANISM: Homo sapiens

<400> SEQUENCE: 97
cagccccccu gcugcugccc ggaggg                                          26

<210> SEQ ID NO 98
<211> LENGTH: 26
<212> TYPE: RNA
<213> ORGANISM: Pan troglodytes

<400> SEQUENCE: 98
cagccccccu gcugcugccc ggaggg                                          26

<210> SEQ ID NO 99
<211> LENGTH: 26
<212> TYPE: RNA
<213> ORGANISM: Macaca mulatta

<400> SEQUENCE: 99
cagccccccu gcugcugccc agaggg                                          26

<210> SEQ ID NO 100
<211> LENGTH: 26
<212> TYPE: RNA
<213> ORGANISM: Otolemur garnettii

<400> SEQUENCE: 100
cagccacccu gcugcugccc agugag                                          26
```

```
<210> SEQ ID NO 101
<211> LENGTH: 26
<212> TYPE: RNA
<213> ORGANISM: Atelerix albiventris

<400> SEQUENCE: 101
ccaccacccu gcugcugccc agagcu                                              26

<210> SEQ ID NO 102
<211> LENGTH: 26
<212> TYPE: RNA
<213> ORGANISM: Canis lupus familiaris

<400> SEQUENCE: 102
cagccacccu gcugcugccc agcgug                                              26

<210> SEQ ID NO 103
<211> LENGTH: 26
<212> TYPE: RNA
<213> ORGANISM: Equus caballus

<400> SEQUENCE: 103
cagccacccu gcugcugccc agugcu                                              26

<210> SEQ ID NO 104
<211> LENGTH: 25
<212> TYPE: RNA
<213> ORGANISM: Bos taurus

<400> SEQUENCE: 104 caccaccug cugcugccca gaggu                                                25

<210> SEQ ID NO 105
<211> LENGTH: 25
<212> TYPE: RNA
<213> ORGANISM: Dasypus novemcinctus

<400> SEQUENCE: 105
aagcaaccug cugcugccca gcaca                                               25

<210> SEQ ID NO 106
<211> LENGTH: 26
<212> TYPE: RNA
<213> ORGANISM: Loxodonta africana

<400> SEQUENCE: 106
caaccacccu gcugcugccc agugca                                              26

<210> SEQ ID NO 107
<211> LENGTH: 25
<212> TYPE: RNA
<213> ORGANISM: Echinops telfairi

<400> SEQUENCE: 107 cauccccug cugcugccca gcaca                                                25

<210> SEQ ID NO 108
<211> LENGTH: 25
<212> TYPE: RNA
<213> ORGANISM: Monodelphis domestica

<400> SEQUENCE: 108
uagcccccug cugcuaccca uugcc                                               25
```

<210> SEQ ID NO 109
<211> LENGTH: 26
<212> TYPE: RNA
<213> ORGANISM: Gallus gallus

<400> SEQUENCE: 109
ccagcccagu gcugcugccg gcugcg                                        26

<210> SEQ ID NO 110
<211> LENGTH: 143
<212> TYPE: DNA
<213> ORGANISM: Artificial sequence
<220> FEATURE:
<223> OTHER INFORMATION: Knock down sequence for miR135

<400> SEQUENCE: 110
gacggcgcta ggatcatcaa ctcacatagg aatgatctaa aagccataca agtattctgg    60
tcacagaata caactcacat aggaatgatc taaaagccat acaagatgat cctagcgccg   120
tcttttttga attcgcggcc cta                                          143

<210> SEQ ID NO 111
<211> LENGTH: 105
<212> TYPE: DNA
<213> ORGANISM: Artificial sequence
<220> FEATURE:
<223> OTHER INFORMATION: Knock down sequence for miR135

<400> SEQUENCE: 111
tcacatagga atgaaaagcc atacgattca cataggaatg aaaagccata accggtcaca    60
taggaatgaa aagccatatc actcacatag gaatgaaaag ccata                  105

<210> SEQ ID NO 112
<211> LENGTH: 100
<212> TYPE: DNA
<213> ORGANISM: Artificial sequence
<220> FEATURE:
<223> OTHER INFORMATION: Knock down sequence for miR135 - antisense
      construct (forward)

<400> SEQUENCE: 112
tcacatagga agcaaagcca taatcgtcac ataggaagca agccataat cgtcacatag    60 gaagcaaagc cataatcgtc acataggaag caaagccata                       100

<210> SEQ ID NO 113
<211> LENGTH: 100
<212> TYPE: DNA
<213> ORGANISM: Artificial sequence
<220> FEATURE:
<223> OTHER INFORMATION: Knock down sequence for miR135 - antisense
      construct (reverse)

<400> SEQUENCE: 113
tatggctttg cttcctatgt gacgattatg ctttgcttc ctatgtgacg attatggctt    60
tgcttcctat gtgacgatta tggctttgct tcctatgtga                       100

<210> SEQ ID NO 114
<211> LENGTH: 143
<212> TYPE: DNA
<213> ORGANISM: Artificial sequence
<220> FEATURE:
<223> OTHER INFORMATION: Knock down sequence for miR335 5p

```
<400> SEQUENCE: 114
gacggcgcta ggatcatcaa cacattttc gttaatcttt gctcttgaca agtattctgg      60
tcacagaata caacacattt ttcgttaatc tttgctcttg acaagatgat cctagcgccg     120
tcttttttga attcgcggcc cta                                             143

<210> SEQ ID NO 115
<211> LENGTH: 105
<212> TYPE: DNA
<213> ORGANISM: Artificial sequence
<220> FEATURE:
<223> OTHER INFORMATION: Knock down sequence for miR335 5p

<400> SEQUENCE: 115 acattttcg ttattgctct tgacgataca tttttcgtta ttgctcttga accggacatt      60
tttcgttatt gctcttgatc acacattttt cgttattgct cttga                    105

<210> SEQ ID NO 116
<211> LENGTH: 100
<212> TYPE: DNA
<213> ORGANISM: Artificial sequence
<220> FEATURE:
<223> OTHER INFORMATION: Knock down sequence for miR335-5p - antisense
      construct (forward)

<400> SEQUENCE: 116 acattttcg agctgctctt gaatcgacat ttttcgagct gctcttgaat cgacattttt      60
cgagctgctc ttgaatcgac attttcgag ctgctcttga                          100

<210> SEQ ID NO 117
<211> LENGTH: 100
<212> TYPE: DNA
<213> ORGANISM: Artificial sequence
<220> FEATURE:
<223> OTHER INFORMATION: Knock down sequence for miR335-5p - antisense
      construct (reverse)

<400> SEQUENCE: 117
tcaagagcag ctcgaaaaat gtcgattcaa gagcagctcg aaaaatgtcg attcaagagc     60
agctcgaaaa atgtcgattc aagagcagct cgaaaaatgt                          100

<210> SEQ ID NO 118
<211> LENGTH: 141
<212> TYPE: DNA
<213> ORGANISM: Artificial sequence
<220> FEATURE:
<223> OTHER INFORMATION: Knock down sequence for miR15a

<400> SEQUENCE: 118
gacggcgcta ggatcatcaa ccacaaacca ttaatcttgt gctgctacaa gtattctggt     60
cacagaatac aaccacaaac cattaatctt gtgctgctac aagatgatcc tagcgccgtc    120 tttttttgaat tcgcggccct a                                             141

<210> SEQ ID NO 119
<211> LENGTH: 101
<212> TYPE: DNA
<213> ORGANISM: Artificial sequence
<220> FEATURE:
<223> OTHER INFORMATION: Knock down sequence for miR15a
```

<400> SEQUENCE: 119
cacaaaccat tatgtgctgc tacgatcaca aaccattatg tgctgctaac cggcacaaac    60
cattatgtgc tgctatcacc acaaaccatt atgtgctgct a    101

<210> SEQ ID NO 120
<211> LENGTH: 96
<212> TYPE: DNA
<213> ORGANISM: Artificial sequence
<220> FEATURE:
<223> OTHER INFORMATION: Knock down sequence for miR15a - antisense
      construct (forward)

<400> SEQUENCE: 120
cacaaaccaa gcgtgctgct aatcgcacaa accaagcgtg ctgctaatcg cacaaaccaa    60
gcgtgctgct aatcgcacaa accaagcgtg ctgcta    96

<210> SEQ ID NO 121
<211> LENGTH: 96
<212> TYPE: DNA
<213> ORGANISM: Artificial sequence
<220> FEATURE:
<223> OTHER INFORMATION: Knock down sequence for miR15a - antisense
      construct (reverse)

<400> SEQUENCE: 121
tagcagcacg cttggtttgt gcgattagca gcacgcttgg tttgtgcgat tagcagcacg    60
cttggtttgt gcgattagca gcacgcttgg tttgtg    96

<210> SEQ ID NO 122
<211> LENGTH: 143
<212> TYPE: DNA
<213> ORGANISM: Artificial sequence
<220> FEATURE:
<223> OTHER INFORMATION: Knock down sequence for miR19

<400> SEQUENCE: 122
gacggcgcta ggatcatcaa ctcagttttg catgatctga tttgcacaca agtattctgg    60
tcacagaata caactcagtt ttgcatgatc tgatttgcac acaagatgat cctagcgccg    120
tcttttttga attcgcggcc cta    143

<210> SEQ ID NO 123
<211> LENGTH: 105
<212> TYPE: DNA
<213> ORGANISM: Artificial sequence
<220> FEATURE:
<223> OTHER INFORMATION: Knock down sequence for miR19

<400> SEQUENCE: 123
tcagttttgc atggatttgc acacgattca gttttgcatg gatttgcaca accggtcagt    60
tttgcatgga tttgcacatc actcagtttt gcatggattt gcaca    105

<210> SEQ ID NO 124
<211> LENGTH: 100
<212> TYPE: DNA
<213> ORGANISM: Artificial sequence
<220> FEATURE:
<223> OTHER INFORMATION: Knock down sequence for miR19 - antisense
      construct (forward)

-continued

<400> SEQUENCE: 124
tcagttttgc atgatttgca caatcgtcag ttttgcatga tttgcacaat cgtcagtttt    60
gcatgatttg cacaatcgtc agttttgcat gatttgcaca                         100

<210> SEQ ID NO 125
<211> LENGTH: 97
<212> TYPE: DNA
<213> ORGANISM: Artificial sequence
<220> FEATURE:
<223> OTHER INFORMATION: Knock down sequence for miR19 - antisense
      construct (forward)

<400> SEQUENCE: 125
tgtgcaaatc atgcaaaact gacgattgtg caaatcatgc aaaactgcga ttgtgcaaat    60
catgcaaaac tgcgattgtg caaatcatgc aaaactg                            97

<210> SEQ ID NO 126
<211> LENGTH: 141
<212> TYPE: DNA
<213> ORGANISM: Artificial sequence
<220> FEATURE:
<223> OTHER INFORMATION: Knock down sequence for miR26

<400> SEQUENCE: 126
gacggcgcta ggatcatcaa cagcctatcc tggatctatt acttgaacaa gtattctggt    60
cacagaatac aacagcctat cctggatcta ttacttgaac aagatgatcc tagcgccgtc   120 tttttttgaat tcgcggccct a                                            141

<210> SEQ ID NO 127
<211> LENGTH: 101
<212> TYPE: DNA
<213> ORGANISM: Artificial sequence
<220> FEATURE:
<223> OTHER INFORMATION: Knock down sequence for miR26

<400> SEQUENCE: 127
agcctatcct ggattacttg aacgatagcc tatcctggat tacttgaaac cggagcctat    60
cctggattac ttgaatcaca gcctatcctg gattacttga a                       101

<210> SEQ ID NO 128
<211> LENGTH: 96
<212> TYPE: DNA
<213> ORGANISM: Artificial sequence
<220> FEATURE:
<223> OTHER INFORMATION: Knock down sequence for miR26 - antisense
      construct (forward)

<400> SEQUENCE: 128
agcctatcct ggttacttga aatcgagcct atcctggtta cttgaaatcg agcctatcct    60
ggttacttga aatcgagcct atcctggtta cttgaa                             96

<210> SEQ ID NO 129
<211> LENGTH: 96
<212> TYPE: DNA
<213> ORGANISM: Artificial sequence
<220> FEATURE:
<223> OTHER INFORMATION: Knock down sequence for miR26 - antisense
      construct (reverse)

<400> SEQUENCE: 129
ttcaagtaac caggataggc tcgatttcaa gtaaccagga taggctcgat ttcaagtaac    60
caggataggc tcgatttcaa gtaaccagga taggct    96

<210> SEQ ID NO 130
<211> LENGTH: 140
<212> TYPE: DNA
<213> ORGANISM: Artificial sequence
<220> FEATURE:
<223> OTHER INFORMATION: Knock down sequence for miR27

<400> SEQUENCE: 130
gacggcgcta ggatcatcaa ctgctcacaa gcaatctgct aagccctcaa gtattctggt    60
cacagaatac aactgctcac aagcaatctg ctaagcccta agatgatcct agcgccgtct   120
tttttgaatt cgcggccta    140

<210> SEQ ID NO 131
<211> LENGTH: 101
<212> TYPE: DNA
<213> ORGANISM: Artificial sequence
<220> FEATURE:
<223> OTHER INFORMATION: Knock down sequence for miR27

<400> SEQUENCE: 131
tgctcacaag cagctaagcc ctcgattgct cacaagcagc taagccctac cggtgctcac    60
aagcagctaa gcccttcact gctcacaagc agctaagccc t    101

<210> SEQ ID NO 132
<211> LENGTH: 92
<212> TYPE: DNA
<213> ORGANISM: Artificial sequence
<220> FEATURE:
<223> OTHER INFORMATION: Knock down sequence for miR27a - antisense
      construct (forward)

<400> SEQUENCE: 132
gcggaactta gcactgtgaa atcggcggaa cttagcactg tgaaatcggc ggaacttagc    60
actgtgaaat cggcggaact tagcactgtg aa    92

<210> SEQ ID NO 133
<211> LENGTH: 92
<212> TYPE: DNA
<213> ORGANISM: Artificial sequence
<220> FEATURE:
<223> OTHER INFORMATION: Knock down sequence for miR27a - antisense
      construct (reverse)

<400> SEQUENCE: 133
ttcacagtgc taagttccgc cgatttcaca gtgctaagtt ccgccgattt cacagtgcta    60
agttccgccg atttcacagt gctaagttcc gc    92

<210> SEQ ID NO 134
<211> LENGTH: 141
<212> TYPE: DNA
<213> ORGANISM: Artificial sequence
<220> FEATURE:
<223> OTHER INFORMATION: Knock down sequence for miR181

```
<400> SEQUENCE: 134
gacggcgcta ggatcatcaa cactcaccga cagatctgtt gaatgttcaa gtattctggt    60
cacagaatac aacactcacc gacagatctg ttgaatgttc aagatgatcc tagcgccgtc    120 tttttttgaat tcgcggccct a                                             141

<210> SEQ ID NO 135
<211> LENGTH: 101
<212> TYPE: DNA
<213> ORGANISM: Artificial sequence
<220> FEATURE:
<223> OTHER INFORMATION: Knock down sequence for miR181

<400> SEQUENCE: 135
actcaccgac aggttgaatg ttcgatactc accgacaggt tgaatgttac cggactcacc    60
gacaggttga atgtttcaca ctcaccgaca ggttgaatgt t                        101

<210> SEQ ID NO 136
<211> LENGTH: 100
<212> TYPE: DNA
<213> ORGANISM: Artificial sequence
<220> FEATURE:
<223> OTHER INFORMATION: Knock down sequence for miR181d - antisense
      construct (forward)

<400> SEQUENCE: 136
acccaccgac agcatgaatg ttatcgaccc accgacagca tgaatgttat cgacccaccg    60
acagcatgaa tgttatcgac ccaccgacag catgaatgtt                          100

<210> SEQ ID NO 137
<211> LENGTH: 102
<212> TYPE: DNA
<213> ORGANISM: Artificial sequence
<220> FEATURE:
<223> OTHER INFORMATION: Knock down sequence for miR181d - antisense
      construct (reverse)

<400> SEQUENCE: 137
aacattcatg ctgtcggtgg gtcgataaca ttcatgctgt cggtgggtac gataacattc    60
atgctgtcgg tgggtcgatt aacattcatg ctgtcggtgg gt                       102

<210> SEQ ID NO 138
<211> LENGTH: 147
<212> TYPE: DNA
<213> ORGANISM: Artificial sequence
<220> FEATURE:
<223> OTHER INFORMATION: Knock down sequence for miR182

<400> SEQUENCE: 138
gacggcgcta ggatcatcaa ccggtgtgag ttctacatct cattgccaaa caagtattct    60
ggtcacagaa tacaaccggt gtgagttcta catctcattg ccaaacaaga tgatcctagc    120
gccgtctttt ttgaattcgc ggccta                                         147

<210> SEQ ID NO 139
<211> LENGTH: 113
<212> TYPE: DNA
<213> ORGANISM: Artificial sequence
<220> FEATURE:
<223> OTHER INFORMATION: Knock down sequence for miR182
```

<400> SEQUENCE: 139
cggtgtgagt tctaccattg ccaaacgatc ggtgtgagtt ctaccattgc caaaaccggc    60
ggtgtgagtt ctaccattgc caaatcaccg gtgtgagttc taccattgcc aaa    113

<210> SEQ ID NO 140
<211> LENGTH: 108
<212> TYPE: DNA
<213> ORGANISM: Artificial sequence
<220> FEATURE:
<223> OTHER INFORMATION: Knock down sequence for miR182 - antisense
      construct (forward)

<400> SEQUENCE: 140
cggtgtgagt tagccattgc caaaatcgcg gtgtgagtta gccattgcca aaatcgcggt    60
gtgagttagc cattgccaaa atcgcggtgt gagttagcca ttgccaaa    108

<210> SEQ ID NO 141
<211> LENGTH: 108
<212> TYPE: DNA
<213> ORGANISM: Artificial sequence
<220> FEATURE:
<223> OTHER INFORMATION: Knock down sequence for miR182 - antisense
      construct (reverse)

<400> SEQUENCE: 141
tttggcaatg gctaactcac accgcgattt tggcaatggc taactcacac cgcgattttg    60
gcaatggcta actcacaccg cgattttggc aatggctaac tcacaccg    108

<210> SEQ ID NO 142
<211> LENGTH: 23
<212> TYPE: RNA
<213> ORGANISM: Artificial sequence
<220> FEATURE:
<223> OTHER INFORMATION: Anti miR-135a oligonucleotide

<400> SEQUENCE: 142
ucacauagga auaaaaagcc aua    23

<210> SEQ ID NO 143
<211> LENGTH: 23
<212> TYPE: RNA
<213> ORGANISM: Artificial sequence
<220> FEATURE:
<223> OTHER INFORMATION: Anti miR-135b oligonucleotide

<400> SEQUENCE: 143
ucacauagga augaaaagcc aua    23

<210> SEQ ID NO 144
<211> LENGTH: 23
<212> TYPE: RNA
<213> ORGANISM: Artificial sequence
<220> FEATURE:
<223> OTHER INFORMATION: Anti miR-335 oligonucleotide

<400> SEQUENCE: 144
acauuuuucg uuauugcucu uga    23

<210> SEQ ID NO 145
<211> LENGTH: 22
<212> TYPE: RNA
<213> ORGANISM: Artificial sequence
<220> FEATURE:

```
<223> OTHER INFORMATION: Anti miR-26a oligonucleotide

<400> SEQUENCE: 145
agccuauccu ggauuacuug aa                                              22

<210> SEQ ID NO 146
<211> LENGTH: 21
<212> TYPE: RNA
<213> ORGANISM: Artificial sequence
<220> FEATURE:
<223> OTHER INFORMATION: Anti miR-26b oligonucleotide

<400> SEQUENCE: 146
accuauccug aauuacuuga a                                               21

<210> SEQ ID NO 147
<211> LENGTH: 25
<212> TYPE: RNA
<213> ORGANISM: Artificial sequence
<220> FEATURE:
<223> OTHER INFORMATION: Anti miR-182 oligonucleotide

<400> SEQUENCE: 147
cggugugagu ucuaccauug ccaaa                                           25

<210> SEQ ID NO 148
<211> LENGTH: 23
<212> TYPE: RNA
<213> ORGANISM: Artificial sequence
<220> FEATURE:
<223> OTHER INFORMATION: Anti miR-19a oligonucleotide

<400> SEQUENCE: 148
ucaguuuugc auagauuugc aca                                             23

<210> SEQ ID NO 149
<211> LENGTH: 23
<212> TYPE: RNA
<213> ORGANISM: Artificial sequence
<220> FEATURE:
<223> OTHER INFORMATION: Anti miR-19b oligonucleotide

<400> SEQUENCE: 149
ucaguuuugc auggauuugc aca                                             23

<210> SEQ ID NO 150
<211> LENGTH: 22
<212> TYPE: RNA
<213> ORGANISM: Artificial sequence
<220> FEATURE:
<223> OTHER INFORMATION: Anti miR-15a oligonucleotide

<400> SEQUENCE: 150
cacaaaccau uaugugcugc ua                                              22

<210> SEQ ID NO 151
<211> LENGTH: 22
<212> TYPE: RNA
<213> ORGANISM: Artificial sequence
<220> FEATURE:
<223> OTHER INFORMATION: Anti miR-15b oligonucleotide

<400> SEQUENCE: 151
uguaaaccau gaugugcugc ua                                              22
```

```
<210> SEQ ID NO 152
<211> LENGTH: 21
<212> TYPE: RNA
<213> ORGANISM: Artificial sequence
<220> FEATURE:
<223> OTHER INFORMATION: Anti miR-27a oligonucleotide

<400> SEQUENCE: 152
gcggaacuua gccacuguga a                                              21

<210> SEQ ID NO 153
<211> LENGTH: 21
<212> TYPE: RNA
<213> ORGANISM: Artificial sequence
<220> FEATURE:
<223> OTHER INFORMATION: Anti miR-27b oligonucleotide

<400> SEQUENCE: 153
gcagaacuua gccacuguga a                                              21

<210> SEQ ID NO 154
<211> LENGTH: 23
<212> TYPE: RNA
<213> ORGANISM: Artificial sequence
<220> FEATURE:
<223> OTHER INFORMATION: Anti miR-181a oligonucleotide

<400> SEQUENCE: 154
acucaccgac agcguugaau guu                                            23

<210> SEQ ID NO 155
<211> LENGTH: 23
<212> TYPE: RNA
<213> ORGANISM: Artificial sequence
<220> FEATURE:
<223> OTHER INFORMATION: Anti miR-181b oligonucleotide

<400> SEQUENCE: 155
acccaccgac agcaaugaau guu                                            23

<210> SEQ ID NO 156
<211> LENGTH: 22
<212> TYPE: RNA
<213> ORGANISM: Artificial sequence
<220> FEATURE:
<223> OTHER INFORMATION: Anti miR-181c oligonucleotide

<400> SEQUENCE: 156
acucaccgac agguugaaug uu                                             22

<210> SEQ ID NO 157
<211> LENGTH: 23
<212> TYPE: RNA
<213> ORGANISM: Artificial Sequence
<220> FEATURE:
<223> OTHER INFORMATION: Anti miR-181d oligonucleotide

<400> SEQUENCE: 157
acccaccgac aacaaugaau guu                                            23

<210> SEQ ID NO 158
<211> LENGTH: 22
<212> TYPE: DNA
<213> ORGANISM: Artificial Sequence
<220> FEATURE:
<223> OTHER INFORMATION: Oligonucleotide primers used for microRNA real
      time PCR
```

```
<400> SEQUENCE: 158
tagcagcacg taaatattgg cg                                              22

<210> SEQ ID NO 159
<211> LENGTH: 22
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 159
gggtttggat agtacgttcg ca                                              22

<210> SEQ ID NO 160
<211> LENGTH: 20
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 160
catacgcccc tcctgatgtc                                                 20

<210> SEQ ID NO 161
<211> LENGTH: 20
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 161
gtgcaccatc agcaaggacc                                                 20

<210> SEQ ID NO 162
<211> LENGTH: 20
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 162
gcgccgaaag tggagtagat                                                 20

<210> SEQ ID NO 163
<211> LENGTH: 23
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 163
agtattttgt ggatgtggcc atg                                             23

<210> SEQ ID NO 164
<211> LENGTH: 21
<212> TYPE: DNA
<213> ORGANISM: Artificial Sequence
<220> FEATURE:
<223> OTHER INFORMATION: Oligonucleotide primers used for mRNA real time
      PCR
```

<400> SEQUENCE: 164
tgggaatggg ctgaccatat t                                              21

<210> SEQ ID NO 165
<211> LENGTH: 18
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 165
catgcccgaa ggctacgt                                                  18

<210> SEQ ID NO 166
<211> LENGTH: 19
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 166
cgatgccctt cagctcgat                                                 19

<210> SEQ ID NO 167
<211> LENGTH: 18
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 167
tcatgtcccg gaagcacc                                                  18

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide primers used for mRNA real time
      PCR

<400> SEQUENCE: 168
aattggccct ttctatgccg                                                20

<210> SEQ ID NO 169
<211> LENGTH: 90
<212> TYPE: DNA
<213> ORGANISM: Mus musculus

<400> SEQUENCE: 169
aggcctcact gttctctatg gcttttttatt cctatgtgat tctattgctc gctcatatag   60
ggattggagc cgtggcgtac ggtgaggata                                     90

<210> SEQ ID NO 170
<211> LENGTH: 90
<212> TYPE: DNA
<213> ORGANISM: Homo sapiens

<400> SEQUENCE: 170
aggcctcgct gttctctatg gcttttttatt cctatgtgat tctactgctc actcatatag   60
ggattggagc cgtggcgcac ggcggggaca                                     90

<210> SEQ ID NO 171
<211> LENGTH: 90
<212> TYPE: DNA
<213> ORGANISM: Pongo pygmaeus

<400> SEQUENCE: 171
aggcctcgct gttctctatg gctttttatt cctatgtgat tctactgctc actcatatag    60
ggattggagc cgtggcgcac ggcggggaca                                     90

<210> SEQ ID NO 172
<211> LENGTH: 90
<212> TYPE: DNA
<213> ORGANISM: Canis familiaris

<400> SEQUENCE: 172
aggcctcgct gttctctatg gctttttatt cctatgtgat tttactgctc actcatatag    60
ggattggagc cgtggcgtac ggcgggggcg                                     90

<210> SEQ ID NO 173
<211> LENGTH: 90
<212> TYPE: DNA
<213> ORGANISM: Equus caballus

<400> SEQUENCE: 173
aggcctcgct gttctctatg gctttttatt cctatgtgat tctactgctc actcatatag    60
ggattggagc cgtggcgcac ggcggggtg                                      90

<210> SEQ ID NO 174
<211> LENGTH: 78
<212> TYPE: DNA
<213> ORGANISM: Caluromys lanatus

<400> SEQUENCE: 174
ctggactata tggctgtgta ttcctatgtg atcccgctgc tcattcacat ggggattgga    60
tgtaccacaa cagggaca                                                  78

<210> SEQ ID NO 175
<211> LENGTH: 96
<212> TYPE: DNA
<213> ORGANISM: Gallus gallus

<400> SEQUENCE: 175
ggccgagcat ggagcgcctc atatggcttt ttattcctat gtgattatac atcccgcttc    60
atatagggat tgaagccgtg caaggcgctg ggtcc                               96

<210> SEQ ID NO 176
<211> LENGTH: 100
<212> TYPE: DNA
<213> ORGANISM: Mus musculus

<400> SEQUENCE: 176
tgaattttca caatgtattt catggcttcc atccctacat gagactttat tacgatcaca    60
taggaataaa aagccataaa gcactagagt gaatttatct                          100

<210> SEQ ID NO 177
<211> LENGTH: 100
<212> TYPE: DNA
<213> ORGANISM: Rattus norvegicus

```
<400> SEQUENCE: 177
tgaattttca caatgtattt catggcttcc atccctacat gagactttat tacgatcaca      60
taggaataaa aagccataaa gcactagagt gaatttatct                          100

<210> SEQ ID NO 178
<211> LENGTH: 100
<212> TYPE: DNA
<213> ORGANISM: Homo sapiens

<400> SEQUENCE: 178 tgattttca caatgtattt catggcttcc atccctacat gagactttat tactatcaca       60
taggaataaa aagccataaa gcactagagt gaatttatct                          100

<210> SEQ ID NO 179
<211> LENGTH: 100
<212> TYPE: DNA
<213> ORGANISM: Pongo pygmaeus

<400> SEQUENCE: 179 tgattttca caatgtattt catggcttcc atccctacat gagactttat tactatcaca       60
taggaataaa aagccataaa gcactagagt gaatttatct                          100

<210> SEQ ID NO 180
<211> LENGTH: 100
<212> TYPE: DNA
<213> ORGANISM: Canis familiaris

<400> SEQUENCE: 180 tgattttca caatgtattt catggcttcc atccctacat gagactttat tactatcaca       60
taggaataaa aagccataaa gcactagagt gaatttatct                          100

<210> SEQ ID NO 181
<211> LENGTH: 100
<212> TYPE: DNA
<213> ORGANISM: Equus caballus

<400> SEQUENCE: 181 tgattttca caatgtattt catggcttcc atccctacat gagactttat tactatcaca       60
taggaataaa aagccataaa gcactagagt gaatttatct                          100

<210> SEQ ID NO 182
<211> LENGTH: 100
<212> TYPE: DNA
<213> ORGANISM: Caluromys lanatus

<400> SEQUENCE: 182
tgacatttca caatgtattt catggcttcc atccctacat gagactttat tactatcaca      60
taggaataaa aagccataag acactagagt gaatttatct                          100

<210> SEQ ID NO 183
<211> LENGTH: 100
<212> TYPE: DNA
<213> ORGANISM: Gallus gallus

<400> SEQUENCE: 183 tgattttca caatgtattt catggcttcc atccctacat gagactttat tactatcaca       60
taggaataaa aagccataaa acactagagt gaatttatct                          100
```

```
<210> SEQ ID NO 184
<211> LENGTH: 97
<212> TYPE: DNA
<213> ORGANISM: Mus musculus

<400> SEQUENCE: 184
cgctctgctg tggcctatgg cttttcattc ctatgtgatt gctgctccga actcatgtag      60
ggctaaaagc catgggctac agtgaggggc aagctcc                              97

<210> SEQ ID NO 185
<211> LENGTH: 97
<212> TYPE: DNA
<213> ORGANISM: Rattus norvegicus

<400> SEQUENCE: 185
cgctctgctg tggcctatgg cttttcattc ctatgtgatt gctgttccga actcatgtag      60
ggctaaaagc catgggctac agtgaggggc aagctcc                              97

<210> SEQ ID NO 186
<211> LENGTH: 99
<212> TYPE: DNA
<213> ORGANISM: Homo sapiens

<400> SEQUENCE: 186
cactctgctg tggcctatgg cttttcattc ctatgtgatt gctgtcccaa actcatgtag      60
ggctaaaagc catgggctac agtgaggggc gagctctcc                            99

<210> SEQ ID NO 187
<211> LENGTH: 101
<212> TYPE: DNA
<213> ORGANISM: Pongo pygmaeus

<400> SEQUENCE: 187
cactctgctg tggcctatgg cttttcattc ctatgtgatt gctgtcccaa actcatgtag      60
ggctaaaagc catgggctac agtgaggggc aagccttctc c                         101

<210> SEQ ID NO 188
<211> LENGTH: 101
<212> TYPE: DNA
<213> ORGANISM: Canis familiaris

<400> SEQUENCE: 188
agctctgctg tggcctatgg cttttcattc ctatgtgatt gctgtttcta attcatgtag      60
ggctaaaagc catgggctac agtgaggggc gtgccttctc c                         101

<210> SEQ ID NO 189
<211> LENGTH: 103
<212> TYPE: DNA
<213> ORGANISM: Equus caballus

<400> SEQUENCE: 189
agctctgctg tggcctatgg cttttcattc ctatgtgatt gctgttctaa actcatgtag      60
ggctaaaagc catgggctac agtgaggggc gtgctccttc tcc                       103

<210> SEQ ID NO 190
<211> LENGTH: 99
<212> TYPE: DNA
<213> ORGANISM: Caluromys lanatus
```

```
<400> SEQUENCE: 190
agctctctgc tgtggcctat ggcttttcat tcctatgtga ttgctgttcc caactcatgt        60
agggctaaaa gccatgggct acagggaggg gagagcctc                              99

<210> SEQ ID NO 191
<211> LENGTH: 97
<212> TYPE: DNA
<213> ORGANISM: Gallus gallus

<400> SEQUENCE: 191
taagccctct gctgtggtct atggcttttt attcctatgt gattgctttt cctaactcat        60
gtagggcgaa aagccatggg ctactcaggg gagggac                                97

<210> SEQ ID NO 192
<211> LENGTH: 22
<212> TYPE: RNA
<213> ORGANISM: Homo sapiens

<400> SEQUENCE: 192
uauagggauu ggagccgugg cg                                                22

<210> SEQ ID NO 193
<211> LENGTH: 22
<212> TYPE: RNA
<213> ORGANISM: Homo sapiens

<400> SEQUENCE: 193
auguagggcu aaaagccaug gg                                                22

<210> SEQ ID NO 194
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (23)..(23)
<223> OTHER INFORMATION: 2' O-Methyl

<400> SEQUENCE: 194
uauggcuuuu uauuccuaug uga                                               23

<210> SEQ ID NO 195
<211> LENGTH: 22
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (22)..(22)
<223> OTHER INFORMATION: 2' O-Methyl

<400> SEQUENCE: 195
uauagggauu ggagccgugg cg                                                22
```

-continued

<210> SEQ ID NO 196
<211> LENGTH: 22
<212> TYPE: RNA
<213> ORGANISM: Artificial Sequence
<220> FEATURE:
<223> OTHER INFORMATION: modified miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (22)..(22)
<223> OTHER INFORMATION: 2' O-Methyl

<400> SEQUENCE: 196
ucauauaggg auuggagccg ug                                              22

<210> SEQ ID NO 197
<211> LENGTH: 23
<212> TYPE: RNA
<213> ORGANISM: Artificial Sequence
<220> FEATURE:
<223> OTHER INFORMATION: modified miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl

<400> SEQUENCE: 197
ucacauagga auaaaaagcc aua                                             23

<210> SEQ ID NO 198
<211> LENGTH: 23
<212> TYPE: RNA
<213> ORGANISM: Artificial Sequence
<220> FEATURE:
<223> OTHER INFORMATION: modified miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (10)..(11)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl

<400> SEQUENCE: 198
uauggcuuuu uauuccuaug uga                                             23

<210> SEQ ID NO 199
<211> LENGTH: 22
<212> TYPE: RNA
<213> ORGANISM: Artificial Sequence
<220> FEATURE:
<223> OTHER INFORMATION: modified miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (10)..(10)
<223> OTHER INFORMATION: 2' O-Methyl

```
<220> FEATURE:
<221> NAME/KEY: misc_feature
<222> LOCATION: (22)..(22)
<223> OTHER INFORMATION: 2' O-Methyl

<400> SEQUENCE: 199
uauagggauu ggagccgugg cg                                             22

<210> SEQ ID NO 200
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (4)..(4)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl

<400> SEQUENCE: 200
uauggcuuuu uauuccuaug uga                                            23

<210> SEQ ID NO 201
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (4)..(4)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl

<400> SEQUENCE: 201
uaauuuaagc uucuuuguuc ugg                                            23

<210> SEQ ID NO 202
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 2' O-Methyl
<220> FEATURE:
<221> NAME/KEY: misc_feature
<222> LOCATION: (23)..(23)
```

```
<223> OTHER INFORMATION: 2' O-Methyl

<400> SEQUENCE: 202
ccagaacaaa gaagcuuaaa uua                                              23

<210> SEQ ID NO 203
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (23)..(23)
<223> OTHER INFORMATION: 2' O-Methyl

<400> SEQUENCE: 203
uauggcuuuu cauuccuaug uga                                              23

<210> SEQ ID NO 204
<211> LENGTH: 22
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (22)..(22)
<223> OTHER INFORMATION: 2' O-Methyl

<400> SEQUENCE: 204
auguagggcu aaaagccaug gg                                               22

<210> SEQ ID NO 205
<211> LENGTH: 22
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(2)
<223> OTHER INFORMATION: 2' O-Methyl

<400> SEQUENCE: 205
ucauguaggg cuaaaagcca ug                                               22

<210> SEQ ID NO 206
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl
```

```
<400> SEQUENCE: 206
ucacauagga augaaaagcc aua                                          23

<210> SEQ ID NO 207
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (11)..(13)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl

<400> SEQUENCE: 207
uauggcuuuu cauuccuaug uga                                          23

<210> SEQ ID NO 208
<211> LENGTH: 22
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (9)..(10)
<223> OTHER INFORMATION: 2' O-Methyl
<220> FEATURE:
<221> NAME/KEY: misc_feature
<222> LOCATION: (22)..(22)
<223> OTHER INFORMATION: 2' O-Methyl

<400> SEQUENCE: 208
auguagggcu aaaagccaug gg                                           22

<210> SEQ ID NO 209
<211> LENGTH: 23
<212> TYPE: RNA
<213> ORGANISM: Artificial Sequence
<220> FEATURE:
<223> OTHER INFORMATION: modified  miR-135 oligonucleotides
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (1)..(2)
<223> OTHER INFORMATION: 2' O-Methyl
<220> FEATURE:
<221> NAME/KEY: misc_feature
<222> LOCATION: (4)..(4)
<223> OTHER INFORMATION: 2' O-Methyl
<220> FEATURE:
<221> NAME/KEY: misc_feature
<222> LOCATION: (23)..(23)
<223> OTHER INFORMATION: 2' O-Methyl
```

<400> SEQUENCE: 209
uauggcuuuu cauuccuaug uga                                           23

<210> SEQ ID NO 210
<211> LENGTH: 177
<212> TYPE: DNA
<213> ORGANISM: Mus musculus

<400> SEQUENCE: 210
acaccctcac gatggaagaa gggcccacag gggccgcccc aggcctcact gttctctatg    60 gcttttatt cctatgtgat tctattgctc gctcatatag ggattggagc cgtggcgtac    120
ggtgaggata agccaacaga gggctctgat gtggaacaag agggctcgag gtaaacc      177

<210> SEQ ID NO 211
<211> LENGTH: 181
<212> TYPE: DNA
<213> ORGANISM: Mus musculus

<400> SEQUENCE: 211 attcccagt tcctgcttt tttaagattg ctgccactgg acccctccgc tctgctgtgg     60
cctatggctt ttcattccta tgtgattgct gctccgaact catgtagggc taaaagccat   120
gggctacagt gaggggcaag ctcctgcaca gctacacatc cctaaggacc agccacagag   180
g                                                                   181

<210> SEQ ID NO 212
<211> LENGTH: 23
<212> TYPE: RNA
<213> ORGANISM: Mus musculus

<400> SEQUENCE: 212
uauggcuuuu uauuccuaug uga                                           23

<210> SEQ ID NO 213
<211> LENGTH: 23
<212> TYPE: RNA
<213> ORGANISM: Mus musculus

<400> SEQUENCE: 213
uauggcuuuu cauuccuaug uga                                           23